US012565485B2

(12) United States Patent
Dipasquale

(10) Patent No.: US 12,565,485 B2
(45) Date of Patent: Mar. 3, 2026

(54) SOLID FORMS OF 1-((S)-4-((R)-7-(6-AMINO-4-METHYL-3-(TRIFLUOROMETHYL)PYRIDIN-2-YL)-6-CHLORO-8-FLUORO-2-(((S)-1-METHYLPYRROLIDIN-2-YL)METHOXY)QUINAZOLIN-4-YL)-3-METHYLPIPERAZIN-1-YL)PROP-2-EN-1-ONE

(71) Applicant: Genentech, Inc., South San Francisco, CA (US)

(72) Inventor: Antonio Giovanni Dipasquale, San Bruno, CA (US)

(73) Assignee: Genentech, Inc., South San Francisco, CA (US)

( * ) Notice: Subject to any disclaimer, the term of this patent is extended or adjusted under 35 U.S.C. 154(b) by 215 days.

(21) Appl. No.: 18/164,277

(22) Filed: Feb. 3, 2023

(65) Prior Publication Data

US 2023/0265074 A1 Aug. 24, 2023

Related U.S. Application Data

(60) Provisional application No. 63/307,526, filed on Feb. 7, 2022.

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01); *C07B 2200/13* (2013.01)

(58) Field of Classification Search
CPC .... C07D 401/14; C07B 2200/13; A61P 35/00
See application file for complete search history.

(56) References Cited

U.S. PATENT DOCUMENTS 11,236,068 B2 2/2022 Malhotra et al.
2022/0081413 A1 3/2022 Lim et al.
2023/0089126 A1 3/2023 Malhotra et al.

FOREIGN PATENT DOCUMENTS

WO WO-2020097537 A2 * 5/2020 ........... C07D 401/04
WO 2022/035790 A1 2/2022
WO 2022/103904 A1 5/2022
WO 2022/125427 A1 6/2022

OTHER PUBLICATIONS

Berge SM, Bighley LD, Monkhouse DC. Pharmaceutical salts. J Pharm Sci. Jan. 1977;66(1):1-19. doi: 10.1002/jps.2600660104. PMID: 833720. (Year: 1977).*
"International Preliminary Report on Patentability—PCT/US2023/061976" (Report Issuance Date: Aug. 6, 2024, Chapter I),:pp. 1-9 (Aug. 22, 2024).
Caira, M.R. Design of Organic Solids—Topics in Chemistry "Chapter 5: Crystalline Polymorphism of Organic Compounds" Weber, E., Aoyama, Y., Caira, M.R., eds., Berlin, Heidelberg—DE:Springer, vol. 198:163-208 (Jan. 1, 1998).

(Continued)

*Primary Examiner* — Clinton A Brooks
*Assistant Examiner* — Josmalen M. Ramos-Lewis
(74) *Attorney, Agent, or Firm* — Kevin M. Clark

(57) ABSTRACT

Provided herein are salts and solid forms of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one, including adipate, fumarate, ethylenesulphonate, besylate, and mesylate salts thereof.

40 Claims, 27 Drawing Sheets

(56) References Cited

OTHER PUBLICATIONS

Hilfiker, R., et al. Polymorphism—in the Pharmaceutical Industry "Chapter 1: Relevance of Solid-sate Properties for Pharmaceutical Products" Hilfiker, R., ed., First edition, Weiheim, Germany: Wiley-VCH Verlag GmBH,: 1-19 (Feb. 6, 2006).

"International Search Report—PCT/US2023/061976" (w/Written Opinion), :pp. 1-16 (Apr. 26, 2023).

USPTO et al., "U.S. Appl. No. 18/164,302 entitled 'Process for Synthesis of Qinazoline Compounds', filed Feb. 3, 2023" (Feb. 2, 2023).

* cited by examiner

Form C

Form D

SOLID FORMS OF 1-((S)-4-((R)-7-(6-AMINO-4-METHYL-3-(TRIFLUOROMETHYL)PYRIDIN-2-YL)-6-CHLORO-8-FLUORO-2-(((S)-1-METHYLPYRROLIDIN-2-YL)METHOXY)QUINAZOLIN-4-YL)-3-METHYLPIPERAZIN-1-YL)PROP-2-EN-1-ONE

CROSS REFERENCE TO RELATED APPLICATIONS

This application claims the benefit of U.S. Provisional Patent Application No. 63/307,526, filed 7 Feb. 2022, and is incorporated herein by reference in its entirety and for all purposes.

FIELD OF THE INVENTION

Provided herein are solid forms of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one and methods of their use in the treatment of cancer.

BACKGROUND

Compounds and pharmaceutically acceptable salts thereof described herein are useful in the treatment of various types of cancers, including for example, lung cancer and colorectal cancer.

It is not possible to predict whether a given molecule will crystallize in one or several crystal forms, whether it will form solvates with different stoichiometries or will combine with other molecules and form stable co-crystals. (Struct Bond (2009) 132: 25-50, 27). The relative stability of varying crystal forms and, for example, the possibility of interconversion between forms or between an amorphous phase and a crystalline phase can significantly and unpredictably affect both physical and chemical properties. Thus, altering the processing, stability, bioavailability, formulation, and/or storage of pharmaceutical compounds. There is no reliable predictability of the solid form and its usefulness as a crystalline solid or amorphous solid.

Accordingly, there is a need for identifying and isolating stable forms of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one.

SUMMARY

Provided herein are solutions to the problems above and other problems in the art.

In one aspect provided herein is a compound of formula 1 as described herein.

In another aspect provided herein is a solid form of the compound of formula 1. In one embodiment, the solid for is Compound A. In one embodiment, the solid for is Compound B. In one embodiment, the solid form is Compound C. In one embodiment, the solid form is Compound D. In one embodiment, the solid form is Compound E. In one embodiment, the solid form is Compound F.

In another aspect provided herein is a solid form of Compound A corresponding to Compound A Form A as described herein. In one embodiment, is a solid form of Compound A corresponding to Compound A Form B as described herein. In one embodiment, is a solid form of Compound A corresponding to Compound A Form C as described herein. In one embodiment, is a solid form of Compound A corresponding to Compound A Form D as described herein.

In another aspect provided herein is a solid form of Compound B corresponding to Compound B Form A. Further provided herein is a solid form of Compound C corresponding to Compound C Form A. Further provided herein is a solid form of Compound D corresponding to Compound D Form A. Further provided herein is a solid form of Compound E corresponding to Compound E Form A. Further provided herein is a solid form of Compound F corresponding to Compound F Form A.

In another aspect provided herein is a method of treating a cancer comprising a KRasG12C mutation in a patient having said cancer, the method comprising administering an effective amount of Compound 1 as described herein or a crystal form corresponding to a Form as described herein of Compound A, Compound B, Compound C, Compound D, Compound E, or Compound F as described herein.

In still another aspect provided herein is a method of treating a cancer comprising a KRasG12C mutation in a patient having said cancer, the method comprising determining if the patient has the mutation and if the patient is determined to have the mutation, then administering an effective amount of Compound 1 as described herein or a crystal form corresponding to a Form as described herein of Compound A, Compound B, Compound C, Compound D, Compound E, or Compound F as described herein.

The present embodiments can be understood more fully by reference to the detailed description and examples, which are intended to exemplify non-limiting embodiments.

DETAILED DESCRIPTION

Figure 1:
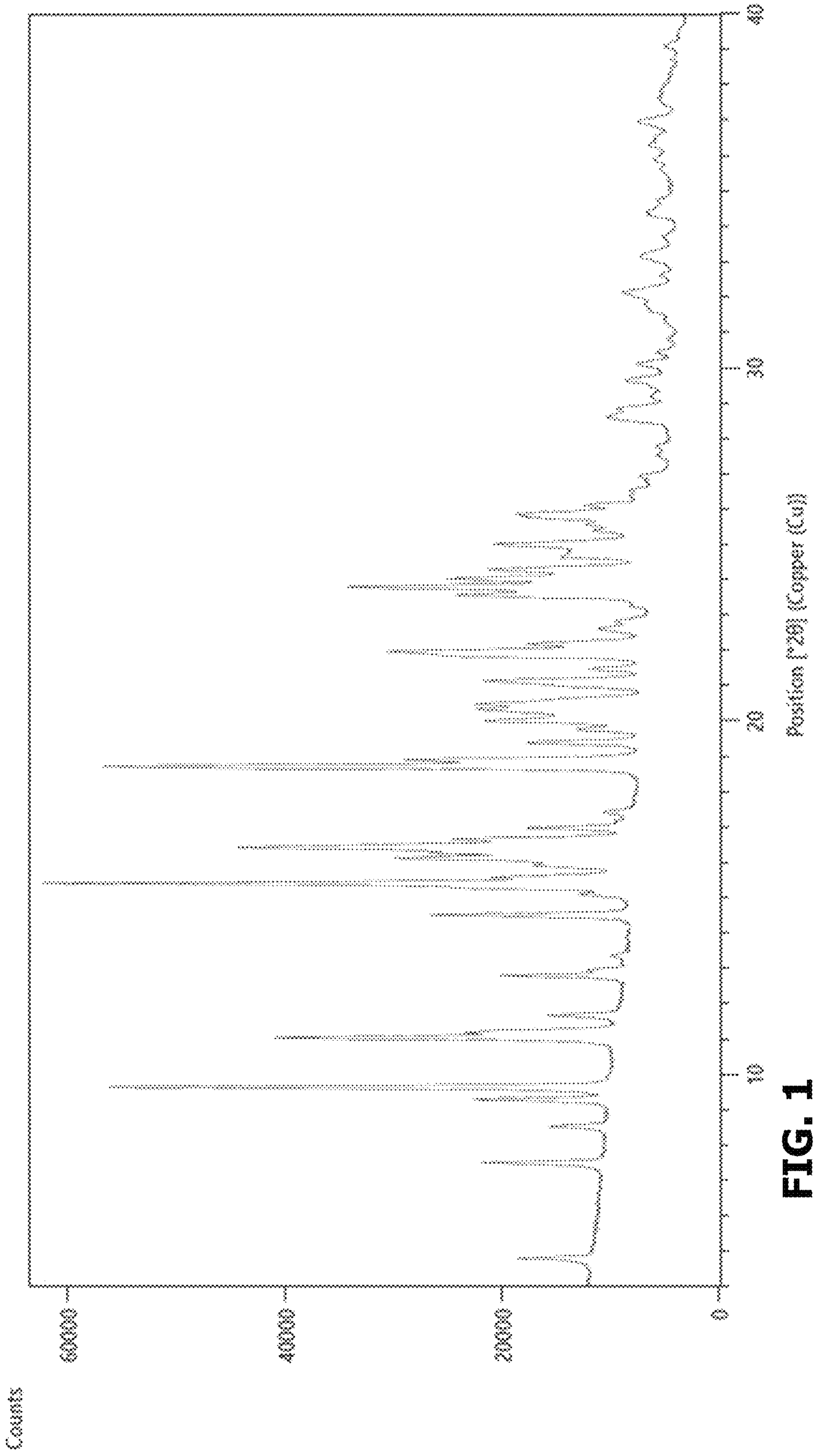
FIG. 1 depicts the XRPD spectrum of Compound A Form A.

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

As used herein, and unless otherwise specified, the terms "about" and "approximately," when referring to a numeric value or range of values used for characterization of a particular solid form described herein (e.g., XRPD peak values) indicate that the value or range of values may deviate from a given value to an extent deemed reasonable to one of ordinary skill in the art while still describing the solid form. In one embodiment, the value of an XRPD peak position may vary by up to $\pm 0.1°$ 2θ (or $\pm 0.05$ degree 2θ) while still describing the particular XRPD peak.

As used herein, and unless otherwise specified, a crystalline that is "pure," i.e., substantially free of other crystalline or amorphous solids or other chemical compounds, and contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by, for example, diffraction analysis, thermal analysis, elemental combustion analysis and/or spectroscopic analysis. The detection of other chemical compounds can be accomplished by, for example, mass spectrometry analysis, spectroscopic analysis, thermal analysis, elemental combustion analysis and/or chromatographic analysis.

Unless otherwise specified, the terms "solvate" and "solvated," as used herein, refer to a solid form of a substance which contains solvent. The terms "hydrate" and "hydrated" refer to a solvate wherein the solvent is water. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

The term "pharmaceutically acceptable," refers to a diluent, excipient, or carrier in a formulation compatible with the other ingredient(s) of the formulation and not deleterious to the recipient thereof.

"Compound 1" refers to a compound having the structure:

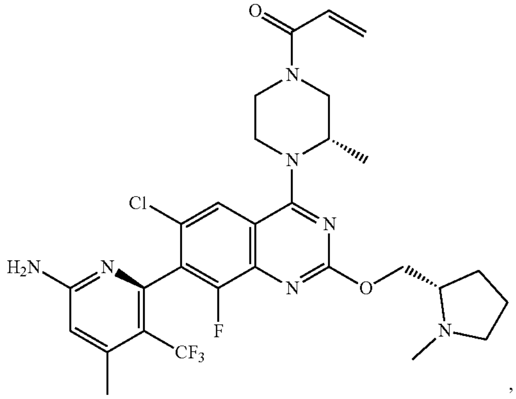

, and having the name 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one.

"Compound A" refers to a compound having the structure:

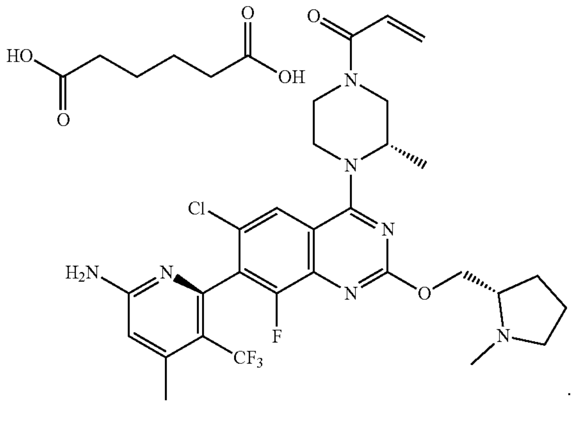

.

In some embodiments, Compound A is also described as Compound 1 adipate.

"Compound B" refers to a compound having the structure:

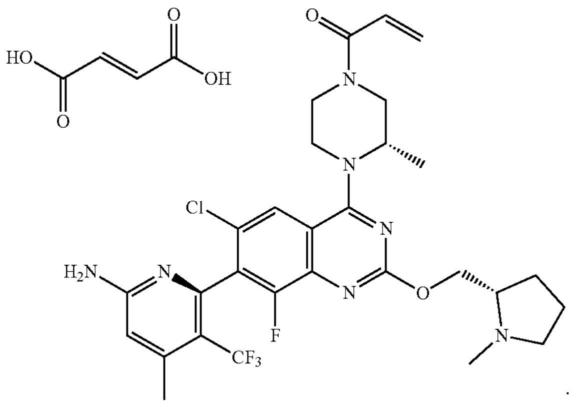

In some embodiments, Compound B is also described as Compound 1 fumarate.

"Compound C" refers to a compound having the structure:

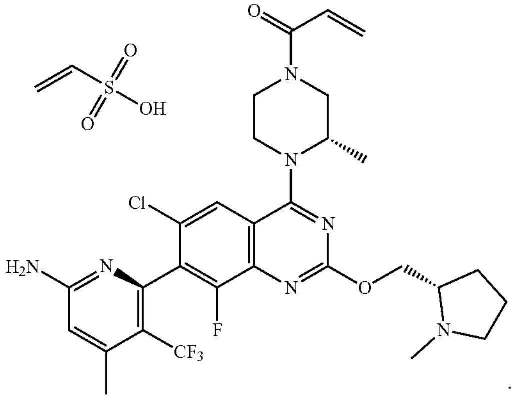

In some embodiments, Compound C is also described as Compound 1 ethylenesulphonate.

"Compound D" refers to a compound having the structure:

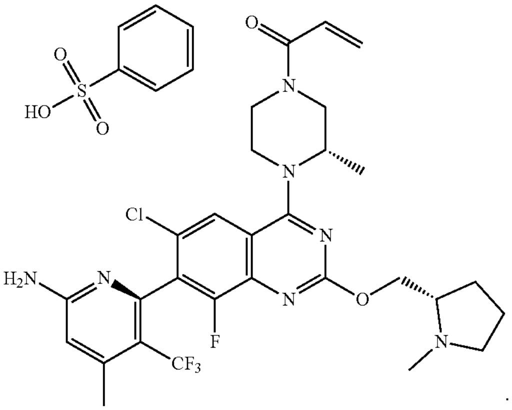

In some embodiments, Compound D is also described as Compound 1 besylate.

"Compound E" refers to a compound having the structure:

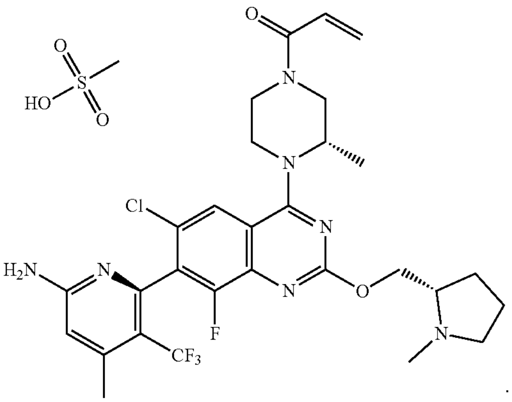

In some embodiments, Compound E is also described as Compound 1 mesylate.

"Compound F" refers to a compound having the structure:

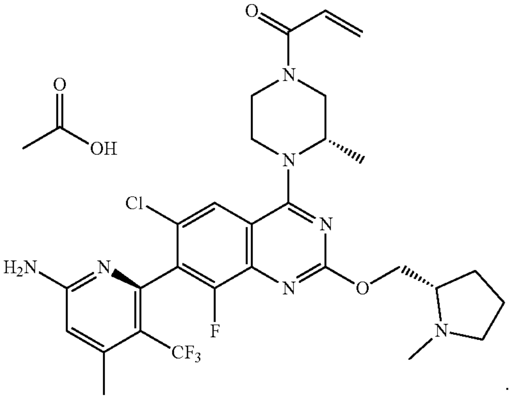

In some embodiments, Compound F is also described as Compound 1 acetate.

The term "solid form" refers to a physical form that is not predominantly in a liquid or a gaseous state. A solid form may be a crystalline form or a mixture thereof. In certain embodiments, a solid form may be a liquid crystal. In certain embodiments, the solid form of Compound A is a solid form corresponding to Compound A Form A, Compound A Form B, Compound A Form C, Compound A Form D, Compound B Form A, Compound C Form A, Compound D Form A, or Compound E Form A, or Compound F Form A, or a mixture thereof.

In one embodiment, the solid form of Compound A is an adipate salt corresponding to Form A. In one embodiment, the solid form of Compound A is an adipate salt corresponding to Form B. In another embodiment, the solid form of Compound A is an adipate salt corresponding to Form C. In still another embodiment, the solid form of Compound A is an adipate salt corresponding to Form D. In one embodiment, the solid form of Compound B is a fumarate salt corresponding to Form A. In another embodiment, the solid form of Compound C is an ethylenesulphonate salt corresponding to Form A. In another embodiment, the solid form of Compound D is a besylate salt corresponding to Form A. In another embodiment, the solid form of Compound E is a mesylate salt corresponding to Form A. In another embodiment, the solid form Compound F is an acetate salt corresponding to Form A.

The term "crystal form" or "crystalline form" refers to a solid form that is crystalline. In certain embodiments, a crystal form of a compound described herein may be substantially free of amorphous solids and/or other crystal forms. In certain embodiments, a crystal form of a compound described herein may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form described herein is pure. In certain embodiments, a crystal form of a compound described herein may be about 99%, 98%, 97%, 96%, 95%, 94%, 93%, 92%, 91%, or 90% pure. In some embodiments, a crystal form is a solid form described herein.

The term "amorphous" or "amorphous solid" refers to a solid form that not substantially crystalline as determined by X-ray diffraction. In particular, the term "amorphous solid" describes a disordered solid form, i.e., a solid form lacking long range crystalline order. In certain embodiments, an amorphous solid of a compound described herein may be substantially free of other amorphous solids and/or crystal forms. In certain embodiments, an amorphous solid may be pure. In certain embodiments, an amorphous solid of a compound described herein may be about 99%, 98%, 97%, 96%, 95%, 94%, 93%, 92%, 91%, or 90% pure.

A "patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for cancer.

As used herein, "essentially" refers to at least 90%, at least 95%, at least 98% or at least 99%.

In the description herein, if there is a discrepancy between a depicted structure and a name given to that structure, then the depicted structure controls. Additionally, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry.

Unless otherwise indicated, the terms "a compound of the formula" or "a compound of formula" or "compounds of the formula" or "compounds of formula" refer to any compound selected from the genus of compounds as defined by the formula (including any pharmaceutically acceptable salt of any such compound if not otherwise noted).

The terms "treat", "treating", and "treatment" refer to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a cancer described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement of a cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. Thus, an "effective amount" may be considered in the context of administering one or more therapeutic agents, and a single agent may be considered to be given in an effective amount if, in conjunction with one or more other agents, a desirable result may be or is achieved.

Exemplary solvent abbreviations used herein

| Abbreviation | Solvent | Abbreviation | Solvent |
|---|---|---|---|
| MeOH | Methanol | ACN | Acetonitrile |
| EtOH | Ethanol | DCM | Dichloromethane |
| IPA | Isopropyl alcohol | EtOAc | Ethyl acetate |
| MIBK | Methyl isobutyl ketone | IPAc | Isopropyl acetate |
| MEK | Methyl ethyl ketone | 2-MeTHF | 2-Methyltetrahydrofuran |
| NMP | N-Methyl pyrrolidone | THF | Tetrahydrofuran |
| DMF | Dimethyl formamide | DMSO | Dimethyl sulfoxide |
| CPME | Cyclopentyl methyl ether | DMAc | Dimethylacetamide |
| MTBE | Methyl tert-butyl ether | — | — |

Polymorphs

Provided herein are solid forms, formulations comprising such solid forms, and methods of using such solid forms of Compound 1 (e.g. Compound A, B, C, D, or E). In one embodiment provided herein are solid forms of Compound 1. Compound 1 can be a freebase as described herein existing in an amorphous solid form.

In one embodiment, Compound 1 is a crystalline adipate salt having the formula of Compound A as described herein. In one embodiment, Compound A exists in one or more forms as described herein. In one such embodiment, Compound A comprises Compound A Form A as described herein. In one such embodiment, Compound A comprises Compound A Form B as described herein. In one such embodiment, Compound A comprises Compound A Form C as described herein. In one such embodiment, Compound A comprises Compound A Form D as described herein. In another such embodiment, Compound A consists of a single Form (e.g. A, B, C, D) as described herein. In one embodiment, a compound or pharmaceutical composition described herein comprises two or more forms of Compound A. In one such embodiment, the compound or pharmaceutically acceptable salt thereof described herein comprises a mixture of Compound A Form A and Compound A Form D as described herein. In one embodiment, the compound or pharmaceutically acceptable salt thereof described herein comprises a mixture of Compound A Form A and Compound A Form C as described herein.

In another embodiment, Compound 1 is a crystalline fumarate salt having the formula of Compound B as described herein. In one such embodiment, Compound B comprises Compound B Form A as described herein.

In another embodiment, Compound 1 is a crystalline ethylenesulphonate salt having the formula of Compound C as described herein. In one such embodiment, Compound C comprises Compound C Form A as described herein.

In another embodiment, Compound 1 is a crystalline besylate salt having the formula of Compound D as described herein. In one such embodiment, Compound D comprises Compound D Form A as described herein.

In another embodiment, Compound 1 is a crystalline mesylate salt having the formula of Compound E as described herein. In one such embodiment, Compound E comprises Compound E Form A as described herein.

In another embodiment, Compound 1 is a crystalline acetate salt having the formula of Compound F as described herein. In one such embodiment, Compound F comprises Compound F Form A as described herein.

Solid forms can be characterized by physical properties such as, for example, stability, solubility and dissolution rate, density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and are unpredictable. There is no protocol of polymorph screening that can guarantee the identification of all crystal forms of a given molecule.

Techniques for characterizing crystal forms and amorphous solids include, for example, thermal analysis (e.g., differential scanning calorimetry (DSC), dynamic vapor sorption (DVS), thermal gravimetric analysis (TGA), and hot-stage microscopy), spectroscopy (e.g., infrared, Raman, and solid-state nuclear magnetic resonance), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy (including $^{1}H$ NMR and F NMR), scanning electron microscopy (SEM), electron crystallography and quantitative analysis, particle size analysis (PSA), surface area analysis, solubility studies, and dissolution studies, ultra-high performance liquid chromatography (UHPLC), and proton nuclear magnetic resonance spectrum.

The purity of the solid forms provided herein can be determined by standard analytical methods, such as thin layer chromatography (TLC), gel electrophoresis, gas chromatography, ultra-high performance liquid chromatography (UHPLC), and mass spectrometry (MS).

Compound A: Form A

In some embodiments, provided herein is a solid form corresponding to Compound A designated as Form A. Form A is an adipate crystalline solid form of Compound 1. In one embodiment, Form A of Compound A is an anhydrate. In one embodiment, Form A of Compound A is obtained from acetone, THF, or EtOAc. In one embodiment, Form A of Compound A is obtained from acetone. In another embodiment, Form A of Compound A is obtained from THF. In another embodiment, Form A of Compound A is obtained from EtOAc. In one embodiment, the stoichiometric ratio of adipic acid:freebase of Form A of Compound A is 0.9, 1.0, 1.01, 1.02, 1.03, 1.04, 1.05, 1.06, 1.07, 1.08, 1.09, or 1.10. In one such embodiment, the stoichiometric ratio of adipic acid:freebase of Form A of Compound A is 1.06.

In one embodiment, a solid form provided herein, e.g., Form A of Compound A, is a adipate salt, and is substantially crystalline, as indicated by X-ray powder diffraction pattern (XRPD) measurements. In one embodiment, the XRPD of a solid form provided herein, e.g., Form A of Compound A, is substantially as shown in FIG. 1. In another embodiment, a solid form provided herein, e.g., Form A of Compound A, has one or more characteristic XRPD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In another embodiment, a solid form provided herein, e.g., Form A of Compound A, has at least 3, 5, 10, 15, or 20 characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In still another embodiment, a solid form provided herein, e.g., Form A of Compound A, has at least five, six, seven, eight, nine, ten, eleven, twelve, thirteen, fourteen, fifteen, sixteen, seventeen, eighteen, nineteen, twenty, or all of the characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein.

In still another embodiment, a solid form provided herein, e.g., Form A of Compound A, has at least 10 characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In another embodiment, a solid form provided herein, e.g., Form A of Compound A, has at least 1, 2, 3, 4, 5, 6, 7, 8, 9, or 10 characteristic XPRD peaks at approximately 9.6474, 11.0365, 14.5086, 15.4059, 16.1353, 16.4193, 16.6719, 18.7038, 18.9135, or 21.9673±0.1° 2θ, as depicted in, for example, FIG. 1, and as found in Table 1 herein.

In still another embodiment, a solid form provided herein, e.g., Form A of Compound A, has at least 5 characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In still another embodiment, a solid form provided herein, e.g., Form A of Compound A, has at least 1, 2, 3, 4, or 5 characteristic XPRD peaks at approximately 9.6474, 11.0365, 15.4059, 16.4193, 18.7038±0.1° 2θ, as depicted in, for example, FIG. 1, and as found in Table 1 herein. In one embodiment, a solid form provided herein, e.g., Form A of Compound A, comprises an X-ray powder diffraction pattern comprising characteristic X-ray powder diffraction peaks using CuKα radiation at 9.6474, 11.0365, 15.4059, 16.4193, 18.7038 (±0.1° 2θ).

In still another embodiment, a solid form provided herein, e.g., Form A of Compound A, has at least 15 characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In still another embodiment, a solid form provided herein, e.g., Form A of Compound A, has at least 20 characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, or 22.1828±0.1° 2θ, as depicted in, for example, FIG. 1, and as found in Table 1 herein. In still another embodiment, a solid form provided herein, e.g., Form A of Compound A, has all of the characteristic XPRD peaks at approximately 4.8059, 7.506, 8.5157, 9.2973, 9.6474, 11.0365, 11.1828, 11.677, 12.7936, 14.5086, 15.4059, 16.1353, 16.4193, 16.6719, 16.9847, 18.7038, 18.9135, 19.3881, 19.7517, 19.9746, 20.5178, 21.1487, 21.4666, 21.9673, and 22.1828±0.1° 2θ, as depicted in, for example, FIG. 1, and as found in Table 1 herein.

TABLE 1

Representative XRPD Peaks for Compound A Form A

| Pos. [° 2θ] | d-spacing [Å] | Rel. Int. [%] |
|---|---|---|
| 4.8059 | 18.37243 | 12.57 |
| 7.506 | 11.76829 | 20.27 |
| 8.5157 | 10.37514 | 6.82 |
| 9.2973 | 9.50454 | 22.86 |
| 9.6474 | 9.16041 | 85.05 |
| 11.0365 | 8.01034 | 57.73 |
| 11.1828 | 7.90589 | 25.7 |
| 11.677 | 7.57235 | 11.66 |
| 12.7936 | 6.91391 | 20.85 |
| 14.5086 | 6.10025 | 33.73 |
| 15.4059 | 5.7469 | 100 |
| 16.1353 | 5.48871 | 40.28 |
| 16.4193 | 5.3944 | 65.37 |
| 16.6719 | 5.31324 | 30.23 |
| 16.9847 | 5.21609 | 18.22 |
| 18.7038 | 4.74037 | 89.52 |
| 18.9135 | 4.68829 | 39.33 |
| 19.3881 | 4.57458 | 19.09 |
| 19.7517 | 4.49117 | 10.64 |
| 19.9746 | 4.44156 | 24.31 |
| 20.5178 | 4.32518 | 24.85 |
| 21.1487 | 4.19755 | 25.86 |
| 21.4666 | 4.13611 | 9.25 |
| 21.9673 | 4.04295 | 43.19 |
| 22.1828 | 4.00415 | 20.22 |

Figure 2:
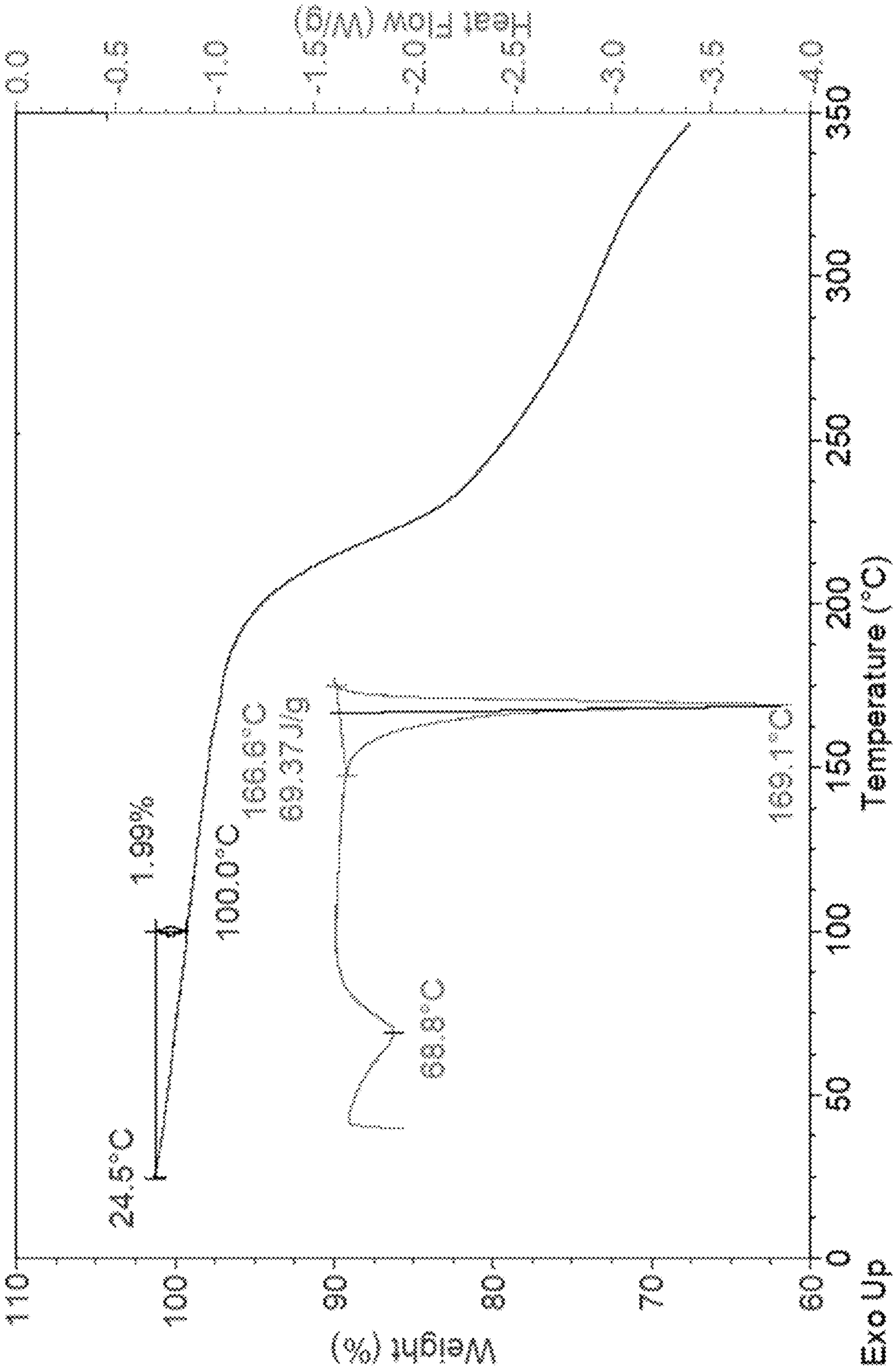
FIG. 2 depicts a TGA thermogram and DSC thermogram overlap for Compound A Form A.

In one embodiment described herein, Form A of Compound A has a TGA thermogram as substantially depicted in FIG. 2, comprising a weight loss of about 2% up to 100° C.

In one such embodiment, Form A of Compound A has a DSC thermogram corresponding to FIG. 2, comprising two endotherms at 68.8° C. and 169.1° C.

Figure 3:
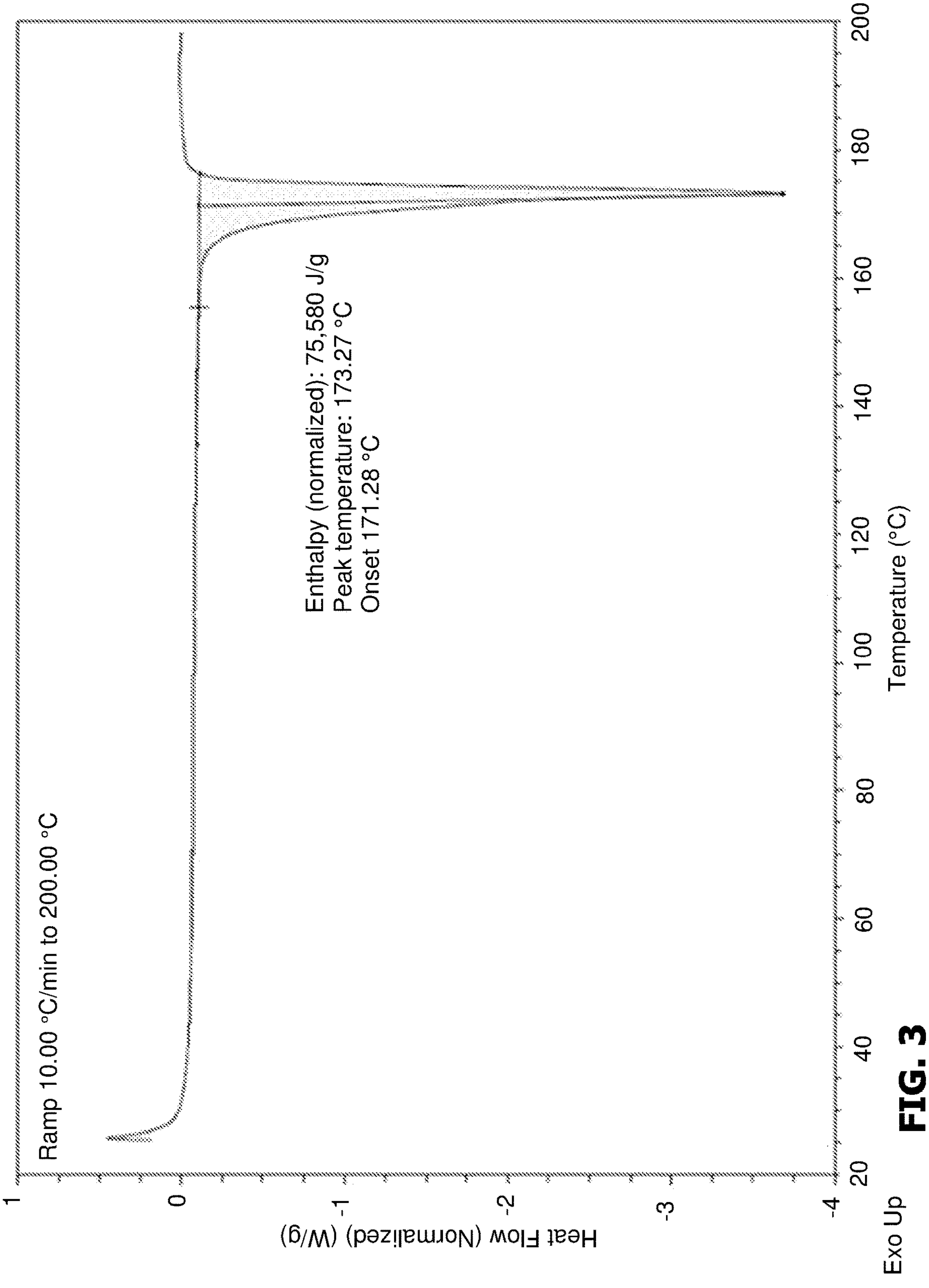
FIG. 3 depicts a DSC thermogram for Compound A Form A.

In one embodiment, Form A of Compound A has a DSC thermogram corresponding to FIG. 3, comprising one endotherm at 173.3° C. (peak).

Figure 4:
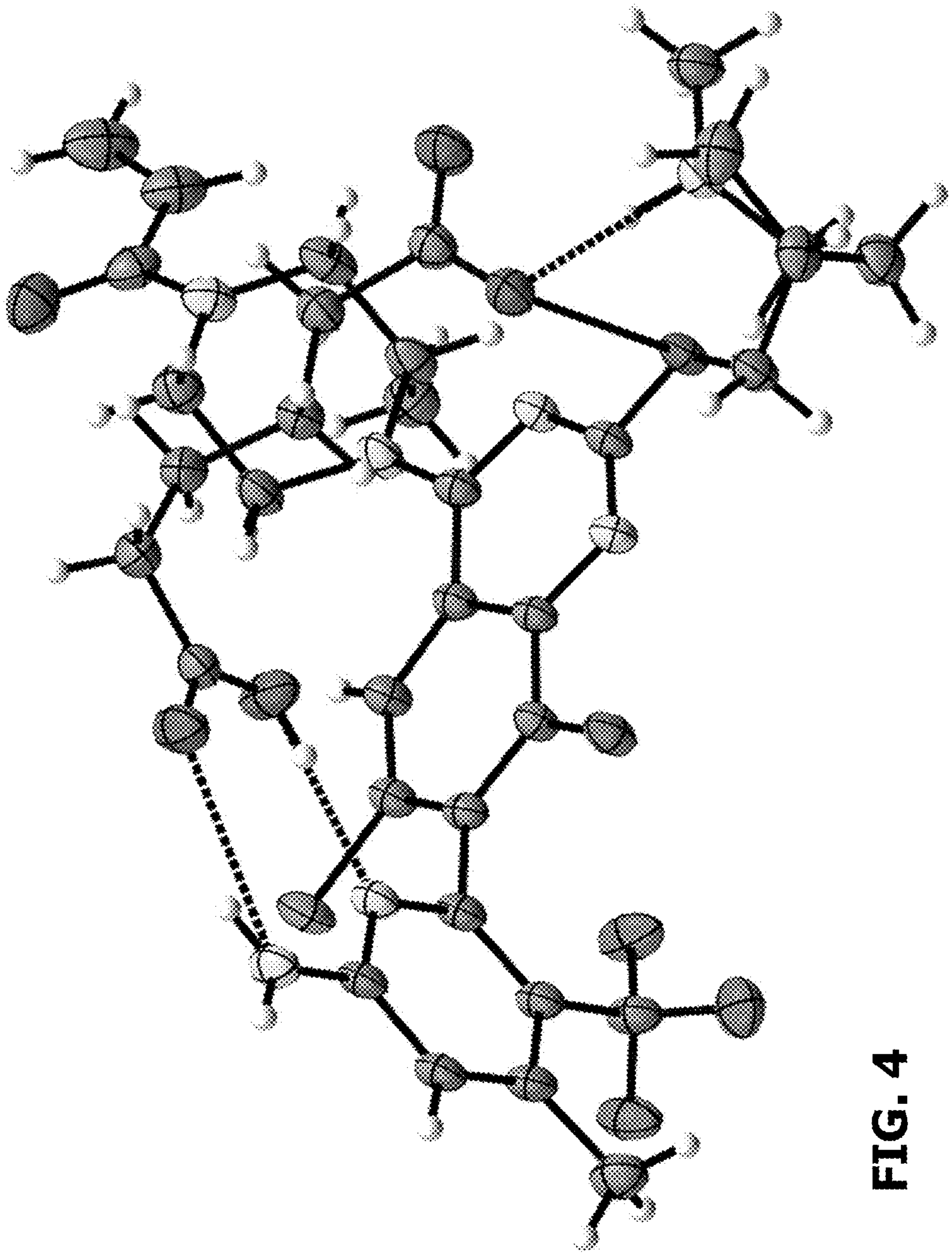
FIG. 4 depicts single crystal XRD of Compound A Form A.

Single crystal XRD for Compound A Form A is shown in FIG. 4. Absolute stereochemistry was unambiguously determined from the diffraction data and is depicted in FIG. 4.

Compound A: Form B

In some embodiments, provided herein is a solid form corresponding to Compound A designated as Form B. Form B is a crystalline solid form of Compound A. In one embodiment, Form B of Compound A is obtained from anti-solvent addition in DCM/toluene, followed by transferring to 5° C. In one embodiment, Form B of Compound A is an anhydrate. In one embodiment, no form change is observed after air drying at RT overnight. In one embodiment, the stoichiometric ratio of adipic acid:freebase of Form B of Compound A is 1.5, 1.55, 1.6, 1.65, 1.7, 1.8, 1.9, 2, 2.05, or 2.10. In one embodiment, the stoichiometric ratio of adipic acid:freebase of Form B of Compound A is 1.65 or 2.10.

Figure 5:
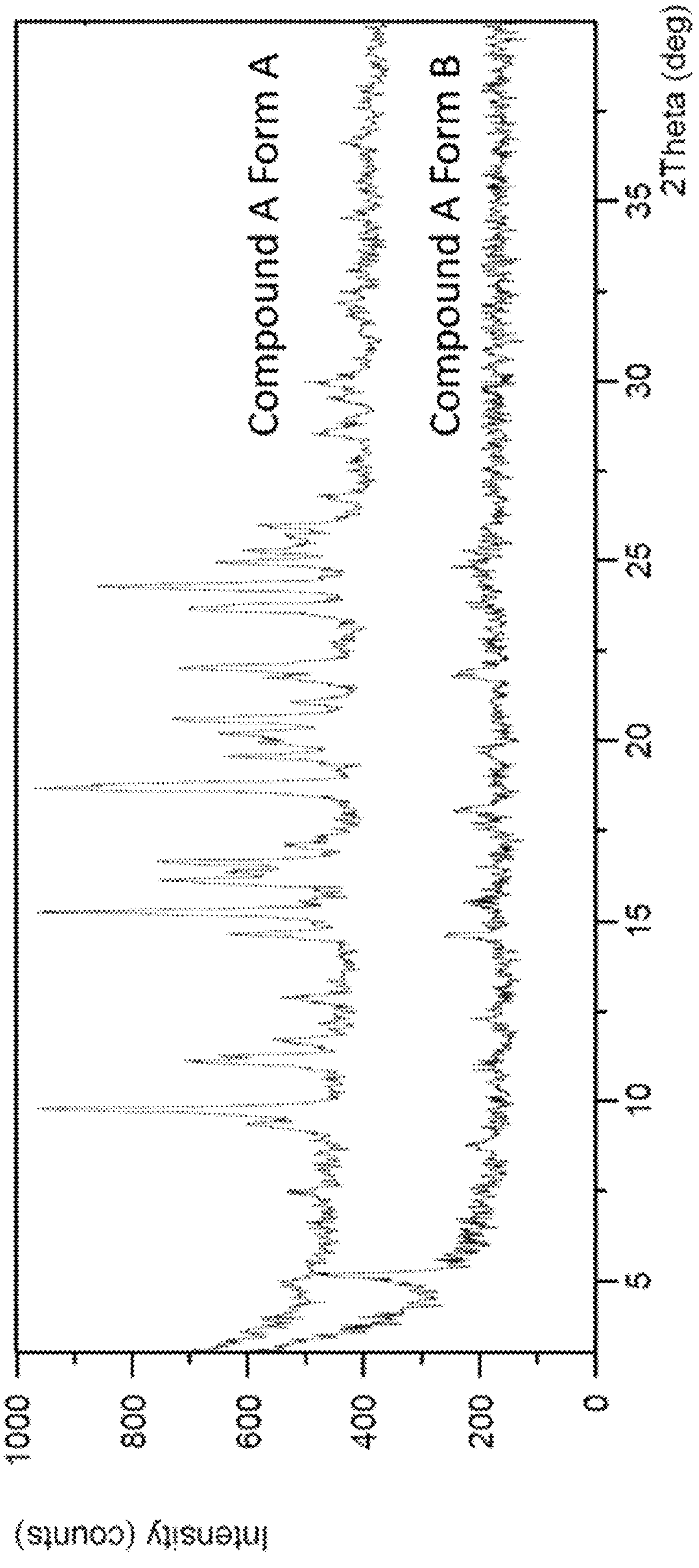
FIG. 5 depicts the XRPD spectrum of Compound A Form B.

In one embodiment, a solid form provided herein, e.g., Form B of Compound A, is a adipate salt, and is substantially crystalline, as indicated by X-ray powder diffraction pattern (XRPD) measurements. In one embodiment, the XRPD of a solid form provided herein, e.g., Form B of Compound A, is substantially as shown in FIG. 5. In another embodiment, a solid form provided herein, e.g., Form B of Compound A, has one or more characteristic XRPD peaks at approximately 5.2063, 8.8524, 11.1301, 12.3721, 14.63, 15.6885, 17.7161, 18.2857, 19.8008, 21.9253, or 25.1335±0.1° 2θ, as depicted in, for example, FIG. 5, and as found in Table 2 herein. In another embodiment, a solid form provided herein, e.g., Form B of Compound A, has at least 3, 5, 7, 9, or 10 characteristic XPRD peaks at approximately 5.2063, 8.8524, 11.1301, 12.3721, 14.63, 15.6885, 17.7161, 18.2857, 19.8008, 21.9253, or 25.1335±0.1° 2θ, as depicted in, for example, FIG. 5, and as found in Table 2 herein. In still another embodiment, a solid form provided herein, e.g., Form B of Compound A, has at least 5, 6, 7, 8, 9, 10 or all of the characteristic XPRD peaks at approximately 5.2063, 8.8524, 11.1301, 12.3721, 14.63, 15.6885, 17.7161, 18.2857, 19.8008, 21.9253, or 25.1335±0.1° 2θ, as depicted in, for example, FIG. 5, and as found in Table 2 herein.

In still another embodiment, a solid form provided herein, e.g., Form B of Compound A, has at least 10 characteristic XPRD peaks at approximately 5.2063, 8.8524, 11.1301, 12.3721, 14.63, 15.6885, 17.7161, 18.2857, 19.8008, 21.9253, or 25.1335±0.1° 2θ, as depicted in, for example, FIG. 5, and as found in Table 2 herein. In another embodiment, a solid form provided herein, e.g., Form B of Compound A, has at least 1, 2, 3, 4, 5, 6, 7, 8, 9, or 10 characteristic XPRD peaks at approximately 5.2063, 8.8524, 12.3721, 14.63, 15.6885, 17.7161, 18.2857, 19.8008, 21.9253, or 25.1335±0.1° 2θ, as depicted in, for example, FIG. 5, and as found in Table 2 herein.

In still another embodiment, a solid form provided herein, e.g., Form B of Compound A, has at least 5 characteristic XPRD peaks at approximately 5.2063, 8.8524, 11.1301, 12.3721, 14.63, 15.6885, 17.7161, 18.2857, 19.8008, 21.9253, or 25.1335±0.1° 2θ, as depicted in, for example, FIG. 5, and as found in Table 2 herein. In still another embodiment, a solid form provided herein, e.g., Form B of Compound A, has at least 1, 2, 3, 4, or 5 characteristic XPRD peaks at approximately 5.2063, 14.63, 17.7161, 21.9253, 25.1335±0.1° 2θ, as depicted in, for example, FIG. 5, and as found in Table 2 herein. In one embodiment, a solid form provided herein, e.g., Form B of Compound A, has an X-ray powder diffraction pattern comprising characteristic X-ray powder diffraction peaks using CuKα radiation at 5.2063, 14.63, 17.7161, 21.9253, 25.1335 (±0.1° 2θ).

TABLE 2

Representative XRPD Peaks for Compound A Form B

| Pos. [° 2θ] | d-spacing [Å] | Rel. Int. [%] |
|---|---|---|
| 5.2063 | 16.96012 | 100 |
| 8.8524 | 9.98124 | 13.93 |
| 11.1301 | 7.94318 | 12.92 |
| 12.3721 | 7.14847 | 19.39 |
| 14.63 | 6.04991 | 31.95 |
| 15.6885 | 5.64402 | 18.78 |
| 17.7161 | 5.00236 | 19.59 |
| 18.2857 | 4.84781 | 18.68 |

TABLE 2-continued

Representative XRPD Peaks for Compound A Form B

| Pos. [° 2θ] | d-spacing [Å] | Rel. Int. [%] |
|---|---|---|
| 19.8008 | 4.48015 | 15.37 |
| 21.9253 | 4.0506 | 22.24 |
| 25.1335 | 3.54035 | 22.89 |

Figure 6:
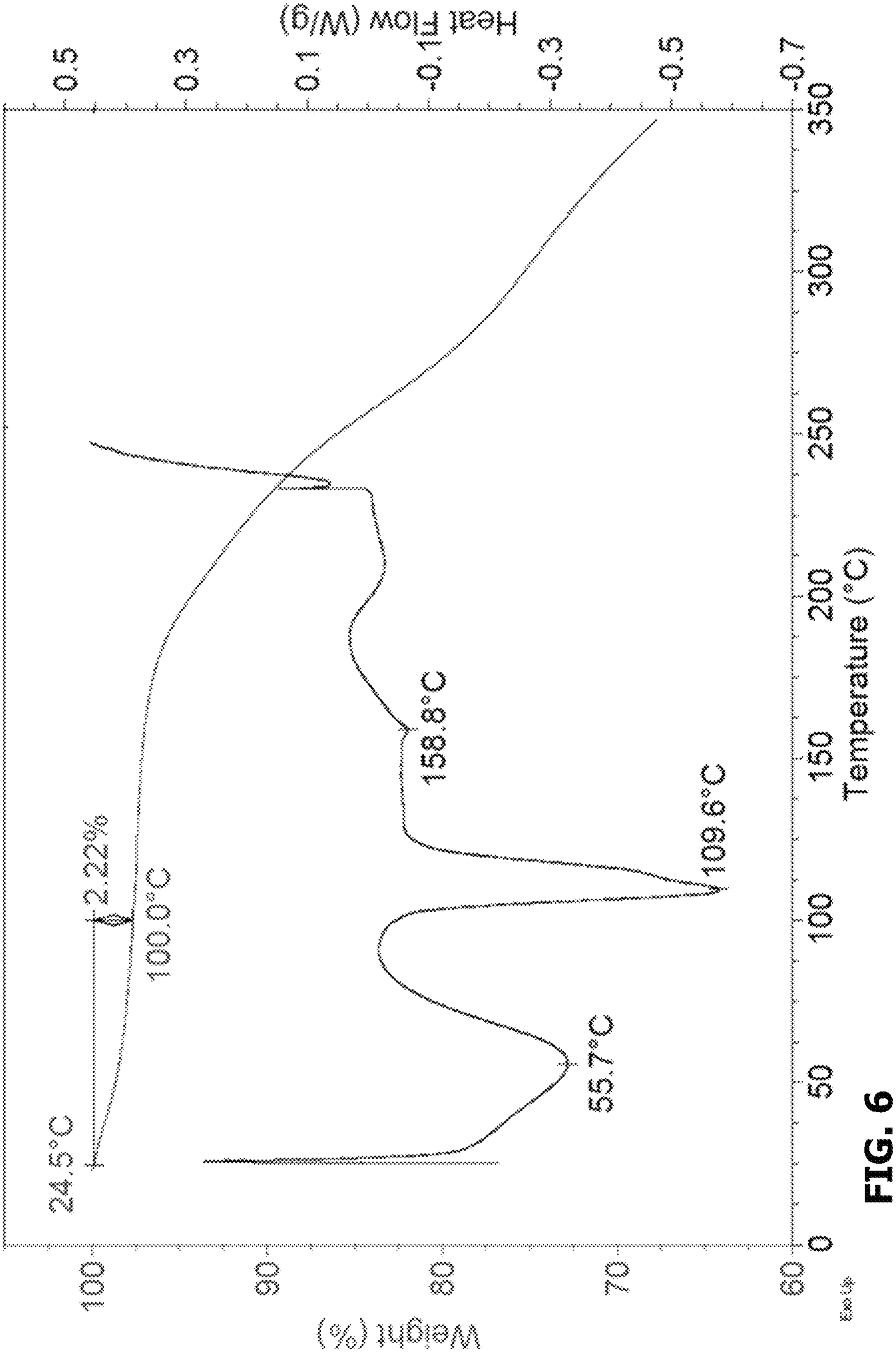
FIG. 6 depicts a TGA thermogram and DSC thermogram overlap for Compound A Form B.

In one embodiment described herein, Form B of Compound A has a TGA thermogram as substantially depicted in FIG. 6, comprising a weight loss of about 2.2% up to 100° C. No form change may be observed after heating Form B of Compound A under nitrogen to about 90° C.

In one such embodiment, Form B of Compound A has a DSC thermogram corresponding to FIG. 6, comprising two broad endotherms at 55.7° C. and 109.6° and a small end other at 158.8° C.

Compound A: Form C

In some embodiments, provided herein is a solid form corresponding to Compound A designated as Form C. Form C is a crystalline solid form of Compound A. In one embodiment, Form C of Compound A is an anhydrate. In one such embodiment, Form C of Compound A is an under-occupied variant of Form D. In one embodiment, Form C is a disordered lattice when compared to Form A or Form D of Compound A. In another such embodiment, the asymmetric unit contains one molecule of Compound A with positionally disordered methylpyrrolidine ring and one adipate anion with one COO— group disordered over two sites (approximately 50/50). (See Examples below). In one embodiment, Form C of Compound A is formed by dehydrating Form D of Compound A. In one such embodiment, the percentage of Form D of Compound A after drying is less than 20%, 15%, 12%, 10%, 8%, 6%, 5%, 2%, or 1%.

In one embodiment, a solid form provided herein, e.g., Form C of Compound A, is a adipate salt, and is substantially crystalline, as indicated by X-ray powder diffraction pattern (XRPD) measurements. In one embodiment, the XRPD of a solid form provided herein, e.g., Form C of Compound A, is equivalent to Form A of Compound A.

Figure 7:
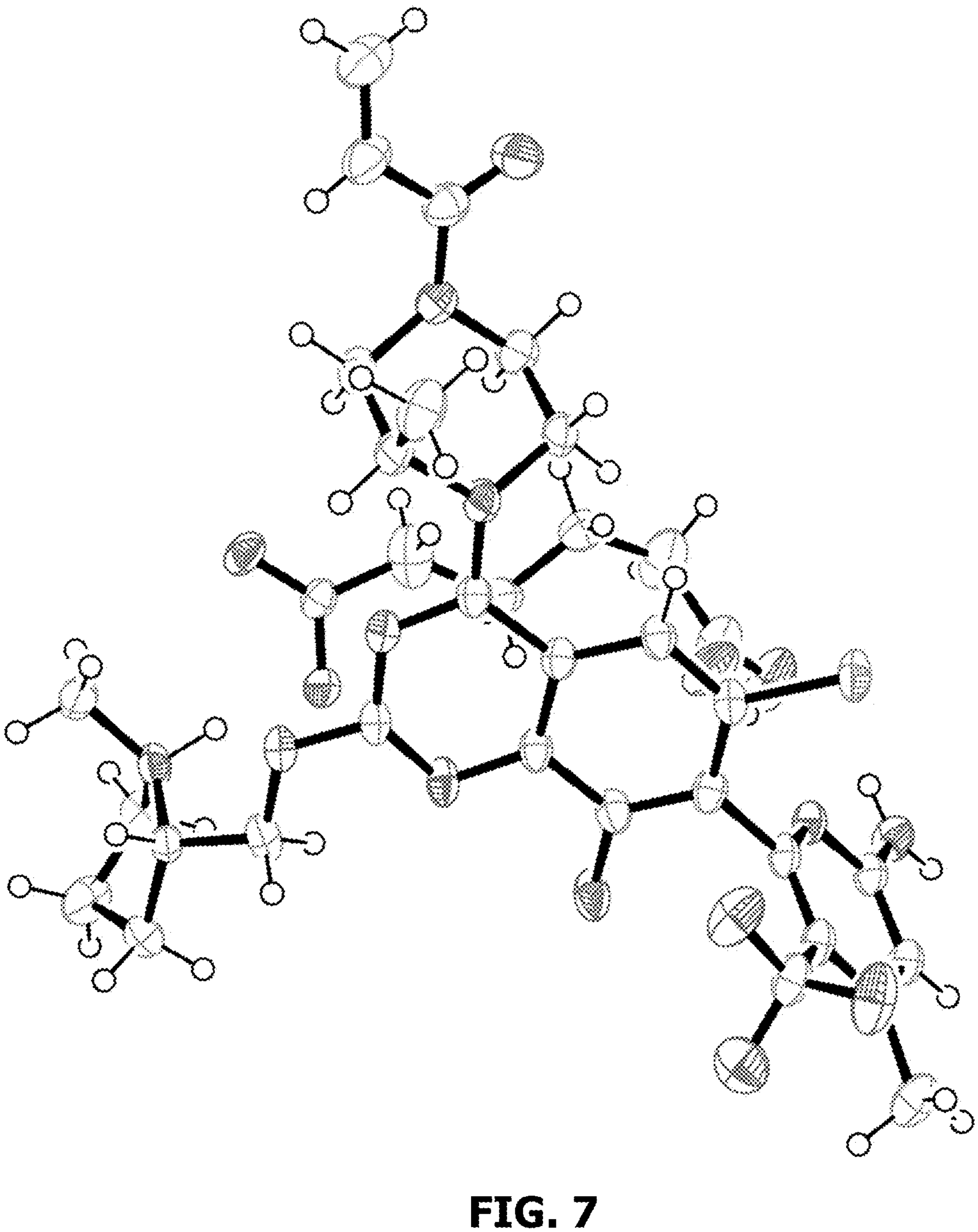
FIG. 7 depicts single crystal XRD of Compound A Form C.

Single Crystal XRD of Compound A Form C is shown in FIG. 7.

Compound A: Form D

In some embodiments, provided herein is a solid form corresponding to Compound A designated as Form D. Form D is a crystalline solid form of Compound B. In one embodiment, Form D of Compound A is a hemihydrate. In one embodiment, Form D of Compound A is formed by exposing Form A or Form C of Compound A as described herein to increasing percentage of relative humidity (rh). In one embodiment, Form D can be dried, thereby reforming Form A and/or Form C of Compound A. In one such embodiment, the percentage of Form D of Compound A after drying is less than 20%, 15%, 12%, 10%, 8%, 6%, 5%, 2%, or 1%.

Figure 8:
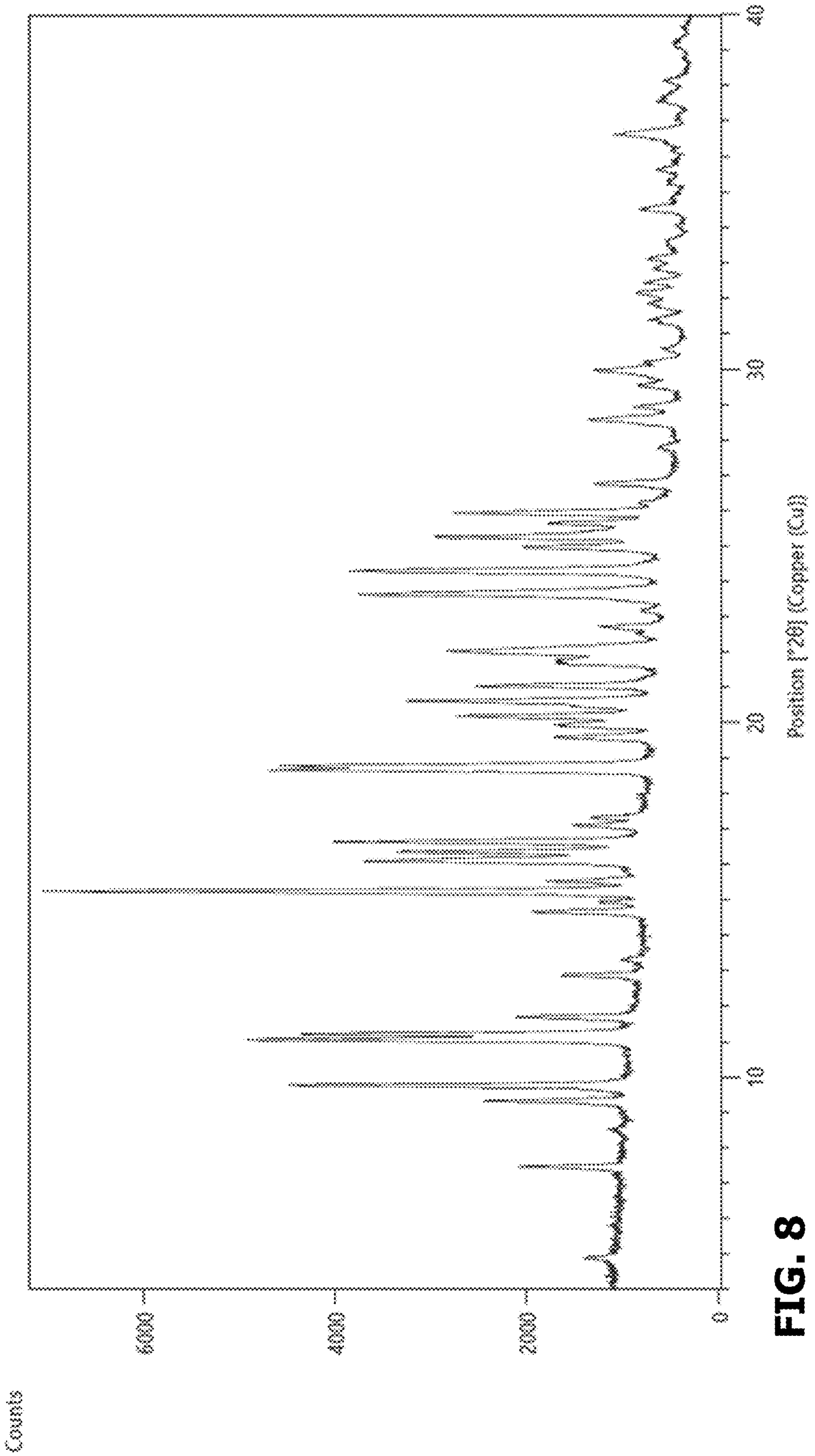
FIG. 8 depicts the XRPD spectrum of Compound A Form D.

In one embodiment, a solid form provided herein, e.g., Form D of Compound A, is a adipate salt, and is substantially crystalline, as indicated by X-ray powder diffraction pattern (XRPD) measurements. In one embodiment, the XRPD of a solid form provided herein, e.g., Form D of Compound A, is substantially as shown in FIG. 8. In another embodiment, a solid form provided herein, e.g., Form D of Compound A, has one or more characteristic XRPD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein. In another embodiment, a solid form provided herein, e.g., Form D of Compound A, has at least 3, 5, 10, 15, or 20 characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein. In still another embodiment, a solid form provided herein, e.g., Form D of Compound A, has at least 5, 6, 7, 8, 9, 10, 11, 12, 13, 14, 14, 15, 16, 17, 18, 19, 20, or all of the characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein.

In still another embodiment, a solid form provided herein, e.g., Form D of Compound A, has at least 10 characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein. In still another embodiment, a solid form provided herein, e.g., Form D of Compound A, has at least 1, 2, 3, 4, 5, 6, 7, 8, 9, or 10 characteristic XPRD peaks at approximately 15.2452, 11.0487, 18.6477, 18.7908, 9.7745, 11.2178, 16.6345, 16.0821, 16.3536, or 20.6308±0.1° 2θ, as depicted in, for example, FIG. 8, and as found in Table 3 herein.

In still another embodiment, a solid form provided herein, e.g., Form D of Compound A, has at least 5 characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein. In still another embodiment, a solid form provided herein, e.g., Form D of Compound A, has at least 1, 2, 3, 4, or 5 characteristic XPRD peaks at approximately 9.7745, 11.0487, 15.2452, 18.6477, 18.7908±0.1° 2θ, as depicted in, for example, FIG. 8, and as found in Table 3 herein. In one embodiment, a solid form provided herein, e.g., Form D of Compound A, has an X-ray powder diffraction pattern comprising characteristic X-ray powder diffraction peaks using CuKα radiation at 9.7745, 11.0487, 15.2452, 18.6477, 18.7908 (±0.1° 2θ)

In still another embodiment, a solid form provided herein, e.g., Form D of Compound A, has at least 15 characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein.

In still another embodiment, a solid form provided herein, e.g., Form D of Compound A, has at least 20 characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein.

In still another embodiment, a solid form provided herein, e.g., Form D of Compound A, has all of the characteristic XPRD peaks at approximately 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, or 22.0397±0.1° 2θ, as depicted in, for example, FIG. 8, and as found in Table 3 herein.

Figure 21:
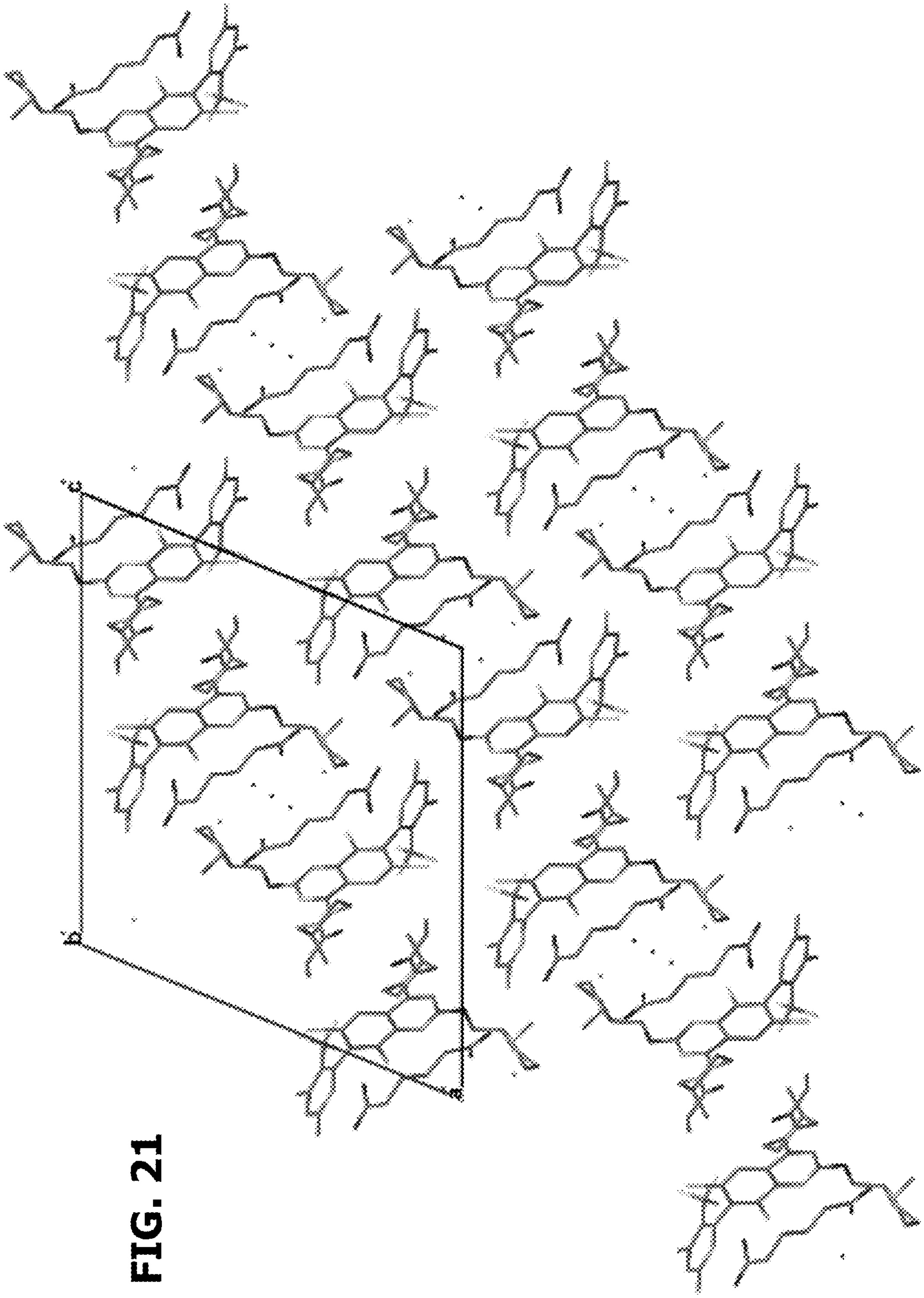
FIG. 21 depicts a view of the crystal packing of Compound A Form D looking down the crystallographic b-axis.

In one embodiment, the single crystal XRD of Compound A Form D is provided in FIG. 21. Crystal packing and other scXRD information for Compound A Form D is as set forth herein (e.g. Examples).

TABLE 3

Representative XRPD Peaks for Compound A Form

| Pos. [° 2θ] | d-spacing [Å] | Rel. Int. [%] |
|---|---|---|
| 7.4529 | 11.85207 | 17.22 |
| 9.309 | 9.49265 | 24.32 |
| 9.7745 | 9.04158 | 56.55 |
| 11.0487 | 8.00156 | 64.53 |
| 11.2178 | 7.88129 | 55.85 |
| 11.6936 | 7.56169 | 20.16 |
| 12.8642 | 6.87607 | 13.15 |
| 14.65 | 6.04167 | 18.46 |
| 14.9254 | 5.93083 | 7.53 |
| 15.2452 | 5.80712 | 100 |
| 15.5252 | 5.70301 | 16.24 |
| 16.0821 | 5.50675 | 46.63 |
| 16.3536 | 5.41595 | 41.59 |
| 16.6345 | 5.32509 | 52.84 |
| 17.1089 | 5.17852 | 12.68 |
| 17.3151 | 5.11731 | 9.61 |
| 18.6477 | 4.75451 | 62.88 |
| 18.7908 | 4.71863 | 58.63 |
| 19.5758 | 4.53114 | 16.41 |
| 19.8874 | 4.46084 | 14.43 |
| 20.2 | 4.39251 | 32.41 |
| 20.6308 | 4.30174 | 41.35 |
| 21.0403 | 4.21895 | 30.63 |
| 21.6587 | 4.09985 | 15.45 |
| 22.0397 | 4.02983 | 35.46 |

Figure 9:
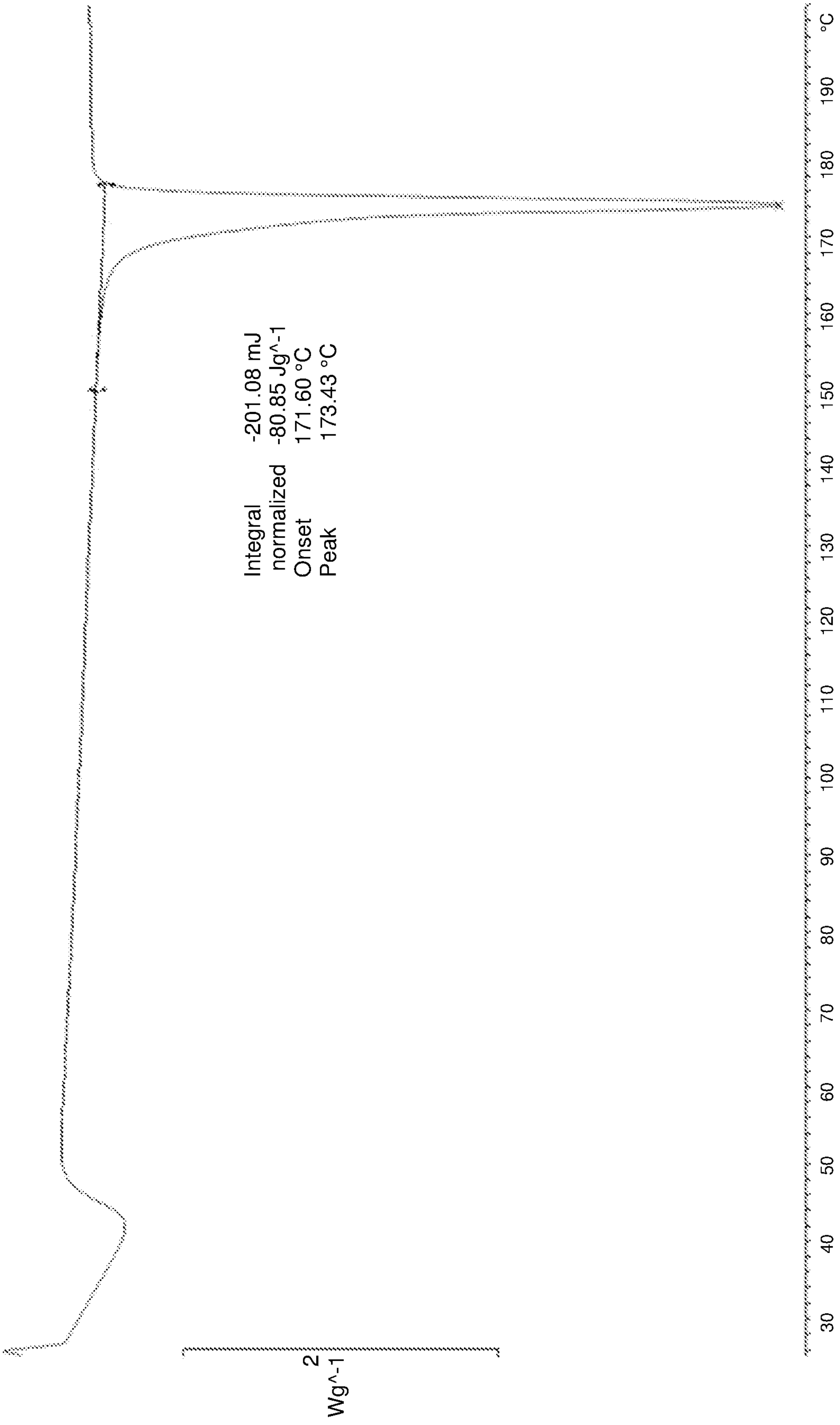
FIG. 9 depicts DSC thermogram for Compound A Form D.

In one embodiment described herein, Compound A Form D has a DSC thermogram as substantially depicted in FIG. 9. In one embodiment, the DSC of Compound A Form D has one endotherm at about 173.4° C. (Peak).

Figure 10:
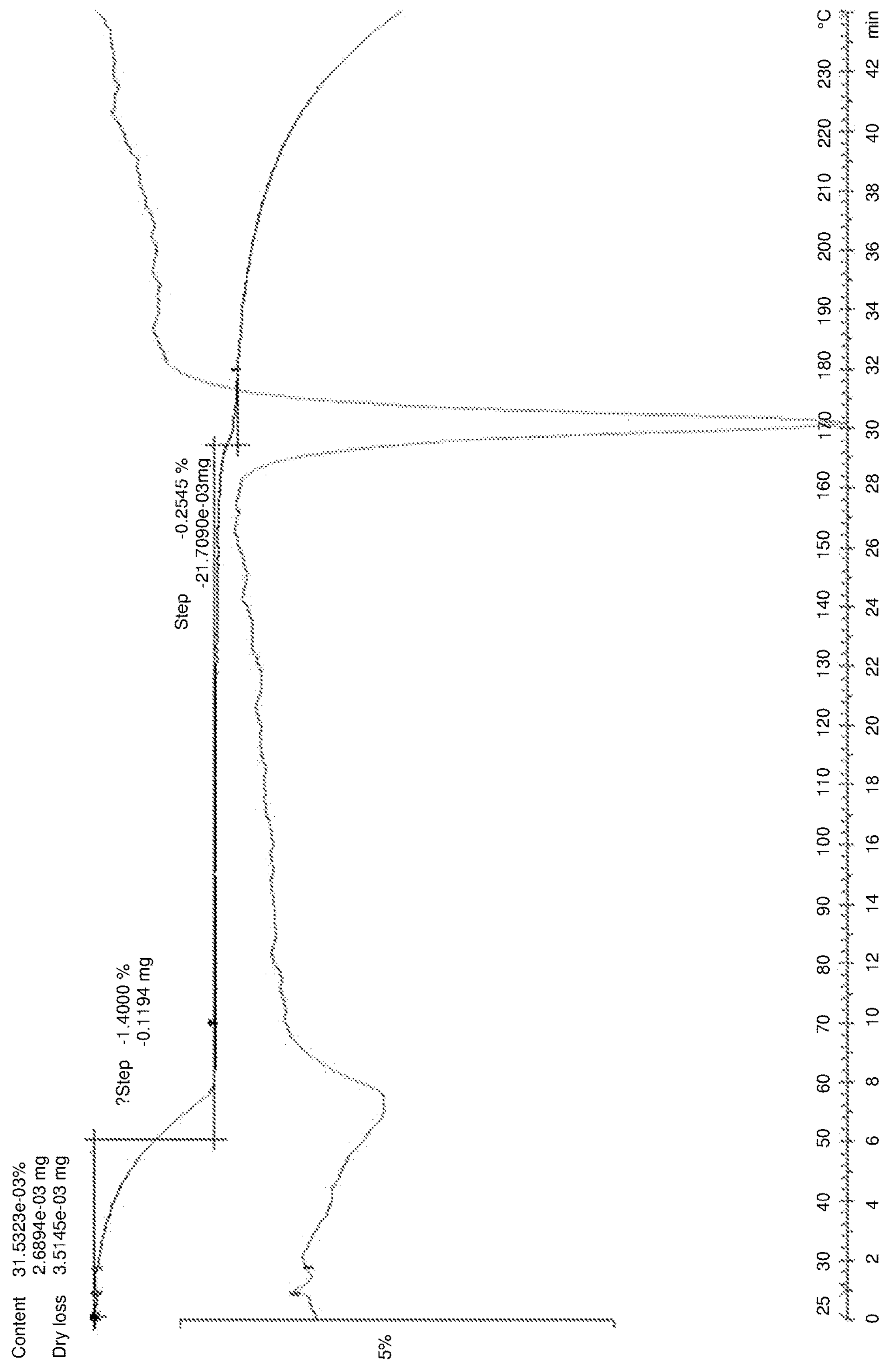
FIG. 10 depicts a TGA thermogram and DSC thermogram overlap for Compound A Form D.

In one embodiment described herein, Form B of Compound A has a TGA thermogram as substantially depicted in FIG. 10, comprising a weight loss of about 1.4% up to 100° C.

Compound B: Form A

In some embodiments, provided herein is a solid form corresponding to Compound B designated as Form A. Compound B Form A is a fumarate crystalline solid form of Compound B. In one embodiment, Compound B Form A is obtained from acetone and air dried at RT. In one embodiment, Compound B Form A is an anhydrate.

In one embodiment, no form change was observed before and after heating Compound B Form A to 100° C. under N2 protection and cooling down and exposed to ambient conditions.

Figure 11:
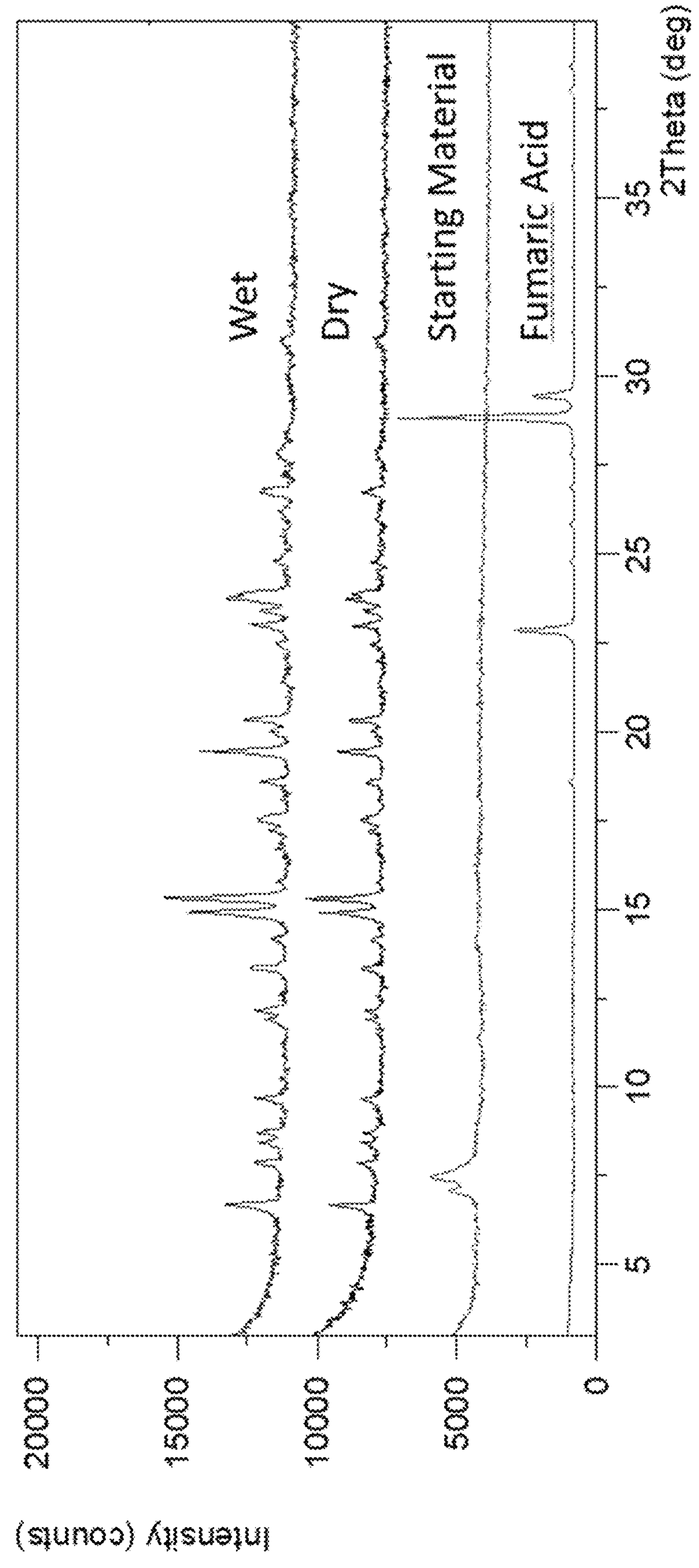
FIG. 11 depicts the XRPD spectrum overlay of Compound B Form A.

In one embodiment, a solid form provided herein, e.g., Form A of Compound B, is a fumarate salt, and is substantially crystalline, as indicated by X-ray powder diffraction pattern (XRPD) measurements. In one embodiment, the XRPD of a solid form provided herein, e.g., Form A of Compound B, is substantially as shown in FIG. 11. In another embodiment, a solid form provided herein, e.g., Form A of Compound B, has one or more characteristic XRPD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein. In another embodiment, a solid form provided herein, e.g., Form A of Compound B, has at least 3, 5, 10, 15, or 20 characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein. In still another embodiment, a solid form provided herein, e.g., Form A of Compound B, has at least 5, 6, 7, 8, 9, 10, 11, 12, 13, 14, 15, 16, 17, 18, 19, 20, or all of the characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein.

In still another embodiment, a solid form provided herein, e.g., Form A of Compound B, has at least 10 characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein. In still another embodiment, a solid form provided herein, e.g., Form A of Compound B, has at least 1, 2, 3, 4, 5, 6, 7, 8, 9, or 10 characteristic XPRD peaks at approximately 6.6796, 13.3393, 14.9097, 15.2963, 17.4837, 19.4416, 20.3394, 23.0009, 23.7124, or 26.7708±0.1° 2θ, as depicted in, for example, FIG. 11, and as found in Table 4 herein.

In still another embodiment, a solid form provided herein, e.g., Form A of Compound B, has at least 5 characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein. In still another embodiment, a solid form provided herein, e.g., Form A of Compound B, has at least 1, 2, 3, 4, or 5 characteristic XPRD peaks at approximately 6.6796, 14.9097, 15.2963, 19.4416, 23.7124±0.1° 2θ, as depicted in, for example, FIG. 11, and as found in Table 4 herein. In one embodiment, a solid form provided herein, e.g., Form A of Compound B, has an X-ray powder diffraction pattern comprising characteristic X-ray powder diffraction peaks using CuKα radiation at 6.6796, 14.9097, 15.2963, 19.4416, 23.7124 (±0.1° 2θ).

In still another embodiment, a solid form provided herein, e.g., Form A of Compound B, has at least 15 characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein.

In still another embodiment, a solid form provided herein, e.g., Form A of Compound B, has at least 20 characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, or 30.9939±0.1° 2θ, as depicted in, for example, FIG. 11, and as found in Table 4 herein.

In still another embodiment, a solid form provided herein, e.g., Form A of Compound B, has all of the characteristic XPRD peaks at approximately 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, and 30.9939±0.1° 2θ, as depicted in, for example, FIG. 11, and as found in Table 4 herein.

TABLE 4

Representative XRPD Peaks for Compound B Form A

| Pos. [° 2θ] | d-spacing [Å] | Rel. Int. [%] |
|---|---|---|
| 6.6796 | 13.22236 | 43.06 |
| 7.8754 | 11.21714 | 22.02 |
| 8.4472 | 10.45905 | 13.58 |
| 8.724 | 10.12778 | 20.88 |
| 9.6832 | 9.1266 | 22.35 |
| 12.1433 | 7.28262 | 25.77 |
| 13.3393 | 6.63225 | 31.01 |
| 14.1386 | 6.25903 | 12.07 |
| 14.9097 | 5.93701 | 77.21 |
| 15.2963 | 5.78782 | 100 |
| 17.4837 | 5.06834 | 27 |
| 18.5763 | 4.77263 | 21.29 |
| 19.4416 | 4.5621 | 66.36 |
| 20.3394 | 4.36271 | 34.81 |
| 21.4642 | 4.13656 | 6.92 |
| 22.4341 | 3.95988 | 12.22 |
| 23.0009 | 3.86356 | 31.5 |
| 23.3901 | 3.80014 | 25.7 |
| 23.7124 | 3.74921 | 52.37 |
| 24.7816 | 3.58982 | 13.39 |
| 26.1995 | 3.39867 | 10 |
| 26.7708 | 3.32742 | 27.07 |
| 27.7302 | 3.21445 | 12.56 |
| 30.9939 | 2.883 | 11.13 |

Figure 12:
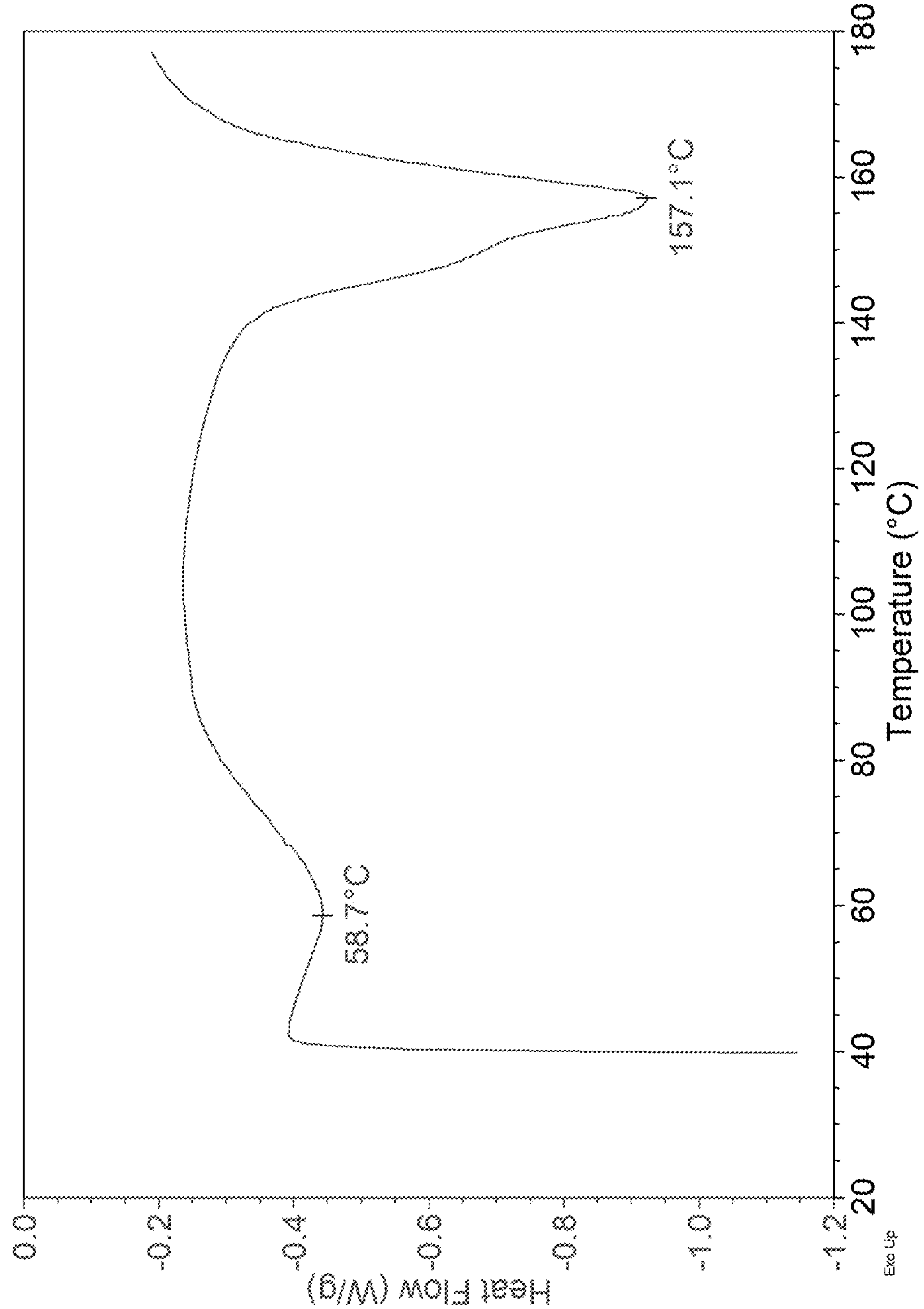
FIG. 12 depicts DSC thermogram for Compound B Form A.

In one embodiment described herein, Form A of Compound B has a DSC thermogram as substantially depicted in FIG. 12.

In one such embodiment, the DSC thermogram comprises one endotherm at about 58.7° C. and an overlapped peak with peak temperature at 157.1° C.

In another embodiment, Form A of Compound B is pure. In one such embodiment, Form A of Compound B is substantially free of other solid forms described herein (e.g. amorphous solid). In another embodiment, the purity of Form A of Compound B is no less than about 95%, no less than about 96%, no less than about 97%, no less than about 98%, no less than about 99%, no less than about 99.5%, or no less than about 99.9%.

Compound C: Form A

In some embodiments, provided herein is a solid form corresponding to Compound C designated as Form A. Form A of Compound C is a ethylsulphonate crystalline solid form of Compound C. In one embodiment, Form A of Compound C is obtained from ethyl acetate and air dried at RT.

In one embodiment, no form change was observed before and after heating Form A of Compound C to 100° C. under N2 protection and cooling down and exposed to ambient conditions.

Figure 13:
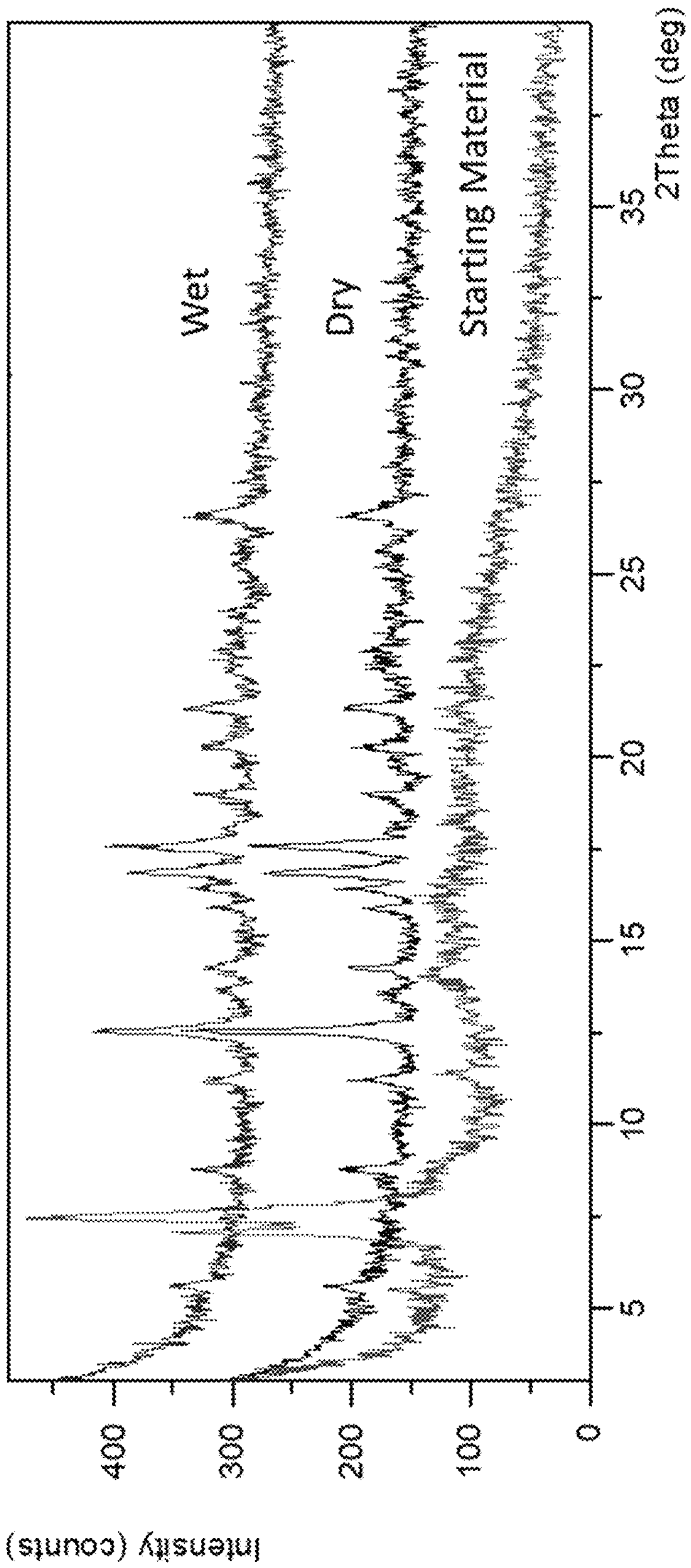
FIG. 13 depicts the XRPD spectrum overlay of Compound C Form A.

In one embodiment, a solid form provided herein, e.g., Form A of Compound C, is an ethylenesulphonate salt, and is substantially crystalline, as indicated by X-ray powder diffraction pattern (XRPD) measurements. In one embodiment, the XRPD of a solid form provided herein, e.g., Form A of Compound C, is substantially as shown in FIG. 13. In another embodiment, a solid form provided herein, e.g., Form A of Compound C, has one or more characteristic XRPD peaks at approximately 5.5814, 8.7554, 11.1932, 12.5401, 13.5091, 14.2557, 15.8682, 16.3963, 16.834, 17.5707, 18.9739, 20.2549, 21.3525, 26.5569±0.1° 2θ, as depicted in, for example, FIG. 13, and as found in Table 5 herein. In another embodiment, a solid form provided herein, e.g., Form A of Compound C, has at least 3, 5, 7, 10, or 12 characteristic XPRD peaks at approximately 5.5814, 8.7554, 11.1932, 12.5401, 13.5091, 14.2557, 15.8682, 16.3963, 16.834, 17.5707, 18.9739, 20.2549, 21.3525, 26.5569±0.1° 2θ, as depicted in, for example, FIG. 13, and as found in Table 5 herein. In still another embodiment, a solid form provided herein, e.g., Form A of Compound C, has at least 5, 6, 7, 8, 9, 10, 11, 12, 13, or all of the characteristic XPRD peaks at approximately 5.5814, 8.7554, 11.1932, 12.5401, 13.5091, 14.2557, 15.8682, 16.3963, 16.834, 17.5707, 18.9739, 20.2549, 21.3525, 26.5569±0.1° 2θ, as depicted in, for example, FIG. 13, and as found in Table 5 herein.

In still another embodiment, a solid form provided herein, e.g., Form A of Compound C, has at least 10 characteristic XPRD peaks at approximately 5.5814, 8.7554, 11.1932, 12.5401, 13.5091, 14.2557, 15.8682, 16.3963, 16.834, 17.5707, 18.9739, 20.2549, 21.3525, 26.5569±0.1° 2θ, as depicted in, for example, FIG. 13, and as found in Table 5 herein. In still another embodiment, a solid form provided herein, e.g., Form A of Compound C, has at least 1, 2, 3, 4, 5, 6, 7, 8, 9, or 10 characteristic XPRD peaks at approximately 12.5401, 17.5707, 16.834, 21.3525, 26.5569, 8.7554, 14.2557, 16.3963, 20.2549, 11.1932±0.1° 2θ, as depicted in, for example, FIG. 13, and as found in Table 5 herein.

In still another embodiment, a solid form provided herein, e.g., Form A of Compound C, has at least 5 characteristic XPRD peaks at approximately 5.5814, 8.7554, 11.1932, 12.5401, 13.5091, 14.2557, 15.8682, 16.3963, 16.834, 17.5707, 18.9739, 20.2549, 21.3525, 26.5569±0.1° 2θ, as depicted in, for example, FIG. 13, and as found in Table 5 herein. In still another embodiment, a solid form provided herein, e.g., Form A of Compound C, has at least 5 characteristic XPRD peaks at approximately 12.5401, 17.5707, 16.834, 21.3525, 26.5569±0.1° 2θ, as depicted in, for example, FIG. 13, and as found in Table 5 herein. In one embodiment, a solid form provided herein, e.g., Form A of Compound C, has an X-ray powder diffraction pattern comprising characteristic X-ray powder diffraction peaks using CuKα radiation at 12.5401, 17.5707, 16.834, 21.3525, 26.5569 (±0.1° 2θ).

TABLE 5

Representative XRPD Peaks for Compound C Form A

| Pos. [° 2θ] | d-spacing [Å] | Rel. Int. [%] |
|---|---|---|
| 5.5814 | 15.82116 | 18.18 |
| 8.7554 | 10.09154 | 27.49 |
| 11.1932 | 7.89859 | 22.06 |

TABLE 5-continued

Representative XRPD Peaks for Compound C Form A

| Pos. [° 2θ] | d-spacing [Å] | Rel. Int. [%] |
|---|---|---|
| 12.5401 | 7.05308 | 100 |
| 13.5091 | 6.54927 | 10.14 |
| 14.2557 | 6.2079 | 26.79 |
| 15.8682 | 5.58052 | 19.33 |
| 16.3963 | 5.40194 | 25.03 |
| 16.834 | 5.26244 | 71.34 |
| 17.5707 | 5.04343 | 73.89 |
| 18.9739 | 4.67349 | 21.79 |
| 20.2549 | 4.38072 | 23.49 |
| 21.3525 | 4.15796 | 32.57 |
| 26.5569 | 3.35374 | 31.51 |

Figure 14:
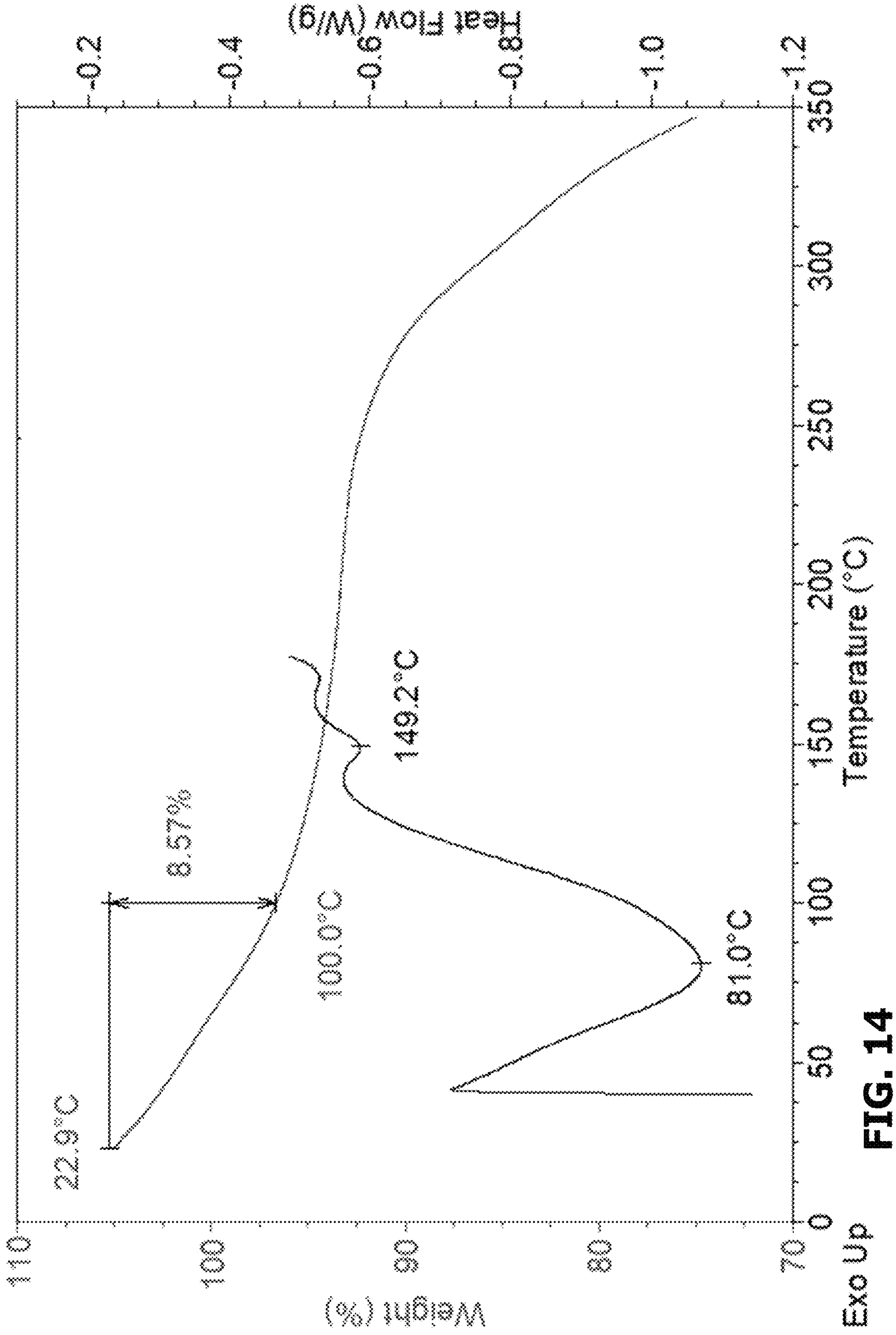
FIG. 14 depicts a TGA thermogram and DSC thermogram overlap for Compound C Form A.

In one embodiment described herein, Form A of Compound C has a TGA thermogram as substantially depicted in FIG. 14. In one embodiment, a weight loss of 8.6% up to 100° C. is observed.

In one embodiment, Form A of Compound C has a DSC thermogram as substantially depicted in FIG. 14, comprising two endotherms at 81.0° C. and 149.2° C. (peak temperature).

In another embodiment, Form A of Compound C is pure. In one such embodiment, Form A of Compound C is substantially free of other solid forms described herein (e.g. amorphous solid). In another embodiment, the purity of Form A of Compound C is no less than about 95%, no less than about 96%, no less than about 97%, no less than about 98%, no less than about 99%, no less than about 99.5%, or no less than about 99.9%.

Compound D: Form A

In some embodiments, provided herein is a solid form corresponding to Compound D designated as Form A. Form A of Compound D is a crystalline solid form of Compound D. In one embodiment, Form A of Compound D is obtained from evaporation of acetone/n-heptane (1:1 v/v).

Figure 15:
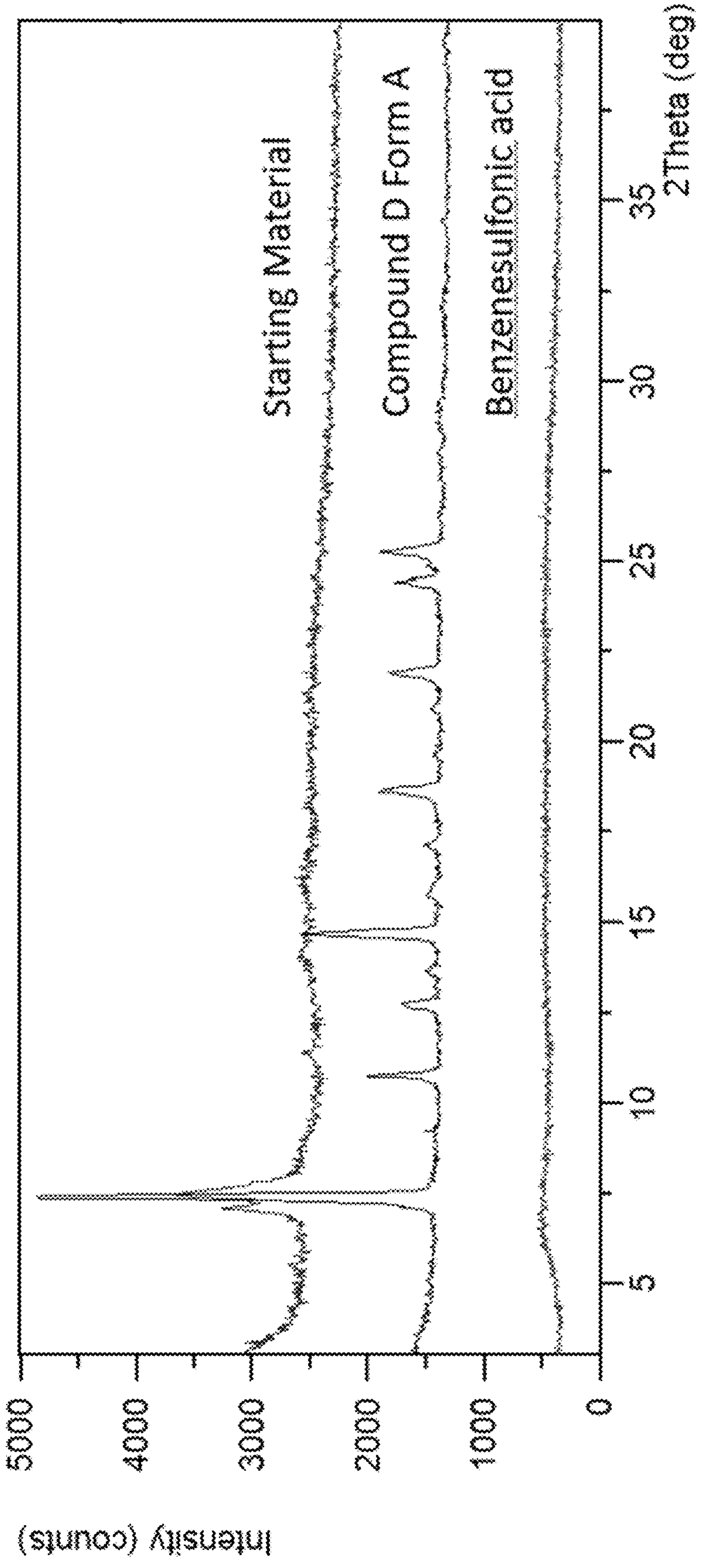
FIG. 15 depicts the XRPD spectrum overlay of Compound D Form A.

In one embodiment, a solid form provided herein, e.g., Form A of Compound D, is an besylate salt, and is substantially crystalline, as indicated by X-ray powder diffraction pattern (XRPD) measurements. In one embodiment, the XRPD of a solid form provided herein, e.g., Form A of Compound D, is substantially as shown in FIG. 15. In another embodiment, a solid form provided herein, e.g., Form A of Compound D, has one or more characteristic XRPD peaks at approximately 7.3809, 9.2213, 10.7407, 12.7588, 13.6799, 14.654, 15.8145, 17.1195, 18.5979, 19.5937, 20.8941, 21.9068, 24.4114, 25.2558±0.1° 2θ, as depicted in, for example, FIG. 15, and as found in Table 6 herein. In another embodiment, a solid form provided herein, e.g., Form A of Compound D, has at least 3, 5, 7, 10 or 12 characteristic XPRD peaks at approximately 7.3809, 9.2213, 10.7407, 12.7588, 13.6799, 14.654, 15.8145, 17.1195, 18.5979, 19.5937, 20.8941, 21.9068, 24.4114, 25.2558±0.1° 2θ, as depicted in, for example, FIG. 15, and as found in Table 6 herein. In still another embodiment, a solid form provided herein, e.g., Form A of Compound D, has at least 5, 6, 7, 8, 9, 10, 11, 12, 13, or all of the characteristic XPRD peaks at approximately 7.3809, 9.2213, 10.7407, 12.7588, 13.6799, 14.654, 15.8145, 17.1195, 18.5979, 19.5937, 20.8941, 21.9068, 24.4114, 25.2558±0.1° 2θ, as depicted in, for example, FIG. 15, and as found in Table 6 herein.

In still another embodiment, a solid form provided herein, e.g., Form A of Compound D, has at least 10 characteristic XPRD peaks at approximately 7.3809, 9.2213, 10.7407, 12.7588, 13.6799, 14.654, 15.8145, 17.1195, 18.5979, 19.5937, 20.8941, 21.9068, 24.4114, 25.2558±0.1° 2θ, as depicted in, for example, FIG. 15, and as found in Table 6 herein. In still another embodiment, a solid form provided herein, e.g., Form A of Compound D, has at least 1, 2, 3, 4, 5, 6, 7, 8, 9, or 10 characteristic XPRD peaks at approximately 7.3809, 10.7407, 12.7588, 14.654, 15.8145, 17.1195, 18.5979, 21.9068, 24.4114, 25.2558±0.1° 2θ, as depicted in, for example, FIG. 15, and as found in Table 6 herein.

In still another embodiment, a solid form provided herein, e.g., Form A of Compound D, has at least 5 characteristic XPRD peaks at approximately 7.3809, 9.2213, 10.7407, 12.7588, 13.6799, 14.654, 15.8145, 17.1195, 18.5979, 19.5937, 20.8941, 21.9068, 24.4114, 25.2558±0.1° 2θ, as depicted in, for example, FIG. 15, and as found in Table 6 herein. In still another embodiment, a solid form provided herein, e.g., Form A of Compound D, has at least 5 characteristic XPRD peaks at approximately 7.3809, 10.7407, 14.654, 18.5979, 25.2558±0.1° 2θ, as depicted in, for example, FIG. 15, and as found in Table 6 herein. In one embodiment, a solid form provided herein, e.g., Form A of Compound D, has an X-ray powder diffraction pattern comprising characteristic X-ray powder diffraction peaks using CuKα radiation at 7.3809, 10.7407, 14.654, 18.5979, 25.2558 (±0.1° 2θ).

TABLE 6

Representative XRPD Peaks for Compound D Form A

| Pos. [° 2θ] | d-spacing [Å] | Rel. Int. [%] |
|---|---|---|
| 7.3809 | 11.96741 | 100 |
| 9.2213 | 9.58275 | 1.19 |
| 10.7407 | 8.23033 | 18.04 |
| 12.7588 | 6.93266 | 8.47 |
| 13.6799 | 6.46789 | 2.68 |
| 14.654 | 6.04005 | 34.95 |
| 15.8145 | 5.59932 | 3.01 |
| 17.1195 | 5.17532 | 3.34 |
| 18.5979 | 4.76713 | 15.98 |
| 19.5937 | 4.52704 | 1.74 |
| 20.8941 | 4.24813 | 2.07 |
| 21.9068 | 4.05397 | 12.77 |
| 24.4114 | 3.64343 | 10.56 |
| 25.2558 | 3.52348 | 15.68 |

Figure 16:
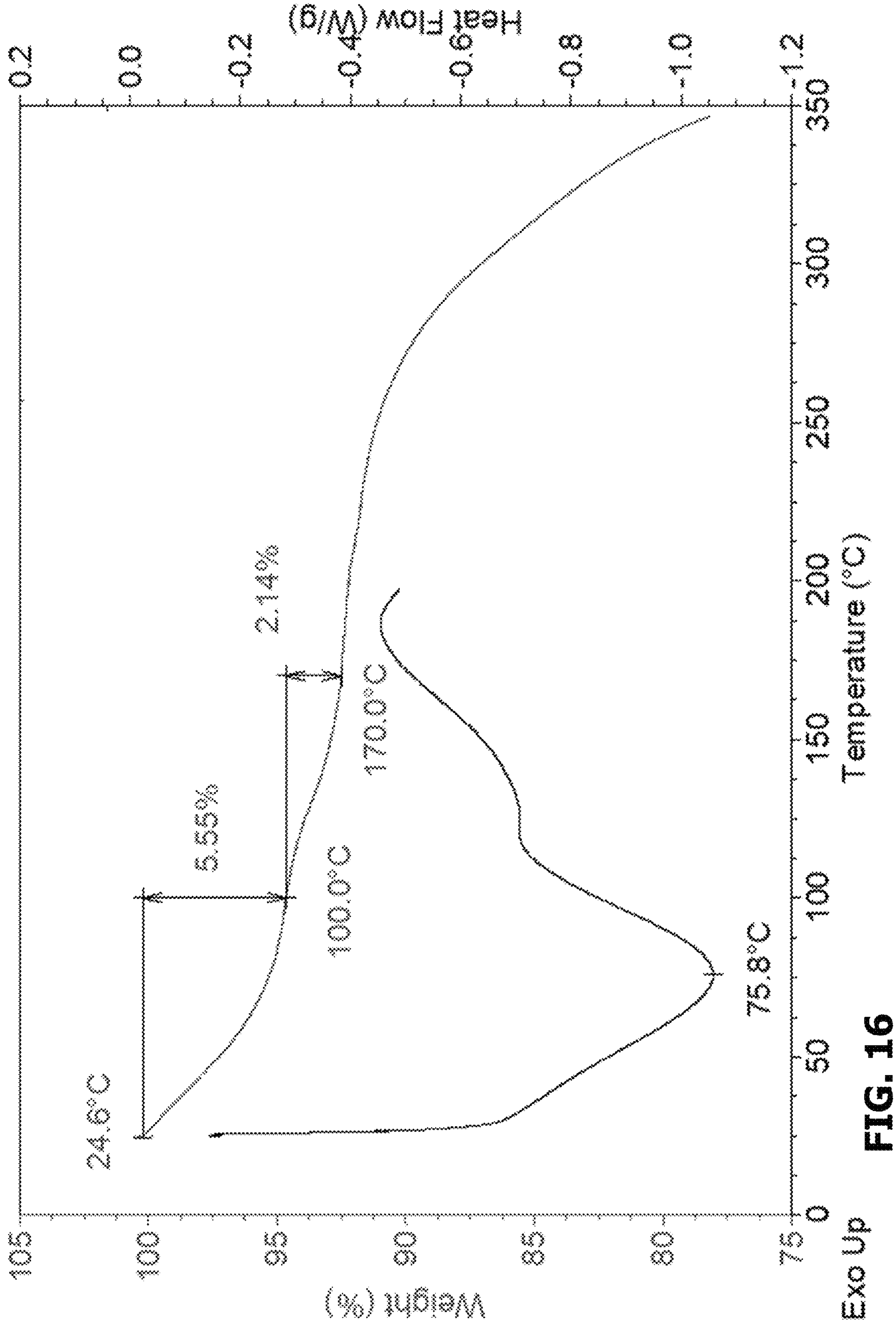
FIG. 16 depicts a TGA thermogram and DSC thermogram overlap for Compound D Form A.

In one embodiment described herein, Form A of Compound D has a TGA thermogram as substantially depicted in FIG. 16. In one embodiment, a weight loss of 7.7% was observed up to 170° C. is observed.

In one embodiment, Form A of Compound D has a DSC thermogram as substantially depicted in FIG. 16, comprising one endotherm at 75.8° C. In one embodiment, the stoichiometric ratio of benzenesulfonic acid:freebase is 1, 1.01, 1.02, or 1.03.

In another embodiment, Form A of Compound D is pure. In one such embodiment, Form A of Compound D is substantially free of other solid forms described herein (e.g. amorphous solid). In another embodiment, the purity of Form A of Compound D is no less than about 95%, no less than about 96%, no less than about 97%, no less than about 98%, no less than about 99%, no less than about 99.5%, or no less than about 99.9%.

Compound E: Form A

In some embodiments, provided herein is a solid form corresponding to Compound E designated as Form A. Form A of Compound E is a crystalline solid form of Compound E. In one embodiment, Form A of Compound E is obtained from acetone.

Figure 17:
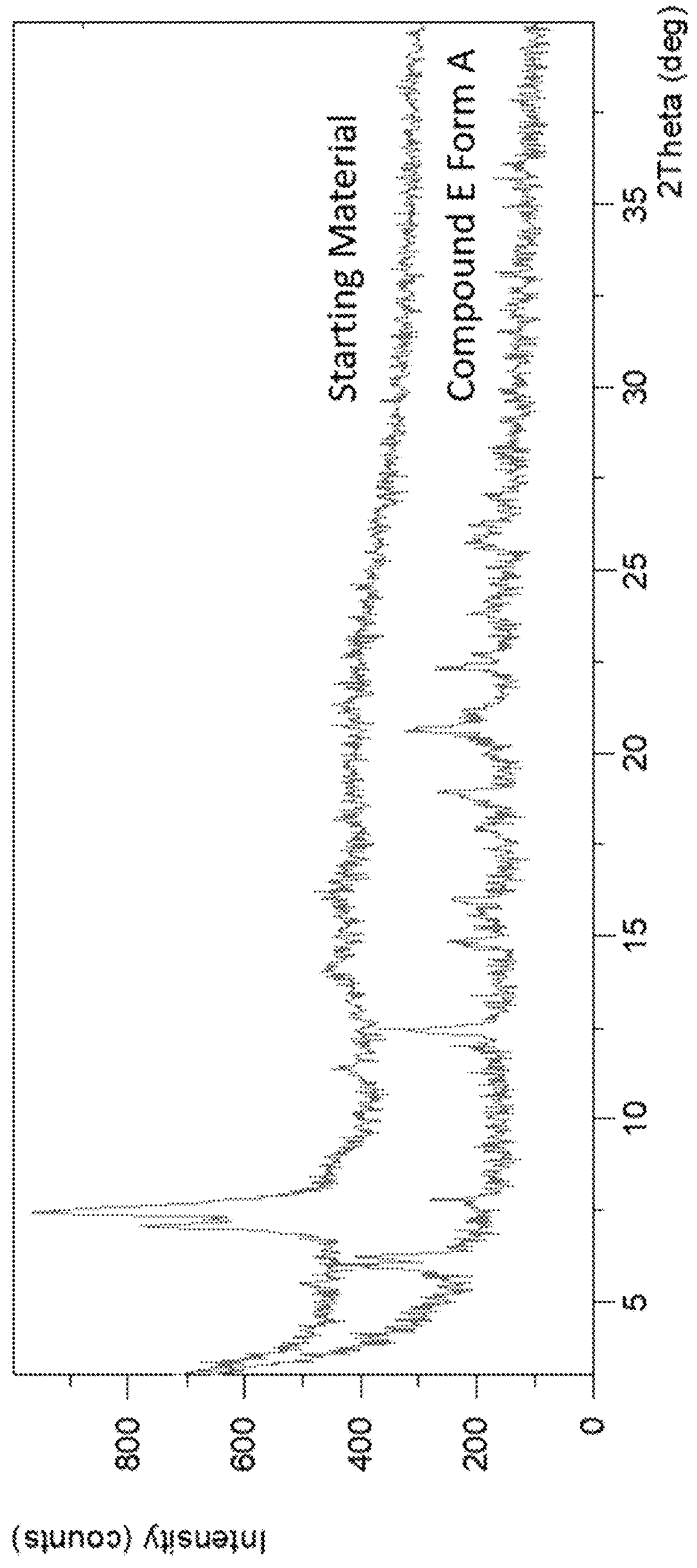
FIG. 17 depicts the XRPD spectrum overlay of Compound E Form A.
Figure 18:
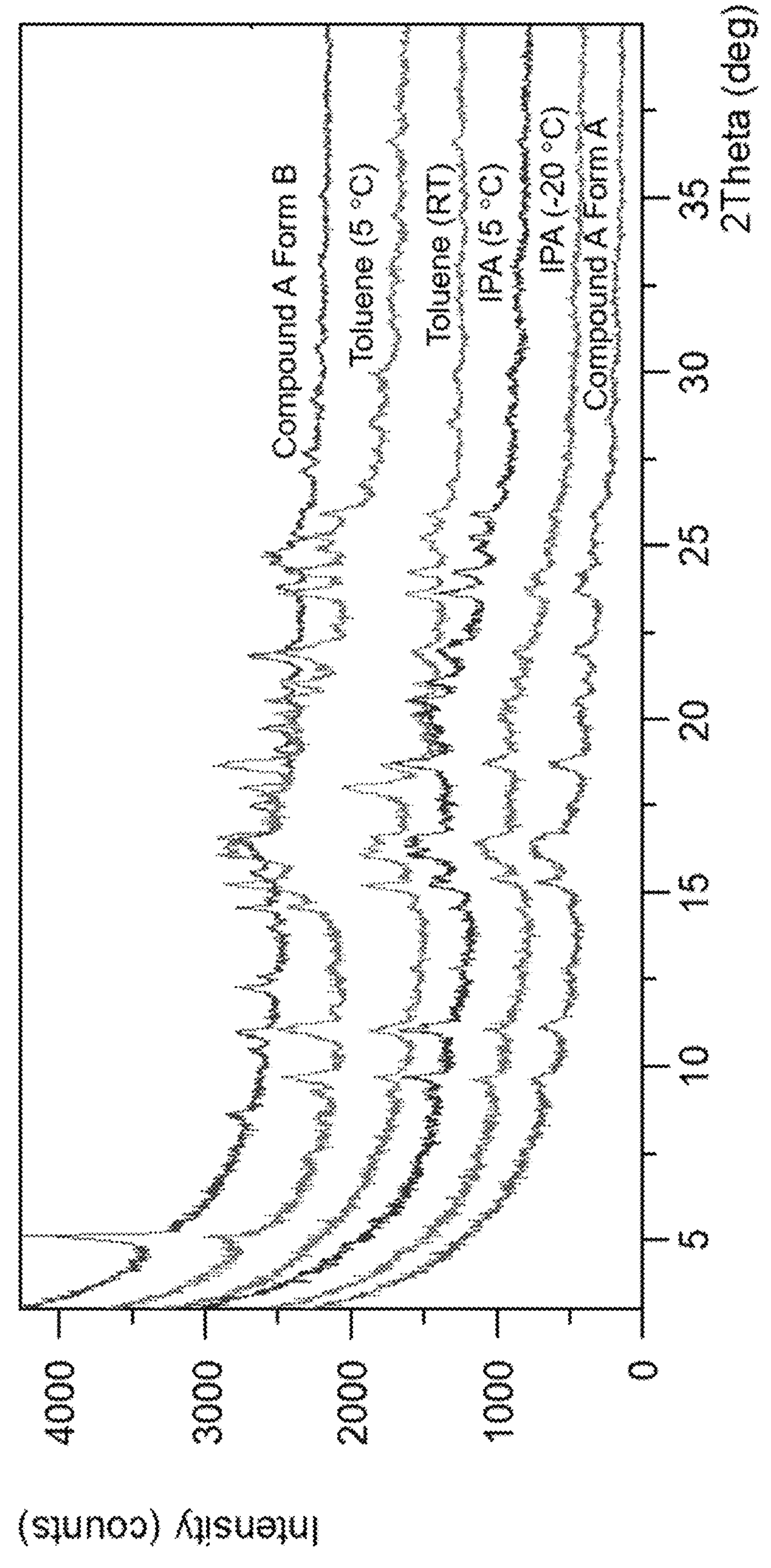
FIG. 18 depicts the XRPD overlay of slurry competition between Compound A Form A and B.

In one embodiment, a solid form provided herein, e.g., Form A of Compound E, is an mesylate salt, and is substantially crystalline, as indicated by X-ray powder diffraction pattern (XRPD) measurements. In one embodiment, the XRPD of a solid form provided herein, e.g., Form A of Compound E, is substantially as shown in FIG. 17. In another embodiment, a solid form provided herein, e.g., Form A of Compound E, has one or more characteristic XRPD peaks at approximately 5.9702, 6.2798, 7.766, 11.9769, 12.4314, 14.8918, 15.5087, 16.002, 17.9217, 18.9264, 20.6365, 22.334, 23.8046, 25.8171, 26.1887±0.1° 2θ, as depicted in, for example, FIG. 17, and as found in Table 7 herein. In another embodiment, a solid form provided herein, e.g., Form A of Compound E, has at least 3, 5, 8, 10, or 12 characteristic XPRD peaks at approximately 5.9702, 6.2798, 7.766, 11.9769, 12.4314, 14.8918, 15.5087, 16.002, 17.9217, 18.9264, 20.6365, 22.334, 23.8046, 25.8171, 26.1887±0.1° 2θ, as depicted in, for example, FIG. 17, and as found in Table 7 herein. In still another embodiment, a solid form provided herein, e.g., Compound E, has at least 5, 6, 7, 8, 9, 10, 11, 12, 13, 14, or all of the characteristic XPRD peaks at approximately 5.9702, 6.2798, 7.766, 11.9769, 12.4314, 14.8918, 15.5087, 16.002, 17.9217, 18.9264, 20.6365, 22.334, 23.8046, 25.8171, 26.1887±0.1° 2θ, as depicted in, for example, FIG. 17 and as found in Table 7 herein.

In still another embodiment, a solid form provided herein, e.g., Form A of Compound E, has at least 10 characteristic XPRD peaks at approximately 5.9702, 6.2798, 7.766, 11.9769, 12.4314, 14.8918, 15.5087, 16.002, 17.9217, 18.9264, 20.6365, 22.334, 23.8046, 25.8171, 26.1887±0.1° 2θ, as depicted in, for example, FIG. 17, and as found in Table 7 herein. In still another embodiment, a solid form provided herein, e.g., Form A of Compound E, has at least 1, 2, 3, 4, 5, 6, 7, 8, 9, or 10 characteristic XPRD peaks at approximately 20.6365, 12.4314, 5.9702, 6.2798, 18.9264, 22.334, 14.8918, 25.8171, 16.002, 23.8046±0.1° 2θ, as depicted in, for example, FIG. 17, and as found in Table 7 herein.

In still another embodiment, a solid form provided herein, e.g., Form A of Compound E, has at least 5 characteristic XPRD peaks at approximately 5.9702, 6.2798, 7.766, 11.9769, 12.4314, 14.8918, 15.5087, 16.002, 17.9217, 18.9264, 20.6365, 22.334, 23.8046, 25.8171, 26.1887±0.1° 2θ, as depicted in, for example, FIG. 17, and as found in Table 7 herein. In still another embodiment, a solid form provided herein, e.g., Form A of Compound E, has at least 5 characteristic XPRD peaks at approximately 5.9702, 6.2798, 12.4314, 18.9264, 20.6365, 0.1° 2θ, as depicted in, for example, FIG. 17, and as found in Table 7 herein. In one embodiment, a solid form provided herein, e.g., Form A of Compound E, has an X-ray powder diffraction pattern comprising characteristic X-ray powder diffraction peaks using CuKα radiation at 5.9702, 6.2798, 12.4314, 18.9264, 20.6365 (±0.1° 2θ).

TABLE 7

Representative XRPD Peaks for Compound E Form A

| Pos. [° 2θ] | d-spacing [Å] | Rel. Int. [%] |
|---|---|---|
| 5.9702 | 14.79172 | 72.39 |
| 6.2798 | 14.0631 | 69.41 |

TABLE 7-continued

Representative XRPD Peaks for Compound E Form A

| Pos. [° 2θ] | d-spacing [Å] | Rel. Int. [%] |
|---|---|---|
| 7.766 | 11.37484 | 23.74 |
| 11.9769 | 7.38342 | 21.81 |
| 12.4314 | 7.11451 | 97.62 |
| 14.8918 | 5.94411 | 41.98 |
| 15.5087 | 5.70906 | 16.92 |
| 16.002 | 5.53413 | 36.61 |
| 17.9217 | 4.94544 | 23.26 |
| 18.9264 | 4.68511 | 63.17 |
| 20.6365 | 4.30057 | 100 |
| 22.334 | 3.97739 | 62.92 |
| 23.8046 | 3.73491 | 31.31 |
| 25.8171 | 3.44814 | 36.87 |
| 26.1887 | 3.40005 | 30.45 |

In another embodiment, Form A of Compound E is pure. In one such embodiment, Form A of Compound E is substantially free of other solid forms described herein (e.g. amorphous solid). In another embodiment, the purity of Form A of Compound E is no less than about 95%, no less than about 96%, no less than about 97%, no less than about 98%, no less than about 99%, no less than about 99.5%, or no less than about 99.9%.

Methods of Treating Cancer

The compounds and solid forms described herein can be administered to the patient in an effective amount (e.g. an amount as described herein) for treating cancer mediated by a $KRas^{G12C}$ mutation. In one such embodiment, the cancer is a solid tumor (e.g. lung cancer, CRC, or pancreatic cancer). It is to be understood that the methods described herein also include treatment with a pharmaceutical composition as described herein comprising a compound (e.g. Compound 1 or a solid form of Compound A, B, C, D, E, or F as described herein. In one embodiment is a method of treating lung cancer mediated by a $KRas^{G12C}$ mutation in a patient having such a cancer, the method comprising administering an effective amount of a solid form corresponding to Compound A, B, C, D, E, or F, or a mixture thereof as described herein) to the patient having cancer.

In one embodiment is a method of treating lung cancer mediated by a $KRas^{G12C}$ mutation in a patient having such a lung cancer, the method comprising administering an effective amount of Compound A as described herein to the patient. In one such embodiment is a method of treating lung cancer mediated by a $KRas^{G12C}$ mutation in a patient having such a lung cancer, the method comprising administering an effective amount of a solid form of Compound A (e.g. Form A, B, C, or D, or a mixture thereof) to the patient as described herein.

In one embodiment, the method comprises administering to the patient having lung cancer comprising a $KRas^{G12C}$ mutation, an effective amount of Compound A Form A as described herein. In one embodiment, the method comprises administering to the patient having lung cancer comprising a $KRas^{G12C}$ mutation, an effective amount of pure Compound A Form A (e.g. substantially free of another solid form such as Compound A Form B, Compound A Form C, or Compound A Form D. In one such embodiment, the crystalline purity of Compound A Form A is 95%, 97%, 98%, 98.5%, 99%, 99.5%, 99.9%. In another embodiment, the method comprises administering to the patient having lung cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount Compound A Form A further comprising a percentage of Compound A Form C. In one such embodiment, the method comprises administering Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having lung cancer comprising a $KRas^{G12C}$ mutation, an effective amount of Compound A Form D as described herein. In one embodiment, the method comprises administering to the patient having lung cancer comprising a $KRas^{G12C}$ mutation, an effective amount of pure Compound A Form D (e.g. substantially free of another solid form such as Compound A Form A, Compound A Form B, or Compound A Form C. In one such embodiment, the crystalline purity of Compound A Form D is 95%, 97%, 98%, 98.5%, 99%, 99.5%, 99.9%. In another embodiment, the method comprises administering to the patient having lung cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount of Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount of Compound A Form A further comprising a percentage of Compound A Form C. In one such embodiment, the method comprises administering to the patient an effective amount of Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having lung cancer comprising a $KRas^{G12C}$ mutation, an effective amount of Compound A Form C as described herein. In one embodiment, the method comprises administering to the patient having lung cancer comprising a $KRas^{G12C}$ mutation, an effective amount of pure Compound A Form C (e.g. substantially free of another solid form such as Compound A Form A, Compound A Form B, or Compound A Form D. In one such embodiment, the crystalline purity of Compound A Form C is 80%, 85%, 90%, 95%, 97%, 98%, 98.5%, 99%, 99.5%, 99.9%. In another embodiment, the method comprises administering to the patient having lung cancer comprising a $KRas^{G12C}$ mutation, an effective amount of Compound A Form c comprising one or more solid form other than Form A Compound c. In one such embodiment, the method comprises administering to the patient an effective amount of Compound A Form C further comprising a percentage of Compound A Form A and/or Form D. In one such embodiment, the method comprises administering to the patient an effective amount of Compound A Form C comprising Compound A Form A and/or Form D at a percentage of about 0.1%-10%, 0.5%-20%, 1%-30%, 1%-40%, 1%-50%, or 10%-50%. In another such embodiment, the mixture of Compound A Form C includes Compound A Form A and/or Form D at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having lung cancer comprising a $KRas^{G12C}$ mutation, an effective amount of Compound A Form B as described herein. In one embodiment, the method comprises administering to the patient having lung cancer comprising a $KRas^{G12C}$ mutation, an effective amount of pure Compound A Form B (e.g. substantially free of another solid form such as Compound A Form A, Compound A Form C, or Compound A Form D. In one such embodiment, the crystalline purity of Compound A Form B is 80%, 85%, 90%, 95%, 97%, 98%, 98.5%, 99%, 99.5%, 99.9%. In another embodiment, the method comprises administering to the patient having lung cancer comprising a $KRas^{G12C}$ mutation, an effective amount of Compound A Form B comprising one or more solid form other than Form A Compound B. In one such embodiment, the method comprises administering to the patient an effective amount of Compound A Form B further comprising a percentage of Compound A Form A, Form C, and/or Form D. In one such embodiment, the method comprises administering to the patient an effective amount of Compound A Form b comprising Compound A Form A, Form C, and/or Form D at a percentage of about 0.1%-10%, 0.5%-20%, 1%-30%, 1%-40%, 1%-50%, 10%-50%, or 25%-75%. In another such embodiment, the mixture of Compound A Form B includes Compound A Form A, Form C and/or Form D at an amount of less than about 0.5%, 1%, 2%, 5%, 7%, 10%, 15%, 20%, 25%, 40%, 50%, 60%, 75%, 80%, or 90%.

In one embodiment is a method of treating lung cancer mediated by a $KRas^{G12C}$ mutation in a patient having such a lung cancer, the method comprising administering an effective amount of Compound B as described herein to the patient. In one such embodiment is a method of treating lung cancer mediated by a $KRas^{G12C}$ mutation in a patient having such a lung cancer, the method comprising administering an effective amount of a solid form of Compound B (e.g. Form A) to the patient as described herein. In one such embodiment is a method of treating lung cancer mediated by a $KRas^{G12C}$ mutation in a patient having such a lung cancer, the method comprising administering an effective amount of Compound B Form A to the patient as described herein.

In one embodiment is a method of treating lung cancer mediated by a $KRas^{G12C}$ mutation in a patient having such a lung cancer, the method comprising administering an effective amount of Compound C as described herein to the patient. In one such embodiment is a method of treating lung cancer mediated by a $KRas^{G12C}$ mutation in a patient having such a lung cancer, the method comprising administering an effective amount of a solid form of Compound C (e.g. Form A) to the patient as described herein. In one such embodiment is a method of treating lung cancer mediated by a $KRas^{G12C}$ mutation in a patient having such a lung cancer, the method comprising administering an effective amount of Compound C Form A to the patient as described herein.

In one embodiment is a method of treating lung cancer mediated by a $KRas^{G12C}$ mutation in a patient having such a lung cancer, the method comprising administering an effective amount of Compound D as described herein to the patient. In one such embodiment is a method of treating lung cancer mediated by a $KRas^{G12C}$ mutation in a patient having such a lung cancer, the method comprising administering an effective amount of a solid form of Compound D (e.g. Form A) to the patient as described herein. In one such embodiment is a method of treating lung cancer mediated by a $KRas^{G12C}$ mutation in a patient having such a lung cancer, the method comprising administering an effective amount of Compound D Form A to the patient as described herein.

In one embodiment is a method of treating lung cancer mediated by a $KRas^{G12C}$ mutation in a patient having such a lung cancer, the method comprising administering an effective amount of Compound E as described herein to the patient. In one such embodiment is a method of treating lung cancer mediated by a $KRas^{G12C}$ mutation in a patient having such a lung cancer, the method comprising administering an effective amount of a solid form of Compound E (e.g. Form A) to the patient as described herein. In one such embodiment is a method of treating lung cancer mediated by a $KRas^{G12C}$ mutation in a patient having such a lung cancer, the method comprising administering an effective amount of Compound E Form A to the patient as described herein.

In one embodiment is a method of treating lung cancer mediated by a $KRas^{G12C}$ mutation in a patient having such a lung cancer, the method comprising administering an effective amount of Compound F as described herein to the patient. In one such embodiment is a method of treating lung cancer mediated by a $KRas^{G12C}$ mutation in a patient having such a lung cancer, the method comprising administering an effective amount of a solid form of Compound F (e.g. Form A) to the patient as described herein. In one such embodiment is a method of treating lung cancer mediated by a $KRas^{G12C}$ mutation in a patient having such a lung cancer, the method comprising administering an effective amount of Compound F Form A to the patient as described herein.

In such embodiments, the lung cancer is non-small cell lung cancer (NSCLC) comprising $KRas^{G12C}$ mutations. In another embodiment of the methods provided herein, the lung cancer is adenocarcinoma, squamous-cell lung carcinoma or large-cell lung carcinoma. In one such embodiment, the cancer is lung adenocarcinoma. In another such embodiment, the lung cancer is a small cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage 11 or IV lung cancer.

Further provided herein is the use (UL1) of Compound 1, Compound A, Compound B, Compound C, Compound D, Compound E, Compound F, or a solid form thereof as described herein for the treatment of lung cancer as described herein. Further provided herein is the use (UL2) of Compound A Form A as described herein for the treatment of lung cancer as described herein. Further provided herein is the use (UL3) of Compound A Form C as described herein for the treatment of lung cancer as described herein. Further provided herein is the use (UL4) of Compound A Form D as described herein for the treatment of lung cancer as described herein.

In one embodiment is a method of treating colorectal cancer mediated by a $KRas^{G12C}$ mutation in a patient having such a cancer, the method comprising administering an effective amount of a solid form corresponding to Compound A, B, C, D, E, or F, or a mixture thereof as described herein) to the patient having cancer.

In one embodiment is a method of treating colorectal cancer mediated by a $KRas^{G12C}$ mutation in a patient having such a colorectal cancer, the method comprising administering an effective amount of Compound A as described herein to the patient. In one such embodiment is a method of treating colorectal cancer mediated by a $KRas^{G12C}$ mutation in a patient having such a colorectal cancer, the method comprising administering an effective amount of a solid form of Compound A (e.g. Form A, B, C, or D, or a mixture thereof) to the patient as described herein.

In one embodiment, the method comprises administering to the patient having colorectal cancer comprising a $KRas^{G12C}$ mutation, an effective amount of Compound A Form A as described herein. In one embodiment, the method comprises administering to the patient having colorectal cancer comprising a $KRas^{G12C}$ mutation, an effective amount of pure Compound A Form A (e.g. substantially free of another solid form such as Compound A Form B, Compound A Form C, or Compound A Form D. In one such embodiment, the crystalline purity of Compound A Form A is 95%, 97%, 98%, 98.5%, 99%, 99.5%, 99.9%. In another embodiment, the method comprises administering to the patient having colorectal cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount Compound A Form A further comprising a percentage of Compound A Form C. In one such embodiment, the method comprises administering Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having colorectal cancer comprising a $KRas^{G12C}$ mutation, an effective amount of Compound A Form D as described herein. In one embodiment, the method comprises administering to the patient having colorectal cancer comprising a $KRas^{G12C}$ mutation, an effective amount of pure Compound A Form D (e.g. substantially free of another solid form such as Compound A Form A, Compound A Form B, or Compound A Form C. In one such embodiment, the crystalline purity of Compound A Form D is 95%, 97%, 98%, 98.5%, 99%, 99.5%, 99.9%. In another embodiment, the method comprises administering to the patient having colorectal cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount of Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount of Compound A Form A further comprising a percentage of Compound A Form C. In one such embodiment, the method comprises administering to the patient an effective amount of Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having colorectal cancer comprising a $KRas^{G12C}$ mutation, an effective amount of Compound A Form C as described herein. In one embodiment, the method comprises administering to the patient having colorectal cancer comprising a $KRas^{G12C}$ mutation, an effective amount of pure Compound A Form C (e.g. substantially free of another solid form such as Compound A Form A, Compound A Form B, or Compound A Form D. In one such embodiment, the crystalline purity of Compound A Form C is 80%, 85%, 90%, 95%, 97%, 98%, 98.5%, 99%, 99.5%, 99.9%. In another embodiment, the method comprises administering to the patient having colorectal cancer comprising a $KRas^{G12C}$ mutation, an effective amount of Compound A Form c comprising one or more solid form other than Form A Compound c. In one such embodiment, the method comprises administering to the patient an effective amount of Compound A Form C further comprising a percentage of Compound A Form A and/or Form D. In one such embodiment, the method comprises administering to the patient an effective amount of Compound A Form C comprising Compound A Form A and/or Form D at a percentage of about 0.1%-10%, 0.5%-20%, 1%-30%, 1%-40%, 1%-50%, or 10%-50%. In another such embodiment, the mixture of Compound A Form C includes Compound A Form A and/or Form D at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having colorectal cancer comprising a $KRas^{G12C}$ mutation, an effective amount of Compound A Form B as described herein. In one embodiment, the method comprises administering to the patient having colorectal cancer comprising a $KRas^{G12C}$ mutation, an effective amount of pure Compound A Form B (e.g. substantially free of another solid form such as Compound A Form A, Compound A Form C, or Compound A Form D. In one such embodiment, the crystalline purity of Compound A Form B is 80%, 85%, 90%, 95%, 97%, 98%, 98.5%, 99%, 99.5%, 99.9%. In another embodiment, the method comprises administering to the patient having colorectal cancer comprising a $KRas^{G12C}$ mutation, an effective amount of Compound A Form B comprising one or more solid form other than Form A Compound B. In one such embodiment, the method comprises administering to the patient an effective amount of Compound A Form B further comprising a percentage of Compound A Form A, Form C, and/or Form D. In one such embodiment, the method comprises administering to the patient an effective amount of Compound A Form b comprising Compound A Form A, Form C, and/or Form D at a percentage of about 0.1%-10%, 0.5%-20%, 1%-30%, 1%-40%, 1%-50%, 10%-50%, or 25%-75%. In another such embodiment, the mixture of Compound A Form B includes Compound A Form A, Form C and/or Form D at an amount of less than about 0.5%, 1%, 2%, 5%, 7%, 10%, 15%, 20%, 25%, 40%, 50%, 60%, 75%, 80%, or 90%.

In one embodiment is a method of treating colorectal cancer mediated by a $KRas^{G12C}$ mutation in a patient having such a colorectal cancer, the method comprising administering an effective amount of Compound B as described herein to the patient. In one such embodiment is a method of treating colorectal cancer mediated by a $KRas^{G12C}$ mutation in a patient having such a colorectal cancer, the method comprising administering an effective amount of a solid form of Compound B (e.g. Form A) to the patient as described herein. In one such embodiment is a method of treating colorectal cancer mediated by a $KRas^{G12C}$ mutation in a patient having such a colorectal cancer, the method comprising administering an effective amount of Compound B Form A to the patient as described herein.

In one embodiment is a method of treating colorectal cancer mediated by a $KRas^{G12C}$ mutation in a patient having such a colorectal cancer, the method comprising administering an effective amount of Compound C as described herein to the patient. In one such embodiment is a method of treating colorectal cancer mediated by a $KRas^{G12C}$ mutation in a patient having such a colorectal cancer, the method comprising administering an effective amount of a solid form of Compound C (e.g. Form A) to the patient as described herein. In one such embodiment is a method of treating colorectal cancer mediated by a $KRas^{G12C}$ mutation in a patient having such a colorectal cancer, the method comprising administering an effective amount of Compound C Form A to the patient as described herein.

In one embodiment is a method of treating colorectal cancer mediated by a $KRas^{G12C}$ mutation in a patient having such a colorectal cancer, the method comprising administering an effective amount of Compound D as described herein to the patient. In one such embodiment is a method of treating colorectal cancer mediated by a $KRas^{G12C}$ mutation in a patient having such a colorectal cancer, the method comprising administering an effective amount of a solid form of Compound D (e.g. Form A) to the patient as described herein. In one such embodiment is a method of treating colorectal cancer mediated by a $KRas^{G12C}$ mutation in a patient having such a colorectal cancer, the method comprising administering an effective amount of Compound D Form A to the patient as described herein.

In one embodiment is a method of treating colorectal cancer mediated by a $KRas^{G12C}$ mutation in a patient having such a colorectal cancer, the method comprising administering an effective amount of Compound E as described herein to the patient. In one such embodiment is a method of treating colorectal cancer mediated by a $KRas^{G12C}$ mutation in a patient having such a colorectal cancer, the method comprising administering an effective amount of a solid form of Compound E (e.g. Form A) to the patient as described herein. In one such embodiment is a method of treating colorectal cancer mediated by a $KRas^{G12C}$ mutation in a patient having such a colorectal cancer, the method comprising administering an effective amount of Compound E Form A to the patient as described herein.

In one embodiment is a method of treating colorectal cancer mediated by a $KRas^{G12C}$ mutation in a patient having such a colorectal cancer, the method comprising administering an effective amount of Compound F as described herein to the patient. In one such embodiment is a method of treating colorectal cancer mediated by a $KRas^{G12C}$ mutation in a patient having such a colorectal cancer, the method comprising administering an effective amount of a solid form of Compound F (e.g. Form A) to the patient as described herein. In one such embodiment is a method of treating colorectal cancer mediated by a $KRas^{G12C}$ mutation in a patient having such a colorectal cancer, the method comprising administering an effective amount of Compound F Form A to the patient as described herein.

Further provided herein is the use (UC1) of Compound 1, Compound A, Compound B, Compound C, Compound D, Compound E, Compound F, or a solid form thereof as described herein for the treatment of colorectal cancer as described herein. Further provided herein is the use (UC2) of Compound A Form A as described herein for the treatment of colorectal cancer as described herein. Further provided herein is the use (UC3) of Compound A Form C as described herein for the treatment of colorectal cancer as described herein. Further provided herein is the use (UC4) of Compound A Form D as described herein for the treatment of colorectal cancer as described herein.

In one embodiment is a method of treating pancreatic cancer mediated by a $KRas^{G12C}$ mutation in a patient having such a cancer, the method comprising administering an effective amount of a solid form corresponding to Compound A, B, C, D, E, or F, or a mixture thereof as described herein) to the patient having cancer.

In one embodiment is a method of treating pancreatic cancer mediated by a $KRas^{G12C}$ mutation in a patient having such a pancreatic cancer, the method comprising administering an effective amount of Compound A as described herein to the patient. In one such embodiment is a method of treating pancreatic cancer mediated by a $KRas^{G12C}$ mutation in a patient having such a pancreatic cancer, the method comprising administering an effective amount of a solid form of Compound A (e.g. Form A, B, C, or D, or a mixture thereof) to the patient as described herein.

In one embodiment, the method comprises administering to the patient having pancreatic cancer comprising a $KRas^{G12C}$ mutation, an effective amount of Compound A Form A as described herein. In one embodiment, the method comprises administering to the patient having pancreatic cancer comprising a $KRas^{G12C}$ mutation, an effective amount of pure Compound A Form A (e.g. substantially free of another solid form such as Compound A Form B, Compound A Form C, or Compound A Form D. In one such embodiment, the crystalline purity of Compound A Form A is 95%, 97%, 98%, 98.5%, 99%, 99.5%, 99.9%. In another embodiment, the method comprises administering to the patient having pancreatic cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount Compound A Form A further comprising a percentage of Compound A Form C. In one such embodiment, the method comprises administering Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having pancreatic cancer comprising a $KRas^{G12C}$ mutation, an effective amount of Compound A Form D as described herein. In one embodiment, the method comprises administering to the patient having pancreatic cancer comprising a $KRas^{G12C}$ mutation, an effective amount of pure Compound A Form D (e.g. substantially free of another solid form such as Compound A Form A, Compound A Form B, or Compound A Form C. In one such embodiment, the crystalline purity of Compound A Form D is 95%, 97%, 98%, 98.5%, 99%, 99.5%, 99.9%. In another embodiment, the method comprises administering to the patient having pancreatic cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount of Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount of Compound A Form A further comprising a percentage of Compound A Form C. In one such embodiment, the method comprises administering to the patient an effective amount of Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having pancreatic cancer comprising a $KRas^{G12C}$ mutation, an effective amount of Compound A Form C as described herein. In one embodiment, the method comprises administering to the patient having pancreatic cancer comprising a $KRas^{G12C}$ mutation, an effective amount of pure Compound A Form C (e.g. substantially free of another solid form such as Compound A Form A, Compound A Form B, or Compound A Form D. In one such embodiment, the crystalline purity of Compound A Form C is 80%, 85%, 90%, 95%, 97%, 98%, 98.5%, 99%, 99.5%, 99.9%. In another embodiment, the method comprises administering to the patient having pancreatic cancer comprising a $KRas^{G12C}$ mutation, an effective amount of Compound A Form c comprising one or more solid form other than Form A Compound c. In one such embodiment, the method comprises administering to the patient an effective amount of Compound A Form C further comprising a percentage of Compound A Form A and/or Form D. In one such embodiment, the method comprises administering to the patient an effective amount of Compound A Form C comprising Compound A Form A and/or Form D at a percentage of about 0.1%-10%, 0.5%-20%, 1%-30%, 1%-40%, 1%-50%, or 10%-50%. In another such embodiment, the mixture of Compound A Form C includes Compound A Form A and/or Form D at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having pancreatic cancer comprising a $KRas^{G12C}$ mutation, an effective amount of Compound A Form B as described herein. In one embodiment, the method comprises administering to the patient having pancreatic cancer comprising a $KRas^{G12C}$ mutation, an effective amount of pure Compound A Form B (e.g. substantially free of another solid form such as Compound A Form A, Compound A Form C, or Compound A Form D. In one such embodiment, the crystalline purity of Compound A Form B is 80%, 85%, 90%, 95%, 97%, 98%, 98.5%, 99%, 99.5%, 99.9%. In another embodiment, the method comprises administering to the patient having pancreatic cancer comprising a $KRas^{G12C}$ mutation, an effective amount of Compound A Form B comprising one or more solid form other than Form A Compound B. In one such embodiment, the method comprises administering to the patient an effective amount of Compound A Form B further comprising a percentage of Compound A Form A, Form C, and/or Form D. In one such embodiment, the method comprises administering to the patient an effective amount of Compound A Form b comprising Compound A Form A, Form C, and/or Form D at a percentage of about 0.1%-10%, 0.5%-20%, 1%-30%, 1%-40%, 1%-50%, 10%-50%, or 25%-75%. In another such embodiment, the mixture of Compound A Form B includes Compound A Form A, Form C and/or Form D at an amount of less than about 0.5%, 1%, 2%, 5%, 7%, 10%, 15%, 20%, 25%, 40%, 50%, 60%, 75%, 80%, or 90%.

In one embodiment is a method of treating pancreatic cancer mediated by a $KRas^{G12C}$ mutation in a patient having such a pancreatic cancer, the method comprising administering an effective amount of Compound B as described herein to the patient. In one such embodiment is a method of treating pancreatic cancer mediated by a $KRas^{G12C}$ mutation in a patient having such a pancreatic cancer, the method comprising administering an effective amount of a solid form of Compound B (e.g. Form A) to the patient as described herein. In one such embodiment is a method of treating pancreatic cancer mediated by a $KRas^{G12C}$ mutation in a patient having such a pancreatic cancer, the method comprising administering an effective amount of Compound B Form A to the patient as described herein.

In one embodiment is a method of treating pancreatic cancer mediated by a $KRas^{G12C}$ mutation in a patient having such a pancreatic cancer, the method comprising administering an effective amount of Compound C as described herein to the patient. In one such embodiment is a method of treating pancreatic cancer mediated by a $KRas^{G12C}$ mutation in a patient having such a pancreatic cancer, the method comprising administering an effective amount of a solid form of Compound C (e.g. Form A) to the patient as described herein. In one such embodiment is a method of treating pancreatic cancer mediated by a $KRas^{G12C}$ mutation in a patient having such a pancreatic cancer, the method comprising administering an effective amount of Compound C Form A to the patient as described herein.

In one embodiment is a method of treating pancreatic cancer mediated by a $KRas^{G12C}$ mutation in a patient having such a pancreatic cancer, the method comprising administering an effective amount of Compound D as described herein to the patient. In one such embodiment is a method of treating pancreatic cancer mediated by a $KRas^{G12C}$ mutation in a patient having such a pancreatic cancer, the method comprising administering an effective amount of a solid form of Compound D (e.g. Form A) to the patient as described herein. In one such embodiment is a method of treating pancreatic cancer mediated by a $KRas^{G12C}$ mutation in a patient having such a pancreatic cancer, the method comprising administering an effective amount of Compound D Form A to the patient as described herein.

In one embodiment is a method of treating pancreatic cancer mediated by a $KRas^{G12C}$ mutation in a patient having such a pancreatic cancer, the method comprising administering an effective amount of Compound E as described herein to the patient. In one such embodiment is a method of treating pancreatic cancer mediated by a $KRas^{G12C}$ mutation in a patient having such a pancreatic cancer, the method comprising administering an effective amount of a solid form of Compound E (e.g. Form A) to the patient as described herein. In one such embodiment is a method of treating pancreatic cancer mediated by a $KRas^{G12C}$ mutation in a patient having such a pancreatic cancer, the method comprising administering an effective amount of Compound E Form A to the patient as described herein.

In one embodiment is a method of treating pancreatic cancer mediated by a $KRas^{G12C}$ mutation in a patient having such a pancreatic cancer, the method comprising administering an effective amount of Compound F as described herein to the patient. In one such embodiment is a method of treating pancreatic cancer mediated by a $KRas^{G12C}$ mutation in a patient having such a pancreatic cancer, the method comprising administering an effective amount of a solid form of Compound F (e.g. Form A) to the patient as described herein. In one such embodiment is a method of treating pancreatic cancer mediated by a $KRas^{G12C}$ mutation in a patient having such a pancreatic cancer, the method comprising administering an effective amount of Compound F Form A to the patient as described herein.

Further provided herein are methods of treating tumor agnostic cancer comprising a $KRas^{G12C}$ mutation in a patient having such a cancer. In one such embodiment, the method comprising treating tumor agnostic cancer comprising a $KRas^{G12C}$ mutation in a patient having such a cancer by (a) determining the absence or presence of a $KRas^{G12C}$ mutation in a sample taken from a patient with a suspected diagnosed cancer; and (b) administering to the patient an effective amount of a solid form of Compound A (e.g. Form A, B, C, or D, or a mixture thereof) to the patient as described herein.

In one embodiment, the method comprises administering to the patient having a tumor agnostic cancer comprising a $KRas^{G12C}$ mutation, an effective amount of Compound A Form A as described herein. In one embodiment, the method comprises administering to the patient having a tumor agnostic cancer comprising a $KRas^{G12C}$ mutation, an effective amount of pure Compound A Form A (e.g. substantially free of another solid form such as Compound A Form B, Compound A Form C, or Compound A Form D. In one such embodiment, the crystalline purity of Compound A Form A is 95%, 97%, 98%, 98.5%, 99%, 99.5%, 99.9%. In another embodiment, the method comprises administering to the patient having a tumor agnostic cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount Compound A Form A further comprising a percentage of Compound A Form C. In one such embodiment, the method comprises administering Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having a tumor agnostic cancer comprising a $KRas^{G12C}$ mutation, an effective amount of Compound A Form D as described herein. In one embodiment, the method comprises administering to the patient having a tumor agnostic cancer comprising a $KRas^{G12C}$ mutation, an effective amount of pure Compound A Form D (e.g. substantially free of another solid form such as Compound A Form A, Compound A Form B, or Compound A Form C. In one such embodiment, the crystalline purity of Compound A Form D is 95%, 97%, 98%, 98.5%, 99%, 99.5%, 99.9%. In another embodiment, the method comprises administering to the patient having a tumor agnostic cancer comprising a $KRas^{G12C}$ mutation, an effective amount of Compound A Form A comprising one or more solid form other than Form A Compound A. In one such embodiment, the method comprises administering to the patient an effective amount of Compound A Form A further comprising a percentage of Compound A Form D. In one such embodiment, the method comprises administering to the patient an effective amount of Compound A Form A comprising Compound A Form D at a percentage of about 0.1%-10%, 0.5%-20%, 1%-30%, 1%-40%, 1%-50%, or 10%-50%. In another such embodiment, the mixture of Compound A Form A and Form D may include Compound A Form D at an amount of less than about 0.5%, 1%, 2%, 5%, 7%, 10%, 15%, 20%, 25%, 40%, 50%, 60%, 75%, 80%, or 90%. In another such embodiment, the method comprises administering to the patient an effective amount of Compound A Form A further comprising a percentage of Compound A Form C. In one such embodiment, the method comprises administering to the patient an effective amount of Compound A Form A comprising Compound A Form C at a percentage of about 0.1%-10%, 0.5%-20%, 1%-30%, 1%-40%, 1%-50%, or 10%-50%. In another such embodiment, the mixture of Compound A Form A and Form C may include Compound A Form C at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having a tumor agnostic cancer comprising a $KRas^{G12C}$ mutation, an effective amount of Compound A Form C as described herein. In one embodiment, the method comprises administering to the patient having a tumor agnostic cancer comprising a $KRas^{G12C}$ mutation, an effective amount of pure Compound A Form C (e.g. substantially free of another solid form such as Compound A Form A, Compound A Form B, or Compound A Form D. In one such embodiment, the crystalline purity of Compound A Form C is 80%, 85%, 90%, 95%, 97%, 98%, 98.5%, 99%, 99.5%, 99.9%. In another embodiment, the method comprises administering to the patient having a tumor agnostic cancer comprising a $KRas^{G12C}$ mutation, an effective amount of Compound A Form c comprising one or more solid form other than Form A Compound c. In one such embodiment, the method comprises administering to the patient an effective amount of Compound A Form C further comprising a percentage of Compound A Form A and/or Form D. In one such embodiment, the method comprises administering to the patient an effective amount of Compound A Form C comprising Compound A Form A and/or Form D at a percentage of about 0.1%-10%, 0.5%-20%, 1%-30%, 1%-40%, 1%-50%, or 10%-50%. In another such embodiment, the mixture of Compound A Form C includes Compound A Form A and/or Form D at an amount of less than about 0.5%, 1%, 2%, 5%, 7%, 10%, 15%, 20%, 25%, 40%, 50%, 60%, 75%, 80%, or 90%.

In one embodiment, the method comprises administering to the patient having a tumor agnostic cancer comprising a $KRas^{G12C}$ mutation, an effective amount of Compound A Form B as described herein. In one embodiment, the method comprises administering to the patient having a tumor agnostic cancer comprising a $KRas^{G12C}$ mutation, an effective amount of pure Compound A Form B (e.g. substantially free of another solid form such as Compound A Form A, Compound A Form C, or Compound A Form D. In one such embodiment, the crystalline purity of Compound A Form B is 80%, 85%, 90%, 95%, 97%, 98%, 98.5%, 99%, 99.5%, 99.9%. In another embodiment, the method comprises administering to the patient having a tumor agnostic cancer comprising a $KRas^{G12C}$ mutation, an effective amount of Compound A Form B comprising one or more solid form other than Form A Compound B. In one such embodiment, the method comprises administering to the patient an effective amount of Compound A Form B further comprising a percentage of Compound A Form A, Form C, and/or Form D. In one such embodiment, the method comprises administering to the patient an effective amount of Compound A Form b comprising Compound A Form A, Form C, and/or Form D at a percentage of about 0.1%-10%, 0.5%-20%, 1%-30%, 1%-40%, 1%-50%, 10%-50%, or 25%-75%. In another such embodiment, the mixture of Compound A Form B includes Compound A Form A, Form C and/or Form D at an amount of less than about 0.5%, 1%, 2%, 5%, 7%, 10%, 15%, 20%, 25%, 40%, 50%, 60%, 75%, 80%, or 90%.

In one embodiment is a method of treating a tumor agnostic cancer mediated by a $KRas^{G12C}$ mutation in a patient having such a tumor agnostic cancer, the method comprising administering an effective amount of Compound B as described herein to the patient. In one such embodiment is a method of treating a tumor agnostic cancer mediated by a $KRas^{G12C}$ mutation in a patient having such a tumor agnostic cancer, the method comprising administering an effective amount of a solid form of Compound B (e.g. Form A) to the patient as described herein. In one such embodiment is a method of treating a tumor agnostic cancer mediated by a $KRas^{G12C}$ mutation in a patient having such a tumor agnostic cancer, the method comprising administering an effective amount of Compound B Form A to the patient as described herein.

In one embodiment is a method of treating a tumor agnostic cancer mediated by a $KRas^{G12C}$ mutation in a patient having such a tumor agnostic cancer, the method comprising administering an effective amount of Compound C as described herein to the patient. In one such embodiment is a method of treating a tumor agnostic cancer mediated by a $KRas^{G12C}$ mutation in a patient having such a tumor agnostic cancer, the method comprising administering an effective amount of a solid form of Compound C (e.g. Form A) to the patient as described herein. In one such embodiment is a method of treating a tumor agnostic cancer mediated by a $KRas^{G12C}$ mutation in a patient having such a tumor agnostic cancer, the method comprising administering an effective amount of Compound C Form A to the patient as described herein.

In one embodiment is a method of treating a tumor agnostic cancer mediated by a $KRas^{G12C}$ mutation in a patient having such a tumor agnostic cancer, the method comprising administering an effective amount of Compound D as described herein to the patient. In one such embodiment is a method of treating a tumor agnostic cancer mediated by a $KRas^{G12C}$ mutation in a patient having such a tumor agnostic cancer, the method comprising administering an effective amount of a solid form of Compound D (e.g. Form A) to the patient as described herein. In one such embodiment is a method of treating a tumor agnostic cancer mediated by a $KRas^{G12C}$ mutation in a patient having such a tumor agnostic cancer, the method comprising administering an effective amount of Compound D Form A to the patient as described herein.

In one embodiment is a method of treating a tumor agnostic cancer mediated by a $KRas^{G12C}$ mutation in a patient having such a tumor agnostic cancer, the method comprising administering an effective amount of Compound E as described herein to the patient. In one such embodiment is a method of treating a tumor agnostic cancer mediated by a $KRas^{G12C}$ mutation in a patient having such a tumor agnostic cancer, the method comprising administering an effective amount of a solid form of Compound E (e.g. Form A) to the patient as described herein. In one such embodiment is a method of treating a tumor agnostic cancer mediated by a $KRas^{G12C}$ mutation in a patient having such a tumor agnostic cancer, the method comprising administering an effective amount of Compound E Form A to the patient as described herein.

In one embodiment is a method of treating a tumor agnostic cancer mediated by a $KRas^{G12C}$ mutation in a patient having such a tumor agnostic cancer, the method comprising administering an effective amount of Compound F as described herein to the patient. In one such embodiment is a method of treating a tumor agnostic cancer mediated by a $KRas^{G12C}$ mutation in a patient having such a tumor agnostic cancer, the method comprising administering an effective amount of a solid form of Compound F (e.g. Form A) to the patient as described herein. In one such embodiment is a method of treating a tumor agnostic cancer mediated by a $KRas^{G12C}$ mutation in a patient having such a tumor agnostic cancer, the method comprising administering an effective amount of Compound F Form A to the patient as described herein.

Further provided herein is the use (UP1) of Compound 1, Compound A, Compound B, Compound C, Compound D, Compound E, Compound F, or a solid form thereof as described herein for the treatment of tumor agnostic cancer as described herein. Further provided herein is the use (UP2) of Compound A Form A as described herein for the treatment of tumor agnostic cancer as described herein. Further provided herein is the use (UP3) of Compound A Form C as described herein for the treatment of tumor agnostic cancer as described herein. Further provided herein is the use (UP4) of Compound A Form D as described herein for the treatment of tumor agnostic cancer as described herein.

In one embodiment of the methods and uses described herein, Compound 1 or a solid form described herein (e.g. Compound A Form A/B/C/D, Compound B, Compound C, Compound D, Compound E, or Compound F) is administered as a fixed dose QD administration. In one embodiment, the administration is oral (PO), where Compound 1 or a solid form described herein (e.g. Compound A Form A/B/C/D, Compound B, Compound C, Compound D, Compound E, or Compound F) is formulated as a tablet or capsule. In one embodiment, Compound 1 or a solid form described herein (e.g. Compound A Form A/B/C/D, Compound B, Compound C, Compound D, Compound E, or Compound F) is administered at an amount of 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a solid form described herein (e.g. Compound A Form A/B/C/D, Compound B, Compound C, Compound D, Compound E, or Compound F) is administered at an amount of about 5 mg, 25 mg, 50 mg, 100 mg, 150 mg, 200 mg, 250 mg, 300 mg, 400 mg or 500 mg. In another embodiment, Compound A Form A or Compound A Form D as described herein is administered at an amount of about 5 mg, 25 mg, 50 mg, 100 mg, 150 mg, 200 mg, 250 mg, 300 mg, 400 mg or 500 mg.

Kits:

Compound 1 and the solid forms described herein (e.g. Compound A, Compound B, Compound C, Compound D, Compound E, and/or Compound F) can be provided as an article of manufacture (i.e a kit) comprising one or more of the compounds described herein for administration. In one embodiment, the kit includes Compound A or a solid form thereof as described herein (e.g. Compound A Form A, B, C, or D) for administration as described herein. In one such embodiment, a kit as described herein comprises Compound A Form A or Compound A Form D as described herein. In another embodiment, the kit includes Compound B Form A. In another embodiment, the kit includes Compound C Form A. In still another embodiment, the kit includes Compound D Form A. In still another embodiment, the kit includes Compound E form A. In still another embodiment, the kit includes Compound F Form A.

In some instances, the article of manufacture further comprises package insert comprising instructions to treat or delay progression of a solid tumor (e.g. lung cancer, CRC, or pancreatic cancer as described herein). In one such embodiment, the cancer is NSCLC. In one embodiment, the article of manufacture further comprises package insert comprising instructions for using Compound 1 or solid forms described herein (e.g. Compound A, Compound B, Compound C, Compound D, Compound E, and/or Compound F) to treat or delay progression of NSCLC in a patient. In one embodiment, the article of manufacture further comprises package insert comprising instructions for using Compound 1 or a solid forms described herein (e.g. Compound A, Compound B, Compound C, Compound D, Compound E, and/or Compound F) to treat or delay progression of pancreatic cancer in a patient. In one embodiment, the article of manufacture further comprises package insert comprising instructions for using Compound 1 or a solid forms described herein (e.g. Compound A, Compound B, Compound C, Compound D, Compound E, and/or Compound F) to treat or delay progression of CRC in a patient.

In such kits, Compound 1 or a solid forms described herein (e.g. Compound A, Compound B, Compound C, Compound D, Compound E, and/or Compound F) is provided in a container. Suitable containers include, for example, bottles, vials, bags and syringes. The container may be formed from a variety of materials such as glass, plastic (such as polyvinyl chloride or polyolefin), or metal alloy (such as stainless steel or hastelloy). In some instances, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some instances, the article of manufacture further includes one or more of another agent (e.g., an additional chemotherapeutic agent or anti-neoplastic agent). Suitable containers for the one or more agents include, for example, bottles, vials, bags and syringes.

Any of the articles of manufacture or kits described herein may include instructions to administer Compound 1 or a solid form described herein (e.g. Compound A, Compound B, Compound C, Compound D, Compound E, and/or Compound F) to a patient in accordance with any of the methods described herein.

Embodiments

Provided below are some exemplary embodiments of the invention.

Embodiment 1. A compound having the structure:

(A)

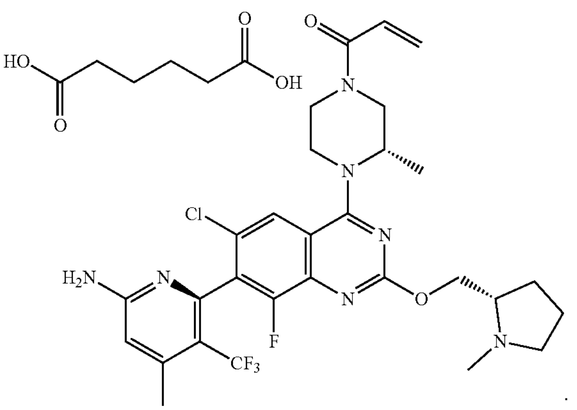

.

Embodiment 2. A crystal form comprising Compound A (A)

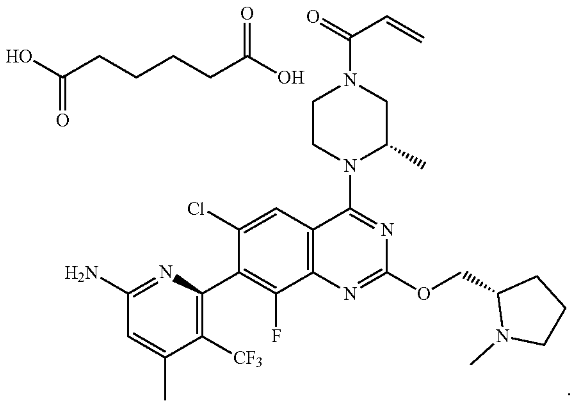

having an X-ray powder diffraction pattern comprising characteristic X-ray powder diffraction peaks using CuKα radiation at 9.6474, 11.0365, 15.4059, 16.4193, 18.7038 (±0.1° 2θ).

Embodiment 3. The crystal form of embodiment 2, wherein the crystal form of Compound A has an X-ray powder diffraction pattern comprising at least 5 characteristic X-ray powder diffraction peaks using CuKα radiation as set forth in Table 1.

Embodiment 4. The crystal form of embodiment 2, wherein the crystal form of Compound A has an X-ray powder diffraction pattern comprising at least 10 characteristic X-ray powder diffraction peaks using CuKα radiation as set forth in Table 1.

Embodiment 5. The crystal form of embodiment 2, wherein the crystal form of Compound A has an X-ray powder diffraction pattern substantially as shown in FIG. 1.

Embodiment 6. The crystal form of embodiment 2, wherein the crystal form of Compound A has a TGA thermograph corresponding substantially to the representative TGA thermogram as depicted in FIG. 2.

Embodiment 7. The crystal form of embodiment 2, wherein the crystal form of Compound A has a DSC thermograph corresponding substantially as depicted in FIG. 2.

Embodiment 8. A crystal form comprising Compound A:

(A)

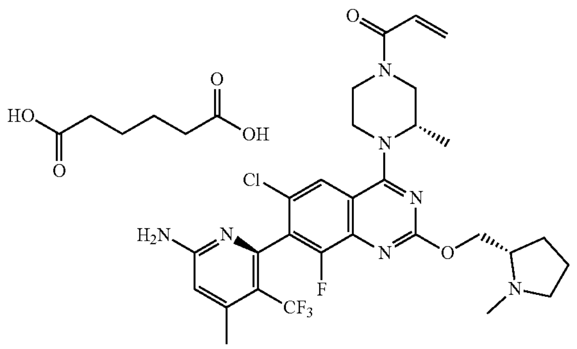

having an X-ray powder diffraction pattern comprising characteristic X-ray powder diffraction peaks using CuKα radiation at 5.2063, 14.63, 17.7161, 21.9253, 25.1335 (±0.1° 2θ).

Embodiment 9. The crystal form of embodiment 8, wherein the crystal form of Compound A has an X-ray powder diffraction pattern comprising at least 5 characteristic X-ray powder diffraction peaks using CuKα radiation as set forth in Table 2.

Embodiment 10. The crystal form of embodiment 8, wherein the crystal form of Compound A has an X-ray powder diffraction pattern comprising at least 10 characteristic X-ray powder diffraction peaks using CuKα radiation as set forth in Table 2.

Embodiment 11. The crystal form of embodiment 8, wherein the crystal form of Compound A has an X-ray powder diffraction pattern substantially as shown in FIG. 5.

Embodiment 12. A crystal form comprising Compound A:

(A)

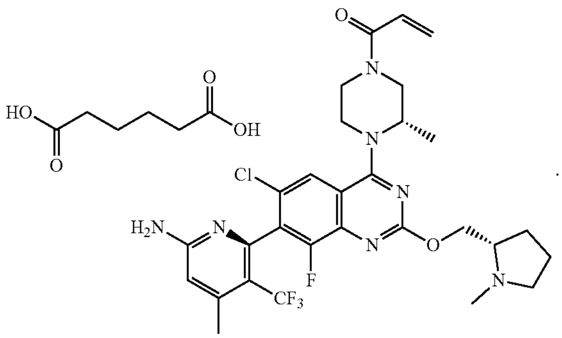

Embodiment 13. A crystal form comprising Compound A:

(A)

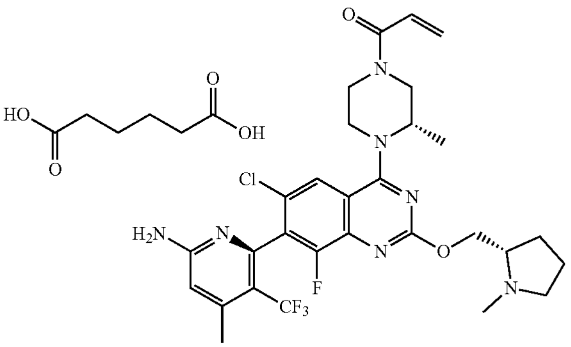

having an X-ray powder diffraction pattern comprising characteristic X-ray powder diffraction peaks using CuKα radiation at 9.7745, 11.0487, 15.2452, 18.6477, 18.7908 (±0.1° 2θ).

Embodiment 14. The crystal form of embodiment 13, wherein the crystal form of Compound A has an X-ray powder diffraction pattern comprising at least 5 characteristic X-ray powder diffraction peaks using CuKα radiation as set forth in Table 3.

Embodiment 15. The crystal form of embodiment 13, wherein the crystal form of Compound A has an X-ray powder diffraction pattern comprising at least 10 characteristic X-ray powder diffraction peaks using CuKα radiation as set forth in Table 3.

Embodiment 16. The crystal form of embodiment 13, wherein the crystal form of Compound A has an X-ray powder diffraction pattern substantially as shown in FIG. 8.

Embodiment 17. The crystal form of embodiment 13, wherein the crystal form of Compound A has a TGA thermograph corresponding substantially to the representative TGA thermogram as depicted in FIG. 10.

Embodiment 18. The crystal form of embodiment 13, wherein the crystal form of Compound A has a DSC thermograph corresponding substantially as depicted in FIG. 9.

Embodiment 19. A crystal form comprising Compound B:

(B)

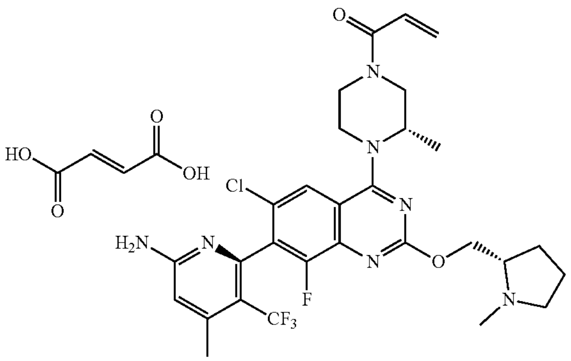

having an X-ray powder diffraction pattern comprising characteristic X-ray powder diffraction peaks using CuKα radiation at 6.6796, 14.9097, 15.2963, 19.4416, 23.7124 (±0.1° 2θ).

Embodiment 20. The crystal form of embodiment 19, wherein the crystal form of Compound B has an X-ray powder diffraction pattern comprising at least 5 characteristic X-ray powder diffraction peaks using CuKα radiation as set forth in Table 4.

Embodiment 21. The crystal form of embodiment 19, wherein the crystal form of Compound B has an X-ray powder diffraction pattern comprising at least 10 characteristic X-ray powder diffraction peaks using CuKα radiation as set forth in Table 4.

Embodiment 22. The crystal form of embodiment 19, wherein the crystal form of Compound B has an X-ray powder diffraction pattern substantially as shown in FIG. 11.

Embodiment 23. The crystal form of embodiment 19, wherein the crystal form of Compound B has a DSC thermograph corresponding substantially as depicted in FIG. 12.

Embodiment 24. A crystal form comprising Compound C:

(C)

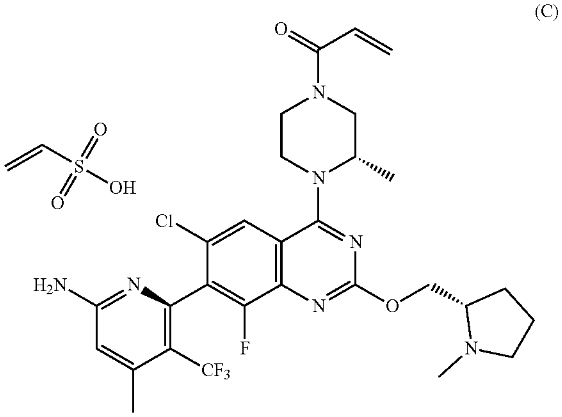

having an X-ray powder diffraction pattern comprising characteristic X-ray powder diffraction peaks using CuKα radiation at 12.5401, 17.5707, 16.834, 21.3525, 26.5569 (±0.1° 2θ).

Embodiment 25. The crystal form of embodiment 24, wherein the crystal form of Compound C has an X-ray powder diffraction pattern comprising at least 5 characteristic X-ray powder diffraction peaks using CuKα radiation as set forth in Table 5.

Embodiment 26. The crystal form of embodiment 24, wherein the crystal form of Compound C has an X-ray powder diffraction pattern comprising at least 10 characteristic X-ray powder diffraction peaks using CuKα radiation as set forth in Table 5.

Embodiment 27. The crystal form of embodiment 24, wherein the crystal form of Compound C has an X-ray powder diffraction pattern substantially as shown in FIG. 13.

Embodiment 28. The crystal form of embodiment 24, wherein the crystal form of Compound C has a TGA thermograph corresponding substantially to the representative TGA thermogram as depicted in FIG. 14.

Embodiment 29. The crystal form of embodiment 24, wherein the crystal form of Compound C has a DSC thermograph corresponding substantially as depicted in FIG. 14.

Embodiment 30. A crystal form comprising Compound D:

(D)

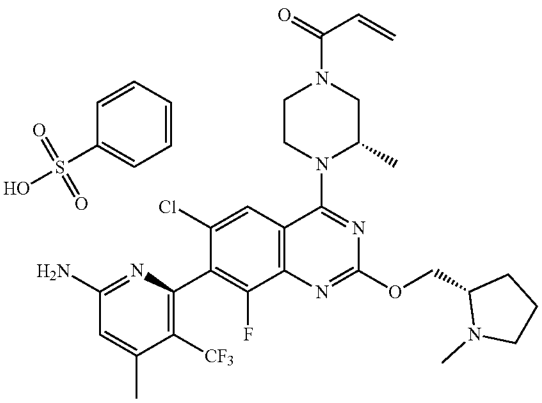

having an X-ray powder diffraction pattern comprising characteristic X-ray powder diffraction peaks using CuKα radiation at 7.3809, 10.7407, 14.654, 18.5979, 25.2558 (±0.1° 2θ).

Embodiment 31. The crystal form of embodiment 30, wherein the crystal form of Compound D has an X-ray powder diffraction pattern comprising at least 5 characteristic X-ray powder diffraction peaks using CuKα radiation as set forth in Table 6.

Embodiment 32. The crystal form of embodiment 30, wherein the crystal form of Compound D has an X-ray powder diffraction pattern comprising at least 10 characteristic X-ray powder diffraction peaks using CuKα radiation as set forth in Table 6.

Embodiment 33. The crystal form of embodiment 30, wherein the crystal form of Compound D has an X-ray powder diffraction pattern substantially as shown in FIG. 15.

Embodiment 34. The crystal form of embodiment 30, wherein the crystal form of Compound D has a TGA thermograph corresponding substantially to the representative TGA thermogram as depicted in FIG. 16.

Embodiment 35. The crystal form of embodiment 30, wherein the crystal form of Compound D has a DSC thermograph corresponding substantially as depicted in FIG. 16.

Embodiment 36. A crystal form comprising Compound E:

(E)

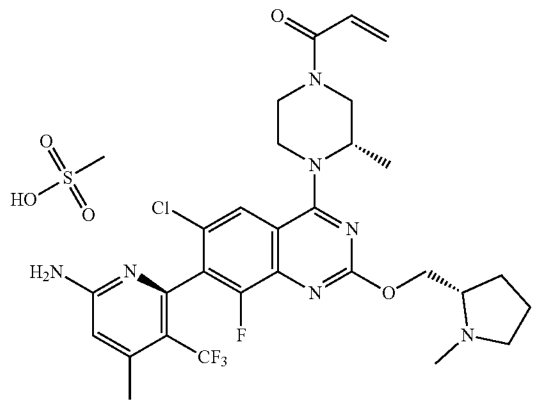

having an X-ray powder diffraction pattern comprising characteristic X-ray powder diffraction peaks using CuKα radiation at 5.9702, 6.2798, 12.4314, 18.9264, 20.6365 (±0.1° 2θ).

Embodiment 37. The crystal form of embodiment 36, wherein the crystal form of Compound E has an X-ray powder diffraction pattern comprising at least 5 characteristic X-ray powder diffraction peaks using CuKα radiation as set forth in Table 7.

Embodiment 38. The crystal form of embodiment 36, wherein the crystal form of Compound E has an X-ray powder diffraction pattern comprising at least 10 characteristic X-ray powder diffraction peaks using CuKα radiation as set forth in Table 7.

Embodiment 39. The crystal form of embodiment 36, wherein the crystal form of Compound E has an X-ray powder diffraction pattern substantially as shown in FIG. 17.

Embodiment 40. A pharmaceutical composition comprising the solid form of any one of claims 2-39 and at least one pharmaceutically acceptable excipient.

Embodiment 41. A pharmaceutical composition of embodiment 40, wherein said composition is formulated for oral administration.

Embodiment 42. A method of treating a cancer comprising a KRasG12C mutation in a patient having said cancer, the method comprising administering an effective amount of a compound of embodiment 1 or a crystal form of any one of embodiments 2-39.

Embodiment 43. A method for treating a cancer comprising a KRasG12C mutation in a patient having said cancer, the method comprising:

determining if the patient has the mutation; and if the patient is determined to have the mutation, then administering to the patient an effective amount of a compound of claim 1 or a crystal form of any one of embodiments 2-39.

Embodiment 44. The method of embodiment 42 or 43, wherein the cancer comprises lung cancer, colorectal cancer, or pancreatic cancer.

Embodiment 45. The method of embodiment 42 or 43, wherein the cancer is lung cancer.

Embodiment 46. The method of embodiment 45, wherein the lung cancer is non-small cell lung cancer (NSCLC).

Embodiment 47. The method of embodiment 42 or 43, wherein the cancer is colorectal cancer.

Embodiment 48. The method of embodiment 42 or 43, wherein the cancer is pancreatic cancer.

Embodiment 49. A method for inhibiting proliferation of a cell population wherein the cell population comprises a KRasG12C mutation, the method comprising contacting the cell population with a compound of claim 1 or a crystal form of any one of embodiments 2-39.

Embodiment 50. A method for inhibiting tumor metastasis comprising administering to an individual in need thereof a therapeutically effective amount of the compound of embodiment 1 or a crystal form of any one of embodiments 2-39.

Embodiment 51. Use of a compound of embodiment 1 or a crystal form of any one of embodiments 2-39 in the manufacture of a medicament for treating a cancer.

Embodiment 52. The use of embodiment 51, wherein the cancer comprises lung cancer, colorectal cancer, or pancreatic cancer.

Embodiment 53. The compound of claim 1 or a crystal form of any one of embodiments 2-39 for use in a method of treating cancer.

Embodiment 54. The compound of embodiment 53, wherein the cancer comprises lung cancer, colorectal cancer, or pancreatic cancer.

EXAMPLES

The following Examples are presented by way of illustration, not limitation.

Example 1

Compound 1 was initially screened with 21 acids and four solvent systems for pharmaceutically acceptable salts and polymorphs. (Table 8). For each solvent of acetone, EtOAc, THF, and MeOH/$H_2O$ (19:1, v/v), freebase and corresponding acid were mixed with a molar charge ratio of 1:1, and stirred at RT overnight. Due to the observation that all the samples were clear solution, all the samples were transferred to stirring at 5° C. overnight. The solids obtained at 5° C. were tested by XRPD. For the clear solutions, anti-solvent (n-heptane for acetone, THF and EtOAc; $H_2O$ for MeOH/

$H_2O$) was added. The mixtures were then stirred at 5° C. for 3 days. The solids obtained were characterized by XRPD, and the other samples were transferred to heating-cooling between 5-50° C. The solids obtained were characterized by XRPD, and the clear solutions were transferred to slow evaporation at RT.

TABLE 8

| Solvent | Acetone | THF | EtOAc | MeOH/$H_2O$ (19:1, v/v) |
|---|---|---|---|---|
| Blank | Freebase Form A[$] | Freebase Form A (Low crystallinity)[$] | Amorphous[$] | Gel[$] |
| $H_3PO_4$ | Amorphous[$] | Amorphous* | Amorphous* | Gel[$] |
| Acetic acid | Compound E Form A[$] | Compound E Form A[$] | Amorphous[$] | Gel[$] |
| Maleic acid | Amorphous[$] | Amorphous[$] | Amorphous[$] | Gel[$] |
| Fumaric acid[&&] | Compound B Form A** | Low crystallinity* | Low crystallinity[&] | Gel[$] |
| | Compound B Form A[&] | Low crystallinity* | Low crystallinity[&] | Gel (EtOH) |
| Succinic acid | Amorphous[$] | Amorphous[$] | Amorphous[$] | Gel[$] |
| L-Malic acid | Amorphous[$] | Amorphous[$] | Amorphous[$] | Gel[$] |
| Adipic acid | Compound A Form A[&] | Compound A Form A* | Adipate Type A[&] | Gel[$] |
| L-Tartaric acid | Amorphous[$] | Amorphous* | Acid* | Gel[$] |
| Hippuric acid | Amorphous[$] | Amorphous[$] | Amorphous[$] | Gel[$] |
| Citric acid | Amorphous[$] | Amorphous* | Acid** | Gel[$] |
| Glycolic acid | Amorphous[$] | Amorphous[$] | Amorphous[$] | Gel[$] |
| Malonic acid | Amorphous[$] | Amorphous[$] | Amorphous[$] | Gel[$] |
| Benzoic acid | Amorphous[$] | Amorphous[$] | Amorphous[$] | Gel[$] |
| Gentisic acid | Amorphous[$] | Amorphous[$] | Amorphous* | Gel[$] |
| Oxalic acid | Amorphous[$] | Amorphous[$] | Amorphous** | Gel[$] |
| R-mandelic acid | Amorphous[$] | Amorphous[$] | Amorphous[$] | Gel[$] |
| S-mandelic acid | Amorphous[$] | Amorphous[$] | Amorphous[$] | Gel[$] |
| p-Toluensulfonic acid | Gel[$] | Amorphous[$] | Amorphous[$] | Gel[$] |
| Benzenesulfonic acid | Compound D Form A[$] | Amorphous[$] | Amorphous[$] | Gel[$] |
| Methylsulfonic acid | Compound E Form A[#] | Amorphous[&] | Amorphous[$] | Gel[$] |
| Ethylsulfonic acid | Amorphous[$] | Amorphous[$] | Compound C Form A[&] | Gel[$] |

[&]: Obtained from slurry at 5° C.

*: Anti-solvent of n-heptane was added and stirred at 5° C.

**: Anti-solvent of n-heptane was added and stirred at 5° C. Heating-cooling between 5° C. and 50° C. was performed.

[#]: Limited solids were observed after stirring at 5° C. During XRPD test, it was observed that the sample may tend to absorb moisture and turn to liquid. The suspension was transferred to −20° C., but limited solids were still observed. Anti-solvent (n-heptane) was added and the sample was transferred to 5° C. However, gel was obtained.

[$]: Anti-solvent was added and stirred at 5° C. Heating-cooling between 5° C. and 50° C. was performed, followed by slow evaporation at RT.

[&&]: For fumaric acid, to try to obtain potential anhydrous/hydrous fumarate hits with good crystallinity, experiments in acetone, THF, and EtOAc were repeated, and one more experiment in EtOH was also set up. However, anhydrous/hydrous fumarate hit with better crystallinity was not obtained.

As summarized in Table 9, a total of six crystalline hits were obtained. The salt hits were characterized by XRPD, TGA, DSC, HPLC and NMR.

TABLE 9

Characterization summary of crystalline salt hits

| Salt | Weight Loss in TGA (%) | Endotherm in DSC (° C., peak) | Purity (area %) | Stoich-iometry (acid/base) |
|---|---|---|---|---|
| Compound A Form A | 2.0 | 68.8, 169.1 | 98.30 | 1.06 |
| Compound B Form A | 0.7 | 53.8, 156.3 | 93.56 | 1.03 |
| Compound C Form A | 8.6 | 81.0, 149.2 | 95.18 | 1.04 |
| Compound D Form A | 7.7 | 75.8 | 96.23 | 1.03 |
| Compound E Form A | NA | NA | NA | NA |
| Compound F Form A | 9.0 | 65.5, 125.4 | 88.42 | 0.69 |

A diverse range of conditions was also explored by carrying out maturation at two different temperatures starting with the amorphous material from a diverse range of solvent/solvent mixtures.

Amorphous material (25 mg) in HPLC vials was treated with 5 vol (125 μl) of solvent and the samples were placed on a shaker at 50° C. or on a stirrer at 5° C. for 7 days with observations noted upon solvent addition. Any solids were filtered using a fritted filter and initially analysed by XRPD. Any solutions were treated with anti-solvent in increasing solvent:anti-solvent ratios until a maximum ratio of 1:5 had been reached at 25° C. The samples were then cooled to 5° C. at 0.1° C./min and held over the weekend. Any solutions from cooling were left to evaporate at RT with the caps removed and any turbid samples were filtered using a fritted filter and initially analysed by XRPD.

Maturation at both low and high temperature for 7 days starting with the amorphous material resulted in the majority of samples remaining as solutions. The solutions from 50° C. maturation were treated with anti-solvent which largely remained as clear solutions after addition of 1:5 solvent: anti-solvent ratio and cooling to 5° C. The samples were subsequently evaporated which largely resulted in amorphous, Compound A Form A/D or gums. The solutions obtained from 5° C. maturation were kept at 5° C. for the duration of the project and remained as solutions.

TABLE 10

| Results and observations from maturation at 5° C. for 7 days starting on amorphous. | | | |
|---|---|---|---|
| Solvent | Upon addition at 5° C. | After 5° C. maturation | XRPD |
| Water | Clear Solution | Clear Solution | N/P |
| Methanol | Clear Solution | Clear Solution | N/P |
| Ethanol | Clear Solution | Clear Solution | N/P |
| 2-propanol | Clear Solution | Suspension | Insufficient material |
| 1-propanol | Clear Solution | Clear Solution | N/P |
| Acetone | Clear Solution | Clear Solution | N/P |
| Ethyl Acetate | Clear Solution | Suspension | Insufficient material |
| Acetonitrile | Clear Solution | Turbid | Insufficient material |
| Toluene | Clear Solution | Solution + fine particles | N/P |
| Isopropyl Acetate | Clear Solution | Solution + fine particles | N/P |
| TBME | Turbid/ Hazy | Hazy Solution | N/P |
| 2-butanone (MEK) | Clear Solution | Clear Solution | N/P |
| THF | Clear Solution | Clear Solution | N/P |
| DMSO | Clear Solution | Clear Solution | N/P |
| NMP | Clear Solution | Clear Solution | N/P |
| Diethyl ether | Hazy Solution | Turbid/ Hazy | Amorphous |
| MIBK | Clear Solution | Turbid/Hazy | Insufficient material |
| DCM | Clear Solution | Clear Solution | N/P |
| Xylene | Partially Dissolved | Solution + large particles | N/P |
| DMI | Clear Solution | Clear Solution | N/P |
| Cumene | Partially Dissolved | Solution + large particles | N/P |
| Sulfolane | Clear Solution | Clear Solution | N/P |
| DMPU | Clear Solution | Clear Solution | N/P |
| 2-Methyl THF | Clear Solution | Clear Solution | N/P |
| Heptane | Turbid/Hazy | Hazy Solution | N/P |
| 1,4-dioxane | Clear Solution | Clear Solution | N/P |
| DMF | Clear Solution | Clear Solution | N/P |
| Nitromethane | Clear Solution | Solution + fine particles | N/P |
| Chloroform | Clear Solution | Clear Solution | N/P |
| 1-butanol | Clear Solution | Clear Solution | N/P |
| 1-Methoxy-2-propanol | Clear Solution | Clear Solution | N/P |
| 3-Methyl-1-butanol | Clear Solution | Clear Solution | N/P |
| Anisole | Clear Solution | Clear Solution | N/P |
| t-butanol/water (1:1) | Clear Solution | Clear Solution | N/P |
| Solvent | Upon addition at 5° C. | After 5° C. maturation | XRPD |
| 10% water/ methanol | Clear Solution | Clear Solution | N/P |
| 5% water/EtOH | Clear Solution | Clear Solution | N/P |
| 20% water/ methanol | Clear Solution | Clear Solution | N/P |
| 10% water/EtOH | Clear Solution | Clear Solution | N/P |
| 10% water/IPA | Clear Solution | Clear Solution | N/P |
| 10% water/ACN | Clear Solution | Clear Solution | N/P |
| 10% water/Acetone | Clear Solution | Clear Solution | N/P |
| PEG 400 | Clear Solution | Clear Solution | N/P |
| Tetralin | Partially Dissolved | Gummy Solution | N/P |
| Cyclohexane | Thin Suspension | Very Thin Suspension | Amorphous |
| Acetic Acid | Clear Solution | Clear Solution | N/P |
| Hexane | Thin Suspension | Turbid | Insufficient material |
| Ethyleneglycol | Clear Solution | Clear Solution | N/P |
| Pyridine | Clear Solution | Clear Solution | N/P |

TABLE 11

| Results and observations from anti-solvent addition from 50 ° C. maturation | | | | | | |
|---|---|---|---|---|---|---|
| | | Antisolvent added at RT (solvent:anti-solvent ratio) | | | Upon cooling | |
| Solvent | Antisolvent | 1:1 | 1:3 | 1:5 | to 5° C. | XRPD |
| Water | 3-Methyl-1-butanol | ✓ | +/− | +/− | Cloudy Solution | Very little solid, poor signal, Form A/D |
| Methanol | Xylene | ✓ | ✓ | ✓ | Frozen | Gummy, amorphous |
| Ethanol | Diethyl ether | ✓ | ✓ | ✓ | Clear Solution | Gummy, very poor signal, Form A/D |

TABLE 11-continued

| Results and observations from anti-solvent addition from 50 ° C. maturation | | | | | | |
|---|---|---|---|---|---|---|
| | | Antisolvent added at RT (solvent:anti-solvent ratio) | | | Upon cooling | |
| Solvent | Antisolvent | 1:1 | 1:3 | 1:5 | to 5° C. | XRPD |
| 2-propanol | Diethyl ether | ✓ | ✓ | ✓ | Clear Solution | Gummy |
| 1-propanol | Diethyl ether | ✓ | ✓ | ✓ | Clear Solution | Gummy, partial match Form A/D, extra peaks |
| Acetone | Diethyl ether | ✓ | ✓ | ✓ | Cloudy Solution | Very Poorly Crystalline |
| 2-butanone (MEK) | Diethyl ether | ✓ | ✓ | ✓ | Clear Solution | Form A/D |
| THF | Diethyl ether | ✓ | ✓ | ✓ | Clear Solution | Form A/D |
| DMSO | Ethyl Acetate | ✓ | ✓ | ✓ | Clear Solution | Amorphous |
| NMP | Ethyl Acetate | ✓ | ✓ | ✓ | Clear Solution | Amorphous |
| DCM | Ethyl Acetate | X | | | Turbid/Hazy | Poorly Crystalline, Form A/D |
| DMI | Ethyl Acetate | ✓ | ✓ | +/− | Clear Solution | Amorphous |
| Sulfolane | Ethyl Acetate | ✓ | ✓ | ✓ | Clear Solution | Clear Solution - after vac drying |
| DMPU | Ethyl Acetate | ✓ | ✓ | ✓ | Clear Solution | Amorphous |
| 2-Methyl THF | Diethyl ether | ✓ | +/− | +/− | Partially Cloudy Solution | Form A/D |
| 1,4-dioxane | Diethyl ether | | | X | Gummy solution | Very little solid, insufficient material |
| DMF | Diethyl ether | ✓ | ✓ | ✓ | Clear Solution | Very little solid, insufficient material |
| Nitromethane | Diethyl ether | ✓ | ✓ | +/− | Gummy solution | Gummy, poor signal, Form A/D |
| Chloroform | Diethyl ether | X | | | Turbid | Poorly Crystalline, Form A/D |
| 1-butanol | Diethyl ether | ✓ | ✓ | ✓ | Clear Solution | Gummy, amorphous |
| 1-Methoxy-2-propanol | IPA | ✓ | ✓ | ✓ | Clear Solution | Gummy |
| 3-Methyl-1-butanol | IPA | ✓ | ✓ | ✓ | Clear Solution | Gummy |
| t-butanol/water (1:1) | IPA | ✓ | ✓ | ✓ | Clear Solution | Gummy |
| 10% water/methanol | IPA | ✓ | ✓ | ✓ | Clear Solution | Gummy |
| 5% water/EtOH | Xylene | ✓ | ✓ | ✓ | Frozen | Form A/D |
| 20% water/methanol | IPA | ✓ | ✓ | ✓ | Clear Solution | Very little solid, insufficient material |
| 10% water/EtOH | Xylene | ✓ | +/− | +/− | Frozen | Very little solid, amorphous |
| 10% water/IPA | Xylene | ✓ | ✓ | ✓ | Frozen | Very Poorly Crystalline |
| 10% water/ACN | Xylene | ✓ | ✓ | ✓ | Frozen | Gummy, amorphous |
| 10% water/Acetone | Xylene | ✓ | ✓ | ✓ | Partially Frozen | Oily Residue |
| PEG 400 | Diethyl ether | ✓ | +/− | +/− | Biphasic Layers | Clear gel like solution |
| Acetic Acid | Diethyl ether | ✓ | ✓ | ✓ | Clear Solution | Very little solid, insufficient material |
| Ethyleneglycol | Diethyl ether | ✓ | ✓ | ✓ | Clear Solution | Amorphous |
| Pyridine | Diethyl ether | ✓ | ✓ | ✓ | Clear Solution | Gummy, amorphous |

Example 2

A total of 62 polymorph screening experiments were performed for freebase through different crystallization methods. Compared with the starting material, better crystallinity was observed for the sample obtained by slow evaporation in ACN with adipic acid, and named as Compound A Form A.

Single crystal data of Compound A Form A was obtained as shown in FIG. 4. According to the single crystal analysis result, Compound A Form A is anhydrous in the lattice, but might contain some surface water.

Compound A Form A was prepared by slurry freebase and adipic acid in EtOAc at RT for 48 hrs and then transferred to 5° C. for 24 hrs to increase the yield. The wet sample was vacuum dried at RT for 3 hrs. No form change was observed before and after drying. A solid was obtained with a yield of 62.2%. As per TGA and DSC, the sample showed a weight loss of 0.6% up to 100° C., and DSC curve showed two endotherms at 56.0° C. and 168.7° C. (peak temperature). Based on the integrals in NMR spectrum, the stoichiometric ratio of adipic acid:freebase was determined to be 1.06. A peak of EtOAc was observed. Around 0.07 molar EtOAc (0.8 wt %) was detected, which was consistent with TGA weight loss.

A disordered version of Compound A Form A, designated as Compound A Form C, was identified via single crystal XRD. See FIG. 7. Further description of this form and its interchangeability with Compound A Form A and Compound A Form D is below.

Compound A Form A was exposed to ambient humidity levels 40%, whereupon Compound A Form D was formed. Compound A Form D is a hemihydrate form of Compound A. For reversibility, Compound A Form D was dehydrated, whereupon Compound A Form D formed Compound A Form C.

Another form of Compound A was obtained and designated as Form B. Compound A Form B was obtained from anti-solvent addition in DCM/toluene, followed by transferring to 5° C. No form change was observed after air drying at RT overnight. A weight loss of 2.2% up to 100° C. was observed in TGA, and two broad endotherms at 55.7° C. and 109.6° C. (peak), and one small endotherm at 158.8° C. (peak) were observed in DSC. Based on the integrals, the stoichiometric ratio of adipic acid:freebase was determined to be 1.65.

VT-XRPD was performed on Compound A Form B for form identification. After heating to 90° C. under N2 protection, no form change was observed, indicating the TGA weight loss was caused by surface water. Thus, Compound A Form B was speculated to be an anhydrate. No peak of DCM was observed. To further confirm the stoichiometric ratio, three batches of Compound A Form B were re-prepared by anti-solvent addition in DCM/toluene, followed by transferring to 5° C. Based on the NMR results, the stoichiometric ratio of adipic acid:freebase for Compound A Form B varied from 1.5 to 1.8.

Slurry Competition between Compound A Form A and B. Slurry competition experiments between Compound A Form A and B were set up to determine the relationship between these two anhydrates. The saturated solution of Compound A Form A was obtained via slurry of Compound A Form A at target temperature overnight. A mixture of Compound A Form A+B was added into ~0.7 mL of saturated solution of Compound A Form A, and suspensions were observed. The suspensions were stirred at a speed of 750 rpm and tested by XRPD in transmission mode. As summarized in Table 12, in toluene, after a mixture of Compound A Form A+B was stirred at 5° C., a mixture of Compound A Form A+B was observed after 5 days. After transferring the sample to RT, Compound A Form A was observed after slurry at RT for 18 days (the peak at ~18.1° was possibly caused by stirrer). In IPA, the mixture turned to Compound A Form A at both 5° C. and −20° C.

TABLE 12

Slurry competition between adipate Type A and B

| Starting Form | Temperature (° C.) | Solvent | Result |
|---|---|---|---|
| Compound A Form A + B | 5 to RT | Toluene | Compound A Form A |
| | 5 | IPA | Compound A Form A |
| | −20 | IPA | Compound A Form A |

Two adipate forms of anhydrates Compound A Form A and Compound A Form B were observed from polymorph screening of adipate with Compound 1. It should be noted that although Compound A Form A was a mono-salt, the stoichiometry of acid/freebase for different Compound A Form B batches varied from 1.5 to 2.1, suggesting Compound A Form B might be a sesqui- or bis-salt. Slurry competition experiments between Compound A Form A and B in toluene (RT) and IPA (5° C. and −20° C.) resulted in Compound A Form A.

Reactive Crystallisation with Adipic Acid. Additional steps were investigated to identify whether additional forms of the adipate salt exist when starting from the free form of Compound 1.

Compound 1 (30 mg) was weighed into HPLC vials with stirrers and dissolved at 50° C. Adipic acid solution in THF (1 M, 1 or 1.5 eq.) was added to each vial and if a solid formed, then an aliquot was taken. The solutions or suspensions were cooled to 40° C. at 0.5° C./min when they were seeded with a very small amount of Compound A Form A. The samples were then further cooled to 5° C. at 0.1° C./min overnight and if a precipitate formed, it was filtered and analysed by XRPD.

Reactive crystallisation with adipic acid largely resulted in Compound A Form A/D or sticky material which was amorphous by XRPD. The results and observations from reactive crystallisation with adipic acid are summarised below in Table 13.

TABLE 13

| Solvent | Acid | Solvent vol. | Obs. After acid addition | Obs. After cooling to 5° C. | XRPD |
|---|---|---|---|---|---|
| Water | 1 equivalent adipic acid | 40* | Became clear | Clear Solution | N/P |
| 10% water/IPA | | 30 | Clear Solution | Clear Solution | Sticky material, amorphous |
| EtOH | | 20 | Clear Solution | Clear Solution | Form A/D |
| Ethyl acetate | | 30 | Light Precipitate | White Precipitate | Form A/D |
| Acetone | | 20 | Clear Solution | Clear Solution | Form A/D |
| Acetonitrile | | 30 | Clear Solution | White Precipitate | Form A/D |
| MEK | | 20 | Clear Solution | Clear Solution | Form A/D |
| THF | | 5 | Clear Solution | White Precipitate, fine | Form A/D |
| TBME | | 40* | White Precipitate | White Precipitate | Form A/D (both & A) |
| Dioxane | | 10 | Clear Solution | Clear Solution | Sticky material, amorphous |
| Anisole | | 20 | Gel-like suspension at 40° C. | White Precipitate | Form A/D (both & A) |
| Acetic acid | | 5 | Clear Solution | Clear Solution | Sticky material, N/P |
| Water | 1.5 equivalents adipic acid | 40* | Partially Clear | Clear Solution | N/P |
| 10% water/IPA | | 30 | Clear Solution | Clear Solution | Sticky material, amorphous |
| EtOH | | 20 | Clear Solution | Clear Solution | Form A/D |

TABLE 13-continued

| Solvent | Acid | Solvent vol. | Obs. After acid addition | Obs. After cooling to 5° C. | XRPD |
|---|---|---|---|---|---|
| Ethyl acetate | | 30 | White Precipitate, at 40° C. | White Precipitate | Form A/D (both & A) |
| Acetone | | 20 | Clear Solution | Clear Solution | Form A/D |
| Acetonitrile | | 30 | Clear Solution | White Precipitate | Form A/D |
| MEK | | 20 | Clear Solution | White Precipitate | Form A/D |
| THF | | 5 | Clear Solution | White Precipitate, fine | Form A/D |
| TBME | | 40* | White Precipitate | White Precipitate | Form A/D (both & A) |
| Dioxane | | 10 | Clear Solution | Clear Solution | Sticky material, amorphous |
| Anisole | | 20 | Gel-like suspension at 40° C. | White Precipitate | Form A/D (both & A) |
| Acetic acid | | 5 | Clear Solution | Clear Solution | Sticky material, amorphous |

Example 3

Instruments and Methods

XRPD. For XRPD analysis, PANalytical X-ray powder diffractometers in reflection mode were used. The XRPD parameters are listed in the table below.

| Parameters | Reflection Mode | | Transmission Mode |
|---|---|---|---|
| Model | Empyrean | X' Pert[3] | X' Pert[3] |
| X-Ray wavelength | Cu, kα, Kα1 (Å): 1.540598 Kα2 (Å): 1.544426 Kα2/Kα1 intensity ratio: 0.50 | | |
| X-Ray tube setting | 45 kV, 40 mA | | |
| Scan mode | Continuous | | |
| Scan range (°2 Theta) | 3°-40° | | |
| Divergence slit | Automatic | 1/8° | 1/2° |
| Scan step time (s) | 17.8 | 46.7 | 31.6 |
| Step size (°2 Theta) | 0.0167 | 0.0263 | 0.013 |
| Test Time | 5 min 30 s | 5 min 4 s | ~7 min |

XRPD was also collected as follows. XRPD diffractograms were collected on a Bruker D8 diffractometer using Cu Kα radiation (40 kV, 40 mA) and a 6-28 goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

Single Crystal X-Ray Diffraction (SCXRD). Data were collected on a Rigaku Synergy Custom MM007-HF using a HyPix-6000 HPAD detector (The Woodlands, Tex., USA). Data were collected in a nitrogen gas stream at 90 K using omega scans. Data were integrated and scaled using CrysAlisPro (Rigaku Oxford Diffraction, 2021). WinGX was used for the solution and refinement of the crystal structures. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

TGA/DSC. TGA data were collected using a TA Q5000 TGA or TA Discovery TGA5500 from TA Instruments and DSC was performed using a TA Discovery DSC2500 from TA Instruments.

General Parameters for TGA and DSC Testing

| Parameters | TGA | DSC |
|---|---|---|
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

Solution NMR. Solution NMR was collected on Bruker 400M NMR Spectrometer using DMSO-d6.

Example 4—Compound A—Amorphous

Compound A (20 mg) was weighed into HPLC vials and solvent was added in 10 vol aliquots (200 µl) at RT on a stirrer plate until sample dissolution or until a maximum of 50 vol had been added and observations were made between additions. The solutions that were obtained were frozen in a dry ice acetone bath before being placed on the freeze dryer under vacuum.

Amorphous material of Compound A (mono adipate salt) was successfully prepared through freeze drying. Characterisation of the initial batch of samples were all shown to be amorphous by XRPD and the NMR's contained ca. 1.1 eq. adipic acid with varying quantities of residual solvent, except for acetonitrile/water (1:1) which contained no residual solvent. The purities were low, between 85-89%, except for 1,4-dioxane which had a very low purity of 57.5%. Static storage at 25° C./97% RH and 40° C./75% RH after 7 days were all shown to have deliquesced.

Liquid asset grinding (LAG) screens: Amorphous material (25 mg) in HPLC vials was treated with two ball bearings and solvent (5 µl, 0.2 vol) and milled on a Fritsch planetary mill fitted with an Automaxion adapter for 2 hours at 500 rpm. Samples that went into solution upon solvent addition were allowed to slowly evaporate with a needle inserted into the cap. The resultant solids from LAG were initially analysed by XRPD.

Example 4—Compound A Form A

Compound A Form A could be obtained in different solvent systems of acetone, THF, and EtOAc from screening. Single crystal data of Compound A Form A shows that Compound A Form A is anhydrous.

Compound A Form A was obtained from THF system and the sample was air dried at RT. No form change was observed before and after drying. A weight loss of 2.0% up to 100° C. was observed in TGA and DSC result showed two endotherms at 68.8° C. and 169.1° C. (peak temperature). Based on the integrals, the stoichiometric ratio of adipic acid:freebase was determined to be 1.06. Peak of THF was observed. Around 0.17 molar THF (1.9 wt %) was detected, which was consistent with TGA weight loss. The purity of Compound A Form A was 98.30 area %. After heating adipate Type A to 100° C. under N2 protection, cooled down and exposed to ambient conditions, very slight differences were observed before and after heating. Peak of THF was observed in the heated sample. Around 0.15 molar THF (1.7 wt %) was still detected, suggesting the organic solvent might be occluded in the crystal form.

Figure 19:
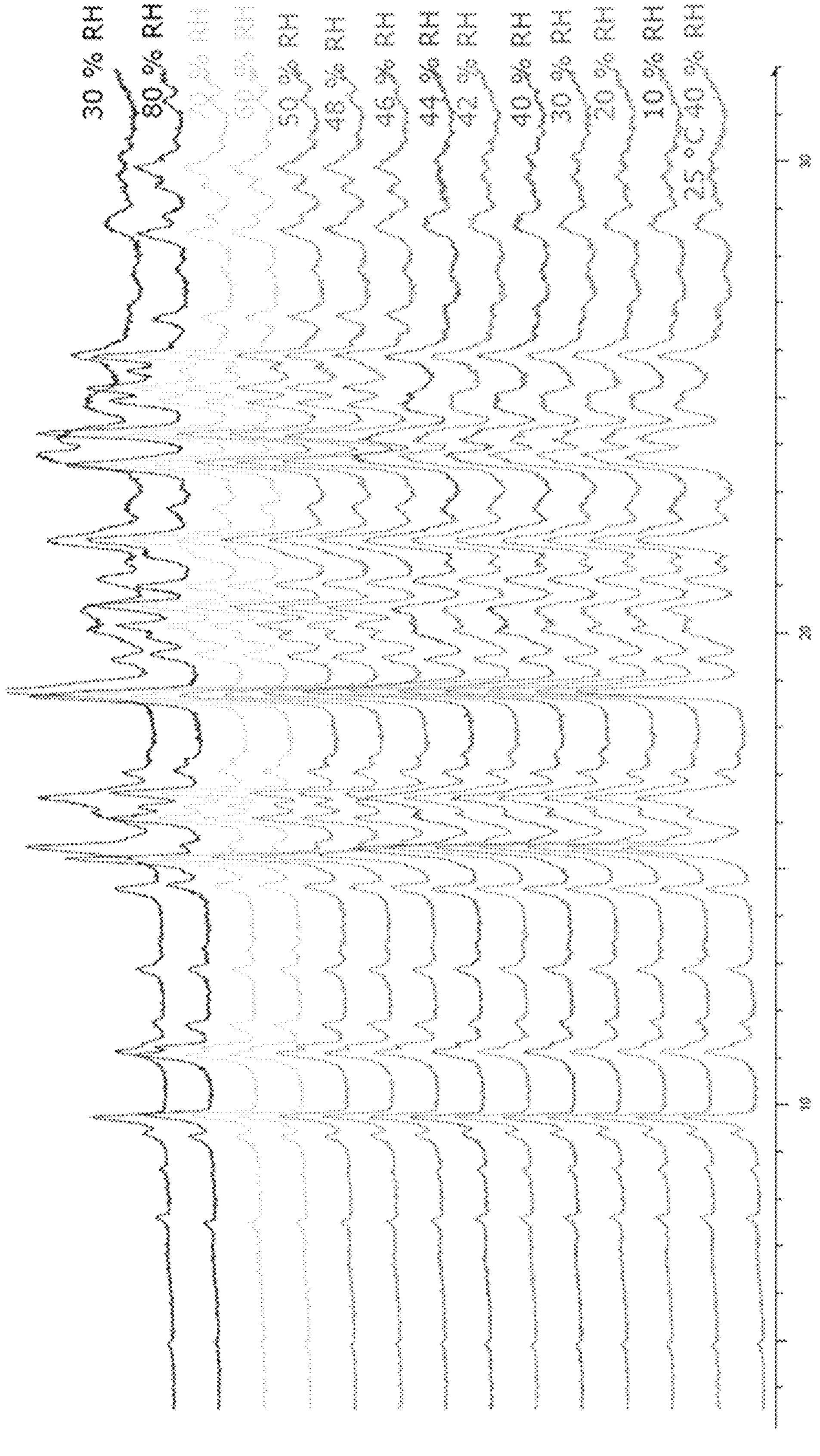
FIG. 19 depicts XRPD of Compound A at varying relative humidity (RH).

VH-XRPD Analysis of Compound A. The VH-XRPD analysis performed on Compound A shows small changes between 44-46% RH which remain up until 80% RH. FIG. 19. The sample then reverts to the original form upon reaching 30% RH. The sample appears to be a channel-like hydrate system which can exist with a range of occupancies of water from 0 to around 1 eq.

Single Crystal XRD. X-ray quality crystals were grown from a saturated isopropanol solution followed by the slow vapor diffusion of heptane to deposit the crystal diffracted. A colorless prism 0.100×0.100×0.100 mm in size was mounted on a Cryoloop with Paratone oil. Data were collected in a nitrogen gas stream at 90(2) K using phi and omega scans. Crystal-to-detector distance was 40 mm and exposure time was 0.2 seconds per frame using a scan width of 1.0°. Data collection was 99.9% complete to 67.000° in θ. A total of 40537 reflections were collected covering the indices, −10<=h<=10, −15<=k<=15, −22<=l<=22. 12985 reflections were found to be symmetry independent, with an $R_{int}$ of 0.0345. Indexing and unit cell refinement indicated a primitive, triclinic lattice. The space group was found to be P 1 (No. 1). The data were integrated and scaled using CrysAlisPro 1.171.40.51a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined from the diffraction data.

TABLE 14

Crystal data and structure refinement for Compound A Form A

| | |
|---|---|
| Empirical formula | C35 H42 Cl F4 N7 O6 |
| Formula weight | 768.20 |
| Temperature | 90(2) K |
| Wavelength | 1.54184 Å |
| Crystal system | Triclinic |
| Space group | P 1 |
| Unit cell dimensions | a = 8.6289(3) Å a = 90.728(2)°. |
| | b = 12.4836(4) Å β = 103.055(2)°. |
| | c = 18.3690(5) Å γ = 110.167(3)°. |
| Volume | 1800.49(10) $Å^3$ |
| Z | 2 |
| Density (calculated) | 1.417 $Mg/m^3$ |
| Absorption coefficient | 1.604 $mm^{-1}$ |
| F(000) | 804 |
| Crystal size | 0.100 × 0.100 × 0.100 $mm^3$ |

TABLE 14-continued

Crystal data and structure refinement for Compound A Form A

| | |
|---|---|
| Theta range for data collection | 2.481 to 75.148° |
| Index ranges | −10 <= h <= 10, −15 <= k <= 15, −22 <= k <= 22 |
| Reflections collected | 40537 |
| Independent reflections | 12985 [R(int) = 0.0345] |
| Completeness to theta = 67.000° | 99.9% |
| Absorption correction | Semi-empirical from equivalents |
| Max. and min. transmission | 1.00000 and 0.84789 |
| Refinement method | Full-matrix least-squares on F2 |
| Data/restraints/parameters | 12985/3/974 |
| Goodness-of-fit on $F^2$ | 1.089 |
| Final R indices [I > 2sigma(I)] | R1 = 0.0471, wR2 = 0.1296 |
| R indices (all data) | R1 = 0.0487, wR2 = 0.1310 |
| Absolute structure parameter | 0.008(14) |
| Extinction coefficient | 0.0016(4) |
| Largest diff. peak and hole | 0.364 and −0.309 e.$Å^{-3}$ |

TABLE 15

Atomic coordinates (×$10^4$) and equivalent isotropic displacement parameters ($Å^2$ × $10^3$) for Compound A Form A. U(eq) is defined as one third of the trace of the orthogonalized $U^{ij}$ tensor.

| | x | y | z | U(eq) |
|---|---|---|---|---|
| C(1) | 561(5) | −64(3) | 3149(2) | 26(1) |
| C(2) | 1896(5) | 1047(3) | 3157(2) | 26(1) |
| C(3) | 2296(5) | 2035(3) | 3650(2) | 28(1) |
| C(4) | 3565(5) | 3031(3) | 3580(2) | 29(1) |
| C(5) | 4519(5) | 3096(3) | 3048(2) | 26(1) |
| C(6) | 4192(5) | 2109(3) | 2613(2) | 26(1) |
| C(7) | 2903(5) | 1058(3) | 2650(2) | 25(1) |
| C(8) | 1564(5) | −816(3) | 2294(2) | 26(1) |
| C(9) | −1348(6) | 632(3) | 3713(2) | 33(1) |
| C(10) | −3268(6) | 209(4) | 3364(3) | 36(1) |
| C(11) | −3402(6) | −1761(4) | 3361(2) | 38(1) |
| C(12) | −1516(6) | −1395(3) | 3739(2) | 33(1) |
| C(13) | −1197(6) | −1450(4) | 4583(3) | 40(1) |
| C(14) | −5275(6) | −1084(4) | 3994(2) | 37(1) |
| C(15) | −5889(6) | −2210(4) | 4304(3) | 43(1) |
| C(16) | −7177(8) | −2464(5) | 4619(3) | 54(1) |
| C(17) | 5723(5) | 4189(3) | 2868(2) | 28(1) |
| C(18) | 7476(5) | 4559(3) | 3083(2) | 29(1) |
| C(19) | 8434(5) | 5557(3) | 2790(2) | 30(1) |
| C(20) | 7546(6) | 6130(3) | 2338(2) | 30(1) |
| C(21) | 5756(5) | 5709(3) | 2144(2) | 29(1) |
| C(22) | 8421(6) | 3966(3) | 3618(2) | 33(1) |
| C(23) | 10347(6) | 5972(4) | 2929(3) | 40(1) |
| C(24) | 2289(6) | −1692(3) | 1334(2) | 32(1) |
| C(25) | 1414(5) | −2762(3) | 784(2) | 31(1) |
| C(26) | 2374(6) | −2759(4) | 182(2) | 38(1) |
| C(27) | 1654(12) | −2118(8) | −390(5) | 33(3) |
| C(27A) | 923(13) | −3304(10) | −570(5) | 47(3) |
| C(28) | −294(7) | −2696(5) | −440(3) | 43(1) |
| C(29) | −1708(6) | −3895(4) | 442(3) | 41(1) |
| C(30) | −2114(6) | −1128(3) | 927(2) | 32(1) |
| C(31) | −2463(6) | −124(4) | 1232(3) | 36(1) |
| C(32) | −1359(6) | 1073(4) | 1105(2) | 34(1) |
| C(33) | −1876(6) | 1973(4) | 1450(3) | 37(1) |
| C(34) | −1243(6) | 3160(4) | 1183(3) | 40(1) |
| C(35) | 627(6) | 3838(3) | 1411(2) | 33(1) |
| C(36) | 7653(5) | 10613(3) | 6751(2) | 28(1) |
| C(37) | 7881(5) | 9510(3) | 6775(2) | 28(1) |
| C(38) | 6880(6) | 8511(4) | 6285(2) | 31(1) |
| C(39) | 7240(6) | 7533(3) | 6375(2) | 31(1) |
| C(40) | 8586(5) | 7468(3) | 6943(2) | 30(1) |
| C(41) | 9591(5) | 8461(3) | 7394(2) | 30(1) |
| C(42) | 9308(5) | 9499(3) | 7325(2) | 28(1) |
| C(43) | 10207(5) | 11397(3) | 7608(2) | 29(1) |
| C(44) | 4522(6) | 9900(4) | 6212(3) | 35(1) |
| C(45) | 3459(7) | 10323(4) | 6626(3) | 41(1) |
| C(46) | 5218(7) | 12289(4) | 6592(3) | 41(1) |
| C(47) | 6296(6) | 11924(4) | 6157(3) | 37(1) |
| C(48) | 5729(7) | 11975(4) | 5316(3) | 44(1) |

TABLE 15-continued

Atomic coordinates (×10^4) and equivalent isotropic displacement parameters (Å^2 × 10^3) for Compound A Form A. U(eq) is defined as one third of the trace of the orthogonalized $U^{ij}$ tensor.

| | x | y | z | U(eq) |
|---|---|---|---|---|
| C(49) | 2036(7) | 11560(4) | 5994(3) | 40(1) |
| C(50) | 2168(7) | 12681(5) | 5690(3) | 47(1) |
| C(51) | 787(9) | 12880(6) | 5368(3) | 55(1) |
| C(52) | 8898(6) | 6387(3) | 7130(2) | 32(1) |
| C(53) | 10055(6) | 6015(3) | 6897(2) | 34(1) |
| C(54) | 10344(7) | 5033(4) | 7197(2) | 38(1) |
| C(55) | 9368(6) | 4466(3) | 7672(2) | 38(1) |
| C(56) | 8175(6) | 4875(4) | 7867(2) | 35(1) |
| C(57) | 11028(7) | 6603(4) | 6348(3) | 40(1) |
| C(58) | 11690(8) | 4619(4) | 7040(3) | 53(1) |
| C(59) | 12759(6) | 12364(3) | 8545(2) | 33(1) |
| C(60) | 12137(6) | 12133(4) | 9265(2) | 38(1) |
| C(61) | 11813(7) | 13135(5) | 9591(3) | 50(1) |
| C(62) | 13569(7) | 13900(4) | 10070(3) | 49(1) |
| C(63) | 14632(7) | 13137(5) | 10203(3) | 51(1) |
| C(64) | 12720(8) | 11266(5) | 10444(3) | 51(1) |
| C(65) | 16230(7) | 11281(5) | 9132(3) | 48(1) |
| C(66) | 17137(8) | 10602(6) | 8843(4) | 61(2) |
| C(67) | 16592(8) | 9320(6) | 8949(3) | 60(2) |
| C(68) | 14934(7) | 8601(5) | 8435(3) | 53(1) |
| C(69) | 14320(9) | 7353(6) | 8609(4) | 63(2) |
| C(70) | 15286(7) | 6618(5) | 8437(3) | 51(1) |
| N(1) | 2756(4) | 125(3) | 2203(2) | 26(1) |
| N(2) | 470(4) | −973(3) | 2731(2) | 26(1) |
| N(3) | −621(5) | −228(3) | 3558(2) | 32(1) |
| N(4) | −4105(5) | −927(3) | 3582(2) | 36(1) |
| N(5) | 4861(4) | 4735(3) | 2399(2) | 28(1) |
| N(6) | 4866(5) | 6245(3) | 1694(2) | 34(1) |
| N(7) | −347(5) | −2823(3) | 360(2) | 33(1) |
| N(8) | 10482(5) | 10454(3) | 7766(2) | 31(1) |
| N(9) | 8879(5) | 11544(3) | 7140(2) | 30(1) |
| N(10) | 6246(5) | 10756(3) | 6320(2) | 33(1) |
| N(11) | 3487(5) | 11455(3) | 6421(2) | 39(1) |
| N(12) | 13474(5) | 11960(3) | 9876(2) | 39(1) |
| N(13) | 7970(5) | 5833(3) | 7604(2) | 33(1) |
| N(14) | 7211(6) | 4359(3) | 8331(2) | 44(1) |
| O(1) | −5807(5) | −325(3) | 4122(2) | 46(1) |
| O(2) | 1324(4) | −1797(2) | 1889(2) | 30(1) |
| O(3) | −3160(5) | −2117(3) | 930(2) | 44(1) |
| O(4) | −798(4) | −932(3) | 691(2) | 39(1) |
| O(5) | 1267(4) | 4690(3) | 1112(2) | 44(1) |
| O(6) | 1515(4) | 3481(3) | 1963(2) | 45(1) |
| O(7) | 668(5) | 10771(3) | 5860(2) | 48(1) |
| O(8) | 11360(4) | 12411(2) | 7968(2) | 34(1) |
| O(9) | 16640(6) | 12316(4) | 9040(3) | 68(1) |
| O(10) | 15093(5) | 10760(3) | 9474(2) | 47(1) |
| O(11) | 15259(5) | 5750(3) | 8737(2) | 52(1) |
| O(12) | 16106(6) | 6985(4) | 7918(2) | 60(1) |
| F(1) | 5128(3) | 2137(2) | 2117(1) | 34(1) |
| F(2) | 7403(3) | 3077(2) | 3890(2) | 46(1) |
| F(3) | 9380(4) | 3549(2) | 3302(2) | 48(1) |
| F(4) | 9486(4) | 4674(2) | 4213(2) | 45(1) |
| F(5) | 10905(3) | 8438(2) | 7938(1) | 39(1) |
| F(6) | 10771(5) | 5868(3) | 5752(2) | 64(1) |
| F(7) | 12714(4) | 7034(3) | 6630(2) | 58(1) |
| F(8) | 10602(4) | 7471(3) | 6067(2) | 53(1) |
| Cl(1) | 4020(1) | 4261(1) | 4170(1) | 37(1) |
| Cl(2) | 5988(2) | 6287(1) | 5777(1) | 42(1) |

TABLE 16

Bond lengths [Å] and angles [°] for Compound A Form A

| | | | |
|---|---|---|---|
| C(1)—N(2) | 1.332(5) | C(14)—C(15) | 1.492(7) |
| C(1)—N(3) | 1.361(5) | C(15)—C(16) | 1.312(7) |
| C(1)—C(2) | 1.463(5) | C(15)—H(15) | 0.9500 |
| C(2)—C(7) | 1.408(5) | C(16)—H(16A) | 0.9500 |
| C(2)—C(3) | 1.413(5) | C(16)—H(16B) | 0.9500 |
| C(3)—C(4) | 1.374(5) | C(17)—N(5) | 1.354(5) |
| C(3)—H(3) | 0.9500 | C(17)—C(18) | 1.378(6) |
| C(4)—C(5) | 1.400(6) | C(18)—C(19) | 1.425(5) |
| C(4)—CI(1) | 1.742(4) | C(18)—C(22) | 1.500(5) |
| C(5)—C(6) | 1.367(5) | C(19)—C(20) | 1.377(6) |
| C(5)—C(17) | 1.497(5) | C(19)—C(23) | 1.508(6) |
| C(6)—F(1) | 1.341(4) | C(20)—C(21) | 1.405(6) |
| C(6)—C(7) | 1.412(5) | C(20)—H(20) | 0.9500 |
| C(7)—N(1) | 1.368(5) | C(21)—N(6) | 1.343(5) |
| C(8)—N(1) | 1.309(5) | C(21)—N(5) | 1.351(5) |
| C(8)—N(2) | 1.340(5) | C(22)—F(4) | 1.335(5) |
| C(8)—O(2) | 1.352(4) | C(22)—F(2) | 1.340(5) |
| C(9)—N(3) | 1.470(5) | C(22)—F(3) | 1.342(5) |
| C(9)—C(10) | 1.531(7) | C(23)—H(23A) | 0.9800 |
| C(9)—H(9A) | 0.9900 | C(23)—H(23B) | 0.9800 |
| C(9)—H(9B) | 0.9900 | C(23)—H(23C) | 0.9800 |
| C(10)—N(4) | 1.460(5) | C(24)—O(2) | 1.436(5) |
| C(10)—H(10A) | 0.9900 | C(24)—C(25) | 1.517(5) |
| C(10)—H(10B) | 0.9900 | C(24)—H(24A) | 0.9900 |
| C(11)—N(4) | 1.468(6) | C(24)—H(24B) | 0.9900 |
| C(11)—C(12) | 1.520(7) | C(25)—N(7) | 1.518(6) |
| C(11)—H(11A) | 0.9900 | C(25)—C(26) | 1.524(6) |
| C(11)—H(11B) | 0.9900 | C(25)—H(25) | 1.0000 |
| C(12)—N(3) | 1.477(5) | C(26)—C(27) | 1.483(9) |
| C(12)—C(13) | 1.518(6) | C(26)—C(27A) | 1.595(10) |
| C(12)—H(12) | 1.0000 | C(26)—H(26A) | 0.9900 |
| C(13)—H(13A) | 0.9800 | C(26)—H(26B) | 0.9900 |
| C(13)—H(13B) | 0.9800 | C(27)—C(28) | 1.564(11) |
| C(13)—H(13C) | 0.9800 | C(27)—H(27A) | 0.9900 |
| C(14)—O(1) | 1.227(6) | C(27)—H(27B) | 0.9900 |
| C(14)—N(4) | 1.357(6) | C(27A)—C(28) | 1.547(11) |

TABLE 16-continued

| Bond lengths [Å] and angles [°] for Compound A Form A | | | |
|---|---|---|---|
| C(27A)—H(27C) | 0.9900 | C(40)—C(52) | 1.494(5) |
| C(27A)—H(27D) | 0.9900 | C(41)—F(5) | 1.340(5) |
| C(28)—N(7) | 1.489(5) | C(41)—C(42) | 1.401 (5) |
| C(28)—H(28A) | 0.9900 | C(42)—N(8) | 1.369(5) |
| C(28)—H(28B) | 0.9900 | C(43)—N(8) | 1.302(5) |
| C(29)—N(7) | 1.482(6) | C(43)—N(9) | 1.337(5) |
| C(29)—H(29A) | 0.9800 | C(43)—O(8) | 1.358(5) |
| C(29)—H(29B) | 0.9800 | C(44)—N(10) | 1.469(6) |
| C(29)—H(29C) | 0.9800 | C(44)—C(45) | 1.528(6) |
| C(30)—O(4) | 1.253(5) | C(44)—H(44A) | 0.9900 |
| C(30)—O(3) | 1.254(5) | C(44)—H(44B) | 0.9900 |
| C(30)—C(31) | 1.516(6) | C(45)—N(11) | 1.461(6) |
| C(31)—C(32) | 1.524(6) | C(45)—H(45A) | 0.9900 |
| C(31)—H(31A) | 0.9900 | C(45)—H(45B) | 0.9900 |
| C(31)—H(31B) | 0.9900 | C(46)—N(11) | 1.457(7) |
| C(32)—C(33) | 1.523(6) | C(46)—C(47) | 1.526(7) |
| C(32)—H(32A) | 0.9900 | C(46)—H(46A) | 0.9900 |
| C(32)—H(32B) | 0.9900 | C(46)—H(46B) | 0.9900 |
| C(33)—C(34) | 1.522(6) | C(47)—N(10) | 1.481(5) |
| C(33)—H(33A) | 0.9900 | C(47)—C(48) | 1.520(6) |
| C(33)—H(33B) | 0.9900 | C(47)—H(47) | 1.0000 |
| C(34)—C(35) | 1.496(6) | C(48)—H(48A) | 0.9800 |
| C(34)—H(34A) | 0.9900 | C(48)—H(48B) | 0.9800 |
| C(34)—H(34B) | 0.9900 | C(48)—H(48C) | 0.9800 |
| C(35)—O(5) | 1.217(5) | C(49)—O(7) | 1.218(6) |
| C(35)—O(6) | 1.308(5) | C(49)—N(11) | 1.368(6) |
| C(36)—N(9) | 1.331(5) | C(49)—C(50) | 1.491 (7) |
| C(36)—N(10) | 1.360(5) | C(50)—C(51) | 1.312(8) |
| C(36)—C(37) | 1.455(5) | C(50)—H(50) | 0.9500 |
| C(37)—C(42) | 1.410(6) | C(51)—H(51A) | 0.9500 |
| C(37)—C(38) | 1.410(6) | C(51)—H(51B) | 0.9500 |
| C(38)—C(39) | 1.362(6) | C(52)—N(13) | 1.350(5) |
| C(38)—H(38) | 0.9500 | C(52)—C(53) | 1.380(6) |
| C(39)—C(40) | 1.402(6) | C(53)—C(54) | 1.427(6) |
| C(39)—CI(2) | 1.748(4) | C(53)—C(57) | 1.495(6) |
| C(40)—C(41) | 1.372(6) | C(54)—C(55) | 1.381(6) |
| C(54)—C(58) | 1.504(7) | C(66)—H(66B) | 0.9900 |
| C(55)—C(56) | 1.405(7) | C(67)—C(68) | 1.492(9) |
| C(55)—H(55) | 0.9500 | C(67)—H(67A) | 0.9900 |
| C(56)—N(14) | 1.339(6) | C(67)—H(67B) | 0.9900 |
| C(56)—N(13) | 1.349(6) | C(68)—C(69) | 1.527(9) |
| C(57)—F(8) | 1.333(5) | C(68)—H(68A) | 0.9900 |
| C(57)—F(7) | 1.337(6) | C(68)—H(68B) | 0.9900 |
| C(57)—F(6) | 1.347(5) | C(69)—C(70) | 1.507(8) |
| C(58)—H(58A) | 0.9800 | C(69)—H(69A) | 0.9900 |
| C(58)—H(58B) | 0.9800 | C(69)—H(69B) | 0.9900 |
| C(58)—H(58C) | 0.9800 | C(70)—O(11) | 1.218(7) |
| C(59)—O(8) | 1.434(5) | C(70)—O(12) | 1.308(6) |
| C(59)—C(60) | 1.530(6) | N(6)—H(6A) | 0.8800 |
| C(59)—H(59A) | 0.9900 | N(6)—H(6B) | 0.8800 |
| C(59)—H(59B) | 0.9900 | N(7)—H(7) | 1.0000 |
| C(60)—N(12) | 1.493(6) | N(12)—H(12) | 1.0000 |
| C(60)—C(61) | 1.516(6) | N(14)—H(14A) | 0.8800 |
| C(60)—H(60) | 1.0000 | N(14)—H(14B) | 0.8800 |
| C(61)—C(62) | 1.537(8) | O(6)—H(6) | 0.8400 |
| C(61)—H(61A) | 0.9900 | O(12)—H(12A) | 0.8400 |
| C(61)—H(61B) | 0.9900 | N(2)—C(1)—N(3) | 117.0(3) |
| C(62)—C(63) | 1.521(7) | N(2)—C(1)—C(2) | 120.0(3) |
| C(62)—H(62A) | 0.9900 | N(3)—C(1)—C(2) | 123.0(3) |
| C(62)—H(62B) | 0.9900 | C(7)—C(2)—C(3) | 119.8(3) |
| C(63)—N(12) | 1.488(6) | C(7)—C(2)—C(1) | 114.1(3) |
| C(63)—H(63A) | 0.9900 | C(3)—C(2)—C(1) | 126.0(3) |
| C(63)—H(63B) | 0.9900 | C(4)—C(3)—C(2) | 119.5(4) |
| C(64)—N(12) | 1.484(6) | C(4)—C(3)—H(3) | 120.2 |
| C(64)—H(64A) | 0.9800 | C(2)—C(3)—H(3) | 120.2 |
| C(64)—H(64B) | 0.9800 | C(3)—C(4)—C(5) | 122.2(3) |
| C(64)—H(64C) | 0.9800 | C(3)—C(4)—CI(1) | 119.6(3) |
| C(65)—O(9) | 1.242(7) | C(5)—C(4)—CI(1) | 118.3(3) |
| C(65)—O(10) | 1.276(6) | C(6)—C(5)—C(4) | 117.3(3) |
| C(65)—C(66) | 1.499(8) | C(6)—C(5)—C(17) | 118.0(3) |
| C(66)—C(67) | 1.534(10) | C(4)—C(5)—C(17) | 124.3(3) |
| C(66)—H(66A) | 0.9900 | F(1)—C(6)—C(5) | 118.6(3) |
| F(1)—C(6)—C(7) | 117.8(3) | H(13A)—C(13)—H(13C) | 109.5 |
| C(5)—C(6)—C(7) | 123.6(3) | H(13B)—C(13)—H(13C) | 109.5 |
| N(1)—C(7)—C(2) | 125.2(3) | O(1)—C(14)—N(4) | 121.8(4) |
| N(1)—C(7)—C(6) | 117.5(3) | O(1)—C(14)—C(15) | 120.1(4) |
| C(2)—C(7)—C(6) | 117.3(3) | N(4)—C(14)—C(15) | 118.0(4) |
| N(1)—C(8)—N(2) | 129.6(3) | C(16)—C(15)—C(14) | 120.5(5) |

TABLE 16-continued

| Bond lengths [Å] and angles [°] for Compound A Form A | | | |
|---|---|---|---|
| N(1)—C(8)—O(2) | 118.2(3) | C(16)—C(15)—H(15) | 119.8 |
| N(2)—C(8)—O(2) | 112.1(3) | C(14)—C(15)—H(15) | 119.8 |
| N(3)—C(9)—C(10) | 111.3(3) | C(15)—C(16)—H(16A) | 120.0 |
| N(3)—C(9)—H(9A) | 109.4 | C(15)—C(16)—H(16B) | 120.0 |
| C(10)—C(9)—H(9A) | 109.4 | H(16A)—C(16)—H(16B) | 120.0 |
| N(3)—C(9)—H(9B) | 109.4 | N(5)—C(17)—C(18) | 123.3(3) |
| C(10)—C(9)—H(9B) | 109.4 | N(5)—C(17)—C(5) | 110.6(3) |
| H(9A)—C(9)—H(9B) | 108.0 | C(18)—C(17)—C(5) | 125.9(3) |
| N(4)—C(10)—C(9) | 110.5(4) | C(17)—C(18)—C(19) | 118.6(4) |
| N(4)—C(10)—H(10A) | 109.5 | C(17)—C(18)—C(22) | 122.9(3) |
| C(9)—C(10)—H(10A) | 109.5 | C(19)—C(18)—C(22) | 118.5(4) |
| N(4)—C(10)—H(10B) | 109.5 | C(20)—C(19)—C(18) | 117.6(4) |
| C(9)—C(10)—H(10B) | 109.5 | C(20)—C(19)—C(23) | 119.4(4) |
| H(10A)—C(10)—H(10B) | 108.1 | C(18)—C(19)—C(23) | 123.0(4) |
| N(4)—C(11)—C(12) | 110.5(3) | C(19)—C(20)—C(21) | 120.8(4) |
| N(4)—C(11)—H(11A) | 109.5 | C(19)—C(20)—H(20) | 119.6 |
| C(12)—C(11)—H(11A) | 109.5 | C(21)—C(20)—H(20) | 119.6 |
| N(4)—C(11)—H(11B) | 109.5 | N(6)—C(21)—N(5) | 117.3(4) |
| C(12)—C(11)—H(11B) | 109.5 | N(6)—C(21)—C(20) | 121.7(3) |
| H(11A)—C(11)—H(11B) | 108.1 | N(5)—C(21)—C(20) | 121.0(3) |
| N(3)—C(12)—C(13) | 111.0(4) | F(4)—C(22)—F(2) | 106.2(3) |
| N(3)—C(12)—C(11) | 109.3(3) | F(4)—C(22)—F(3) | 105.9(4) |
| C(13)—C(12)—C(11) | 112.1(4) | F(2)—C(22)—F(3) | 105.9(3) |
| N(3)—C(12)—H(12) | 108.1 | F(4)—C(22)—C(18) | 112.0(3) |
| C(13)—C(12)—H(12) | 108.1 | F(2)—C(22)—C(18) | 113.7(4) |
| C(11)—C(12)—H(12) | 108.1 | F(3)—C(22)—C(18) | 112.5(3) |
| C(12)—C(13)—H(13A) | 109.5 | C(19)—C(23)—H(23A) | 109.5 |
| C(12)—C(13)—H(13B) | 109.5 | C(19)—C(23)—H(23B) | 109.5 |
| H(13A)—C(13)—H(13B) | 109.5 | H(23A)—C(23)—H(23B) | 109.5 |
| C(12)—C(13)—H(13C) | 109.5 | C(19)—C(23)—H(23C) | 109.5 |
| H(23A)—C(23)—H(23C) | 109.5 | C(27)—C(28)—H(28A) | 111.2 |
| H(23B)—C(23)—H(23C) | 109.5 | N(7)—C(28)—H(28B) | 111.2 |
| O(2)—C(24)—C(25) | 107.2(3) | C(27)—C(28)—H(28B) | 111.2 |
| O(2)—C(24)—H(24A) | 110.3 | H(28A)—C(28)—H(28B) | 109.1 |
| C(25)—C(24)—H(24A) | 110.3 | N(7)—C(29)—H(29A) | 109.5 |
| O(2)—C(24)—H(24B) | 110.3 | N(7)—C(29)—H(29B) | 109.5 |
| C(25)—C(24)—H(24B) | 110.3 | H(29A)—C(29)—H(29B) | 109.5 |
| H(24A)—C(24)—H(24B) | 108.5 | N(7)—C(29)—H(29C) | 109.5 |
| C(24)—C(25)—N(7) | 110.9(3) | H(29A)—C(29)—H(29C) | 109.5 |
| C(24)—C(25)—C(26) | 111.6(4) | H(29B)—C(29)—H(29C) | 109.5 |
| N(7)—C(25)—C(26) | 105.2(3) | O(4)—C(30)—O(3) | 123.6(4) |
| C(24)—C(25)—H(25) | 109.7 | O(4)—C(30)—C(31) | 118.7(4) |
| N(7)—C(25)—H(25) | 109.7 | O(3)—C(30)—C(31) | 117.8(4) |
| C(26)—C(25)—H(25) | 109.7 | C(30)—C(31)—C(32) | 117.2(4) |
| C(27)—C(26)—C(25) | 102.2(4) | C(30)—C(31)—H(31A) | 108.0 |
| C(25)—C(26)—C(27A) | 104.8(5) | C(32)—C(31)—H(31A) | 108.0 |
| C(27)—C(26)—H(26A) | 111.3 | C(30)—C(31)—H(31B) | 108.0 |
| C(25)—C(26)—H(26A) | 111.3 | C(32)—C(31)—H(31B) | 108.0 |
| C(27)—C(26)—H(26B) | 111.3 | H(31A)—C(31)—H(31B) | 107.2 |
| C(25)—C(26)—H(26B) | 111.3 | C(33)—C(32)—C(31) | 110.1(4) |
| H(26A)—C(26)—H(26B) | 109.2 | C(33)—C(32)—H(32A) | 109.6 |
| C(26)—C(27)—C(28) | 101.2(6) | C(31)—C(32)—H(32A) | 109.6 |
| C(26)—C(27)—H(27A) | 111.5 | C(33)—C(32)—H(32B) | 109.6 |
| C(28)—C(27)—H(27A) | 111.5 | C(31)—C(32)—H(32B) | 109.6 |
| C(26)—C(27)—H(27B) | 111.5 | H(32A)—C(32)—H(32B) | 108.1 |
| C(28)—C(27)—H(27B) | 111.5 | C(34)—C(33)—C(32) | 115.4(4) |
| H(27A)—C(27)—H(27B) | 109.3 | C(34)—C(33)—H(33A) | 108.4 |
| C(28)—C(27A)—C(26) | 97.1(5) | C(32)—C(33)—H(33A) | 108.4 |
| C(28)—C(27A)—H(27C) | 112.3 | C(34)—C(33)—H(33B) | 108.4 |
| C(26)—C(27A)—H(27C) | 112.3 | C(32)—C(33)—H(33B) | 108.4 |
| C(28)—C(27A)—H(27D) | 112.3 | H(33A)—C(33)—H(33B) | 107.5 |
| C(26)—C(27A)—H(27D) | 112.3 | C(35)—C(34)—C(33) | 118.1(4) |
| H(27C)—C(27A)—H(27D) | 109.9 | C(35)—C(34)—H(34A) | 107.8 |
| N(7)—C(28)—C(27A) | 104.3(5) | C(33)—C(34)—H(34A) | 107.8 |
| N(7)—C(28)—C(27) | 103.0(4) | C(35)—C(34)—H(34B) | 107.8 |
| N(7)—C(28)—H(28A) | 111.2 | C(33)—C(34)—H(34B) | 107.8 |
| H(34A)—C(34)—H(34B) | 107.1 | C(44)—C(45)—H(45A) | 109.5 |
| O(5)—C(35)—O(6) | 122.3(4) | N(11)—C(45)—H(45B) | 109.5 |
| O(5)—C(35)—C(34) | 121.7(4) | C(44)—C(45)—H(45B) | 109.5 |
| O(6)—C(35)—C(34) | 116.0(4) | H(45A)—C(45)—H(45B) | 108.1 |
| N(9)—C(36)—N(10) | 117.1(3) | N(11)—C(46)—C(47) | 110.5(4) |
| N(9)—C(36)—C(37) | 120.0(4) | N(11)—C(46)—H(46A) | 109.5 |
| N(10)—C(36)—C(37) | 122.8(4) | C(47)—C(46)—H(46A) | 109.5 |
| C(42)—C(37)—C(38) | 119.1(3) | N(11)—C(46)—H(46B) | 109.5 |
| C(42)—C(37)—C(36) | 114.5(4) | C(47)—C(46)—H(46B) | 109.5 |
| C(38)—C(37)—C(36) | 126.3(4) | H(46A)—C(46)—H(46B) | 108.1 |
| C(39)—C(38)—C(37) | 120.0(4) | N(10)—C(47)—C(48) | 110.5(4) |
| C(39)—C(38)—H(38) | 120.0 | N(10)—C(47)—C(46) | 109.7(4) |

TABLE 16-continued

| Bond lengths [Å] and angles [°] for Compound A Form A | | | |
|---|---|---|---|
| C(37)—C(38)—H(38) | 120.0 | C(48)—C(47)—C(46) | 112.3(4) |
| C(38)—C(39)—C(40) | 122.6(4) | N(10)—C(47)—H(47) | 108.0 |
| C(38)—C(39)—CI(2) | 120.2(3) | C(48)—C(47)—H(47) | 108.0 |
| C(40)—C(39)—CI(2) | 117.2(3) | C(46)—C(47)—H(47) | 108.0 |
| C(41)—C(40)—C(39) | 116.6(4) | C(47)—C(48)—H(48A) | 109.5 |
| C(41)—C(40)—C(52) | 118.4(4) | C(47)—C(48)—H(48B) | 109.5 |
| C(39)—C(40)—C(52) | 124.8(4) | H(48A)—C(48)—H(48B) | 109.5 |
| F(5)—C(41)—C(40) | 118.5(3) | C(47)—C(48)—H(48C) | 109.5 |
| F(5)—C(41)—C(42) | 117.9(3) | H(48A)—C(48)—H(48C) | 109.5 |
| C(40)—C(41)—C(42) | 123.6(4) | H(48B)—C(48)—H(48C) | 109.5 |
| N(8)—C(42)—C(41) | 118.2(4) | O(7)—C(49)—N(11) | 122.0(5) |
| N(8)—C(42)—C(37) | 123.8(3) | O(7)—C(49)—C(50) | 120.2(5) |
| C(41)—C(42)—C(37) | 117.9(4) | N(11)—C(49)—C(50) | 117.9(5) |
| N(8)—C(43)—N(9) | 129.6(4) | C(51)—C(50)—C(49) | 120.2(6) |
| N(8)—C(43)—O(8) | 119.0(4) | C(51)—C(50)—H(50) | 119.9 |
| N(9)—C(43)—O(8) | 111.4(3) | C(49)—C(50)—H(50) | 119.9 |
| N(10)—C(44)—C(45) | 111.2(4) | C(50)—C(51)—H(51A) | 120.0 |
| N(10)—C(44)—H(44A) | 109.4 | C(50)—C(51)—H(51B) | 120.0 |
| C(45)—C(44)—H(44A) | 109.4 | H(51A)—C(51)—H(51B) | 120.0 |
| N(10)—C(44)—H(44B) | 109.4 | N(13)—C(52)—C(53) | 123.0(4) |
| C(45)—C(44)—H(44B) | 109.4 | N(13)—C(52)—C(40) | 111.4(3) |
| H(44A)—C(44)—H(44B) | 108.0 | C(53)—C(52)—C(40) | 125.5(4) |
| N(11)—C(45)—C(44) | 110.6(4) | C(52)—C(53)—C(54) | 118.5(4) |
| N(11)—C(45)—H(45A) | 109.5 | C(52)—C(53)—C(57) | 122.8(4) |
| C(54)—C(53)—C(57) | 118.7(4) | C(62)—C(61)—H(61A) | 110.9 |
| C(55)—C(54)—C(53) | 117.8(4) | C(60)—C(61)—H(61B) | 110.9 |
| C(55)—C(54)—C(58) | 119.1(4) | C(62)—C(61)—H(61B) | 110.9 |
| C(53)—C(54)—C(58) | 123.1(4) | H(61A)—C(61)—H(61B) | 109.0 |
| C(54)—C(55)—C(56) | 120.5(4) | C(63)—C(62)—C(61) | 105.7(4) |
| C(54)—C(55)—H(55) | 119.7 | C(63)—C(62)—H(62A) | 110.6 |
| C(56)—C(55)—H(55) | 119.7 | C(61)—C(62)—H(62A) | 110.6 |
| N(14)—C(56)—N(13) | 116.5(4) | C(63)—C(62)—H(62B) | 110.6 |
| N(14)—C(56)—C(55) | 122.6(4) | C(61)—C(62)—H(62B) | 110.6 |
| N(13)—C(56)—C(55) | 120.9(4) | H(62A)—C(62)—H(62B) | 108.7 |
| F(8)—C(57)—F(7) | 105.8(4) | N(12)—C(63)—C(62) | 106.7(4) |
| F(8)—C(57)—F(6) | 105.8(4) | N(12)—C(63)—H(63A) | 110.4 |
| F(7)—C(57)—F(6) | 105.5(4) | C(62)—C(63)—H(63A) | 110.4 |
| F(8)—C(57)—C(53) | 114.3(4) | N(12)—C(63)—H(63B) | 110.4 |
| F(7)—C(57)—C(53) | 113.8(4) | C(62)—C(63)—H(63B) | 110.4 |
| F(6)—C(57)—C(53) | 110.9(4) | H(63A)—C(63)—H(63B) | 108.6 |
| C(54)—C(58)—H(58A) | 109.5 | N(12)—C(64)—H(64A) | 109.5 |
| C(54)—C(58)—H(58B) | 109.5 | N(12)—C(64)—H(64B) | 109.5 |
| H(58A)—C(58)—H(58B) | 109.5 | H(64A)—C(64)—H(64B) | 109.5 |
| C(54)—C(58)—H(58C) | 109.5 | N(12)—C(64)—H(64C) | 109.5 |
| H(58A)—C(58)—H(58C) | 109.5 | H(64A)—C(64)—H(64C) | 109.5 |
| H(58B)—C(58)—H(58C) | 109.5 | H(64B)—C(64)—H(64C) | 109.5 |
| O(8)—C(59)—C(60) | 107.4(4) | O(9)—C(65)—O(10) | 123.6(5) |
| O(8)—C(59)—H(59A) | 110.2 | O(9)—C(65)—C(66) | 118.6(5) |
| C(60)—C(59)—H(59A) | 110.2 | O(10)—C(65)—C(66) | 117.7(5) |
| O(8)—C(59)—H(59B) | 110.2 | C(65)—C(66)—C(67) | 118.0(5) |
| C(60)—C(59)—H(59B) | 110.2 | C(65)—C(66)—H(66A) | 107.8 |
| H(59A)—C(59)—H(59B) | 108.5 | C(67)—C(66)—H(66A) | 107.8 |
| N(12)—C(60)—C(61) | 103.8(4) | C(65)—C(66)—H(66B) | 107.8 |
| N(12)—C(60)—C(59) | 110.5(4) | C(67)—C(66)—H(66B) | 107.8 |
| C(61)—C(60)—C(59) | 113.4(4) | H(66A)—C(66)—H(66B) | 107.1 |
| N(12)—C(60)—H(60) | 109.6 | C(68)—C(67)—C(66) | 114.2(5) |
| C(61)—C(60)—H(60) | 109.6 | C(68)—C(67)—H(67A) | 108.7 |
| C(59)—C(60)—H(60) | 109.6 | C(66)—C(67)—H(67A) | 108.7 |
| C(60)—C(61)—C(62) | 104.1(4) | C(68)—C(67)—H(67B) | 108.7 |
| C(60)—C(61)—H(61A) | 110.9 | C(66)—C(67)—H(67B) | 108.7 |
| H(67A)—C(67)—H(67B) | 107.6 | C(29)—N(7)—C(28) | 111.8(4) |
| C(67)—C(68)—C(69) | 113.2(5) | C(29)—N(7)—C(25) | 112.7(3) |
| C(67)—C(68)—H(68A) | 108.9 | C(28)—N(7)—C(25) | 106.8(3) |
| C(69)—C(68)—H(68A) | 108.9 | C(29)—N(7)—H(7) | 108.5 |
| C(67)—C(68)—H(68B) | 108.9 | C(28)—N(7)—H(7) | 108.5 |
| C(69)—C(68)—H(68B) | 108.9 | C(25)—N(7)—H(7) | 108.5 |
| H(68A)—C(68)—H(68B) | 107.7 | C(43)—N(8)—C(42) | 113.7(3) |
| C(70)—C(69)—C(68) | 117.6(5) | C(36)—N(9)—C(43) | 117.4(3) |
| C(70)—C(69)—H(69A) | 107.9 | C(36)—N(10)—C(44) | 122.9(3) |
| C(68)—C(69)—H(69A) | 107.9 | C(36)—N(10)—C(47) | 119.6(3) |
| C(70)—C(69)—H(69B) | 107.9 | C(44)—N(10)—C(47) | 114.4(3) |
| C(68)—C(69)—H(69B) | 107.9 | C(49)—N(11)—C(46) | 128.3(4) |
| H(69A)—C(69)—H(69B) | 107.2 | C(49)—N(11)—C(45) | 119.1(4) |
| O(11)—C(70)—O(12) | 123.5(5) | C(46)—N(11)—C(45) | 111.4(4) |
| O(11)—C(70)—C(69) | 123.1(5) | C(64)—N(12)—C(63) | 112.0(4) |
| O(12)—C(70)—C(69) | 113.4(5) | C(64)—N(12)—C(60) | 111.5(4) |
| C(8)—N(1)—C(7) | 113.1(3) | C(63)—N(12)—C(60) | 104.8(4) |
| C(1)—N(2)—C(8) | 117.9(3) | C(64)—N(12)—H(12) | 109.5 |

TABLE 16-continued

| Bond lengths [Å] and angles [°] for Compound A Form A | | | |
|---|---|---|---|
| C(1)—N(3)—C(9) | 124.3(3) | C(63)—N(12)—H(12) | 109.5 |
| C(1)—N(3)—C(12) | 119.6(3) | C(60)—N(12)—H(12) | 109.5 |
| C(9)—N(3)—C(12) | 114.9(3) | C(56)—N(13)—C(52) | 119.2(4) |
| C(14)—N(4)—C(10) | 120.2(4) | C(56)—N(14)—H(14A) | 120.0 |
| C(14)—N(4)—C(11) | 128.0(4) | C(56)—N(14)—H(14B) | 120.0 |
| C(10)—N(4)—C(11) | 111.6(3) | H(14A)—N(14)—H(14B) | 120.0 |
| C(21)—N(5)—C(17) | 118.6(4) | C(8)—O(2)—C(24) | 116.3(3) |
| C(21)—N(6)—H(6A) | 120.0 | C(35)—O(6)—H(6) | 109.5 |
| C(21)—N(6)—H(6B) | 120.0 | C(43)—O(8)—C(59) | 117.1(3) |
| H(6A)—N(6)—H(6B) | 120.0 | C(70)—O(12)—H(12A) | 109.5 |

TABLE 17

Anisotropic displacement parameters ($Å^2 \times 10^3$) for Compound A Form A. The anisotropic displacement factor exponent takes the form: $-2\pi^2[h^2a^{*2}U^{11} + \ldots + 2hka^*b^*U^{12}]$

| | $U^{11}$ | $U^{22}$ | $U^{33}$ | $U^{23}$ | $U^{13}$ | $U^{12}$ |
|---|---|---|---|---|---|---|
| C(1) | 30(2) | 20(2) | 27(2) | 3(1) | 6(2) | 6(2) |
| C(2) | 28(2) | 20(2) | 27(2) | 2(1) | 4(2) | 6(2) |
| C(3) | 31(2) | 22(2) | 27(2) | 0(1) | 7(2) | 6(2) |
| C(4) | 34(2) | 20(2) | 29(2) | 0(1) | 4(2) | 7(2) |
| C(5) | 27(2) | 20(2) | 26(2) | 2(1) | 1(2) | 5(2) |
| C(6) | 28(2) | 19(2) | 29(2) | 2(1) | 7(2) | 6(2) |
| C(7) | 28(2) | 18(2) | 26(2) | 2(1) | 4(2) | 5(2) |
| C(8) | 32(2) | 17(2) | 26(2) | 1(1) | 5(2) | 6(2) |
| C(9) | 38(2) | 22(2) | 40(2) | 1 (2) | 16(2) | 8(2) |
| C(10) | 37(2) | 32(2) | 39(2) | 5(2) | 12(2) | 10(2) |
| C(11) | 48(3) | 25(2) | 37(2) | 0(2) | 17(2) | 5(2) |
| C(12) | 40(2) | 24(2) | 39(2) | 7(2) | 19(2) | 8(2) |
| C(13) | 43(3) | 35(2) | 42(2) | 11(2) | 13(2) | 12(2) |
| C(14) | 29(2) | 41(2) | 31(2) | −2(2) | 2(2) | 5(2) |
| C(15) | 39(3) | 43(2) | 37(2) | 0(2) | 9(2) | 1(2) |
| C(16) | 55(3) | 53(3) | 38(2) | −4(2) | 17(2) | −1(3) |
| C(17) | 33(2) | 18(2) | 28(2) | 0(1) | 5(2) | 5(2) |
| C(18) | 31(2) | 20(2) | 29(2) | 1(1) | 2(2) | 5(2) |
| C(19) | 31(2) | 20(2) | 31(2) | −1(1) | 4(2) | 2(2) |
| C(20) | 36(2) | 17(2) | 31(2) | 1(1) | 5(2) | 4(2) |
| C(21) | 35(2) | 16(2) | 29(2) | 0(1) | 4(2) | 5(2) |
| C(22) | 32(2) | 24(2) | 34(2) | 5(2) | 2(2) | 1(2) |
| C(23) | 35(2) | 31(2) | 46(2) | 9(2) | 5(2) | 5(2) |
| C(24) | 36(2) | 23(2) | 36(2) | −1(2) | 11(2) | 7(2) |
| C(25) | 36(2) | 24(2) | 32(2) | 1(2) | 8(2) | 11(2) |
| C(26) | 42(3) | 39(2) | 36(2) | −2(2) | 9(2) | 17(2) |
| C(27) | 38(5) | 42(5) | 26(4) | 4(3) | 10(3) | 21(4) |
| C(27A) | 45(6) | 58(6) | 32(4) | −12(4) | 4(4) | 15(5) |
| C(28) | 46(3) | 58(3) | 33(2) | 10(2) | 10(2) | 28(2) |
| C(29) | 38(3) | 31(2) | 47(2) | −2(2) | 11(2) | 4(2) |
| C(30) | 35(2) | 26(2) | 34(2) | 4(2) | 8(2) | 11(2) |
| C(31) | 37(2) | 30(2) | 42(2) | 2(2) | 12(2) | 12(2) |
| C(32) | 31(2) | 29(2) | 39(2) | −1(2) | 7(2) | 9(2) |
| C(33) | 30(2) | 31(2) | 48(2) | −3(2) | 9(2) | 9(2) |
| C(34) | 32(2) | 30(2) | 54(3) | −3(2) | 3(2) | 12(2) |
| C(35) | 33(2) | 24(2) | 41(2) | −2(2) | 2(2) | 12(2) |
| C(36) | 31(2) | 26(2) | 28(2) | 3(1) | 10(2) | 10(2) |
| C(37) | 32(2) | 26(2) | 27(2) | 2(1) | 8(2) | 10(2) |
| C(38) | 32(2) | 31(2) | 26(2) | 2(2) | 5(2) | 9(2) |
| C(39) | 37(2) | 24(2) | 25(2) | −3(1) | 7(2) | 6(2) |
| C(40) | 35(2) | 25(2) | 31(2) | 0(2) | 10(2) | 10(2) |
| C(41) | 30(2) | 27(2) | 31(2) | 1(2) | 3(2) | 11(2) |
| C(42) | 32(2) | 24(2) | 27(2) | 1(1) | 7(2) | 11(2) |
| C(43) | 32(2) | 23(2) | 29(2) | 1(1) | 6(2) | 9(2) |
| C(44) | 31(2) | 26(2) | 42(2) | −1(2) | 2(2) | 7(2) |
| C(45) | 44(3) | 33(2) | 50(3) | 7(2) | 14(2) | 14(2) |
| C(46) | 50(3) | 29(2) | 39(2) | 1(2) | 1 (2) | 16(2) |
| C(47) | 36(2) | 28(2) | 42(2) | 8(2) | 0(2) | 11(2) |
| C(48) | 50(3) | 46(3) | 42(2) | 15(2) | 12(2) | 22(2) |
| C(49) | 45(3) | 43(2) | 38(2) | −2(2) | 15(2) | 20(2) |
| C(50) | 54(3) | 48(3) | 46(3) | 3(2) | 11(2) | 27(2) |
| C(51) | 72(4) | 63(3) | 37(2) | −4(2) | 0(2) | 40(3) |
| C(52) | 39(2) | 23(2) | 28(2) | −2(1) | 7(2) | 7(2) |
| C(53) | 44(3) | 20(2) | 38(2) | 2(2) | 14(2) | 11(2) |
| C(54) | 55(3) | 24(2) | 36(2) | 3(2) | 15(2) | 14(2) |
| C(55) | 53(3) | 23(2) | 36(2) | 4(2) | 12(2) | 12(2) |

TABLE 17-continued

Anisotropic displacement parameters ($Å^2 \times 10^3$) for Compound A Form A. The anisotropic displacement factor exponent takes the form: $-2\pi^2[h^2a^{*2}U^{11} + \ldots + 2hka^*b^*U^{12}]$

| | $U^{11}$ | $U^{22}$ | $U^{33}$ | $U^{23}$ | $U^{13}$ | $U^{12}$ |
|---|---|---|---|---|---|---|
| C(56) | 45(3) | 27(2) | 28(2) | 1(2) | 9(2) | 7(2) |
| C(57) | 59(3) | 28(2) | 44(2) | 7(2) | 26(2) | 21(2) |
| C(58) | 79(4) | 35(2) | 66(3) | 17(2) | 38(3) | 31(3) |
| C(59) | 33(2) | 24(2) | 35(2) | 0(2) | 1(2) | 8(2) |
| C(60) | 34(2) | 38(2) | 37(2) | −4(2) | 3(2) | 12(2) |
| C(61) | 50(3) | 53(3) | 47(3) | −11(2) | 4(2) | 26(2) |
| C(62) | 55(3) | 40(2) | 50(3) | −9(2) | 10(2) | 16(2) |
| C(63) | 44(3) | 40(3) | 58(3) | −3(2) | −2(2) | 10(2) |
| C(64) | 52(3) | 52(3) | 51(3) | 13(2) | 18(2) | 19(2) |
| C(65) | 42(3) | 63(3) | 41(2) | 15(2) | 11(2) | 22(2) |
| C(66) | 46(3) | 86(4) | 54(3) | −2(3) | 19(3) | 22(3) |
| C(67) | 57(4) | 89(4) | 50(3) | −4(3) | 9(3) | 48(3) |
| C(68) | 53(3) | 72(4) | 44(3) | 2(2) | 13(2) | 34(3) |
| C(69) | 68(4) | 76(4) | 65(3) | 14(3) | 37(3) | 36(3) |
| C(70) | 50(3) | 61(3) | 48(3) | 4(2) | 18(2) | 24(3) |
| N(1) | 28(2) | 19(1) | 28(2) | 1(1) | 6(1) | 4(1) |
| N(2) | 30(2) | 19(1) | 28(2) | 1(1) | 7(1) | 5(1) |
| N(3) | 37(2) | 18(2) | 41(2) | 5(1) | 17(2) | 8(1) |
| N(4) | 36(2) | 29(2) | 37(2) | 2(1) | 10(2) | 4(2) |
| N(5) | 32(2) | 18(1) | 30(2) | 2(1) | 5(1) | 6(1) |
| N(6) | 34(2) | 21(2) | 41(2) | 6(1) | 2(2) | 7(1) |
| N(7) | 37(2) | 28(2) | 34(2) | 0(1) | 9(2) | 12(2) |
| N(8) | 36(2) | 24(2) | 30(2) | 2(1) | 4(1) | 11(1) |
| N(9) | 33(2) | 26(2) | 30(2) | 2(1) | 6(1) | 11(1) |
| N(10) | 31(2) | 24(2) | 38(2) | 5(1) | 2(2) | 8(1) |
| N(11) | 42(2) | 32(2) | 45(2) | 4(2) | 9(2) | 16(2) |
| N(12) | 38(2) | 35(2) | 39(2) | 3(2) | 8(2) | 10(2) |
| N(13) | 39(2) | 26(2) | 31(2) | 0(1) | 9(2) | 8(2) |
| N(14) | 57(3) | 36(2) | 43(2) | 11(2) | 22(2) | 15(2) |
| O(1) | 43(2) | 54(2) | 47(2) | 5(2) | 17(2) | 19(2) |
| O(2) | 37(2) | 18(1) | 32(1) | 0(1) | 11(1) | 5(1) |
| O(3) | 46(2) | 28(2) | 55(2) | 8(1) | 16(2) | 9(1) |
| O(4) | 39(2) | 29(1) | 49(2) | 2(1) | 13(1) | 11(1) |
| O(5) | 41(2) | 29(2) | 54(2) | 9(1) | 0(2) | 10(1) |
| O(6) | 33(2) | 36(2) | 54(2) | 14(2) | −1(2) | 5(1) |
| O(7) | 41(2) | 52(2) | 50(2) | −2(2) | 9(2) | 17(2) |
| O(8) | 36(2) | 22(1) | 37(1) | 0(1) | −3(1) | 8(1) |
| O(9) | 63(3) | 70(3) | 84(3) | 37(2) | 34(2) | 28(2) |
| O(10) | 50(2) | 52(2) | 47(2) | 10(2) | 18(2) | 23(2) |
| O(11) | 56(2) | 59(2) | 47(2) | 11(2) | 23(2) | 22(2) |
| O(12) | 79(3) | 74(3) | 60(2) | 28(2) | 44(2) | 50(2) |
| F(1) | 39(1) | 22(1) | 39(1) | 0(1) | 19(1) | 3(1) |
| F(2) | 37(2) | 34(1) | 54(2) | 24(1) | 1(1) | 3(1) |
| F(3) | 48(2) | 43(2) | 57(2) | 11(1) | 9(1) | 25(1) |
| F(4) | 47(2) | 33(1) | 38(1) | 0(1) | −12(1) | 6(1) |
| F(5) | 41(1) | 25(1) | 46(1) | 0(1) | −4(1) | 14(1) |
| F(6) | 107(3) | 39(2) | 56(2) | 1(1) | 51(2) | 17(2) |
| F(7) | 54(2) | 55(2) | 71(2) | 22(2) | 30(2) | 17(2) |
| F(8) | 77(2) | 45(2) | 63(2) | 31(1) | 43(2) | 36(2) |
| Cl(1) | 48(1) | 22(1) | 36(1) | −6(1) | 12(1) | 5(1) |
| Cl(2) | 55(1) | 26(1) | 36(1) | −8(1) | 0(1) | 10(1) |

TABLE 18

Hydrogen coordinates (×10[4]) and isotropic displacement parameters ($Å^2 \times 10^3$) for Compound A Form A

| | x | y | z | U(eq) |
|---|---|---|---|---|
| H(3) | 1693 | 2012 | 4026 | 33 |
| H(9A) | −784 | 1352 | 3506 | 39 |
| H(9B) | −1128 | 799 | 4262 | 39 |
| H(10A) | −3749 | 754 | 3534 | 43 |
| H(10B) | −3483 | 176 | 2811 | 43 |
| H(11A) | −3566 | −1822 | 2808 | 45 |
| H(11B) | −4016 | −2524 | 3504 | 45 |
| H(12) | −1056 | −1930 | 3529 | 40 |
| H(13A) | 32 | −1203 | 4804 | 60 |
| H(13B) | −1753 | −2239 | 4689 | 60 |
| H(13C) | −1662 | −943 | 4799 | 60 |
| H(15) | −5344 | −2747 | 4274 | 52 |
| H(16A) | −7726 | −1929 | 4650 | 64 |
| H(16B) | −7562 | −3183 | 4815 | 64 |
| H(20) | 8150 | 6819 | 2154 | 36 |
| H(23A) | 10662 | 5511 | 2593 | 60 |
| H(23B) | 10845 | 5897 | 3452 | 60 |
| H(23C) | 10776 | 6779 | 2831 | 60 |
| H(24A) | 3472 | −1624 | 1575 | 38 |
| H(24B) | 2323 | −1000 | 1070 | 38 |
| H(26A) | 1319 | −3458 | 1061 | 37 |
| H(26A) | 3616 | −2363 | 381 | 46 |
| H(26B) | 2149 | −3549 | −26 | 46 |
| H(27A) | 1917 | −2223 | −877 | 39 |
| H(27B) | 2077 | −1289 | −222 | 39 |
| H(27C) | 1338 | 3090 | −1027 | 57 |
| H(27D) | 401 | −4149 | −590 | 5 |
| H(28A) | −924 | −2203 | −663 | 52 |
| H(28B) | −779 | −3451 | −741 | 52 |
| H(29A) | −2815 | −3890 | 160 | 61 |
| H(29B) | −1706 | −3948 | 974 | 61 |
| H(29C) | −1505 | −4555 | 247 | 61 |
| H(31A) | −2335 | −159 | 1780 | 43 |
| H(31B) | −3667 | −228 | 1006 | 43 |
| H(32A) | −147 | 1205 | 1337 | 40 |
| H(32B) | −1491 | 1138 | 560 | 40 |
| H(33A) | −3135 | 1698 | 1338 | 44 |
| H(33B) | −1446 | 2042 | 2003 | 44 |
| H(34A) | −1598 | 3072 | 627 | 48 |
| H(34B) | −1839 | 3620 | 1363 | 48 |
| H(38) | 5956 | 8520 | 5893 | 37 |
| H(44A) | 4597 | 9176 | 6401 | 42 |
| H(44B) | 3956 | 9741 | 5670 | 42 |
| H(45A) | 2269 | 9774 | 6497 | 50 |
| H(45B) | 3917 | 10362 | 7175 | 50 |
| H(46A) | 5735 | 12357 | 7138 | 49 |
| H(46B) | 5194 | 13050 | 6457 | 49 |
| H(47) | 7501 | 12464 | 6336 | 44 |
| H(48A) | 6429 | 11710 | 5059 | 66 |
| H(48B) | 5861 | 12766 | 5215 | 66 |
| H(48C) | 4531 | 11481 | 5133 | 66 |
| H(50) | 3256 | 13252 | 5729 | 57 |
| H(51A) | −302 | 12310 | 5329 | 66 |
| H(51B) | 877 | 13595 | 5175 | 66 |
| H(55) | 9504 | 3795 | 7867 | 45 |
| H(58A) | 11988 | 4157 | 7438 | 80 |
| H(58B) | 12704 | 5279 | 7025 | 80 |
| H(58C) | 11255 | 4151 | 6555 | 80 |
| H(59A) | 13732 | 13100 | 8622 | 39 |
| H(59B) | 13134 | 11743 | 8403 | 39 |
| H(60) | 11077 | 11436 | 9166 | 45 |
| H(61A) | 10983 | 12871 | 9904 | 60 |
| H(61B) | 11374 | 13550 | 9188 | 60 |
| H(62A) | 14095 | 14559 | 9801 | 59 |
| H(62B) | 13468 | 14196 | 10553 | 59 |
| H(63A) | 15587 | 13411 | 9956 | 61 |
| H(63B) | 15106 | 13145 | 10748 | 61 |
| H(64A) | 13585 | 11037 | 10778 | 76 |
| H(64B) | 11764 | 10580 | 10189 | 76 |
| H(64C) | 12312 | 11723 | 10739 | 76 |
| H(66B) | 18366 | 10963 | 9088 | 74 |
| H(66B) | 17005 | 10680 | 8299 | 74 |
| H(67A) | 17488 | 9039 | 8868 | 72 |
| H(67B) | 16509 | 9219 | 9474 | 72 |

TABLE 18-continued

Hydrogen coordinates (×10[4]) and isotropic displacement parameters ($Å^2 \times 10^3$) for Compound A Form A

| | x | y | z | U(eq) |
|---|---|---|---|---|
| H(68A) | 15055 | 8626 | 7912 | 63 |
| H(68B) | 14062 | 8933 | 8473 | 63 |
| H(69A) | 14340 | 7347 | 9150 | 76 |
| H(69B) | 13117 | 6984 | 8326 | 76 |
| H(6A) | 3746 | 5959 | 1576 | 41 |
| H(6B) | 5403 | 6882 | 1516 | 41 |
| H(7) | −576 | −2158 | 559 | 40 |
| H(12) | 14118 | 11567 | 9654 | 46 |
| H(14A) | 6493 | 4649 | 8448 | 53 |
| H(14B) | 7297 | 3731 | 8518 | 53 |
| H(6) | 2554 | 3875 | 2029 | 67 |
| H(12A) | 16607 | 6541 | 7840 | 90 |

Example 5—Compound A Form D

The crystal structure of Compound A Form D was determined using X-ray data collected at 100 K on a crystal isolated from the batch. The structure of Compound A Form D was solved and refined in the non-centrosymmetric, monoclinic space group I2 with the final R1[I>2σ(I)] =3.54%. The asymmetric unit was found to contain one molecule of Compound A, one fully ordered adipate anion, one 50% occupied water molecule (O7), which is positioned on a crystallographic special position (2-fold axis) and one partially occupied water molecule (O8, 20% occupancy) disordered about a special position (2-fold axis). In the structure, the molecule also shows positional disorder with the methylpyrrolidine ring disordered over two sites and modelled with a 64.6:35.4 ratio. The absolute stereochemistry of the compound has been determined with stereocentres C6 and C25 in the S configuration. The Flack parameter for this structure is 0.007(8). The XRPD pattern simulated from the crystal structure data (collected at 100 K) is consistent with the reference experimental diffractogram of Form D (collected at RT). Slight differences in the simulated and experimental diffractograms are attributable to lattice variations with temperature and preferred orientation.

An overlay with calculated diffractogram of hydrated Form D shows that calculated XRPDs of these two Forms are similar, however there are some differences. The simulated diffractogram is consistent with the experimental VH diffractogram of Compound A Form A at 10% RH. Slight differences in the simulated and experimental diffractograms are attributable to lattice variations with temperature and preferred orientation.

Compound A Form A, C and D are structurally similar and interconvert rapidly depending upon the ambient relative humidity with the majority of water uptake occurring between 40-50% RH at 25° C.

Transitions of Forms of Compound A at varying RH.

| % Relative Humidity | XRPD |
|---|---|
| 0%-44% | Compound A Form A |
| 49%-54% | Transition |
| 58%-76%-49% | Compound A Form D |
| 44% | Transition |

-continued

| % Relative Humidity | XRPD |
|---|---|
| 39%-0%-44% | Compound A Form A |
| 49% | Transition |
| 54%-76%-53% | Compound A Form D |
| 48% | Transition |
| 44%-0% | Compound A Form A |

Single crystal experiments. The single crystal X-ray structure of Compound A Form D was determined at 100 K using a crystal grown by slow evaporation from THF. A crystal of sufficient size and quality for analysis by single crystal X-ray diffraction was isolated with approximate dimensions 0.22×0.20×0.08 mm.

The crystals were monoclinic, group I2 with the final R1=[I>2σ(I)]=3.54%. The compound was confirmed as Compound A Form D. The asymmetric unit contained one molecule of Compound A Form D, one fully ordered adipate anion, one 50% occupied water molecule, O7, sitting on a crystallographic special position (2-fold axis) and one partially occupied water molecule, O8, disordered about a special position (2-fold axis). The refined atomic occupancy of O8 is 0.195 (approximately 20% water). The molecule also showed positional disorder at carbon C27 methylpyrrolidine ring which has been modelled over two sites with a 64.6:35.4 ratio.

TABLE 19

Crystal data and structure refinement for Compound A Form D

| | | |
|---|---|---|
| Empirical formula | C35 H44 CI F4 N7 06.50 | |
| Formula weight | 778.22 | |
| Temperature | 90(2) K | |
| Wavelength | 1.54184 Å | |
| Crystal system | Monoclinic | |
| Space group | I 2 | |
| Unit cell dimensions | a = 20.2510(3) Å | α = 90°. |
| | b = 8.73850(10) Å | ß = 112.156(2)°. |
| | c = 22.2870(3) Å | γ = 90°. |
| Volume | 3652.76(10) $Å^3$ | |
| Z | 4 | |
| Density (calculated) | 1.415 $Mg/m^3$ | |
| Absorption coefficient | 1.598 $mm^{-1}$ | |
| F(000) | 1632 | |
| Crystal size | 0.200 × 0.120 × 0.100 $mm^3$ | |
| Theta range for data collection | 2.516 to 75.031°. | |
| Index ranges | −24 <= h <= 24, | −9 <= k <= 10, −27 <= k <= 27 |
| Reflections collected | 28840 | |
| Independent reflections | 6849 [R(int) = 0.0256] | |
| Completeness to theta = 67.000° | 100.0 % | |
| Absorption correction | Gaussian | |
| Max. and min. transmission | 1.000 and 0.671 | |
| Refinement method | Full-matrix least-squares on $F^2$ | |
| Data/restraints/parameters | 6849/1/509 | |
| Goodness-of-fit on $F^2$ | 1.048 | |
| Final R indices [I>2sigma(I)] | R1 = 0.0320, wR2 = 0.0899 | |
| R indices (all data) | R1 = 0.0323, wR2 = 0.0902 | |
| Absolute structure parameter | −0.009(5) | |
| Extinction coefficient | 0.00030(8) | |
| Largest diff. peak and hole | 1.072 and −0.188 e.$Å^{-3}$ | |

TABLE 20

Atomic coordinates ($\times 10^4$)and equivalent isotropic displacement parameters ($Å^2 \times 10^3$)for Compound A Form D. U(eq) is defined as one third of the trace of the orthogonalized $U^{ij}$ tensor.

| | x | y | z | U(eq) |
|---|---|---|---|---|
| C(1) | 3573(1) | 5230(3) | 6770(1) | 23(1) |
| C(2) | 3021(1) | 5999(3) | 6231(1) | 23(1) |
| C(3) | 2279(1) | 5675(3) | 5985(1) | 25(1) |
| C(4) | 1829(1) | 6460(3) | 5458(1) | 25(1) |
| C(5) | 2072(1) | 7610(3) | 5151(1) | 23(1) |
| C(6) | 2777(1) | 7969(3) | 5421(1) | 23(1) |
| C(7) | 3269(1) | 7229(3) | 5965(1) | 22(1) |
| C(8) | 4368(1) | 7039(3) | 6722(1) | 23(1) |
| C(9) | 3956(1) | 3494(3) | 7706(1) | 31(1) |
| C(10) | 4306(1) | 1966(3) | 7677(1) | 32(1) |
| C(11) | 3297(1) | 1196(3) | 6730(1) | 30(1) |
| C(12) | 2936(1) | 2738(3) | 6713(1) | 28(1) |
| C(13) | 3568(2) | 3460(4) | 8177(1) | 37(1) |
| C(14) | 3642(1) | −507(3) | 7667(1) | 30(1) |
| C(15) | 4070(2) | −760(4) | 8367(1) | 40(1) |
| C(16) | 4045(2) | −2070(4) | 8646(2) | 46(1) |
| C(17) | 1622(1) | 8320(3) | 4514(1) | 23(1) |
| C(18) | 1326(1) | 9766(3) | 4430(1) | 25(1) |
| C(19) | 974(1) | 10322(3) | 3785(1) | 27(1) |
| C(20) | 917(1) | 9355(3) | 3286(1) | 27(1) |
| C(21) | 1231(1) | 7892(3) | 3405(1) | 25(1) |
| C(22) | 1350(1) | 10762(3) | 4983(1) | 31(1) |
| C(23) | 690(2) | 11921(4) | 3637(1) | 38(1) |
| C(24) | 5276(1) | 8670(3) | 6669(1) | 27(1) |
| C(25) | 6079(1) | 8610(3) | 6908(1) | 29(1) |
| C(26) | 6375(1) | 9814(3) | 6575(2) | 36(1) |
| C(27) | 6974(2) | 8987(5) | 6419(2) | 34(1) |
| C(28) | 6658(2) | 7409(3) | 6254(1) | 36(1) |

TABLE 20-continued

Atomic coordinates (×$10^4$)and equivalent isotropic displacement parameters (Å$^2$ × $10^3$)for Compound A Form D. U(eq) is defined as one third of the trace of the orthogonalized $U^{ij}$ tensor.

| | x | y | z | U(eq) |
|---|---|---|---|---|
| C(26A) | 6375(1) | 9814(3) | 6575(2) | 36(1) |
| C(27A) | 6369(4) | 9037(10) | 6025(4) | 36(2) |
| C(28A) | 6658(2) | 7409(3) | 6254(1) | 36(1) |
| C(29) | 6818(1) | 6274(3) | 7315(1) | 35(1) |
| C(30) | 5218(1) | 4019(3) | 6244(1) | 28(1) |
| C(31) | 4551(2) | 3104(3) | 5891(1) | 32(1) |
| C(32) | 4066(1) | 3634(3) | 5219(1) | 30(1) |
| C(33) | 3427(2) | 2568(3) | 4943(1) | 40(1) |
| C(34) | 2995(2) | 2726(4) | 4220(2) | 47(1) |
| C(35) | 2497(1) | 4066(3) | 3987(1) | 32(1) |
| N(1) | 3952(1) | 7773(3) | 6207(1) | 24(1) |
| N(2) | 4228(1) | 5819(2) | 7016(1) | 24(1) |
| N(3) | 3458(1) | 3928(3) | 7051(1) | 27(1) |
| N(4) | 3766(1) | 794(3) | 7388(1) | 31(1) |
| N(5) | 1585(1) | 7400(2) | 4018(1) | 25(1) |
| N(6) | 1200(1) | 6941(3) | 2921(1) | 32(1) |
| N(7) | 6321(1) | 7079(3) | 6737(1) | 29(1) |
| O(1) | 3181(1) | −1430(2) | 7363(1) | 39(1) |
| O(2) | 5052(1) | 7512(2) | 7011(1) | 26(1) |
| O(3) | 5243(1) | 5376(2) | 6049(1) | 33(1) |
| O(4) | 5704(1) | 3432(2) | 6711(1) | 39(1) |
| O(5) | 2191(1) | 4320(2) | 3410(1) | 38(1) |
| O(6) | 2414(1) | 4910(2) | 4440(1) | 35(1) |
| O(7) | 5000 | 7215(5) | 5000 | 84(2) |
| F(1) | 3023(1) | 9104(2) | 5150(1) | 32(1) |
| F(2) | 696(1) | 11166(2) | 4942(1) | 44(1) |
| F(3) | 1665(1) | 10118(2) | 5567(1) | 43(1) |
| F(4) | 1703(1) | 12087(2) | 5009(1) | 45(1) |
| Cl(1) | 922(1) | 6035(1) | 5145(1) | 34(1) |

TABLE 21

Bond lengths [Å] and angles [°] for Compound A Form D.

| | | | |
|---|---|---|---|
| C(1)—N(2) | 1.332(3) | C(14)—O(1) | 1.227(4) |
| C(1)—N(3) | 1.361(3) | C(14)—N(4) | 1.365(3) |
| C(1)—C(2) | 1.461(3) | C(14)—C(15) | 1.487(4) |
| C(2)—C(7) | 1.409(3) | C(15)—C(16) | 1.312(4) |
| C(2)—C(3) | 1.419(3) | C(15)—H(15) | 0.9500 |
| C(3)—C(4) | 1.368(3) | C(16)—H(16A) | 0.9500 |
| C(3)—H(3) | 0.9500 | C(16)—H(16B) | 0.9500 |
| C(4)—C(5) | 1.404(3) | C(17)—N(5) | 1.347(3) |
| C(4)—CI(1) | 1.741(2) | C(17)—C(18) | 1.381(3) |
| C(5)—C(6) | 1.360(3) | C(18)—C(19) | 1.428(3) |
| C(5)—C(17) | 1.501(3) | C(18)—C(22) | 1.494(3) |
| C(6)—F(1) | 1.351(3) | C(19)—C(20) | 1.367(4) |
| C(6)—C(7) | 1.403(3) | C(19)—C(23) | 1.499(4) |
| C(7)—N(1) | 1.366(3) | C(20)—C(21) | 1.408(4) |
| C(8)—N(1) | 1.308(3) | C(20)—H(20) | 0.9500 |
| C(8)—N(2) | 1.336(3) | C(21)—N(6) | 1.344(3) |
| C(8)—O(2) | 1.354(3) | C(21)—N(5) | 1.351(3) |
| C(9)—N(3) | 1.478(3) | C(22)—F(3) | 1.337(3) |
| C(9)—C(10) | 1.525(4) | C(22)—F(2) | 1.339(3) |
| C(9)—C(13) | 1.531 (3) | C(22)—F(4) | 1.351(3) |
| C(9)—H(9) | 1.0000 | C(23)—H(23A) | 0.9800 |
| C(10)—N(4) | 1.458(4) | C(23)—H(23B) | 0.9800 |
| C(10)—H(10A) | 0.9900 | C(23)—H(23C) | 0.9800 |
| C(10)—H(10B) | 0.9900 | C(24)—O(2) | 1.438(3) |
| C(11)—N(4) | 1.458(3) | C(24)—C(25) | 1.509(3) |
| C(11)—C(12) | 1.527(4) | C(24)—H(24A) | 0.9900 |
| C(11)—H(11A) | 0.9900 | C(24)—H(24B) | 0.9900 |
| C(11)—H(11B) | 0.9900 | C(25)—N(7) | 1.521(4) |
| C(12)—N(3) | 1.471(3) | C(25)—C(26) | 1.533(4) |
| C(12)—H(12A) | 0.9900 | C(25)—C(26A) | 1.533(4) |
| C(12)—H(12B) | 0.9900 | C(25)—H(25) | 1.0000 |
| C(13)—H(13A) | 0.9800 | C(26)—C(27) | 1.560(5) |
| C(13)—H(13B) | 0.9800 | C(26)—H(26A) | 0.9900 |
| C(13)—H(13C) | 0.9800 | C(26)—H(26B) | 0.9900 |
| C(27)—C(28) | 1.506(5) | N(6)—H(6A) | 0.8800 |
| C(27)—H(27A) | 0.9900 | N(6)—H(6B) | 0.8800 |
| C(27)—H(27B) | 0.9900 | N(7)—H(7) | 1.0000 |
| C(28)—N(7) | 1.504(3) | O(6)—H(6) | 0.8400 |
| C(28)—H(28A) | 0.9900 | O(7)—H(7X) | 1.05(7) |
| C(28)—H(28B) | 0.9900 | N(2)—C(1)—N(3) | 116.8(2) |
| C(26A)—C(27A) | 1.399(9) | N(2)—C(1)—C(2) | 119.7(2) |
| C(26A)—H(26C) | 0.9900 | N(3)—C(1)—C(2) | 123.5(2) |
| C(26A)—H(26D) | 0.9900 | C(7)—C(2)—C(3) | 118.9(2) |
| C(27A)—C(28A) | 1.550(9) | C(7)—C(2)—C(1) | 114.4(2) |
| C(27A)—H(27C) | 0.9900 | C(3)—C(2)—C(1) | 126.6(2) |
| C(27A)—H(27D) | 0.9900 | C(4)—C(3)—C(2) | 119.8(2) |
| C(28A)—N(7) | 1.504(3) | C(4)—C(3)—H(3) | 120.1 |
| C(28A)—H(28C) | 0.9900 | C(2)—C(3)—H(3) | 120.1 |
| C(28A)—H(28D) | 0.9900 | C(3)—C(4)—C(5) | 122.3(2) |
| C(29)—N(7) | 1.480(3) | C(3)—C(4)—CI(1) | 119.84(18) |
| C(29)—H(29A) | 0.9800 | C(5)—C(4)—CI(1) | 117.85(17) |
| C(29)—H(29B) | 0.9800 | C(6)—C(5)—C(4) | 116.8(2) |

TABLE 21-continued

Bond lengths [Å] and angles [°] for Compound A Form D.

| | | | |
|---|---|---|---|
| C(29)—H(29C) | 0.9800 | C(6)—C(5)—C(17) | 119.0(2) |
| C(30)—O(4) | 1.241(3) | C(4)—C(5)—C(17) | 123.8(2) |
| C(30)—O(3) | 1.271(3) | F(1)—C(6)—C(5) | 118.3(2) |
| C(30)—C(31) | 1.511(4) | F(1)—C(6)—C(7) | 117.51(19) |
| C(31)—C(32) | 1.520(3) | C(5)—C(6)—C(7) | 124.2(2) |
| C(31)—H(31A) | 0.9900 | N(1)—C(7)—C(6) | 117.7(2) |
| C(31)—H(31B) | 0.9900 | N(1)—C(7)—C(2) | 124.6(2) |
| C(32)—C(33) | 1.523(4) | C(6)—C(7)—C(2) | 117.7(2) |
| C(32)—H(32A) | 0.9900 | N(1)—C(8)—N(2) | 129.6(2) |
| C(32)—H(32B) | 0.9900 | N(1)—C(8)—O(2) | 118.1(2) |
| C(33)—C(34) | 1.523(4) | N(2)—C(8)—O(2) | 112.30(19) |
| C(33)—H(33A) | 0.9900 | N(3)—C(9)—C(10) | 109.7(2) |
| C(33)—H(33B) | 0.9900 | N(3)—C(9)—C(13) | 110.3(2) |
| C(34)—C(35) | 1.504(4) | C(10)—C(9)—C(13) | 112.3(2) |
| C(34)—H(34A) | 0.9900 | N(3)—C(9)—H(9) | 108.1 |
| C(34)—H(34B) | 0.9900 | C(10)—C(9)—H(9) | 108.1 |
| C(35)—O(5) | 1.219(3) | C(13)—C(9)—H(9) | 108.1 |
| C(35)—O(6) | 1.312(3) | N(4)—C(10)—C(9) | 110.5(2) |
| N(4)—C(10)—H(10A) | 109.5 | C(17)—C(18)—C(22) | 123.0(2) |
| C(9)—C(10)—H(10A) | 109.5 | C(19)—C(18)—C(22) | 118.8(2) |
| N(4)—C(10)—H(10B) | 109.5 | C(20)—C(19)—C(18) | 117.8(2) |
| C(9)—C(10)—H(10B) | 109.5 | C(20)—C(19)—C(23) | 119.3(2) |
| H(10A)—C(10)—H(10B) | 108.1 | C(18)—C(19)—C(23) | 122.9(2) |
| N(4)—C(11)—C(12) | 111.2(2) | C(19)—C(20)—C(21) | 120.9(2) |
| N(4)—C(11)—H(11A) | 109.4 | C(19)—C(20)—H(20) | 119.5 |
| C(12)—C(11)—H(11A) | 109.4 | C(21)—C(20)—H(20) | 119.5 |
| N(4)—C(11)—H(11B) | 109.4 | N(6)—C(21)—N(5) | 117.5(2) |
| C(12)—C(11)—H(11B) | 109.4 | N(6)—C(21)—C(20) | 121.9(2) |
| H(11A)—C(11)—H(11B) | 108.0 | N(5)—C(21)—C(20) | 120.6(2) |
| N(3)—C(12)—C(11) | 111.5(2) | F(3)—C(22)—F(2) | 105.9(2) |
| N(3)—C(12)—H(12A) | 109.3 | F(3)—C(22)—F(4) | 105.6(2) |
| C(11)—C(12)—H(12A) | 109.3 | F(2)—C(22)—F(4) | 105.7(2) |
| N(3)—C(12)—H(12B) | 109.3 | F(3)—C(22)—C(18) | 114.3(2) |
| C(11)—C(12)—H(12B) | 109.3 | F(2)—C(22)—C(18) | 112.0(2) |
| H(12A)—C(12)—H(12B) | 108.0 | F(4)—C(22)—C(18) | 112.8(2) |
| C(9)—C(13)—H(13A) | 109.5 | C(19)—C(23)—H(23A) | 109.5 |
| C(9)—C(13)—H(13B) | 109.5 | C(19)—C(23)—H(23B) | 109.5 |
| H(13A)—C(13)—H(13B) | 109.5 | H(23A)—C(23)—H(23B) | 109.5 |
| C(9)—C(13)—H(13C) | 109.5 | C(19)—C(23)—H(23C) | 109.5 |
| H(13A)—C(13)—H(13C) | 109.5 | H(23A)—C(23)—H(23C) | 109.5 |
| H(13B)—C(13)—H(13C) | 109.5 | H(23B)—C(23)—H(23C) | 109.5 |
| O(1)—C(14)—N(4) | 121.9(2) | O(2)—C(24)—C(25) | 107.61(19) |
| O(1)—C(14)—C(15) | 120.2(3) | O(2)—C(24)—H(24A) | 110.2 |
| N(4)—C(14)—C(15) | 117.9(3) | C(25)—C(24)—H(24A) | 110.2 |
| C(16)—C(15)—C(14) | 120.9(3) | O(2)—C(24)—H(24B) | 110.2 |
| C(16)—C(15)—H(15) | 119.5 | C(25)—C(24)—H(24B) | 110.2 |
| C(14)—C(15)—H(15) | 119.5 | H(24A)—C(24)—H(24B) | 108.5 |
| C(15)—C(16)—H(16A) | 120.0 | C(24)—C(25)—N(7) | 110.4(2) |
| C(15)—C(16)—H(16B) | 120.0 | C(24)—C(25)—C(26) | 111.8(2) |
| H(16A)—C(16)—H(16B) | 120.0 | N(7)—C(25)—C(26) | 105.2(2) |
| N(5)—C(17)—C(18) | 123.3(2) | C(24)—C(25)—C(26A) | 111.8(2) |
| N(5)—C(17)—C(5) | 110.8(2) | N(7)—C(25)—C(26A) | 105.2(2) |
| C(18)—C(17)—C(5) | 125.7(2) | C(24)—C(25)—H(25) | 109.8 |
| C(17)—C(18)—C(19) | 118.3(2) | N(7)—C(25)—H(25) | 109.8 |
| C(26)—C(25)—H(25) | 109.8 | H(28C)—C(28A)—H(28D) | 109.3 |
| C(25)—C(26)—C(27) | 105.6(3) | N(7)—C(29)—H(29A) | 109.5 |
| C(25)—C(26)—H(26A) | 110.6 | N(7)—C(29)—H(29B) | 109.5 |
| C(27)—C(26)—H(26A) | 110.6 | H(29A)—C(29)—H(29B) | 109.5 |
| C(25)—C(26)—H(26B) | 110.6 | N(7)—C(29)—H(29C) | 109.5 |
| C(27)—C(26)—H(26B) | 110.6 | H(29A)—C(29)—H(29C) | 109.5 |
| H(26A)—C(26)—H(26B) | 108.8 | H(29B)—C(29)—H(29C) | 109.5 |
| C(28)—C(27)—C(26) | 100.6(3) | O(4)—C(30)—O(3) | 123.5(2) |
| C(28)—C(27)—H(27A) | 111.6 | O(4)—C(30)—C(31) | 119.3(2) |
| C(26)—C(27)—H(27A) | 111.6 | O(3)—C(30)—C(31) | 117.3(2) |
| C(28)—C(27)—H(27B) | 111.6 | C(30)—C(31)—C(32) | 118.1(2) |
| C(26)—C(27)—H(27B) | 111.6 | C(30)—C(31)—H(31A) | 107.8 |
| H(27A)—C(27)—H(27B) | 109.4 | C(32)—C(31)—H(31A) | 107.8 |
| N(7)—C(28)—C(27) | 105.4(2) | C(30)—C(31)—H(31B) | 107.8 |
| N(7)—C(28)—H(28A) | 110.7 | C(32)—C(31)—H(31B) | 107.8 |
| C(27)—C(28)—H(28A) | 110.7 | H(31A)—C(31)—H(31B) | 107.1 |
| N(7)—C(28)—H(28B) | 110.7 | C(31)—C(32)—C(33) | 110.2(2) |
| C(27)—C(28)—H(28B) | 110.7 | C(31)—C(32)—H(32A) | 109.6 |
| H(28A)—C(28)—H(28B) | 108.8 | C(33)—C(32)—H(32A) | 109.6 |
| C(27A)—C(26A)—C(25) | 102.4(4) | C(31)—C(32)—H(32B) | 109.6 |
| C(27A)—C(26A)—H(26C) | 111.3 | C(33)—C(32)—H(32B) | 109.6 |
| C(25)—C(26A)—H(26C) | 111.3 | H(32A)—C(32)—H(32B) | 108.1 |
| C(27A)—C(26A)—H(26D) | 111.3 | C(34)—C(33)—C(32) | 115.7(3) |
| C(25)—C(26A)—H(26D) | 111.3 | C(34)—C(33)—H(33A) | 108.4 |

TABLE 21-continued

| Bond lengths [Å] and angles [°] for Compound A Form D. | | | |
|---|---|---|---|
| H(26C)—C(26A)—H(26D) | 109.2 | C(32)—C(33)—H(33A) | 108.4 |
| C(26A)—C(27A)—C(28A) | 106.2(5) | C(34)—C(33)—H(33B) | 108.4 |
| C(26A)—C(27A)—H(27C) | 110.5 | C(32)—C(33)—H(33B) | 108.4 |
| C(28A)—C(27A)—H(27C) | 110.5 | H(33A)—C(33)—H(33B) | 107.4 |
| C(26A)—C(27A)—H(27D) | 110.5 | C(35)—C(34)—C(33) | 118.6(3) |
| C(28A)—C(27A)—H(27D) | 110.5 | C(35)—C(34)—H(34A) | 107.7 |
| H(27C)—C(27A)—H(27D) | 108.7 | C(33)—C(34)—H(34A) | 107.7 |
| N(7)—C(28A)—C(27A) | 101.2(3) | C(35)—C(34)—H(34B) | 107.7 |
| N(7)—C(28A)—H(28C) | 111.5 | C(33)—C(34)—H(34B) | 107.7 |
| C(27A)—C(28A)—H(28C) | 111.5 | H(34A)—C(34)—H(34B) | 107.1 |
| N(7)—C(28A)—H(28D) | 111.5 | O(5)—C(35)—O(6) | 123.2(2) |
| C(27A)—C(28A)—H(28D) | 111.5 | O(5)—C(35)—C(34) | 121.0(2) |
| O(6)—C(35)—C(34) | 115.8(2) | H(6A)—N(6)—H(6B) | 120.0 |
| C(8)—N(1)—C(7) | 113.4(2) | C(29)—N(7)—C(28A) | 111.8(2) |
| C(1)—N(2)—C(8) | 117.93(19) | C(29)—N(7)—C(28) | 111.8(2) |
| C(1)—N(3)—C(12) | 124.79(19) | C(29)—N(7)—C(25) | 112.2(2) |
| C(1)—N(3)—C(9) | 119.8(2) | C(28A)—N(7)—C(25) | 106.6(2) |
| C(12)—N(3)—C(9) | 114.6(2) | C(28)—N(7)—C(25) | 106.6(2) |
| C(14)—N(4)—C(11) | 119.8(2) | C(29)—N(7)—H(7) | 108.7 |
| C(14)—N(4)—C(10) | 128.3(2) | C(28)—N(7)—H(7) | 108.7 |
| C(11)—N(4)—C(10) | 111.7(2) | C(25)—N(7)—H(7) | 108.7 |
| C(17)—N(5)—C(21) | 119.0(2) | C(8)—O(2)—C(24) | 115.77(17) |
| C(21)—N(6)—H(6A) | 120.0 | C(35)—O(6)—H(6) | 109.5 |
| C(21)—N(6)—H(6B) | 120.0 | H(6A)—N(6)—H(6B) | 120.0 |

TABLE 22

Anisotropic displacement parameters (Å$^2$ × 10$^3$)for Compound A Form D. The anisotropic displacement factor exponent takes the form: $-2\pi^2[h^2a^{*2}U^{11} + \ldots + 2hka^*b^*U^{12}]$.

| | U11 | U22 | U33 | U23 | U13 | U12 |
|---|---|---|---|---|---|---|
| C(1) | 25(1) | 26(1) | 18(1) | 0(1) | 7(1) | 1(1) |
| C(2) | 23(1) | 26(1) | 19(1) | 2(1) | 7(1) | 3(1) |
| C(3) | 25(1) | 28(1) | 23(1) | 2(1) | 11(1) | −1(1) |
| C(4) | 21(1) | 31(1) | 23(1) | −1(1) | 9(1) | 1(1) |
| C(5) | 23(1) | 26(1) | 18(1) | 0(1) | 6(1) | 3(1) |
| C(6) | 23(1) | 24(1) | 21(1) | 4(1) | 7(1) | −1(1) |
| C(7) | 21(1) | 24(1) | 19(1) | 0(1) | 6(1) | 1(1) |
| C(8) | 21(1) | 25(1) | 20(1) | 1(1) | 5(1) | 0(1) |
| C(9) | 32(1) | 33(1) | 22(1) | 8(1) | 4(1) | −3(1) |
| C(10) | 27(1) | 39(2) | 27(1) | 10(1) | 7(1) | 2(1) |
| C(11) | 33(1) | 31(1) | 25(1) | 4(1) | 9(1) | 0(1) |
| C(12) | 26(1) | 28(1) | 26(1) | 4(1) | 7(1) | −3(1) |
| C(13) | 47(2) | 39(2) | 25(1) | 5(1) | 12(1) | 2(1) |
| C(14) | 35(1) | 28(1) | 33(1) | 6(1) | 19(1) | 9(1) |
| C(15) | 43(2) | 42(2) | 37(1) | 10(1) | 18(1) | 8(1) |
| C(16) | 43(2) | 51(2) | 50(2) | 23(1) | 24(1) | 15(1) |
| C(17) | 19(1) | 28(1) | 20(1) | 2(1) | 6(1) | 1(1) |
| C(18) | 22(1) | 31(1) | 21(1) | 2(1) | 5(1) | 4(1) |
| C(19) | 21(1) | 34(1) | 24(1) | 3(1) | 5(1) | 4(1) |
| C(20) | 23(1) | 35(1) | 20(1) | 4(1) | 3(1) | 3(1) |
| C(21) | 23(1) | 31(1) | 21(1) | 1(1) | 7(1) | −1(1) |
| C(22) | 27(1) | 37(2) | 24(1) | 1(1) | 6(1) | 9(1) |
| C(23) | 42(2) | 37(2) | 27(1) | 4(1) | 5(1) | 14(1) |
| C(24) | 22(1) | 27(1) | 29(1) | 5(1) | 5(1) | −2(1) |
| C(25) | 25(1) | 29(1) | 29(1) | −1(1) | 4(1) | −2(1) |
| C(26) | 29(1) | 30(2) | 48(2) | 2(1) | 13(1) | −3(1) |
| C(27) | 30(2) | 35(2) | 37(2) | −2(2) | 13(2) | −2(2) |
| C(28) | 41(1) | 34(2) | 34(1) | −1(1) | 16(1) | −3(1) |
| C(26A) | 29(1) | 30(2) | 48(2) | 2(1) | 13(1) | −3(1) |
| C(27A) | 42(5) | 33(5) | 41(5) | 1(3) | 24(4) | −5(3) |
| C(28A) | 41(1) | 34(2) | 34(1) | −1(1) | 16(1) | −3(1) |
| C(29) | 33(1) | 34(2) | 32(1) | 3(1) | 5(1) | 4(1) |
| C(30) | 35(1) | 27(1) | 23(1) | 2(1) | 11(1) | 2(1) |
| C(31) | 35(1) | 26(1) | 31(1) | 3(1) | 8(1) | −1(1) |
| C(32) | 31(1) | 25(1) | 31(1) | 1(1) | 8(1) | −1(1) |
| C(33) | 35(1) | 27(1) | 46(2) | 2(1) | 1(1) | −1(1) |
| C(34) | 38(2) | 36(2) | 48(2) | −17(1) | −6(1) | 6(1) |
| C(35) | 27(1) | 31(1) | 32(1) | −6(1) | 4(1) | 0(1) |
| N(1) | 20(1) | 28(1) | 21(1) | 4(1) | 4(1) | 0(1) |
| N(2) | 23(1) | 27(1) | 19(1) | 3(1) | 5(1) | 1(1) |
| N(3) | 29(1) | 28(1) | 20(1) | 6(1) | 3(1) | −3(1) |
| N(4) | 33(1) | 31(1) | 28(1) | 7(1) | 9(1) | 1(1) |

TABLE 22-continued

Anisotropic displacement parameters (Å$^2$ × 10$^3$)for Compound A Form D. The anisotropic displacement factor exponent takes the form: $-2\pi^2[h^2a^{*2}U^{11} + \ldots + 2hka^*b^*U^{12}]$.

| | U11 | U22 | U33 | U23 | U13 | U12 |
|---|---|---|---|---|---|---|
| N(5) | 22(1) | 30(1) | 20(1) | 1(1) | 4(1) | 2(1) |
| N(6) | 35(1) | 36(1) | 20(1) | −1(1) | 4(1) | 7(1) |
| N(7) | 26(1) | 28(1) | 28(1) | 2(1 | 5(1) | −1(1) |
| O(1) | 45(1) | 32(1) | 44(1) | 6(1) | 20(1) | −2(1) |
| O(2) | 22(1) | 29(1) | 21(1) | 4(1) | 3(1) | −2(1) |
| O(3) | 36(1) | 27(1) | 28(1) | 2(1) | 4(1) | −5(1) |
| O(4) | 41(1) | 37(1) | 28(1) | 3(1) | 1(1) | 4(1) |
| O(5) | 37(1) | 41(1) | 29(1) | −8(1) | 5(1) | 6(1) |
| O(6) | 40(1) | 35(1) | 27(1) | −2(1) | 7(1) | 10(1) |
| O(7) | 160(5) | 47(2) | 28(2) | 0 | 17(2) | 0 |
| F(1) | 25(1) | 34(1) | 30(1) | 14(1) | 3(1) | −4(1) |
| F(2) | 32(1) | 63(1) | 34(1) | −11(1) | 11(1) | 16(1) |
| F(3) | 58(1) | 45(1) | 19(1) | 1(1) | 8(1) | 22(1) |
| F(4) | 53(1) | 36(1) | 42(1) | −11(1) | 15(1) | −6(1) |
| Cl(1) | 19(1) | 48(1) | 33(1) | 10(1) | 6(1) | −2(1) |

TABLE 23

Hydrogen coordinates (×10$^4$) and isotropic displacement parameters (Å$^2$ × 10$^3$) for Compound A Form D.

| | x | y | z | U(eq) |
|---|---|---|---|---|
| H(3) | 2096 | 4916 | 6185 | 30 |
| H(9) | 4338 | 4290 | 7859 | 37 |
| H(10A) | 4606 | 2079 | 7417 | 38 |
| H(10B) | 4618 | 1649 | 8120 | 38 |
| H(11A) | 2929 | 394 | 6556 | 36 |
| H(11B) | 3578 | 1242 | 6450 | 36 |
| H(12A) | 2677 | 3049 | 6257 | 33 |
| H(12B) | 2583 | 2634 | 6920 | 33 |
| H(13A) | 3335 | 4448 | 8166 | 56 |
| H(13B) | 3912 | 3264 | 8617 | 56 |
| H(13C) | 3208 | 2647 | 8050 | 56 |
| H(15) | 4366 | 39 | 8616 | 47 |
| H(16A) | 3751 | −2873 | 8400 | 55 |
| H(16B) | 4322 | −2215 | 9093 | 55 |
| H(20) | 661 | 9674 | 2852 | 33 |
| H(23A) | 1089 | 12646 | 3764 | 56 |
| H(23B) | 385 | 12144 | 3879 | 56 |

TABLE 23-continued

Hydrogen coordinates (×10^4) and isotropic displacement parameters ($Å^2 \times 10^3$) for Compound A Form D.

| | x | y | z | U(eq) |
|---|---|---|---|---|
| H(23C) | 411 | 12017 | 3172 | 56 |
| H(24A) | 5119 | 9692 | 6754 | 33 |
| H(24B) | 5065 | 8475 | 6197 | 33 |
| H(25) | 6289 | 8764 | 7388 | 35 |
| H(26A) | 6572 | 10697 | 6866 | 43 |
| H(26B) | 5996 | 10186 | 6173 | 43 |
| H(27A) | 7049 | 9467 | 6048 | 41 |
| H(27B) | 7430 | 8971 | 6799 | 41 |
| H(28A) | 6296 | 7382 | 5806 | 43 |
| H(28B) | 7034 | 6648 | 6291 | 43 |
| H(26C) | 6066 | 10732 | 6456 | 43 |
| H(26D) | 6864 | 10125 | 6856 | 43 |
| H(27C) | 6677 | 9566 | 5835 | 43 |
| H(27D) | 5879 | 8983 | 5694 | 43 |
| H(28C) | 6502 | 6667 | 5891 | 43 |
| H(28D) | 7185 | 7400 | 6460 | 13 |
| H(29A) | 6941 | 5275 | 7187 | 53 |
| H(29B) | 6590 | 6129 | 7629 | 53 |
| H(29C) | 7252 | 6885 | 7513 | 53 |
| H(31A) | 4265 | 3079 | 6166 | 38 |
| H(31B) | 4696 | 2038 | 5853 | 38 |
| H(32A) | 4335 | 3644 | 4929 | 36 |
| H(32B) | 3899 | 4688 | 5244 | 36 |
| H(33A) | 3598 | 1500 | 5032 | 48 |
| H(33B) | 3105 | 2753 | 5178 | 48 |
| H(34A) | 3335 | 2762 | 3997 | 56 |
| H(34B) | 2709 | 1781 | 4074 | 56 |
| H(6A) | 1406 | 6037 | 3009 | 39 |
| H(6B) | 974 | 7223 | 2516 | 39 |
| H(7) | 5892 | 6419 | 6525 | 34 |
| H(6) | 2113 | 5599 | 4268 | 53 |
| H(7X) | 4400 | 5674 | 5035 | 101 |
| H(7X) | 4950(40) | 6470(80) | 5350(30) | 110(20) |

TABLE 24

Torsion angles [°] for Compound A Form D.

| | |
|---|---|
| N(2)—C(1)—C(2)—C(7) | 7.6(3) |
| N(3)—C(1)—C(2)—C(7) | −173.2(2) |
| N(2)—C(1)—C(2)—C(3) | −168.9(2) |
| N(3)—C(1)—C(2)—C(3) | 10.2(4) |
| C(7)—C(2)—C(3)—C(4) | 6.1(3) |
| C(1)—C(2)—C(3)—C(4) | −177.5(2) |
| C(2)—C(3)—C(4)—C(5) | −1.1(4) |
| C(2)—C(3)—C(4)—Cl(1) | 178.61(18) |
| C(3)—C(4)—C(5)—C(6) | −3.2(3) |
| Cl(1)—C(4)—C(5)—C(6) | 177.16(18) |
| C(3)—C(4)—C(5)—C(17) | 169.9(2) |
| Cl(1)—C(4)—C(5)—C(17) | −9.8(3) |
| C(4)—C(5)—C(6)—F(1) | −177.9(2) |
| C(17)—C(5)—C(6)—F(1) | 8.7(3) |
| C(4)—C(5)—C(6)—C(7) | 2.4(3) |
| C(17)—C(5)—C(6)—C(7) | −171.0(2) |
| F(1)—C(6)—C(7)—N(1) | 4.2(3) |
| C(5)—C(6)—C(7)—N(1) | −176.1(2) |
| F(1)—C(6)—C(7)—C(2) | −177.2(2) |
| C(5)—C(6)—C(7)—C(2) | 2.5(3) |
| C(3)—C(2)—C(7)—N(1) | 171.8(2) |
| C(1)—C(2)—C(7)—N(1) | −5.0(3) |
| C(3)—C(2)—C(7)—C(6) | −6.7(3) |
| C(1)—C(2)—C(7)—C(6) | 176.5(2) |
| N(3)—C(9)—C(10)—N(4) | −55.9(3) |
| C(13)—C(9)—C(10)—N(4) | 67.1(3) |
| N(4)—C(11)—C(12)—N(3) | 50.9(3) |
| O(1)—C(14)—C(15)—C(16) | 10.9(4) |
| N(4)—C(14)—C(15)—C(16) | −171.1(3) |
| C(6)—C(5)—C(17)—N(5) | 93.6(3) |
| C(4)—C(5)—C(17)—N(5) | −79.2(3) |
| C(6)—C(5)—C(17)—C(18) | −81.4(3) |
| C(4)—C(5)—C(17)—C(18) | 105.7(3) |
| N(5)—C(17)—C(18)—C(19) | −0.9(3) |

TABLE 24-continued

Torsion angles [°] for Compound A Form D.

| | |
|---|---|
| C(5)—C(17)—C(18)—C(19) | 173.5(2) |
| N(5)—C(17)—C(18)—C(22) | 178.1(2) |
| C(5)—C(17)—C(18)—C(22) | −7.4(4) |
| C(17)—C(18)—C(19)—C(20) | 3.4(3) |
| C(22)—C(18)—C(19)—C(20) | −175.7(2) |
| C(17)—C(18)—C(19)—C(23) | −174.6(2) |
| C(22)—C(18)—C(19)—C(23) | 6.3(4) |
| C(18)—C(19)—C(20)—C(21) | −3.6(4) |
| C(23)—C(19)—C(20)—C(21) | 174.4(2) |
| C(19)—C(20)—C(21)—N(6) | −177.9(2) |
| C(19)—C(20)—C(21)—N(5) | 1.3(4) |
| C(17)—C(18)—C(22)—F(3) | −1.7(3) |
| C(19)—C(18)—C(22)—F(3) | 177.4(2) |
| C(17)—C(18)—C(22)—F(2) | −122.1(2) |
| C(19)—C(18)—C(22)—F(2) | 56.9(3) |
| C(17)—C(18)—C(22)—F(4) | 118.9(2) |
| C(19)—C(18)—C(22)—F(4) | −62.0(3) |
| O(2)—C(24)—C(25)—N(7) | 63.7(2) |
| O(2)—C(24)—C(25)—C(26) | −179.6(2) |
| O(2)—C(24)—C(25)—C(26A) | −179.6(2) |
| C(24)—C(25)—C(26)—C(27) | −137.9(3) |
| N(7)—C(25)—C(26)—C(27) | −18.1(3) |
| C(25)—C(26)—C(27)—C(28) | 35.9(3) |
| C(26)—C(27)—C(28)—N(7) | −40.4(3) |
| C(24)—C(25)—C(26A)—C(27A) | −88.5(4) |
| N(7)—C(25)—C(26A)—C(27A) | 31.3(4) |
| C(25)—C(26A)—C(27A)—C(28A) | −43.3(5) |
| C(26A)—C(27A)—C(28A)—N(7) | 38.8(5) |
| O(4)—C(30)—C(31)—C(32) | −162.5(2) |
| O(3)—C(30)—C(31)—C(32) | 18.5(3) |
| C(30)—C(31)—C(32)—C(33) | 179.9(2) |
| C(31)—C(32)—C(33)—C(34) | −165.8(2) |
| C(32)—C(33)—C(34)—C(35) | −76.3(4) |
| C(33)—C(34)—C(35)—O(5) | 173.2(3) |
| C(33)—C(34)—C(35)—O(6) | −7.6(4) |
| N(2)—C(8)—N(1)—C(7) | 3.4(4) |
| O(2)—C(8)—N(1)—C(7) | −178.41(19) |
| C(6)—C(7)—N(1)—C(8) | 178.4(2) |
| C(2)—C(7)—N(1)—C(8) | −0.1(3) |
| N(3)—C(1)—N(2)—C(8) | 175.6(2) |
| C(2)—C(1)—N(2)—C(8) | −5.2(3) |
| N(1)—C(8)—N(2)—C(1) | −0.7(4) |
| O(2)—C(8)—N(2)—C(1) | −178.91(19) |
| N(2)—C(1)—N(3)—C(12) | −150.4(2) |
| C(2)—C(1)—N(3)—C(12) | 30.4(3) |
| N(2)—C(1)—N(3)—C(9) | 18.5(3) |
| C(2)—C(1)—N(3)—C(9) | −160.7(2) |
| C(11)—C(12)—N(3)—C(1) | 119.6(2) |
| C(11)—C(12)—N(3)—C(9) | −49.9(3) |
| C(10)—C(9)—N(3)—C(1) | −117.9(2) |
| C(13)—C(9)—N(3)—C(1) | 117.9(3) |
| C(10)—C(9)—N(3)—C(12) | 52.1(3) |
| C(13)—C(9)—N(3)—C(12) | −72.1(3) |
| O(1)—C(14)—N(4)—C(11) | 6.3(4) |
| C(15)—C(14)—N(4)—C(11) | 171.7(2) |
| O(1)—C(14)—N(4)—C(10) | −177.8(2) |
| C(15)—C(14)—N(4)—C(10) | 4.2(4) |
| C(12)—C(11)—N(4)—C(14) | 119.4(2) |
| C(12)—C(11)—N(4)—C(10) | −57.1(3) |
| C(9)—C(10)—N(4)—C(14) | −116.2(3) |
| C(9)—C(10)—N(4)—C(11) | 60.0(3) |
| C(18)—C(17)—N(5)—C(21) | −1.4(3) |
| C(5)—C(17)—N(5)—C(21) | −176.6(2) |
| N(6)—C(21)—N(5)—C(17) | −179.4(2) |
| C(20)—C(21)—N(5)—C(17) | 1.3(3) |
| C(27A)—C(28A)—N(7)—C(29) | −140.1(4) |
| C(27A)—C(28A)—N(7)—C(25) | −17.2(4) |
| C(27)—C(28)—N(7)—C(29) | −92.4(3) |
| C(27)—C(28)—N(7)—C(25) | 30.6(3) |
| C(24)—C(25)—N(7)—C(29) | −123.6(2) |
| C(26)—C(25)—N(7)—C(29) | 115.7(2) |
| C(26A)—C(25)—N(7)—C(29) | 115.7(2) |
| C(24)—C(25)—N(7)—C(28A) | 113.7(2) |
| C(26A)—C(25)—N(7)—C(28A) | −7.0(2) |
| C(24)—C(25)—N(7)—C(28) | 113.7(2) |

TABLE 24-continued

| Torsion angles [°] for Compound A Form D. | |
|---|---|
| C(26)—C(25)—N(7)—C(28) | −7.0(2) |
| N(1)—C(8)—O(2)—C(24) | −7.4(3) |
| N(2)—C(8)—O(2)—C(24) | 171.03(19) |
| C(25)—C(24)—O(2)—C(8) | −158.6(2) |

Figure 20:
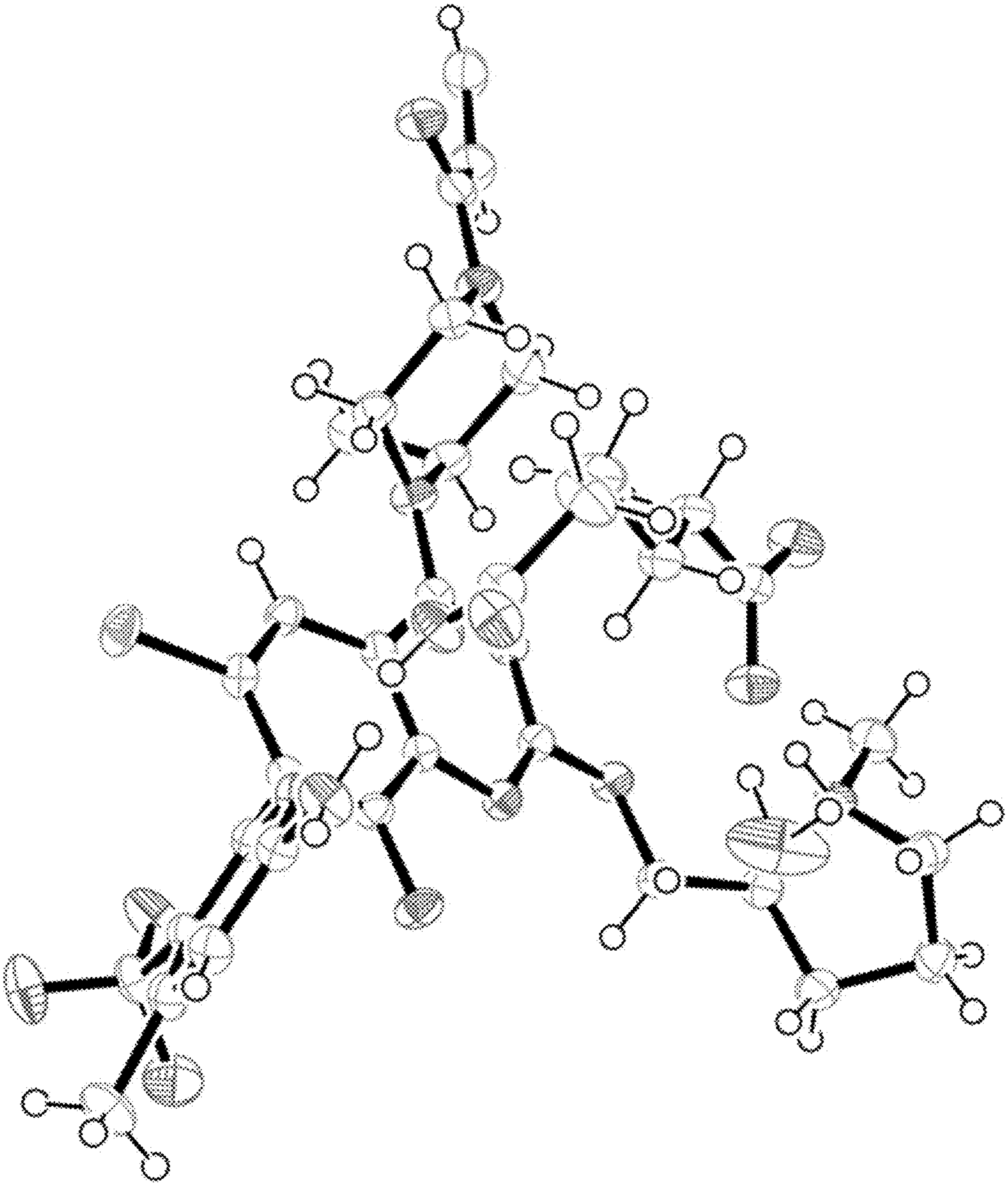
FIG. 20 depicts single crystal XRD of Compound A Form D.

The single crystal structure of Compound A Form D is shown in FIG. 20. C6 and C25 of Compound A Form D are in the S configuration. The Flack [2] parameter for this structure is 0.007(8). For the inverted structure, with C6 and C25 in the R configuration the Flack parameter is 0.996(8). Determination of the absolute structure using Bayesian statistics on Bijvoet differences [3] reveals that the probability of the absolute structure as presented being correct is 1.000, while the probabilities of the absolute structure being a racemic twin or false are both 0.000. The Flack equivalent and its uncertainty are calculated through this program to be 0.011(6). The calculation was based on 3344 Bijvoet pairs with a coverage of 92%.

Figure 22:
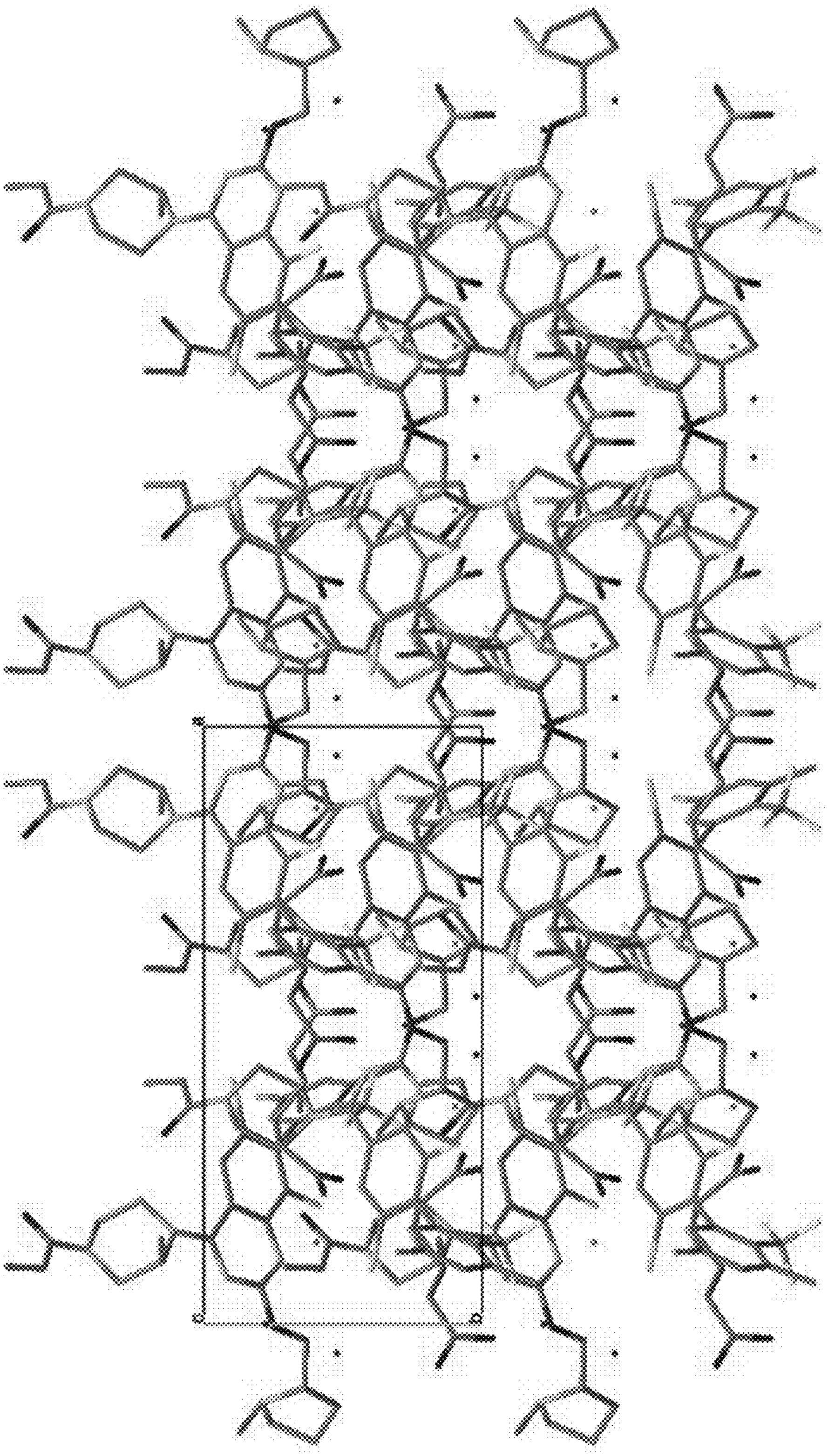
FIG. 22 depicts a view of the crystal packing of Compound A Form D looking down the crystallographic c-axis.

There are five intermolecular hydrogen bonds in the crystal structure of Form D. A water molecule (O7) sits on a 2-fold axis and is hydrogen bonded to two symmetry related carbonyl oxygen atoms (O4). The carboxylic group of the adipate forms a heterodimer through the O—H . . . N and O . . . H—N intramolecular interactions with nitrogen N5 and N6 of the API molecule. Anime nitrogen atom N6 is also involved in a hydrogen bond interaction to oxygen O3 of the adipate. Additionally, nitrogen N7 of disordered 1-methylpyrrolidine is involved in one N—H . . . O intermolecular interaction to oxygen O4 of the —COO— group of adipate. Views of the crystal packing within the unit cell can be seen in FIG. 21 and FIG. 22. For clarity all hydrogen atoms have been removed from packing diagrams.

Overall Summary. Compound A was the most stable form for further development of Compound 1. The amorphous form is considered for development purposes to be unstable for further development. Not only is the adipate salt of Compound A far more stable than the other identified salt forms, but it is also useful in the crystallization and purification of the compound during large scale synthesis.

Example 6—Compound A Form C

X-ray quality crystals were grown from a saturated methylethylketone solution that was allowed to slowly evaporate under ambient conditions. A colorless prism 0.170×0.080×0.060 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 43859 reflections were collected covering the indices, −25<=h<=25, −10<=k<=10, −27<=l<=27. 7083 reflections were found to be symmetry independent, with an $R_{int}$ of 0.0360. Indexing and unit cell refinement indicated an I-centered, monoclinic lattice. The space group was found to be I 2 (No. 5). The data were integrated and scaled using CrysAlisPro 1.171.41.76a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

TABLE 25

Hydrogen bond information for Form C

| D—H . . . A | d(D—H) | d(H . . . A) | d(D . . . A) | <(DHA) |
|---|---|---|---|---|
| N6—H6B . . . O5 | 0.85(7) | 2.13(7) | 2.976(8) | 175(5) |
| N6—H6A . . . O3#1 | 0.90(7) | 1.96(7) | 2.799(8) | 156(6) |
| N6—H6A . . . O3A#1 | 0.90(7) | 1.95(7) | 2.800(10) | 158(6) |
| O6—H6C . . . N5 | 0.84 | 1.85 | 2.662(6) | 163.2 |
| N7A—H7A . . . O4A#2 | 1.00 | 1.58 | 2.559(13) | 163.5 |
| N7—H7 . . . O4 | 1.00 | 1.64 | 2.62(2) | 166.2 |

#1 x + 1/2, y + 1/2, z + 1/2
#2 x, y + 1, z

TABLE 26

| Crystal data and structure refinement for Compound A Form C | | |
|---|---|---|
| Empirical formula | C35 H42 Cl F4 N7 O6 | |
| Formula weight | 768.20 | |
| Temperature | 90(2) K | |
| Wavelength | 1.54184 Å | |
| Crystal system | Monoclinic | |
| Space group | I 2 | |
| Unit cell dimensions | a = 20.4022(2) Å | α = 90°. |
| | b = 8.63050(10) Å | β = 113.7020(10)°. |
| | c = 22.3422(3) Å | γ = 90°. |
| Volume | 3602.20(8) Å$^3$ | |
| Z | 4 | |
| Density (calculated) | 1.417 Mg/m$^3$ | |
| Absorption coefficient | 1.604 mm$^{-1}$ | |
| F(000) | 1608 | |
| Crystal size | 0.170 × 0.080 × 0.060 mm3 | |
| Theta range for data collection | 2.480 to 75.125°. | |
| Index ranges | −25 <= h <= 25, −10 <= k <= 10, −27 <= k <= 27 | |
| Reflections collected | 43859 | |
| Independent reflections | 7083 [R(int) = 0.0360] | |
| Completeness to theta = 67.000° | 100.0% | |
| Absorption correction | Gaussian | |
| Max. and min. transmission | 1.000 and 0.678 | |
| Refinement method | Full-matrix least-squares on F$^2$ | |
| Data/restraints/parameters | 7083/1/574 | |
| Goodness-of-fit on F2 | 1.082 | |
| Final R indices [I > 2sigma(I)] | R1 = 0.0333, wR2 = 0.0862 | |
| R indices (all data) | R1 = 0.0337, wR2 = 0.0864 | |
| Absolute structure parameter | 0.009(5) | |
| Extinction coefficient | 0.00053(7) | |
| Largest diff. peak and hole | 0.211 and −0.190 e.Å$^{-3}$ | |

TABLE 27

Atomic coordinates (×10$^4$) and equivalent isotropic displacement parameters (Å$^2$ × 10$^3$) for Compound A Form C. U(eq) is defined as one third of the trace of the orthogonalized $U^{ij}$ tensor.

| | x | y | z | U(eq) |
|---|---|---|---|---|
| C(1) | 3569(1) | 5187(3) | 6766(1) | 28(1) |
| C(2) | 3022(1) | 5959(3) | 6211(1) | 27(1) |
| C(3) | 2277(1) | 5656(3) | 5958(1) | 29(1) |
| C(4) | 1824(1) | 6453(3) | 5424(1) | 30(1) |
| C(5) | 2064(1) | 7612(3) | 5116(1) | 30(1) |
| C(6) | 2781(1) | 7942(3) | 5392(1) | 32(1) |
| C(7) | 3277(1) | 7176(3) | 5942(1) | 29(1) |
| C(8) | 4381(1) | 6963(3) | 6725(1) | 29(1) |
| C(9) | 2944(1) | 2666(3) | 6687(1) | 35(1) |
| C(10) | 3349(2) | 1165(4) | 6713(1) | 40(1) |
| C(11) | 4321(2) | 1985(4) | 7702(1) | 38(1) |

TABLE 27-continued

Atomic coordinates (×$10^4$) and equivalent isotropic displacement parameters ($Å^2$ × $10^3$) for Compound A Form C. U(eq) is defined as one third of the trace of the orthogonalized $U^{ij}$ tensor.

| | x | y | z | U(eq) |
|---|---|---|---|---|
| C(12) | 3936(2) | 3479(4) | 7725(1) | 37(1) |
| C(13) | 3534(2) | 3353(5) | 8168(2) | 51(1) |
| C(14) | 3665(2) | −542(4) | 7659(2) | 39(1) |
| C(15) | 4067(2) | −775(4) | 8372(2) | 48(1) |
| C(16) | 4021(2) | −2091(5) | 8648(2) | 56(1) |
| C(17) | 1612(1) | 8368(3) | 4481(1) | 29(1) |
| C(18) | 1315(1) | 9823(3) | 4409(1) | 31(1) |
| C(19) | 966(1) | 10437(4) | 3766(1) | 33(1) |
| C(20) | 914(1) | 9507(3) | 3251(1) | 33(1) |
| C(21) | 1218(1) | 8023(3) | 3356(1) | 30(1) |
| C(22) | 1342(2) | 10781(4) | 4979(1) | 38(1) |
| C(23) | 685(2) | 12064(4) | 3633(2) | 46(1) |
| C(24) | 5314(1) | 8584(4) | 6710(1) | 37(1) |
| C(25) | 6106(3) | 8603(6) | 6915(2) | 28(1) |
| C(26) | 6685(3) | 7468(7) | 6261(3) | 38(1) |
| C(27) | 7039(8) | 9033(17) | 6491(8) | 48(3) |
| C(28) | 6404(3) | 9875(7) | 6613(3) | 34(1) |
| C(29) | 6845(3) | 6234(7) | 7308(3) | 36(1) |
| C(30) | 5223(3) | 4190(6) | 6172(2) | 29(1) |
| C(31) | 4575(2) | 3362(5) | 5781(2) | 61(1) |
| C(24A) | 5314(1) | 8584(4) | 6710(1) | 37(1) |
| C(25A) | 5580(3) | 7619(6) | 6293(3) | 32(1) |
| C(26A) | 6541(4) | 9165(9) | 6316(5) | 44(2) |
| C(27A) | 6865(3) | 7775(8) | 6773(3) | 43(1) |
| C(28A) | 6236(10) | 6689(19) | 6628(9) | 38(3) |
| C(29A) | 5735(4) | 8081(8) | 5271(3) | 44(1) |
| C(24X) | 5314(1) | 8584(4) | 6710(1) | 37(1) |
| C(25X) | 6106(3) | 8603(6) | 6915(2) | 28(1) |
| C(26X) | 6685(3) | 7468(7) | 6261(3) | 38(1) |
| C(27X) | 6359(8) | 9077(16) | 5978(7) | 35(3) |
| C(28X) | 6404(3) | 9875(7) | 6613(3) | 34(1) |
| C(29X) | 6845(3) | 6234(7) | 7308(3) | 36(1) |
| C(30A) | 5080(4) | 2199(7) | 5921(3) | 43(1) |
| C(31A) | 4575(2) | 3362(5) | 5781(2) | 61(1) |
| C(32) | 4027(2) | 3718(4) | 5108(2) | 49(1) |
| C(33) | 3397(2) | 2605(4) | 4900(2) | 43(1) |
| C(34) | 2910(2) | 2681(5) | 4181(2) | 63(1) |
| C(35) | 2454(2) | 4099(4) | 3935(2) | 48(1) |
| N(1) | 3972(1) | 7681(3) | 6192(1) | 32(1) |
| N(2) | 4233(1) | 5756(3) | 7026(1) | 29(1) |
| N(3) | 3436(1) | 3900(3) | 7054(1) | 34(1) |
| N(4) | 3806(1) | 759(3) | 7383(1) | 38(1) |
| N(5) | 1573(1) | 7475(3) | 3971(1) | 29(1) |
| N(6) | 1184(1) | 7084(3) | 2865(1) | 38(1) |
| N(7) | 6365(8) | 7098(15) | 6742(7) | 35(2) |
| N(7A) | 5795(3) | 8759(6) | 5901(2) | 34(1) |
| N(7X) | 6365(8) | 7098(15) | 6742(7) | 35(2) |
| O(1) | 3208(1) | −1477(3) | 7332(1) | 48(1) |
| O(2) | 5072(1) | 7420(2) | 7032(1) | 34(1) |
| O(3) | 5233(2) | 5533(4) | 5952(2) | 35(1) |
| O(4) | 5711(2) | 3642(5) | 6664(2) | 39(1) |
| O(3A) | 4993(2) | 1157(5) | 5494(2) | 43(1) |
| O(4A) | 5551(3) | 2146(6) | 6493(2) | 62(1) |
| O(5) | 2368(2) | 4928(3) | 4384(1) | 54(1) |
| O(6) | 2169(1) | 4400(3) | 3354(1) | 60(1) |
| F(1) | 3028(1) | 9071(2) | 5121(1) | 45(1) |
| F(2) | 1703(1) | 12108(2) | 5040(1) | 54(1) |
| F(3) | 682(1) | 11204(3) | 4915(1) | 56(1) |
| F(4) | 1643(1) | 10074(2) | 5554(1) | 53(1) |
| Cl(1) | 906(1) | 6064(1) | 5100(1) | 38(1) |

TABLE 28

Bond lengths [A] and angles [°] for Compound A Form C.

| | | | |
|---|---|---|---|
| C(1)—N(2) | 1.334(3) | C(14)—C(15) | 1.482(4) |
| C(1)—N(3) | 1.364(4) | C(15)—C(16) | 1.315(5) |
| C(1)—C(2) | 1.455(3) | C(15)—H(15) | 0.9500 |
| C(2)—C(7) | 1.410(4) | C(16)—H(16A) | 0.9500 |
| C(2)—C(3) | 1.416(3) | C(16)—H(16B) | 0.9500 |
| C(3)—C(4) | 1.365(4) | C(17)—N(5) | 1.352(3) |
| C(3)—H(3) | 0.9500 | C(17)—C(18) | 1.375(4) |
| C(4)—C(5) | 1.409(4) | C(18)—C(19) | 1.425(4) |
| C(4)—Cl(1) | 1.747(3) | C(18)—C(22) | 1.501(4) |
| C(5)—C(6) | 1.369(4) | C(19)—C(20) | 1.370(4) |
| C(5)—C(17) | 1.496(3) | C(19)—C(23) | 1.500(4) |
| C(6)—F(1) | 1.348(3) | C(20)—C(21) | 1.401(4) |
| C(6)—C(7) | 1.404(4) | C(20)—H(20) | 0.9500 |
| C(7)—N(1) | 1.368(3) | C(21)—N(6) | 1.344(4) |
| C(8)—N(1) | 1.303(3) | C(21)—N(5) | 1.355(3) |
| C(8)—N(2) | 1.340(4) | C(22)—F(4) | 1.329(3) |
| C(8)—O(2) | 1.354(3) | C(22)—F(2) | 1.339(4) |
| C(9)—N(3) | 1.467(4) | C(22)—F(3) | 1.347(3) |
| C(9)—C(10) | 1.525(4) | C(23)—H(23A) | 0.9800 |
| C(9)—H(9A) | 0.9900 | C(23)—H(23B) | 0.9800 |
| C(9)—H(9B) | 0.9900 | C(23)—H(23C) | 0.9800 |
| C(10)—N(4) | 1.452(3) | C(24)—O(2) | 1.434(4) |
| C(10)—H(10A) | 0.9900 | C(24)—C(25) | 1.491(5) |
| C(10)—H(10B) | 0.9900 | C(24)—H(24A) | 0.9900 |
| C(11)—N(4) | 1.460(4) | C(24)—H(24B) | 0.9900 |
| C(11)—C(12) | 1.521(4) | C(25)—N(7) | 1.510(15) |
| C(11)—H(11A) | 0.9900 | C(25)—C(28) | 1.537(8) |
| C(11)—H(11B) | 0.9900 | C(25)—H(25) | 1.0000 |
| C(12)—N(3) | 1.480(3) | C(26)—N(7) | 1.499(17) |
| C(12)—C(13) | 1.522(4) | C(26)—C(27) | 1.521(18) |
| C(12)—H(12) | 1.0000 | C(26)—H(26A) | 0.9900 |
| C(13)—H(13A) | 0.9800 | C(26)—H(26B) | 0.9900 |
| C(13)—H(13B) | 0.9800 | C(27)—C(28) | 1.603(14) |
| C(13)—H(13C) | 0.9800 | C(27)—H(27A) | 0.9900 |
| C(14)—O(1) | 1.228(4) | C(27)—H(27B) | 0.9900 |
| C(14)—N(4) | 1.366(4) | C(28)—H(28A) | 0.9900 |

TABLE 28-continued

| Bond lengths [A] and angles [°] for Compound A Form C. | | | |
|---|---|---|---|
| C(28)—H(28B) | 0.9900 | C(25X)—C(28X) | 1.537(8) |
| C(29)—N(7) | 1.456(17) | C(25X)—H(25X) | 1.0000 |
| C(29)—H(29A) | 0.9800 | C(26X)—N(7X) | 1.499(17) |
| C(29)—H(29B) | 0.9800 | C(26X)—C(27X) | 1.560(16) |
| C(29)—H(29C) | 0.9800 | C(26X)—H(26E) | 0.9900 |
| C(30)—O(4) | 1.242(6) | C(26X)—H(26F) | 0.9900 |
| C(30)—O(3) | 1.263(7) | C(27X)—C(28X) | 1.546(14) |
| C(30)—C(31) | 1.448(7) | C(27X)—H(27E) | 0.9900 |
| C(31)—C(32) | 1.501(5) | C(27X)—H(27F) | 0.9900 |
| C(31)—H(31A) | 0.9900 | C(28X)—H(28E) | 0.9900 |
| C(31)—H(31B) | 0.9900 | C(28X)—H(28F) | 0.9900 |
| C(24A)—O(2) | 1.434(4) | C(29X)—N(7X) | 1.456(17) |
| C(24A)—C(25A) | 1.504(6) | C(29X)—H(29G) | 0.9800 |
| C(24A)—H(24C) | 0.9900 | C(29X)—H(29H) | 0.9800 |
| C(24A)—H(24D) | 0.9900 | C(29X)—H(291) | 0.9800 |
| C(25A)—C(28A) | 1.48(2) | C(30A)—O(4A) | 1.253(8) |
| C(25A)—N(7A) | 1.495(7) | C(30A)—O(3A) | 1.271(8) |
| C(25A)—H(25A) | 1.0000 | C(30A)—C(31A) | 1.383(8) |
| C(26A)—N(7A) | 1.470(9) | C(31A)—C(32) | 1.501(5) |
| C(26A)—C(27A) | 1.542(10) | C(31A)—H(31C) | 0.9900 |
| C(26A)—H(26C) | 0.9900 | C(31A)—H(31D) | 0.9900 |
| C(26A)—H(26D) | 0.9900 | C(32)—C(33) | 1.520(5) |
| C(27A)—C(28A) | 1.516(15) | C(32)—H(32A) | 0.9900 |
| C(27A)—H(27C) | 0.9900 | C(32)—H(32B) | 0.9900 |
| C(27A)—H(27D) | 0.9900 | C(33)—C(34) | 1.514(5) |
| C(28A)—H(28C) | 0.9900 | C(33)—H(33A) | 0.9900 |
| C(28A)—H(28D) | 0.9900 | C(33)—H(33B) | 0.9900 |
| C(29A)—N(7A) | 1.482(8) | C(34)—C(35) | 1.501(5) |
| C(29A)—H(29D) | 0.9800 | C(34)—H(34A) | 0.9900 |
| C(29A)—H(29E) | 0.9800 | C(34)—H(34B) | 0.9900 |
| C(29A)—H(29F) | 0.9800 | C(35)—O(6) | 1.219(4) |
| C(24X)—O(2) | 1.434(4) | C(35)—O(5) | 1.300(4) |
| C(24X)—C(25X) | 1.491(5) | N(6)—H(6A) | 0.8800 |
| C(24X)—H(24E) | 0.9900 | N(6)—H(6B) | 0.8800 |
| C(24X)—H(24F) | 0.9900 | N(7)—H(7) | 1.0000 |
| C(25X)—N(7X) | 1.510(15) | N(7A)—H(7A) | 1.0000 |
| N(7X)—H(7X) | 1.0000 | C(9)—C(10)—H(10B) | 109.4 |
| O(5)—H(5) | 0.8400 | H(10A)—C(10)—H(10B) | 108.0 |
| N(2)—C(1)—N(3) | 117.1(2) | N(4)—C(11)—C(12) | 110.5(2) |
| N(2)—C(1)—C(2) | 119.9(2) | N(4)—C(11)—H(11A) | 109.5 |
| N(3)—C(1)—C(2) | 123.0(2) | C(12)—C(11)—H(11A) | 109.5 |
| C(7)—C(2)—C(3) | 119.2(2) | N(4)—C(11)—H(11B) | 109.5 |
| C(7)—C(2)—C(1) | 114.6(2) | C(12)—C(11)—H(11B) | 109.5 |
| C(3)—C(2)—C(1) | 126.0(2) | H(11A)—C(11)—H(11B) | 108.1 |
| C(4)—C(3)—C(2) | 119.9(2) | N(3)—C(12)—C(11) | 109.2(2) |
| C(4)—C(3)—H(3) | 120.1 | N(3)—C(12)—C(13) | 110.2(2) |
| C(2)—C(3)—H(3) | 120.1 | C(11)—C(12)—C(13) | 112.4(3) |
| C(3)—C(4)—C(5) | 122.5(2) | N(3)—C(12)—H(12) | 108.3 |
| C(3)—C(4)—Cl(1) | 120.2(2) | C(11)—C(12)—H(12) | 108.3 |
| C(5)—C(4)—Cl(1) | 117.35(19) | C(13)—C(12)—H(12) | 108.3 |
| C(6)—C(5)—C(4) | 116.5(2) | C(12)—C(13)—H(13A) | 109.5 |
| C(6)—C(5)—C(17) | 118.4(2) | C(12)—C(13)—H(13B) | 109.5 |
| C(4)—C(5)—C(17) | 124.7(2) | H(13A)—C(13)—H(13B) | 109.5 |
| F(1)—C(6)—C(5) | 118.2(2) | C(12)—C(13)—H(13C) | 109.5 |
| F(1)—C(6)—C(7) | 117.7(2) | H(13A)—C(13)—H(13C) | 109.5 |
| C(5)—C(6)—C(7) | 124.1(2) | H(13B)—C(13)—H(13C) | 109.5 |
| N(1)—C(7)—C(6) | 118.2(2) | O(1)—C(14)—N(4) | 121.2(3) |
| N(1)—C(7)—C(2) | 124.2(2) | O(1)—C(14)—C(15) | 120.7(3) |
| C(6)—C(7)—C(2) | 117.6(2) | N(4)—C(14)—C(15) | 118.1(3) |
| N(1)—C(8)—N(2) | 129.5(2) | C(16)—C(15)—C(14) | 120.6(4) |
| N(1)—C(8)—O(2) | 118.6(2) | C(16)—C(15)—H(15) | 119.7 |
| N(2)—C(8)—O(2) | 111.8(2) | C(14)—C(15)—H(15) | 119.7 |
| N(3)—C(9)—C(10) | 110.9(2) | C(15)—C(16)—H(16A) | 120.0 |
| N(3)—C(9)—H(9A) | 109.5 | C(15)—C(16)—H(16B) | 120.0 |
| C(10)—C(9)—H(9A) | 109.5 | H(16A)—C(16)—H(16B) | 120.0 |
| N(3)—C(9)—H(9B) | 109.5 | N(5)—C(17)—C(18) | 123.2(2) |
| C(10)—C(9)—H(9B) | 109.5 | N(5)—C(17)—C(5) | 110.9(2) |
| H(9A)—C(9)—H(9B) | 108.1 | C(18)—C(17)—C(5) | 125.8(2) |
| N(4)—C(10)—C(9) | 110.9(2) | C(17)—C(18)—C(19) | 118.4(2) |
| N(4)—C(10)—H(10A) | 109.4 | C(17)—C(18)—C(22) | 122.6(2) |
| C(9)—C(10)—H(10A) | 109.4 | C(19)—C(18)—C(22) | 119.0(3) |
| N(4)—C(10)—H(10B) | 109.4 | C(20)—C(19)—C(18) | 117.9(3) |
| C(20)—C(19)—C(23) | 119.2(2) | C(27)—C(26)—H(26B) | 111.1 |
| C(18)—C(19)—C(23) | 122.9(3) | H(26A)—C(26)—H(26B) | 109.0 |
| C(19)—C(20)—C(21) | 121.0(2) | C(26)—C(27)—C(28) | 98.8(9) |
| C(19)—C(20)—H(20) | 119.5 | C(26)—C(27)—H(27A) | 112.0 |
| C(21)—C(20)—H(20) | 119.5 | C(28)—C(27)—H(27A) | 112.0 |
| N(6)—C(21)—N(5) | 116.7(3) | C(26)—C(27)—H(27B) | 112.0 |

TABLE 28-continued

| Bond lengths [A] and angles [°] for Compound A Form C. | | | |
|---|---|---|---|
| N(6)—C(21)—C(20) | 122.7(2) | C(28)—C(27)—H(27B) | 112.0 |
| N(5)—C(21)—C(20) | 120.6(2) | H(27A)—C(27)—H(27B) | 109.7 |
| F(4)—C(22)—F(2) | 105.8(2) | C(25)—C(28)—C(27) | 103.9(7) |
| F(4)—C(22)—F(3) | 106.3(2) | C(25)—C(28)—H(28A) | 111.0 |
| F(2)—C(22)—F(3) | 105.4(3) | C(27)—C(28)—H(28A) | 111.0 |
| F(4)—C(22)—C(18) | 114.4(3) | C(25)—C(28)—H(28B) | 111.0 |
| F(2)—C(22)—C(18) | 112.9(2) | C(27)—C(28)—H(28B) | 111.0 |
| F(3)—C(22)—C(18) | 111.4(2) | H(28A)—C(28)—H(28B) | 109.0 |
| C(19)—C(23)—H(23A) | 109.5 | N(7)—C(29)—H(29A) | 109.5 |
| C(19)—C(23)—H(23B) | 109.5 | N(7)—C(29)—H(29B) | 109.5 |
| H(23A)—C(23)—H(23B) | 109.5 | H(29A)—C(29)—H(29B) | 109.5 |
| C(19)—C(23)—H(23C) | 109.5 | N(7)—C(29)—H(29C) | 109.5 |
| H(23A)—C(23)—H(23C) | 109.5 | H(29A)—C(29)—H(29C) | 109.5 |
| H(23B)—C(23)—H(23C) | 109.5 | H(29B)—C(29)—H(29C) | 109.5 |
| O(2)—C(24)—C(25) | 113.8(3) | O(4)—C(30)—O(3) | 124.2(5) |
| O(2)—C(24)—H(24A) | 108.8 | O(4)—C(30)—C(31) | 124.0(5) |
| C(25)—C(24)—H(24A) | 108.8 | O(3)—C(30)—C(31) | 111.8(4) |
| O(2)—C(24)—H(24B) | 108.8 | C(30)—C(31)—C(32) | 129.4(4) |
| C(25)—C(24)—H(24B) | 108.8 | C(30)—C(31)—H(31A) | 104.9 |
| H(24A)—C(24)—H(24B) | 107.7 | C(32)—C(31)—H(31A) | 104.9 |
| C(24)—C(25)—N(7) | 111.0(6) | C(30)—C(31)—H(31B) | 104.9 |
| C(24)—C(25)—C(28) | 116.3(4) | C(32)—C(31)—H(31B) | 104.9 |
| N(7)—C(25)—C(28) | 105.1(7) | H(31A)—C(31)—H(31B) | 105.8 |
| C(24)—C(25)—H(25) | 108.0 | O(2)—C(24A)—C(25A) | 101.9(3) |
| N(7)—C(25)—H(25) | 108.0 | O(2)—C(24A)—H(24C) | 111.4 |
| C(28)—C(25)—H(25) | 108.0 | C(25A)—C(24A)—H(24C) | 111.4 |
| N(7)—C(26)—C(27) | 103.4(7) | O(2)—C(24A)—H(24D) | 111.4 |
| N(7)—C(26)—H(26A) | 111.1 | C(25A)—C(24A)—H(24D) | 111.4 |
| C(27)—C(26)—H(26A) | 111.1 | H(24C)—C(24A)—H(24D) | 109.2 |
| N(7)—C(26)—H(26B) | 111.1 | C(28A)—C(25A)—N(7A) | 103.7(8) |
| C(28A)—C(25A)—C(24A) | 117.6(8) | C(24X)—C(25X)—C(28X) | 116.3(4) |
| N(7A)—C(25A)—C(24A) | 105.2(4) | N(7X)—C(25X)—C(28X) | 105.1(7) |
| C(28A)—C(25A)—H(25A) | 110.0 | C(24X)—C(25X)—H(25X) | 108.0 |
| N(7A)—C(25A)—H(25A) | 110.0 | N(7X)—C(25X)—H(25X) | 108.0 |
| C(24A)—C(25A)—H(25A) | 110.0 | C(28X)—C(25X)—H(25X) | 108.0 |
| N(7A)—C(26A)—C(27A) | 107.0(5) | N(7X)—C(26X)—C(27X) | 104.0(9) |
| N(7A)—C(26A)—H(26C) | 110.3 | N(7X)—C(26X)—H(26E) | 110.9 |
| C(27A)—C(26A)—H(26C) | 110.3 | C(27X)—C(26X)—H(26E) | 110.9 |
| N(7A)—C(26A)—H(26D) | 110.3 | N(7X)—C(26X)—H(26F) | 110.9 |
| C(27A)—C(26A)—H(26D) | 110.3 | C(27X)—C(26X)—H(26F) | 110.9 |
| H(26C)—C(26A)—H(26D) | 108.6 | H(26E)—C(26X)—H(26F) | 109.0 |
| C(28A)—C(27A)—C(26A) | 103.8(9) | C(28X)—C(27X)—C(26X) | 99.6(9) |
| C(28A)—C(27A)—H(27C) | 111.0 | C(28X)—C(27X)—H(27E) | 111.9 |
| C(26A)—C(27A)—H(27C) | 111.0 | C(26X)—C(27X)—H(27E) | 111.9 |
| C(28A)—C(27A)—H(27D) | 111.0 | C(28X)—C(27X)—H(27F) | 111.9 |
| C(26A)—C(27A)—H(27D) | 111.0 | C(26X)—C(27X)—H(27F) | 111.9 |
| H(27C)—C(27A)—H(27D) | 109.0 | H(27E)—C(27X)—H(27F) | 109.6 |
| C(25A)—C(28A)—C(27A) | 106.7(11) | C(25X)—C(28X)—C(27X) | 101.4(6) |
| C(25A)—C(28A)—H(28C) | 110.4 | C(25X)—C(28X)—H(28E) | 111.5 |
| C(27A)—C(28A)—H(28C) | 110.4 | C(27X)—C(28X)—H(28E) | 111.5 |
| C(25A)—C(28A)—H(28D) | 110.4 | C(25X)—C(28X)—H(28F) | 111.5 |
| C(27A)—C(28A)—H(28D) | 110.4 | C(27X)—C(28X)—H(28F) | 111.5 |
| H(28C)—C(28A)—H(28D) | 108.6 | H(28E)—C(28X)—H(28F) | 109.3 |
| N(7A)—C(29A)—H(29D) | 109.5 | N(7X)—C(29X)—H(29G) | 109.5 |
| N(7A)—C(29A)—H(29E) | 109.5 | N(7X)—C(29X)—H(29H) | 109.5 |
| H(29D)—C(29A)—H(29E) | 109.5 | H(29G)—C(29X)—H(29H) | 109.5 |
| N(7A)—C(29A)—H(29F) | 109.5 | N(7X)—C(29X)—H(291) | 109.5 |
| H(29D)—C(29A)—H(29F) | 109.5 | H(29G)—C(29X)—H(291) | 109.5 |
| H(29E)—C(29A)—H(29F) | 109.5 | H(29H)—C(29X)—H(291) | 109.5 |
| O(2)—C(24X)—C(25X) | 113.8(3) | O(4A)—C(30A)—O(3A) | 124.0(6) |
| O(2)—C(24X)—H(24E) | 108.8 | O(4A)—C(30A)—C(31A) | 116.9(5) |
| C(25X)—C(24X)—H(24E) | 108.8 | O(3A)—C(30A)—C(31A) | 118.5(6) |
| O(2)—C(24X)—H(24F) | 108.8 | C(30A)—C(31A)—C(32) | 124.2(4) |
| C(25X)—C(24X)—H(24F) | 108.8 | C(30A)—C(31A)—H(31C) | 106.3 |
| H(24E)—C(24X)—H(24F) | 107.7 | C(32)—C(31A)—H(31C) | 106.3 |
| C(24X)—C(25X)—N(7X) | 111.0(6) | C(30A)—C(31A)—H(31D) | 106.3 |
| C(32)—C(31A)—H(31D) | 106.3 | C(14)—N(4)—C(10) | 120.0(3) |
| H(31C)—C(31A)—H(31D) | 106.4 | C(14)—N(4)—C(11) | 128.0(2) |
| C(31A)—C(32)—C(33) | 112.0(3) | C(10)—N(4)—C(11) | 111.5(2) |
| C(31)—C(32)—C(33) | 112.0(3) | C(17)—N(5)—C(21) | 118.8(2) |
| C(31)—C(32)—H(32A) | 109.2 | C(21)—N(6)—H(6A) | 120.0 |
| C(33)—C(32)—H(32A) | 109.2 | C(21)—N(6)—H(6B) | 120.0 |
| C(31)—C(32)—H(32B) | 109.2 | H(6A)—N(6)—H(6B) | 120.0 |
| C(33)—C(32)—H(32B) | 109.2 | C(29)—N(7)—C(26) | 113.4(11) |
| H(32A)—C(32)—H(32B) | 107.9 | C(29)—N(7)—C(25) | 113.6(9) |
| C(34)—C(33)—C(32) | 114.3(3) | C(26)—N(7)—C(25) | 107.4(9) |
| C(34)—C(33)—H(33A) | 108.7 | C(29)—N(7)—H(7) | 107.4 |
| C(32)—C(33)—H(33A) | 108.7 | C(26)—N(7)—H(7) | 107.4 |

TABLE 28-continued

Bond lengths [A] and angles [°] for Compound A Form C.

| | | | |
|---|---|---|---|
| C(34)—C(33)—H(33B) | 108.7 | C(25)—N(7)—H(7) | 107.4 |
| C(32)—C(33)—H(33B) | 108.7 | C(26A)—N(7A)—C(29A) | 111.2(6) |
| H(33A)—C(33)—H(33B) | 107.6 | C(26A)—N(7A)—C(25A) | 105.0(5) |
| C(35)—C(34)—C(33) | 118.0(3) | C(29A)—N(7A)—C(25A) | 111.4(5) |
| C(35)—C(34)—H(34A) | 107.8 | C(26A)—N(7A)—H(7A) | 109.7 |
| C(33)—C(34)—H(34A) | 107.8 | C(29A)—N(7A)—H(7A) | 109.7 |
| C(35)—C(34)—H(34B) | 107.8 | C(25A)—N(7A)—H(7A) | 109.7 |
| C(33)—C(34)—H(34B) | 107.8 | C(29X)—N(7X)—C(26X) | 113.4(11) |
| H(34A)—C(34)—H(34B) | 107.1 | C(29X)—N(7X)—C(25X) | 113.6(9) |
| O(6)—C(35)—O(5) | 123.4(3) | C(26X)—N(7X)—C(25X) | 107.4(9) |
| O(6)—C(35)—C(34) | 121.6(3) | C(29X)—N(7X)—H(7X) | 107.4 |
| O(5)—C(35)—C(34) | 115.0(3) | C(26X)—N(7X)—H(7X) | 107.4 |
| C(8)—N(1)—C(7) | 113.6(2) | C(25X)—N(7X)—H(7X) | 107.4 |
| C(1)—N(2)—C(8) | 117.6(2) | C(8)—O(2)—C(24X) | 116.7(2) |
| C(1)—N(3)—C(9) | 123.3(2) | C(8)—O(2)—C(24) | 116.7(2) |
| C(1)—N(3)—C(12) | 119.4(2) | C(8)—O(2)—C(24A) | 116.7(2) |
| C(9)—N(3)—C(12) | 115.2(2) | C(35)—O(5)—H(5) | 109.5 |

TABLE 29

Anisotropic displacement parameters ($Å^2 \times 10^3$)for Compound A Form C. The anisotropic displacement factor exponent takes the form: $-2\pi^2[h^2a^{*2}U^{11} + \ldots + 2\ h\ k\ a^*\ b^*\ U^{12}]$.

| | U11 | U22 | U33 | U23 | U13 | U12 |
|---|---|---|---|---|---|---|
| C(1) | 26(1) | 36(1) | 22(1) | −2(1) | 9(1) | 0(1) |
| C(2) | 25(1) | 36(1) | 20(1) | −1(1) | 9(1) | 1(1) |
| C(3) | 24(1) | 39(1) | 25(1) | −2(1) | 11(1) | −3(1) |
| C(4) | 22(1) | 43(2) | 25(1) | −2(1) | 8(1) | −2(1) |
| C(5) | 26(1) | 41(1) | 20(1) | 1(1) | 7(1) | 2(1) |
| C(6) | 27(1) | 46(2) | 22(1) | 4(1) | 8(1) | −6(1) |
| C(7) | 23(1) | 43(1) | 21(1) | 1(1) | 8(1) | −2(1) |
| C(8) | 21(1) | 39(1) | 23(1) | −6(1) | 6(1) | −1(1) |
| C(9) | 28(1) | 41(2) | 28(1) | 3(1) | 4(1) | −4(1) |
| C(10) | 41(1) | 41(2) | 30(1) | 3(1) | 7(1) | −2(1) |
| C(11) | 29(1) | 53(2) | 28(1) | 8(1) | 9(1) | −2(1) |
| C(12) | 35(1) | 45(2) | 24(1) | 4(1) | 4(1) | −2(1) |
| C(13) | 48(2) | 73(2) | 29(2) | 3(2) | 13(1) | 10(2) |
| C(14) | 39(2) | 39(2) | 43(2) | 6(1) | 20(1) | 6(1) |
| C(15) | 43(2) | 59(2) | 44(2) | 18(2) | 18(1) | 8(2) |
| C(16) | 46(2) | 71(2) | 61(2) | 28(2) | 32(2) | 17(2) |
| C(17) | 22(1) | 43(2) | 20(1) | −1(1) | 6(1) | −1(1) |
| C(18) | 25(1) | 43(2) | 21(1) | −3(1) | 5(1) | 2(1) |
| C(19) | 26(1) | 47(2) | 24(1) | 1(1) | 7(1) | 5(1) |
| C(20) | 29(1) | 44(2) | 21(1) | 0(1) | 5(1) | 1(1) |
| C(21) | 26(1) | 41(1) | 22(1) | 1(1) | 6(1) | −2(1) |
| C(22) | 33(1) | 52(2) | 24(1) | −2(1) | 7(1) | 9(1) |
| C(23) | 46(2) | 53(2) | 31(1) | −1(1) | 8(1) | 17(2) |
| C(24) | 27(1) | 42(2) | 40(2) | −8(1) | 11(1) | −8(1) |
| C(25) | 22(2) | 31(2) | 27(2) | −1(2) | 6(2) | −2(2) |
| C(26) | 43(3) | 44(3) | 33(3) | −3(2) | 22(2) | −2(3) |
| C(27) | 35(7) | 59(9) | 63(8) | 18(7) | 32(7) | 12(6) |
| C(28) | 32(3) | 35(3) | 37(3) | −4(3) | 16(2) | −5(2) |
| C(29) | 30(2) | 39(3) | 35(3) | 4(2) | 10(2) | 3(2) |
| C(30) | 30(2) | 33(3) | 23(2) | −1(2) | 9(2) | 4(2) |
| C(31) | 45(2) | 75(3) | 57(2) | −23(2) | 16(2) | 3(2) |
| C(24A) | 27(1) | 42(2) | 40(2) | −8(1) | 11(1) | −8(1) |
| C(25A) | 33(3) | 29(3) | 34(3) | −4(2) | 14(2) | −6(2) |
| C(26A) | 36(5) | 45(4) | 47(5) | 5(4) | 13(4) | −15(3) |
| C(27A) | 29(3) | 44(3) | 49(4) | 4(3) | 7(3) | −1(3) |
| C(28A) | 25(6) | 45(8) | 42(7) | 5(5) | 11(5) | −3(5) |
| C(29A) | 51(3) | 42(3) | 37(3) | −8(3) | 16(3) | −8(3) |
| C(24X) | 27(1) | 42(2) | 40(2) | −8(1) | 11(1) | −8(1) |
| C(25X) | 22(2) | 31(2) | 27(2) | −1(2) | 6(2) | −2(2) |
| C(26X) | 43(3) | 44(3) | 33(3) | −3(2) | 22(2) | −2(3) |
| C(27X) | 44(9) | 37(6) | 23(6) | −4(6) | 13(6) | −5(6) |
| C(28X) | 32(3) | 35(3) | 37(3) | −4(3) | 16(2) | −5(2) |
| C(29X) | 30(2) | 39(3) | 35(3) | 4(2) | 10(2) | 3(2) |
| C(30A) | 64(4) | 37(3) | 38(3) | −3(3) | 31(3) | −5(3) |
| C(31A) | 45(2) | 75(3) | 57(2) | −23(2) | 16(2) | 3(2) |
| C(32) | 46(2) | 35(2) | 68(2) | 13(2) | 26(2) | 6(1) |
| C(33) | 43(2) | 35(2) | 49(2) | 3(1) | 16(1) | 6(1) |
| C(34) | 58(2) | 62(2) | 53(2) | −19(2) | 5(2) | 20(2) |
| C(35) | 47(2) | 55(2) | 38(2) | −8(1) | 12(1) | 12(2) |

TABLE 29-continued

Anisotropic displacement parameters ($Å^2 \times 10^3$)for Compound A Form C. The anisotropic displacement factor exponent takes the form: $-2\pi^2[h^2a^{*2}U^{11} + \ldots + 2\ h\ k\ a^*\ b^*\ U^{12}]$.

| | U11 | U22 | U33 | U23 | U13 | U12 |
|---|---|---|---|---|---|---|
| N(1) | 22(1) | 51(1) | 21(1) | −1(1) | 6(1) | −4(1) |
| N(2) | 24(1) | 35(1) | 26(1) | −1(1) | 7(1) | 2(1) |
| N(3) | 31(1) | 40(1) | 24(1) | 2(1) | 4(1) | −3(1) |
| N(4) | 38(1) | 41(1) | 30(1) | 6(1) | 7(1) | −1(1) |
| N(5) | 25(1) | 39(1) | 22(1) | 0(1) | 7(1) | 0(1) |
| N(6) | 42(1) | 44(1) | 22(1) | −3(1) | 6(1) | 3(1) |
| N(7) | 21(5) | 43(6) | 36(5) | −1(4) | 8(4) | −4(4) |
| N(7A) | 34(3) | 36(2) | 32(2) | −3(2) | 12(2) | −6(2) |
| N(7X) | 21(5) | 43(6) | 36(5) | −1(4) | 8(4) | −4(4) |
| ○(1) | 50(1) | 41(1) | 56(1) | 4(1) | 23(1) | −3(1) |
| ?(2) | 23(1) | 41(1) | 33(1) | −2(1) | 4(1) | −2(1) |
| O(3) | 34(2) | 33(2) | 30(2) | 0(2) | 5(2) | −1(2) |
| O(4) | 43(2) | 41(2) | 24(2) | 5(2) | 4(2) | 7(2) |
| O(3A) | 53(2) | 39(2) | 35(2) | −4(2) | 17(2) | −2(2) |
| O(4A) | 97(4) | 44(3) | 37(2) | −1(2) | 18(3) | 1(3) |
| O(5) | 71(2) | 54(1) | 35(1) | 2(1) | 18(1) | 29(1) |
| O(6) | 58(1) | 81(2) | 35(1) | −7(1) | 12(1) | 26(1) |
| F(1) | 31(1) | 68(1) | 29(1) | 15(1) | 3(1) | −14(1) |
| F(2) | 62(1) | 53(1) | 43(1) | −18(1) | 16(1) | −7(1) |
| F(3) | 38(1) | 89(2) | 40(1) | −15(1) | 13(1) | 18(1) |
| F(4) | 67(1) | 65(1) | 20(1) | 0(1) | 12(1) | 20(1) |
| Cl(1) | 20(1) | 58(1) | 33(1) | 5(1) | 7(1) | −1(1) |

TABLE 30

Hydrogen coordinates ($\times 10^4$) and isotropic displacement parameters ($Å^2 \times 10^3$) for Compound A Form C.

| | x | y | z | U(eq) |
|---|---|---|---|---|
| H(3) | 2094 | 4900 | 6159 | 35 |
| H(9A) | 2686 | 2991 | 6226 | 41 |
| H(9B) | 2585 | 2488 | 6875 | 41 |
| H(10A) | 3003 | 318 | 6513 | 47 |
| H(10B) | 3645 | 1290 | 6458 | 47 |
| H(11A) | 4627 | 2163 | 7459 | 45 |
| H(11B) | 4633 | 1662 | 8152 | 45 |
| H(12) | 4301 | 4321 | 7896 | 45 |
| H(13A) | 3300 | 4343 | 8170 | 76 |
| H(13B) | 3872 | 3101 | 8613 | 76 |
| H(13C) | 3172 | 2535 | 8006 | 76 |
| H(15) | 4360 | 34 | 8631 | 58 |
| H(16A) | 3729 | −2904 | 8391 | 67 |
| H(16B) | 4281 | −2230 | 9105 | 67 |
| H(20) | 667 | 9873 | 2817 | 40 |
| H(23A) | 371 | 12255 | 3860 | 69 |
| H(23B) | 415 | 12205 | 3162 | 69 |

TABLE 30-continued

Hydrogen coordinates (×$10^4$) and isotropic displacement parameters ($Å^2 \times 10^3$) for Compound A Form C.

| | x | y | z | U(eq) |
|---|---|---|---|---|
| H(23C) | 1087 | 12794 | 3790 | 69 |
| H(24A) | 5159 | 9612 | 6800 | 44 |
| H(24B) | 5083 | 8408 | 6232 | 44 |
| H(25) | 6334 | 8724 | 7401 | 3 |
| H(26A) | 6310 | 7535 | 5811 | 45 |
| H(26B) | 7041 | 6676 | 6273 | 45 |
| H(27A) | 7151 | 9561 | 6150 | 58 |
| H(27B) | 7479 | 8946 | 6897 | 58 |
| H(28A) | 6587 | 10761 | 6916 | 41 |
| H(28B) | 6031 | 10253 | 6197 | 41 |
| H(29A) | 7274 | 6855 | 7546 | 54 |
| H(29B) | 6984 | 5264 | 7163 | 54 |
| H(29C) | 6601 | 6002 | 7597 | 54 |
| H(31A) | 4300 | 3303 | 6059 | 73 |
| H(31B) | 4732 | 2290 | 5753 | 73 |
| H(24C) | 5704 | 9215 | 7028 | 44 |
| H(24D) | 4918 | 9273 | 6440 | 44 |
| H(25A) | 5186 | 6942 | 5995 | 38 |
| H(26C) | 6557 | 10107 | 6574 | 53 |
| H(26D) | 6812 | 9367 | 6043 | 53 |
| H(27C) | 7247 | 7275 | 6675 | 52 |
| H(27D) | 7066 | 8103 | 7237 | 52 |
| H(28C) | 6258 | 5826 | 6345 | 45 |
| H(28D) | 6240 | 6248 | 7039 | 45 |
| H(29D) | 6112 | 7305 | 5353 | 66 |
| H(29E) | 5788 | 8902 | 4991 | 66 |
| H(29F) | 5266 | 7589 | 5053 | 66 |
| H(24E) | 5159 | 9612 | 6800 | 44 |
| H(24F) | 5083 | 8408 | 6232 | 44 |
| H(25X) | 6334 | 8724 | 7401 | 33 |
| H(26E) | 6551 | 6676 | 5911 | 45 |
| H(26F) | 7213 | 7526 | 6480 | 45 |
| H(27E) | 6648 | 9625 | 5780 | 42 |
| H(27F) | 5858 | 8986 | 5653 | 42 |
| H(28E) | 6903 | 10143 | 6901 | 41 |
| H(28F) | 6105 | 10822 | 6518 | 41 |
| H(29G) | 6606 | 6030 | 7603 | 54 |
| H(29H) | 6972 | 5249 | 7164 | 54 |
| H(291) | 7280 | 6841 | 7539 | 54 |
| H(31C) | 4843 | 4335 | 5948 | 73 |
| H(31D) | 4304 | 3155 | 6055 | 73 |
| H(32A) | 4255 | 3655 | 4793 | 58 |
| H(32B) | 3851 | 4790 | 5100 | 58 |
| H(33A) | 3583 | 1536 | 5007 | 52 |
| H(33B) | 3112 | 2832 | 5159 | 52 |
| H(34A) | 3211 | 2570 | 3929 | 76 |
| H(34B) | 2587 | 1771 | 4077 | 76 |
| H(6A) | 1386 | 6164 | 2951 | 45 |
| H(6B) | 959 | 7389 | 2457 | 45 |
| H(7) | 5935 | 6435 | 6512 | 42 |
| H(7A) | 5487 | 9704 | 5816 | 41 |
| H(7X) | 5935 | 6435 | 6512 | 42 |
| H(5) | 2083 | 5659 | 4208 | 82 |

Similarly to Compound A Form D, the carboxylic group of the adipate forms a heterodimer with the API molecule through the O—H . . . N and O—H . . . N intramolecular interactions. The hydrogen H6A of amine N6 forms one intermolecular N—H . . . O bond to either O3 or O3A oxygen atoms of positionally disordered —COO— group of the adipate anion (50/50). Additionally, the nitrogen atom N7 of one component of positionally disordered 1-methylpyrrolidine is involved in one N—H . . . O intermolecular interaction to oxygen O4 of also disordered —COO— group of adipate. Nitrogen N7A of the second component is hydrogen bonded to the analogous oxygen O4A. There appear to be no further hydrogen bonding interactions and as such the crystal structure packing is further stabilised by Van der Waals interactions only.

Figure 23:
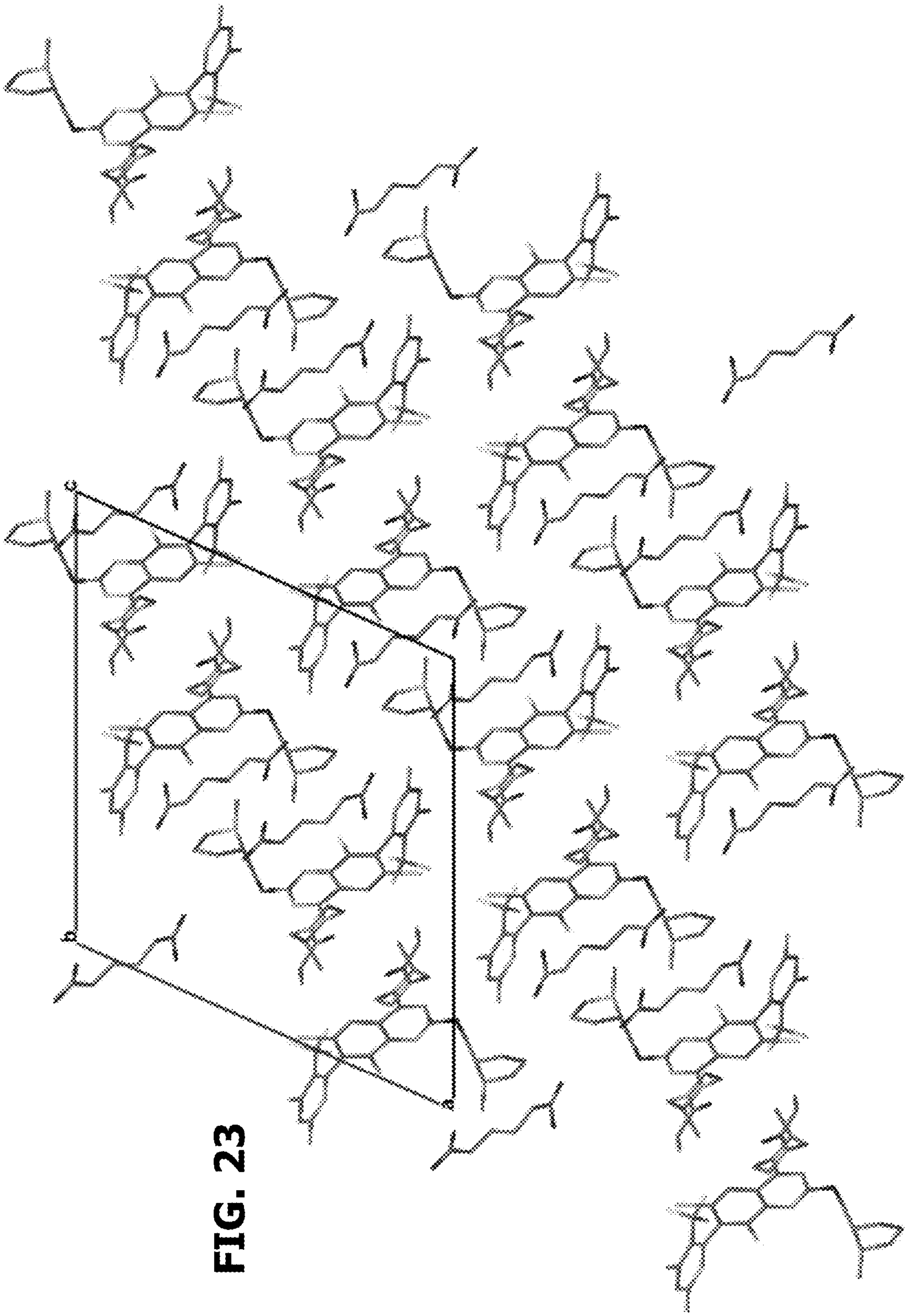
FIG. 23 depicts a view of the crystal packing of Form C looking down the crystallographic b-axis. Only major components of disorder are shown.
Figure 24:
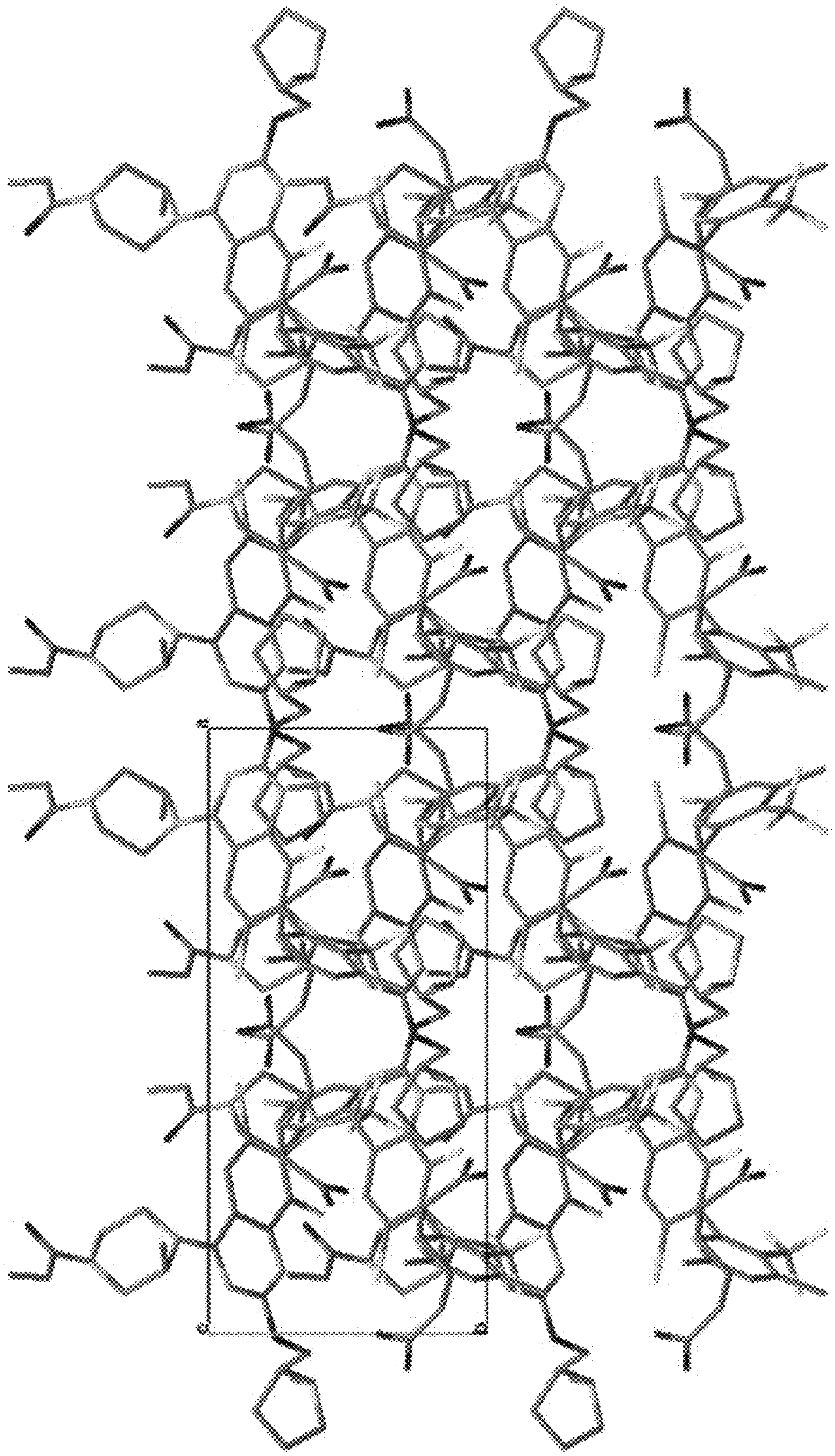
FIG. 24 depicts a view of the crystal packing of Form C looking down the crystallographic c-axis. Only major components of disorder are shown.
Figure 25:
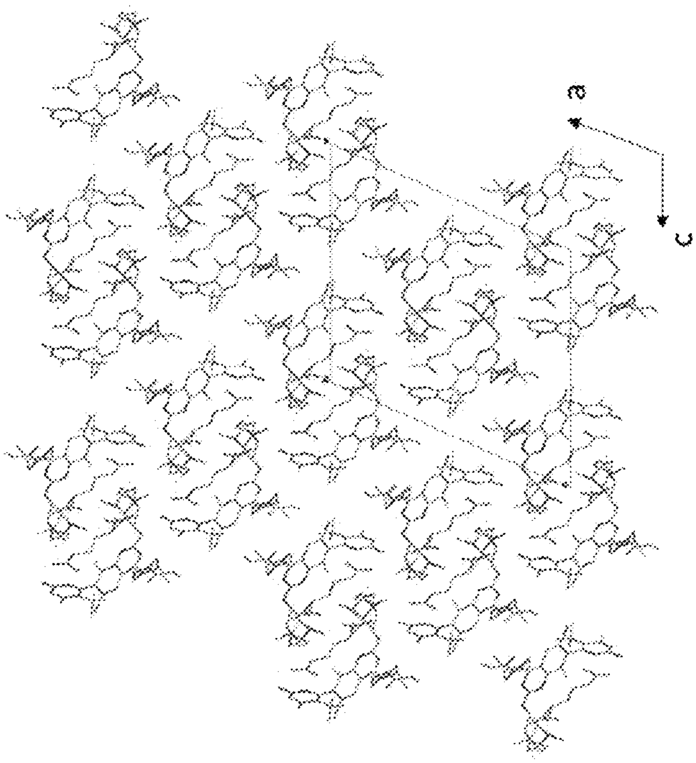
FIG. 25 depicts a comparison of crystal packing between hydrated Form D and anhydrous Form C, viewed down crystallographic b-axis.
Figure 25:
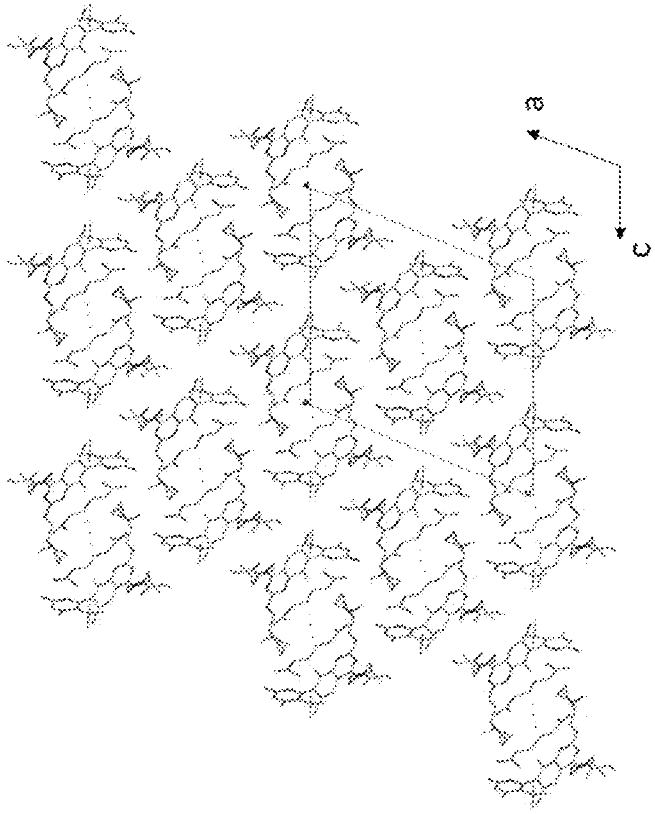

Views of the crystal packing within the unit cell can be seen in FIG. 23 and FIG. 24. A comparison of the crystal packing of Compound A Form C and Compound A Form D is shown in FIG. 25. For clarity all hydrogen atoms have been removed from packing diagrams.

Example 6—Compound B Form A

Compound B Form A was obtained from an acetone system and the sample was air dried at RT. No form change was observed before and after drying (FIG. 11). A weight loss of 0.7% up to 100° C. was observed in TGA and DSC result showed one endotherm at 53.8° C. (peak temperature) before the possible overlapped peak with peak temperature at 156.3° C. (FIG. 12). Based on the integrals, the stoichiometric ratio of fumaric acid:freebase was determined to be 1.03. A peak of acetone was observed and approximately 0.49 molar acetone (4.4 wt %) was detected. The HPLC purity of Compound B Form A was determined to be 93.56 area %. After heating Compound B Form A to 100° C. under N2 protection, cooled down and exposed to ambient conditions, no form change was observed before and after heating. Peak of acetone was observed in the heated sample. Around 0.39 molar acetone (3.5 wt %) was still detected. One endotherm at 58.7° C. and an overlapped peak with peak temperature at 157.1° C. were still observed on the sample obtained after heating. The first endotherm might be caused by re-adsorption of moisture. Since ~3.5 wt % acetone was still detected from NMR, Compound B Form A is expected to be an acetone/$H_2O$ co-solvate.

Example 7—Compound C Form A

Compound C Form A was obtained from EtOAc system and the sample was air dried at RT. No form change was observed before and after drying (FIG. 13). A weight loss of 8.6% up to 100° C. was observed in TGA and two endotherms at 81.0° C. and 149.2° C. (peak temperature) were observed in DSC curve (FIG. 14). HPLC purity of Compound C Form A was determined to be 95.18 area %.

Example 8—Compound D Form A

Compound D Form A was obtained from evaporation of acetone/n-heptane (1:1, v/v) solution. The XRPD result is displayed in FIG. 15. A weight loss of 7.7% was observed up to 170° C. in TGA, and DSC result (FIG. 16) showed one endotherm at 75.8° C. (peak temperature). Based on the integrals by NMR analysis, the stoichiometric ratio of benzenesulfonic acid:freebase was determined to be 1.03. Peak of acetone was observed. Around 0.30 molar acetone (2.7 wt %) was detected. HPLC purity of Compound D Form A was determined to be 96.23 area %.

Example 9: Compound E Form A

Compound E Form A was obtained from acetone system. The XRPD spectrum overlay is shown in FIG. 17. Limited solids were observed after stirring at 5° C. During XRPD test, it was observed that the sample tended to absorb moisture and turn to liquid. The suspension was transferred to −20° C., but limited solids were still observed. Anti-solvent (n-heptane) was added and the sample was transferred to 5° C. However, gel was obtained.

Example 10: Compound F Form A

Figure 26:
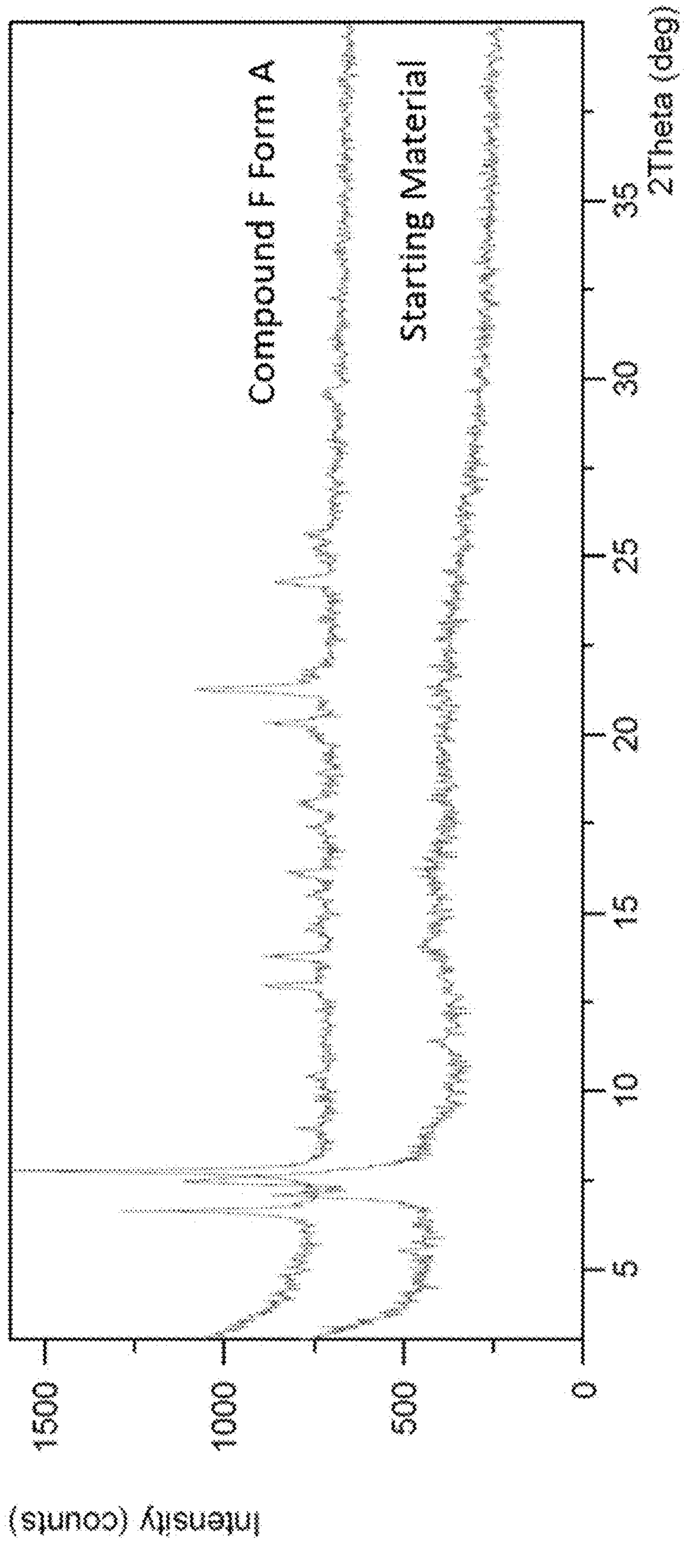
FIG. 26 depicts the XRPD spectrum overlay of Compound F Form A.

Compound F Form A (810935-03-A2) was obtained from acetone/n-heptane (1:1, v/v) system by evaporation at RT (FIG. 26).

Figure 27:
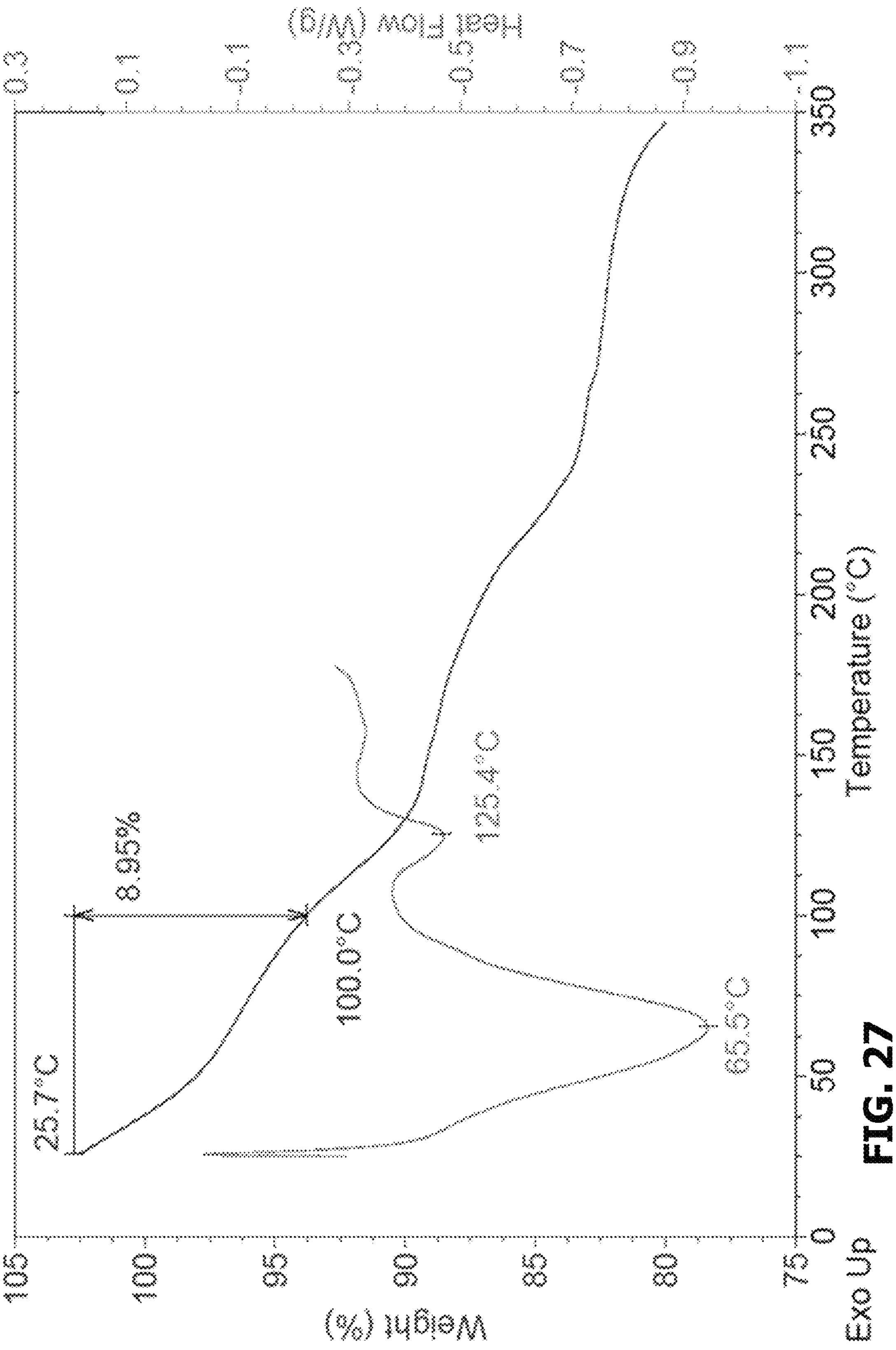
FIG. 27 depicts a TGA thermogram and DSC thermogram overlap for Compound F Form A.

A weight loss of 9.0% up to 100° C. was observed in TGA and DSC result showed two endotherms at 65.5° C. and 125.4° C. (peak temperature) (FIG. 27).

Based on the integrals, the stoichiometric ratio of acetic acid:freebase was determined to be 0.69. Peak of acetone was observed. Around 0.16 molar acetone (1.5 wt %) was detected. The purity of Compound F Form A was 88.42 area %.

After heating Compound F Form A to 100° C. under N2 protection, cooled down and exposed to ambient conditions, no form change was observed. Two broad DSC endotherms at 64.2° C. and 124.2° C. (peak temperature) were still observed on the sample obtained after heating, suggesting the re-adsorption of moisture. Since no form change was observed after heating, Compound F Form A is likely a hydrate.

TABLE 31

Representative XRPD Peaks for Compound F Form A.

| Pos. [°2θ] | d-spacing [Å] | Rel. Int. [%] |
|---|---|---|
| 6.6132 | 13.35494 | 55.67 |
| 7.7347 | 11.42087 | 100 |
| 8.9607 | 9.86079 | 6.47 |
| 10.3787 | 8.51654 | 4.48 |
| 12.9417 | 6.83509 | 21.07 |
| 13.7826 | 6.41992 | 16.86 |
| 14.5599 | 6.07887 | 4.79 |
| 16.0886 | 5.50455 | 12.29 |
| 17.4322 | 5.08318 | 4.97 |
| 18.0779 | 4.90307 | 9.75 |
| 20.3112 | 4.36871 | 20.73 |
| 21.2392 | 4.17987 | 43.46 |
| 24.2764 | 3.66337 | 20.25 |
| 25.6495 | 3.47029 | 8.21 |
| 29.6647 | 3.00907 | 5.28 |

Example 10—Freebase Screening Procedure

The solubility of starting material was estimated at RT in 20 solvents. For each experiment, approximately 2 mg of sample was added into a 3-mL glass vial. Solvents in Table 32 were then added stepwise (50, 50, 200, 700 μL) into the vials until the solids were dissolved visually or a total volume of 1 mL was reached. Solubility results are summarized in Table 5-11 and were used to guide the solvent selection in salt screening and crystal form screening.

TABLE 32

Approximate solubility of starting material at RT

| Solvent | Solubility (mg/mL) | Solvent | Solubility (mg/mL) |
|---|---|---|---|
| MeOH | S > 42.0 | 1,4-Dioxane | S > 38.0 |
| EtOH | 7.0 < S < 21.0 | ACN | 6.7 < S < 20.0 |
| IPA | 2.1 < S < 7.0 | MTBE | 2.2 < S < 7.3 |
| Acetone | S > 40.0 | n-Heptane | S < 2.0 |
| MEK | S > 46.0 | Toluene | S > 40.0 |
| EtOAc | S > 40.0 | DMSO | S > 38.0 |
| IPAc | S > 40.0 | $H_2O$ | S < 2.1 |
| MIBK | S > 42.0 | DCM | S > 38.0 |
| THF | S > 44.0 | CPME | S > 40.0 |
| 2-MeTHF | S > 40.0 | Anisole | S > 38.0 |

A total of 64 polymorph screening experiments were performed for freebase Compound 1 using the sample received as starting material through different crystallization methods. The methods utilized and crystal forms identified are summarized in Table 33. As a result, Form A was obtained from polymorph screening.

TABLE 33

Summary of polymorph screening experiments of freebase

| Method | Result |
|---|---|
| Slurry at RT/5 ° C./50 ° C. | Form A, amorphous, gel, |
| Liquid Vapor Diffusion | Form A, amorphous, gel, clear |
| Slow Evaporation | Form A, amorphous, gel |
| Anti-solvent Addition | Form A, amorphous, gel, |
| Total | Form A, amorphous, gel, clear |

Slurry at RT

Slurry conversion experiments were conducted at RT in different solvent systems. About 15~20 mg of freebase starting material (Compound 1) was suspended in 0.5 mL of solvent in an HPLC vial. Solids were isolated for XRPD analysis after magnetically stirring at RT. Results summarized in Table 34 indicated that Form A and amorphous were obtained.

TABLE 34

Summary of slurry conversion experiments at RT

| Solvent, v:v | Result |
|---|---|
| IPA | Form A (Low crystallinity) |
| MTBE | Gel |
| ACN | Form A |
| EtOH | Form A |
| EtOH/$H_2O$, 1:1 | Form A |
| ACN/$H_2O$, 1:1 | Form A (Low crystallinity) |
| Acetone/$H_2O$, 1:4 | Form A |
| 1,4-Dioxane/$H_2O$, 1:4 | Amorphous |
| Benzyl alcohol/n-Heptane, 1:4 | Gel |
| THF/n-Heptane, 1:4 | Form A |
| DCM/n-Heptane, 1:4 | Form A |
| Anisole/n-Heptane, 1:4 | Gel |
| Toluene/Cyclohexane, 1:4 | Amorphous |
| CPME/Cyclohexane, 1:4 | Amorphous |
| MEK/Cyclohexane, 1:4 | Amorphous |
| EtOAc/Cyclohexane, 1:4 | Amorphous |

Slurry at 5°. Slurry conversion experiments were conducted at 5° C. in different solvent systems. About 15~20 mg of freebase starting material (Compound 1) was suspended in 0.5 mL of solvent in an HPLC vial. Solids were isolated for XRPD analysis after magnetically stirring at 5° C. Results summarized in Table 35 indicated that Form A and amorphous were obtained.

TABLE 35

Summary of slurry conversion experiments at 5° C.

| Solvent, v:v | Result |
|---|---|
| ACN | Form A |
| MIBK/n-Heptane, 1:3 | Gel |
| IPAc/n-Heptane, 1:3 | Amorphous |
| 2-MeTHF/n-Heptane, 1:3 | Gel |
| Xylene/n-Heptane, 1:3 | Amorphous |
| DMAc/n-Heptane, 1:3 | Gel |
| NMP/$H_2O$, 1:4 | Amorphous |
| Ethyl lactate/$H_2O$, 1:3 | Gel |
| DMF/$H_2O$, 1:3 | Amorphous |

Slurry at 50°. Slurry conversion experiments were conducted at 50° C. in different solvent systems. About 20 mg of freebase starting material (Compound 1) was suspended in 0.5 mL of solvent in an HPLC vial. Solids were isolated for XRPD analysis after magnetical stirring at 50° C. Results summarized in Table 36 indicated that amorphous was obtained.

TABLE 36

| Solvent | Result |
|---|---|
| $H_2O$ | Amorphous |
| n-Heptane | Amorphous |

Liquid vapor diffusion. Liquid vapor diffusion experiments were conducted in different solvent systems. Approximate 20 mg of freebase starting material (Compound 1) was dissolved in 0.3~1.5 mL corresponding solvent to obtain a clear solution in a 3-mL vial (if a suspension was observed, the sample was filtered through a PTFE filter with 0.45 μm pore size). This solution was then placed into a 20-mL vial with 3 mL of corresponding anti-solvent. The 20-mL vial was sealed with a cap and kept at RT allowing sufficient time for organic vapor to interact with the solution. The precipitates were isolated for XRPD analysis. The results summarized in Table 37 showed that Form A and amorphous were observed.

TABLE 37

| Solvent | Anti-solvent | Result |
|---|---|---|
| IPAc | n-Heptane | Amorphous |
| Toluene | | Gel |
| 1.4-Dioxane | | Gel |
| 2-Butanol | | Gel |
| DMF | $H_2O$ | Clear solution |
| ACN | | Form A |
| DMSO | | Amorphous |
| THF | | Form A (Low crystallinity) |
| CPME | n-Pentane | Gel |
| Anisole | | Gel |
| Acetone | | Form A |
| EtOAc | | Gel |
| Xylene | | Gel |

Slow evaporation. Slow evaporation experiments were performed under 10 conditions. Briefly, about 15~20 mg of freebase starting material (810935-01-A) was dissolved in 0.5~1.0 mL of solvent in a 3-mL glass vial. The visually clear solutions were subjected to evaporation at RT with vials sealed by Parafilm®. The solids were isolated for XRPD analysis, and the results summarized in Table 38 indicated that Form A and amorphous were obtained.

TABLE 38

| Solvent | Result |
|---|---|
| ACN | Form A |
| DCM | Form A (Low crystallinity) |
| MEK | Amorphous |
| EtOAc | Amorphous |
| IPAc | Gel |
| MeOH | Amorphous |
| EtOH | Form A |
| Acetone | Form A |
| THF | Amorphous |
| 2-MeTHF | Gel |

Anti-solvent addition. A total of 12 anti-solvent addition experiments were carried out. About 20 mg of freebase starting material (Compound 1) was dissolved in 0.5~1.5 mL solvent to obtain a clear solution (if a suspension was observed, the sample was filtered through a PTFE filter with 0.45 μm pore size), and the solution was magnetically stirred followed by addition of anti-solvent stepwise till precipitate appeared or the total amount of anti-solvent reached 10.0 mL. The obtained precipitate was isolated for XRPD analysis. Results summarized in Table 39 showed that Compound A Form A with low crystallinity and amorphous were generated.

TABLE 39

| Solvent | Anti-solvent | Result |
|---|---|---|
| Toluene | n-Heptane | Amorphous |
| EtOAc | | Amorphous |
| CPME | | Amorphous |
| Acetone | | Form A (Low crystallinity) |
| ACN | | Form A (Low crystallinity) |
| 1.4-Dioxane | $H_2O$ | Gel |
| MeOH | | Amorphous |
| DMSO | | Low crystallinity |
| THF | | Form A (Low crystallinity) |
| Anisole | Cyclohexane | Gel |
| MEK | | Gel |
| DCM | | Form A (Low crystallinity) |

Example 11—Polymorphic Screening of Compound A

The solubility of Compound A Form A (810935-33-A) was estimated at RT, following similar procedure as described herein. Results summarized in Table 40 were used to guide the solvent selection in polymorph screening of adipate. The methods utilized and crystal forms identified are summarized in Table 41.

TABLE 40

Approximate solubility of Compound A Form A at RT

| Solvent | Solubility (mg/mL) | Solvent | Solubility (mg/mL) |
|---|---|---|---|
| MeOH | S > 48.0 | 1,4-Dioxane | 7.0 < S < 21.0 |
| EtOH | S > 42.0 | ACN | 2.4 < S < 8.0 |
| IPA | 2.2 < S < 7.3 | MTBE | S < 1.9 |
| Acetone | 6.0 < S < 18.0 | n-Heptane | S < 2.0 |
| MEK | 6.7 < S < 20.0 | Toluene | S < 1.9 |
| EtOAc | S < 2.0 | DMSO | S > 44.0 |
| IPAc | S < 1.9 | $H_2O$ | 22.0 < S < 44.0 |
| MIBK | S < 2.0 | DCM | 19.0 < S < 38.0 |
| THF | S > 48.0 | CPME | S < 2.0 |
| 2-MeTHF | 20.0 < S < 40.0 | Anisole | S < 1.9 |

TABLE 41

Summary of polymorph screening experiments of adipate

| Method | Result |
|---|---|
| Slurry at RT/50° C. | Compound A Form A, gel, clear |
| Liquid Vapor Diffusion | Amorphous, clear, gel |
| Slow Evaporation | Gel, clear |
| Solid Vapor Diffusion | Compound A Form A |
| Anti-solvent Addition | Compound A Form A, B, clear, gel |
| Slow Cooling | Compound A Form A |
| Total | Compound A Form A, Compound A Form B, clear, gel |

Slurry at RT for Compound A. Slurry conversion experiments were conducted at RT in different solvent systems.

About 15 mg of Compound A Form A was suspended in 0.5 mL of solvent in an HPLC vial. Solids were isolated for XRPD analysis after magnetic stirring at RT. Results summarized in Table 42 indicated that adipate Type A was obtained.

TABLE 42

| Solvent, v:v | Result |
|---|---|
| IPA | Compound A Form A |
| ACN | Compound A Form A |
| Acetone | Compound A Form A |
| MEK | Compound A Form A |
| 1,4-Dioxane | Compound A Form A |
| $H_2O$ | Clear solution |
| $H_2O$/ACN, 1:4 | Gel |
| $H_2O$/IPA, 1:4 | Gel |
| DCM/IPA, 1:4 | Compound A Form A |
| 2-MeTHF/Toluene, 1:4 | Compound A Form A |
| Acetone/n-Heptane, 1:3 | Compound A Form A |
| Acetone/Anisole, 1:3 | Compound A Form A |
| MEK/n-Heptane, 1:3 | Compound A Form A |
| MEK/MTBE, 1:3 | Compound A Form A |
| 1,4-Dioxane/n-Heptane, 1:3 | Compound A Form A |
| 1,4-Dioxane/IPAc, 1:3 | Compound A Form A |
| DMSO/$H_2O$, 1:6 | Clear solution |
| THF/$H_2O$, 1:6 | Clear solution |
| EtOH/n-Heptane, 1:6 | Compound A Form A |
| MeOH/CPME, 1:6 | Compound A Form A |

*: Clear solution was transferred to 5° C., followed by transferring to −20° C.

**: Clear solution was transferred to 5° C., followed by transferring to −20° C. Clear solution was still observed, so anti-solvent was added.

#: Clear solution was transferred to 5° C., followed by transferring to −20° C. Clear solution was still observed, so anti-solvent was added. Since clear solution was still observed, the sample was transferred to evaporation at RT.

&: The clear solution was transferred to evaporation at RT

Slurry at 50° for Compound A. Slurry conversion experiments were conducted at 50° C. in different solvent systems. About 15 mg of Compound A Form A was suspended in 0.5 mL of solvent in an HPLC vial. Solids were isolated for XRPD analysis after magnetic stirring at 50° C. Results summarized in Table 43 indicated that Compound A Form A was obtained.

TABLE 43

| Solvent | Result |
|---|---|
| MIBK | Compound A Form A |
| EtOAc | Compound A Form A |
| IPAc | Compound A Form A |
| Anisole | Compound A Form A |
| n-Heptane | Compound A Form A |
| CPME | Compound A Form A |
| MTBE | Compound A Form A |
| Toluene | Compound A Form A |

Liquid vapor diffusion Compound A. Liquid vapor diffusion experiments were conducted in different solvent systems. Approximate 15 mg of Compound A Form A was dissolved in 0.5 mL corresponding solvent to obtain a clear solution in a 3-mL vial. This solution was then placed into a 20-mL vial with 3 mL of corresponding anti-solvent. The 20-mL vial was sealed with a cap and kept at RT allowing sufficient time for organic vapor to interact with the solution. The precipitates were isolated for XRPD analysis. The results summarized in Table 44 showed that amorphous was obtained.

TABLE 44

| Solvent | Anti-solvent | Result |
|---|---|---|
| DMSO | EtOAc | Clear solution |
| THF | n-Heptane | Amorphous |
| | MTBE | Gel |
| EtOH | n-Pentane | Gel |
| | MTBE | Gel |
| $H_2O$ | IPA | Gel |
| | ACN | Gel |

*: clear solutions obtained from liquid vapor diffusion were transferred to evaporation at RT.

Slow evaporation Compound A. Slow evaporation experiments were performed under seven conditions. Briefly, about 15 mg of Compound A Form A was dissolved in 0.5~1.0 mL of solvent in a 3-mL glass vial. The visually clear solutions were subjected to evaporation at RT with vials sealed by Parafilm® with a few pinholes. The results summarized in Table 45 indicated that only gel or clear solution was obtained.

TABLE 45

| Solvent | Result |
|---|---|
| MeOH | Gel |
| EtOH | Gel |
| THF | Gel |
| DCM | Gel |
| 2-MeTHF | Gel |
| $H_2O$ | Clear solution |
| Acetone | Gel |

Solid vapor diffusion Compound A. Solid vapor diffusion experiments were conducted using 12 different solvents. Approximate 15 mg of Compound A Form A (810935-40-A) was weighed into a 3-mL vial, which was placed into a 20-mL vial with 2 mL of corresponding solvent. The 20-mL vial was sealed with a cap and kept at RT allowing solvent vapor to interact with the sample. The solids were tested by XRPD and the results summarized in Table 46 showed that Compound A Form A was obtained.

TABLE 46

| Solvent | Result |
|---|---|
| $H_2O$ | Compound A Form A |
| DCM | Compound A Form A |
| EtOH | Compound A Form A |
| MeOH | Compound A Form A |
| ACN | Compound A Form A |
| THF | Compound A Form A |
| Acetone | Compound A Form A |
| DMF | Compound A Form A |
| EtOAc | Compound A Form A |
| 1,4-Dioxane | Compound A Form A |
| IPA | Compound A Form A |
| DMSO | Compound A Form A |

Anti-solvent addition Compound A. A total of 14 anti-solvent addition experiments were carried out. About 15 mg of Compound A Form A was dissolved in 0.5~1.5 mL solvent to obtain a clear solution (if a suspension was observed, the sample was filtered through a PTFE filter with 0.45 μm pore size), and the solution was magnetically stirred followed by addition of anti-solvent stepwise until precipitate appeared or the total amount of anti-solvent reached 10.0 mL. The obtained precipitate was isolated for XRPD analysis. Results summarized in Table 47 showed that Compound A Form A and Compound A Form B were generated.

TABLE 47

| Solvent | Anti-solvent | Result |
|---|---|---|
| THF | n-Heptane | Compound A Form A |
| EtOH | | Compound A Form A |
| DCM | | Compound A Form A |
| 2-MeTHF | | Gel |
| EtOH | Anisole | Clear solution |
| DMSO | EtOAc | Clear |
| THF | | Compound A Form A |
| MeOH | Toluene | Compound A Form A |
| THF | | Compound A Form A |
| DCM | | Compound A Form B |
| MeOH | MTBE | Gel |
| EtOH | | Gel |
| DCM | | Compound A Form A |
| THF | | Compound A Form A |

Slow cooling Compound A. Slow cooling experiments were conducted in four solvent systems. About 15 mg of Compound A Form A was suspended in 1.0 mL of solvent in a 3-mL glass vial at RT. The suspension was then heated to 50° C., equilibrated for about 2 hr and filtered to a new vial using a seal membrane (PTFE, pore size of 0.45 μm). Filtrates were slowly cooled down to 5° C. at a rate of 0.1° C./min. The obtained solids were kept isothermal at 5° C. before isolation for XRPD analysis. Results summarized in Table 48 indicated Compound A Form A was obtained.

TABLE 48

| Solvent | Result |
|---|---|
| Acetone | Compound A Form A |
| MEK | Compound A Form A |
| IPA | Compound A Form A |
| ACN | Compound A Form A |

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A crystal form comprising Compound A, Form A:

(A)

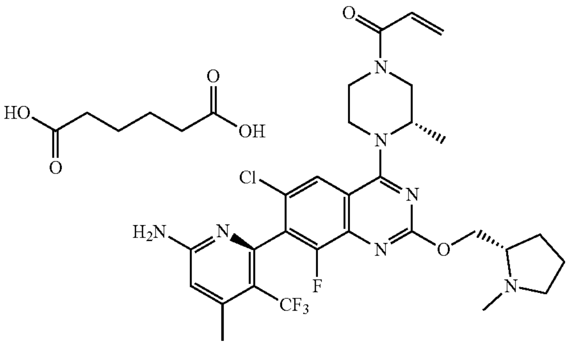

having an X-ray powder diffraction pattern comprising characteristic X-ray powder diffraction peaks using CuKα radiation at 9.6474, 11.0365, 15.4059, 16.4193, and 18.7038 (±0.1° 2θ).

2. The crystal form of claim 1, wherein the crystal form of Compound A, Form A has an X-ray powder diffraction pattern comprising at least 15 additional characteristic X-ray powder diffraction peaks using CuKα radiation at 4.8059, 7.506, 8.5157, 9.2973, 11.1828, 11.677, 12.7936, 14.5086, 16.1353, 16.6719, 16.9847, 18.9135, 19.3881, 19.7517, 19.9746, 20.5178, 21.1487, 21.4666, 21.9673, or 22.1828 (±0.1° 2θ).

3. The crystal form of claim 1, wherein the crystal form of Compound A, Form A has an X-ray powder diffraction pattern comprising at least 10 additional characteristic X-ray powder diffraction peaks using CuKα radiation at 4.8059, 7.506, 8.5157, 9.2973, 11.1828, 11.677, 12.7936, 14.5086, 16.1353, 16.6719, 16.9847, 18.9135, 19.3881, 19.7517, 19.9746, 20.5178, 21.1487, 21.4666, 21.9673, or 22.1828 (±0.1°2θ).

4. The crystal form of claim 1, wherein the crystal form of Compound A, Form A has an X-ray powder diffraction pattern comprising characteristic X-ray powder diffraction peaks using CuKα radiation at 4.8059, 7.506, 8.5157, 9.2973, 9.6474, 11.0365, 11.1828, 11.677, 12.7936, 14.5086, 15.4059, 16.1353, 16.4193, 16.6719, 16.9847, 22.7038, 18.9135, 19.3881, 19.7517, 19.9746, 20.5178, 21.1487, 21.4666, 21.9673, and 22.1828 (±0.1° 2θ) and comprising corresponding d-spacings at 18.37243 11.76829, 10.37514, 9.50454, 9.16041, 8.01034, 7.90589, 7.57235, 6.91391, 6.10025, 5.7469, 5.48871, 5.3944, 4.31324, 5.21609, 4.74037, 4.68829, 4.57458, 4.49117, 4.44156, 4.32518, 4.19755, 4.13611, 4.04295, and 4.00415 ([Å]).

5. The crystal form of claim 1, wherein the crystal form of Compound A, Form A has a weight loss of about 2% up to 100° C. as measured by TGA thermograph and two endotherms at 68.8° C. and 169.1° C. as measured by DSC thermograph.

6. A pharmaceutical composition comprising the solid form of claim 1 and at least one pharmaceutically acceptable excipient.

7. A pharmaceutical composition of claim 6, wherein said composition is formulated for oral administration.

8. The crystal form of claim 1, wherein the crystal form of Compound A, Form A is an anhydrate.

9. The crystal form of claim 1, wherein the crystal form of Compound A, Form A comprises a stoichiometric ratio of adipic acid:freebase of 0.9, 1.0, 1.01, 1.02, 1.03, 1.04, 10.5, 1.06, 1.07, 1.08, 1.09, or 1.10.

10. The crystal form of claim 1, wherein the crystal form of Compound A, Form A comprises a stoichiometric ratio of adipic acid:freebase of 1.06.

11. A crystal form comprising Compound A, Form B:

(A)

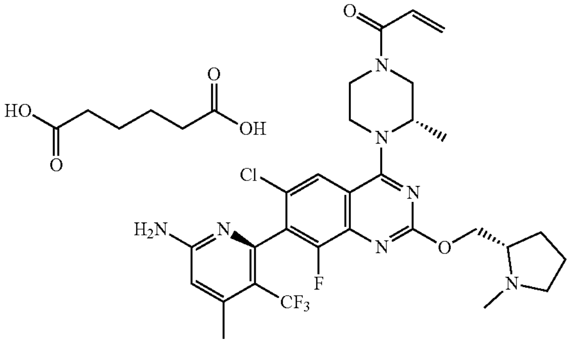

having an X-ray powder diffraction pattern comprising characteristic X-ray powder diffraction peaks using CuKα radiation at 5.2063, 14.63, 17.7161, 21.9253, and 25.1335 (±0.1° 2θ).

12. The crystal form of claim 11, wherein the crystal form of Compound A, Form B has an X-ray powder diffraction pattern comprising at least 5 additional characteristic X-ray powder diffraction peaks using CuKα radiation at 8.8524, 11.1301, 12.3721, 15.6885, 18.2857, or 19.8008 (±0.1° 2θ).

13. The crystal form of claim 11, wherein the crystal form of Compound A, Form B has an X-ray powder diffraction pattern comprising characteristic X-ray powder diffraction peaks using CuKα radiation at 5.2063, 8.8524, 11.1301, 12.3721, 14.63, 15.6885, 17.7161, 18.2857, 19.8008, 21.9253, and 25.1335 (±0.1°2θ) and comprising corresponding d-spacings at 16.96012, 9.98124, 7.94318, 7.14847, 6.04991, 5.64402, 5.00236, 4.84781, 4.48015, 4.0506, and 3.54035 ([Å]).

14. The crystal form of claim 11, wherein the crystal form of Compound A, Form B is an anhydrate.

15. The crystal form of claim 11, wherein the crystal form of Compound A, Form B comprises a stoichiometric ratio of adipic acid:freebase of 1.5, 1.55, 1.6, 1.65, 1.7, 1.8, 1.9, 2, 2.05, or 2.10.

16. A crystal form comprising Compound A, Form D:

(A)

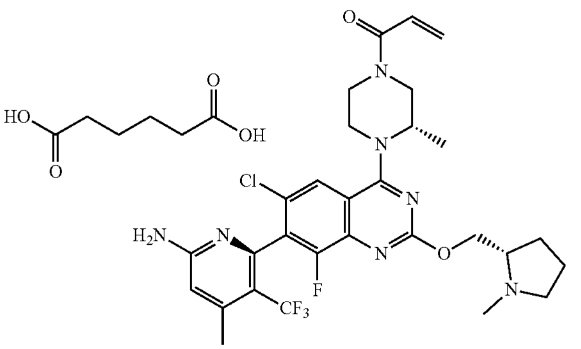

having an X-ray powder diffraction pattern comprising characteristic X-ray powder diffraction peaks using CuKα radiation at 9.7745, 11.0487, 15.2452, 18.6477, and 18.7908 (±0.1°2θ).

17. The crystal form of claim 16, wherein the crystal form of Compound A, Form D has an X-ray powder diffraction pattern comprising at least 15 additional characteristic X-ray powder diffraction peaks using CuKα radiation at 7.4529, 9.309, 11.2178, 11.6936, 12.8642, 14.65, 14.9254, 15.5252, 16.0821, 16.3536, 16.6345, 17.1089, 17.3151, 19.5758, 19.8874, 20.2, 20.6308, 21.0403, 21.6587, or 22.0397 (±0.1° 2θ).

18. The crystal form of claim 16, wherein the crystal form of Compound A, Form D has an X-ray powder diffraction pattern comprising at least 10 additional characteristic X-ray powder diffraction peaks using CuKα radiation at 7.4529, 9.309, 11.2178, 11.6936, 12.8642, 14.65, 14.9254, 15.5252, 16.0821, 16.3536, 16.6345, 17.1089, 17.3151, 19.5758, 19.8874, 20.2, 20.6308, 21.0403, 21.6587, or 22.0397 (±0.1° 2θ).

19. The crystal form of claim 16, wherein the crystal form of Compound A, Form D has an X-ray powder diffraction pattern comprising X-ray powder diffraction peaks using CuKα radiation at 7.4529, 9.309, 9.7745, 11.0487, 11.2178, 11.6936, 12.8642, 14.65, 14.9254, 15.2452, 15.5252, 16.0821, 16.3536, 16.6345, 17.1089, 17.3151, 18.6477, 18.7908, 19.5758, 19.8874, 20.2, 20.6308, 21.0403, 21.6587, and 22.0397 (±0.1°2θ) and comprising corresponding d-spacings at 11.85207, 9.49265, 9.04158, 8.00156, 7.88129, 7.56169, 6.87607, 6.04167, 5.93083, 5.80712, 5.70301, 5.50675, 5.41595, 5.32509, 5.17852, 4.11731, 4.75451, 4.71863, 4.53114, 4.46084, 4.39251, 4.30174, 4.21895, 4.09985, and 4.02983 ([Π]).

20. The crystal form of claim 16, wherein the crystal form of Compound A, Form D has a weight loss of about 1.4% up to 100° C. as measured by TGA thermograph.

21. The crystal form of claim 16, wherein the crystal form of Compound A, Form D is a hemihydrate.

22. A crystal form comprising Compound B:

(B)

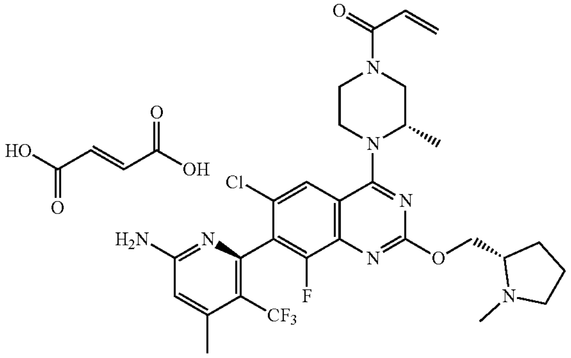

having an X-ray powder diffraction pattern comprising characteristic X-ray powder diffraction peaks using CuKα radiation at 6.6796, 14.9097, 15.2963, 19.4416, and 23.7124 (±0.1°2θ).

23. The crystal form of claim 22, wherein the crystal form of Compound B has an X-ray powder diffraction pattern comprising at least 15 additional characteristic X-ray powder diffraction peaks using CuKα radiation at 7.8754, 8.4472, 8.724, 9.6832, 12.1433, 13.3393, 14.1386, 17.4837, 18.5763, 20.3394, 21.4642, 22.4341, 23.0009, 23.3901, 24.7816, 26.1995, 26.7708, 27.7302, or 30.9939 (±0.1° 2θ).

24. The crystal form of claim 22, wherein the crystal form of Compound B has an X-ray powder diffraction pattern comprising at least 10 additional characteristic X-ray powder diffraction peaks using CuKα radiation at 7.8754, 8.4472, 8.724, 9.6832, 12.1433, 13.3393, 14.1386, 17.4837, 18.5763, 20.3394, 21.4642, 22.4341, 23.0009, 23.3901, 24.7816, 26.1995, 26.7708, 27.7302, or 30.9939 (±0.1° 2θ).

25. The crystal form of claim 22, wherein the crystal form of Compound B has an X-ray powder diffraction pattern comprising characteristic X-ray powder diffraction peaks using CuKα radiation at 6.6796, 7.8754, 8.4472, 8.724, 9.6832, 12.1433, 13.3393, 14.1386, 14.9097, 15.2963, 17.4837, 18.5763, 19.4416, 20.3394, 21.4642, 22.4341, 23.0009, 23.3901, 23.7124, 24.7816, 26.1995, 26.7708, 27.7302, and 30.9939 (±0.1° 2θ) and comprising corresponding d-spacings at 13.22236, 11.21714, 10.45905, 10.12778, 9.1266, 7.28262, 6.63225, 6.25903, 5.93701, 5.78782, 5.06834, 4.77263, 4.5621, 4.36271, 4.13656, 3.95988, 3.86356, 3.80014, 3.74921, 3.58982, 3.39867, 3.32742, 3.21445, and 2.883 ([Å]).

26. The crystal form of claim 22, wherein the crystal form of Compound B is an anhydrate.

27. The crystal form of claim 22, wherein the crystal form of Compound B comprises a stoichiometric ratio of fumaric acid:freebase of 1.03.

28. A crystal form comprising Compound C:

(C)

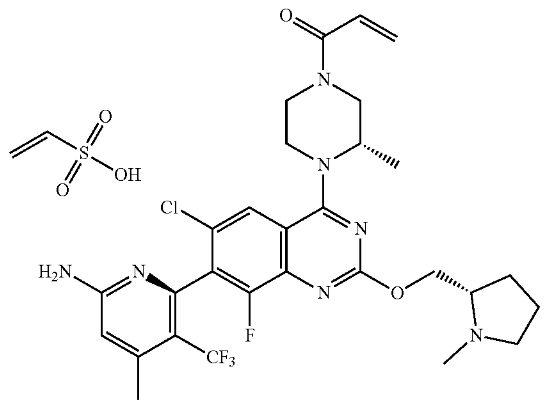

having an X-ray powder diffraction pattern comprising characteristic X-ray powder diffraction peaks using CuKα radiation at 12.5401, 17.5707, 16.834, 21.3525, and 26.5569 (±0.1°2θ).

29. The crystal form of claim 28, wherein the crystal form of Compound C has an X-ray powder diffraction pattern comprising at least 5 additional characteristic X-ray powder diffraction peaks using CuKα radiation at 5.5814, 8.7554, 11.1932, 13.5091, 14.2557, 15.8682, 16.3963, 18.9739, 20.2549, or 26.5569±0.1° 2θ.

30. The crystal form of claim 28, wherein the crystal form of Compound C has an X-ray powder diffraction pattern comprising characteristic X-ray powder diffraction peaks using CuKα radiation at 5.5814, 8.7554, 11.1932, 12.5401, 13.5091, 14.2557, 15.8682, 16.3963, 16.834, 17.5707, 18.9739, 20.2549, 21.3525, and 26.5569±0.1° 2θ and comprising corresponding d-spacings at 15.82116, 10.09154, 7.89859, 7.05308, 6.54927, 6.2079, 5.58052, 5.40194, 5.26244, 5.04343, 4.67349, 4.38072, 4.15796, and 3.35374 ([Å]).

31. The crystal form of claim 28, wherein the crystal form of Compound C has a weight loss of 8.6% up to 100° C. as measured by TGA thermograph two endotherms at 81.0° C. and 149.2° C. as measured by DSC thermograph.

32. The crystal form of claim 28 wherein the crystal form of Compound C comprises a stoichiometric ratio of ethylenesulphonic acid:freebase of 1.04.

33. A crystal form comprising Compound D:

(D)

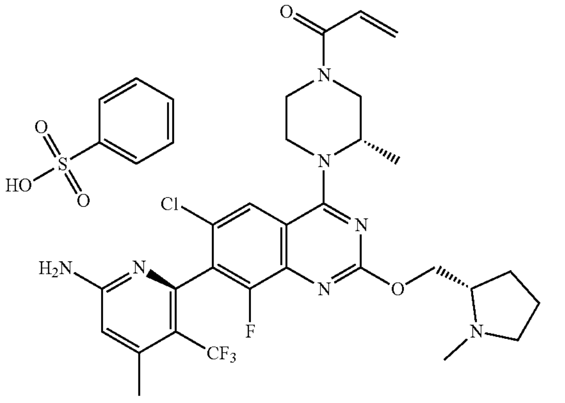

having an X-ray powder diffraction pattern comprising characteristic X-ray powder diffraction peaks using CuKα radiation at 7.3809, 10.7407, 14.654, 18.5979, and 25.2558 (±0.1° 2θ).

34. The crystal form of claim 33, wherein the crystal form of Compound D has an X-ray powder diffraction pattern comprising at least 5 additional characteristic X-ray powder diffraction peaks using CuKα radiation at 9.2213, 12.7588, 13.6799, 15.8145, 17.1195, 19.5937, 20.8941, 21.9068, or 24.4114±0.1° 2θ.

35. The crystal form of claim 33, wherein the crystal form of Compound D has an X-ray powder diffraction pattern comprising X-ray powder diffraction peaks using CuKα radiation at 7.3809, 9.2213, 10.7407, 12.7588, 13.6799, 14.654, 15.8145, 17.1195, 18.5979, 19.5937, 20.8941, 21.9068, 24.4114, and 25.2558±0.1° 2θ and comprising corresponding d-spacings at 11.96741, 9.58275, 8.23033, 6.93266, 6.46789, 6.04005, 5.59932, 5.17532, 4.76713, 4.52704, 4.24813, 4.05397, 3.64343, and 3.52348.

36. The crystal form of claim 33, wherein the crystal form of Compound D has a weight loss of 7.7% was observed up to 170° C. as measured by TGA thermograph and one endotherm at 75.8° C. as measured by DSC thermograph.

37. The crystal form of claim 33, wherein the crystal form of Compound D comprises a stoichiometric ratio of benzenesulfonic acid:freebase of 1.03.

38. A crystal form comprising Compound E:

(E)

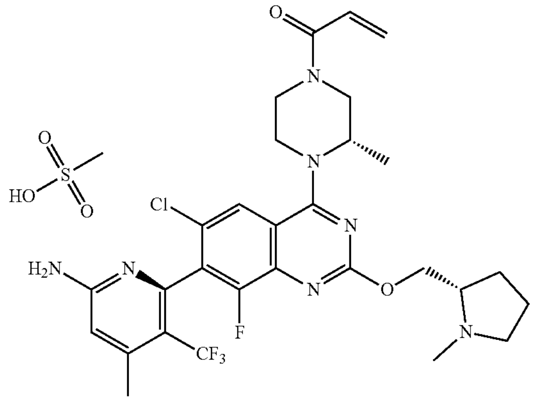

having an X-ray powder diffraction pattern comprising characteristic X-ray powder diffraction peaks using CuKα radiation at 5.9702, 6.2798, 12.4314, 18.9264, and 20.6365 (±0.1° 2θ).

39. The crystal form of claim 38, wherein the crystal form of Compound E has an X-ray powder diffraction pattern comprising at least 5 additional characteristic X-ray powder diffraction peaks using CuKα radiation at 7.766, 11.9769, 14.8918, 15.5087, 16.002, 17.9217, 22.334, 23.8046, 25.8171, or 26.1887±0.1° 2θ.

40. The crystal form of claim 38, wherein the crystal form of Compound E has an X-ray powder diffraction pattern comprising characteristic X-ray powder diffraction peaks using CuKα radiation at 5.9702, 6.2798, 7.766, 11.9769, 12.4314, 14.8918, 15.5087, 16.002, 17.9217, 18.9264, 20.6365, 22.334, 23.8046, 25.8171, and 26.1887±0.1° 2θ and comprising corresponding d-spacings at 14.79172, 14.0631, 11.37484, 7.38342, 7.11451, 5.94411, 5.70906, 5.53413, 4.94544, 4.68511, 4.30057, 3.97739, 3.73491, 3.44814, and 3.40005 ([Å]).

* * * * *